US012565511B2

(12) United States Patent
Zhang et al.

(10) Patent No.: US 12,565,511 B2
(45) Date of Patent: Mar. 3, 2026

(54) SOS1 INHIBITOR CONTAINING PHOSPHORUS

(71) Applicant: Chia Tai Tianqing Pharmaceutical Group Co., Ltd., Lianyungang (CN)

(72) Inventors: Yinsheng Zhang, Nanjing (CN); Baomin Liu, Nanjing (CN); Zhengbang Chen, Nanjing (CN); Jinfa Hu, Nanjing (CN); Yuchen Chen, Nanjing (CN); Kewen Sun, Nanjing (CN); Jinan Wang, Nanjing (CN); Lijuan Zhu, Nanjing (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 645 days.

(21) Appl. No.: 17/998,244

(22) PCT Filed: May 10, 2021

(86) PCT No.: PCT/CN2021/092672

§ 371 (c)(1),
(2) Date: Nov. 8, 2022

(87) PCT Pub. No.: WO2021/228028

PCT Pub. Date: Nov. 18, 2021

(65) Prior Publication Data

US 2024/0254151 A1 Aug. 1, 2024

(30) Foreign Application Priority Data

May 9, 2020 (CN) ......................... 202010387620.0
Apr. 25, 2021 (CN) ......................... 202110450032.1

(51) Int. Cl.

| | |
|---|---|
| ***A61K 31/675*** | (2006.01) |
| ***C07F 9/6512*** | (2006.01) |
| ***C07F 9/6561*** | (2006.01) |
| ***C07F 9/6568*** | (2006.01) |
| ***C07F 9/6571*** | (2006.01) |
| ***C07F 9/6584*** | (2006.01) |

(52) U.S. Cl.

CPC ........ *C07F 9/65128* (2013.01); *A61K 31/675* (2013.01); *C07F 9/6561* (2013.01); *C07F 9/6568* (2013.01); *C07F 9/657163* (2013.01); *C07F 9/6584* (2013.01)

(58) Field of Classification Search

None
See application file for complete search history.

(56) References Cited

U.S. PATENT DOCUMENTS

2019/0358230 A1* 11/2019 Gmachl ............... C07D 403/10

FOREIGN PATENT DOCUMENTS

| | | | | |
|---|---|---|---|---|
| CN | 110167928 A | 8/2019 | | |
| EP | 4074317 A1 * | 10/2022 | ............ C07F 9/6561 | |
| JP | 2024-513595 A | 3/2024 | | |
| WO | WO 2004/058267 A1 | 7/2004 | | |
| WO | WO 2018/115380 A1 | 6/2018 | | |
| WO | WO 2018/172250 A1 | 9/2018 | | |
| WO | WO 2019/201848 A1 | 10/2019 | | |
| WO | WO 2022/148442 A1 | 7/2022 | | |

OTHER PUBLICATIONS

Zeng, Yi. Design, synthesis, and evaluation of dual son of sevenless 1 (SOS1) and epidermal growth factor receptor (EGFR) inhibitors for the treatment of cancers. Bioorganic Chemistry 153 (2024) 107833 (Year: 2024).*
Office Action for JP 2022-568428 issued on Mar. 25, 2025.
Supplementary European Search Report for EP 21804515 dated Apr. 15, 2024.
Abbott, Jason R. et al., "Discovery of Quinazolines That Activate SOS1-Mediated Nucleotide Exchange on RAS" ACS Medicinal Chemistry Letters, Aug. 2018, pp. 941-946, vol. 9, No. 9.
Akan, Denis T. et al., "Small Molecule SOS1 Agonists Modulate MAPK and PI3K Signaling via Independent Cellular Responses" ACS Chem. Biol., 2019, pp. 325-331, vol. 14.
Hillig, Roman C. et al., "Discovery of potent SOS1 inhibitors that block RAS activation via disruption of the RAS-SOS1 interaction" PNAS, Jan. 2019, pp. 2551-2560, vol. 116, No. 7.
International Search Report for PCT/CN2021/092672 dated Jun. 29, 2021.

* cited by examiner

*Primary Examiner* — Clinton A Brooks
*Assistant Examiner* — Nicola Maria Bauer
(74) *Attorney, Agent, or Firm* — Knobbe, Martens, Olson & Bear, LLP

(57) ABSTRACT

The present application relates to the field of pharmaceutical chemistry, relates to an SOS1 inhibitor containing phosphorus, i.e., a compound of formula (I) and a preparation method therefor, and a pharmaceutical composition containing the compound, and relates to use thereof in the preparation of a drug for treating a disease and/or disorder related to SOS1 or regulated by SOS1.

(I)

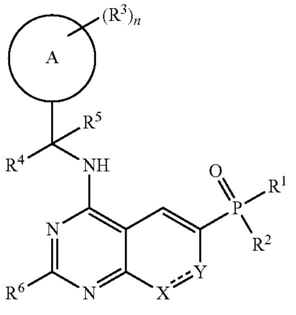

19 Claims, No Drawings

SOS1 INHIBITOR CONTAINING PHOSPHORUS

CROSS-REFERENCE TO RELATED APPLICATIONS

This application is a U.S. National Phase Application of PCT International Application Number PCT/CN2021/092672, filed on May 10, 2021, designating the United States of America and published in the Chinese language, which is an International Application of and claims the benefit of priority to Chinese Patent Application No. 202010387620.0, filed on May 9, 2020, and Chinese Patent Application No. 202110450032.1, filed on Apr. 25, 2021. The disclosures of the above-referenced applications are hereby expressly incorporated by reference in their entireties.

TECHNICAL FIELD

The present application relates to an SOS1 inhibitor containing phosphorus, a preparation method therefor, a pharmaceutical composition containing the inhibitor, and use thereof in the treatment of a disease and/or disorder related to SOS1 or regulated by SOS1.

BACKGROUND

RAS is the most frequently mutated oncogene in human cancers, while KRAS is the most frequently occurring subtype in the RAS family, with KRAS gene mutations accounting for 86% of the total RAS gene mutations.

The binding of guanine nucleotide exchange factors (GEFs) such as SOS1 (Son of Sevenless 1) promote release of GDP from RAS-family proteins, enabling GTP binding (Chardin et al., *Science,* 1993, 260(5112):1338-43). When in the GTP-bound state, RAS-family proteins are active and engage effector proteins including C-RAF and phosphoinositide 3-kinase (PI3K) to promote the RAF/mitogen or extracellular signal-regulated kinase (MEK/ERK) pathway, the PI3K/AKT/mammalian target of rapamycin (mTOR) pathway and the RalGDS (Ral guanine nucleotide dissociation stimulator) pathway (McCormick et al., *J. Mol. Med. (Berl).*, 2016, 94(3):253-8; Rodriguez-Viciana et al., *Cancer Cell.,* 2005, 7(3):205-6). These pathways affect diverse cellular processes such as proliferation, survival, metabolism, motility, angiogenesis, immunity and growth (Young et al., *Adv. Cancer Res.,* 2009, 102:1-17; Rodriguez-Viciana et al., *Cancer Cell.,* 2005, 7(3):205-6).

Selective inhibition of the binding of the catalytic site of SOS1 to RAS-family proteins can prevent SOS1-mediated activation of RAS-family proteins to the GTP-bound form. Thus, SOS1 inhibitor compounds can inhibit signaling in cells downstream of RAS-family proteins (e.g., ERK phosphorylation). A desirable SOS1 inhibitor compound should have high potency towards selective inhibition of SOS1: RAS-family protein binding and ERK phosphorylation in cells.

Recently, researchers from Bayer have reported the discovery of a selective SOS1 inhibitor containing a quinazoline parent nucleus (*Proc Natl Acad Sci.* 2019; 116(7):2551-2560), representing the compound BAY-293, which can block RAS activation by interfering with the RAS-SOS1 interaction.

BAY-293

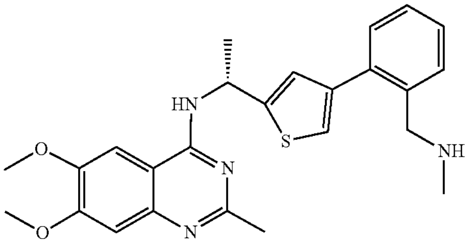

Herein, provided is a novel SOS1 inhibitor compound that can inhibit ERK phosphorylation in cells by interfering with the RAS-SOS1 interaction.

SUMMARY

In one aspect, the present application provides a compound of formula (I), a stereoisomer thereof or a pharmaceutically acceptable salt thereof, (I)

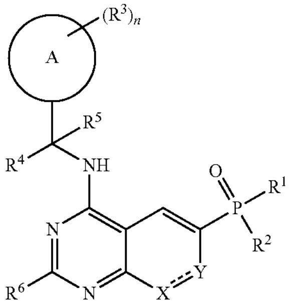

wherein,

X and Y are each independently selected from the group consisting of $CR^a$, C(O), N and $NR^b$;

“------” represents a single bond or a double bond depending on X and Y;

$R^a$ is selected from the group consisting of hydrogen, hydroxy, halogen, cyano, $C_{1-6}$ alkyl and $C_{1-6}$ alkoxy, wherein the $C_{1-6}$ alkyl or $C_{1-6}$ alkoxy is optionally substituted with one or more deuterium or halogens;

$R^b$ is selected from the group consisting of hydrogen, $C_{1-6}$ alkyl and $C_{1-6}$ alkoxy;

$R^1$ and $R^2$ are each independently selected from the group consisting of $C_{1-6}$ alkyl, $NH(R^c)$—$C_{1-6}$ alkyl- and $N(R^c)(C_{1-6}$ alkyl)-$C_{1-6}$ alkyl-, or $R^1$, $R^2$ and the phosphorus atom to which they are both connected together form 5-10 membered heterocyclyl, wherein the $C_{1-6}$ alkyl or 5-10 membered heterocyclyl is optionally substituted with one or more $R^c$;

each $R^c$ is independently selected from the group consisting of hydrogen, O═, HN═, $C_{1-6}$ alkyl-N═, $C_{1-6}$ alkyl-, $C_{1-6}$ alkyl-C(O)—, $C_{1-6}$ alkyl-$S(O)_2$—, 3-6 membered cycloalkyl-$S(O)_2$—, $C_{1-6}$ alkyl OC(O)—, $C_{1-6}$ alkyl-O—$C_{1-6}$ alkyl-, $C_{1-6}$ alkyl-O—$C_{1-6}$ alkyl-C(O)—, amino-C(O)—, mono($C_{1-6}$ alkyl)amino-C(O)—, di($C_{1-6}$ alkyl)amino-C(O)—, amino-$C_{1-6}$ alkyl-C(O)—, mono($C_{1-6}$ alkyl)amino-$C_{1-6}$ alkyl-C(O)—, di($C_{1-6}$ alkyl)amino-$C_{1-6}$ alkyl-C(O)—, amino-C(O)—$C_{1-6}$ alkyl-, mono($C_{1-6}$ alkyl)amino-C(O)—$C_{1-6}$ alkyl-, di($C_{1-6}$ alkyl)amino-C(O)—$C_{1-6}$ alkyl-, 3-6 membered cycloalkyl-, 3-6 membered cycloalkyl-C(O)—, 3-6 membered cycloalkyl-$C_{1-6}$ alkyl-, 3-6 membered heterocycloalkyl-, 3-6 membered heterocycloalkyl-C(O)—, 3-6 membered heterocycloalkyl-$C_{1-6}$ alkyl-, $C_{6-10}$ aryl-$C_{1-6}$ alkyl- and $C_{1-6}$ alkyl-substituted with one or more hydroxy or cyano, wherein the $R^c$ is optionally substituted with one or more halogens when it is not hydrogen and O=;

ring A is selected from the group consisting of $C_{6-10}$ aryl, 5-10 membered heteroaryl, 8-12 membered fused ring and 8-12 membered fused heterocyclic ring;

n is 0, 1, 2 or 3;

each $R^3$ is independently selected from the group consisting of amino, nitro, halogen, $C_{1-8}$ alkyl-, 3-6 membered cycloalkyl- and phenyl, wherein the $C_{1-8}$ alkyl-, 3-6 membered cycloalkyl- or phenyl is optionally substituted with one or more $R^d$;

$R^d$ is selected from the group consisting of hydroxy, halogen and $C_{1-6}$ alkyl-NH—$C_{1-6}$ alkyl-;

$R^4$ and $R^5$ are each independently selected from the group consisting of hydrogen, deuterium and $C_{1-6}$ alkyl, wherein the $C_{1-6}$ alkyl is optionally substituted with one or more halogens;

$R^6$ is selected from the group consisting of hydrogen, halogen and $C_{1-6}$ alkyl, wherein the $C_{1-6}$ alkyl is optionally substituted with one or more halogens.

In some embodiments, X is selected from the group consisting of $CR^a$ and $NR^b$, and Y is selected from the group consisting of $CR^a$, C(O), N and $NR^b$. In some embodiments, X is selected from the group consisting of $CR^a$ and $NR^b$, and Y is selected from the group consisting of $CR^a$, C(O) and N.

In some embodiments, X is selected from $CR^a$, and Y is selected from the group consisting of $CR^a$, C(O), N and $NR^b$. In some embodiments, X is selected from $CR^a$, and Y is selected from the group consisting of $CR^a$, C(O) and N. In some embodiments, X is selected from $CR^a$, and Y is selected from N.

In some embodiments, X is selected from $NR^b$, and Y is selected from the group consisting of $CR^a$, C(O), N and $NR^b$. In some embodiments, X is selected from $NR^b$, and Y is selected from the group consisting of $CR^a$, C(O) and N. In some embodiments, X is selected from $NR^b$, and Y is selected from C(O).

In some embodiments, X and Y are both selected from $CR^a$. In some embodiments, X is selected from CH, and Y is selected from $CR^a$.

In some embodiments, $R^a$ is selected from the group consisting of hydrogen, hydroxy, halogen, cyano, $C_{1-4}$ alkyl and $C_{1-4}$ alkoxy, wherein the $C_{1-4}$ alkyl or $C_{1-4}$ alkoxy is optionally substituted with one or more deuterium or halogens.

In some embodiments, $R^a$ is selected from the group consisting of hydrogen, hydroxy, halogen, cyano, $C_{1-4}$ alkyl and $C_{1-4}$ alkoxy, wherein the $C_{1-4}$ alkyl is optionally substituted with one or more halogens, and the $C_{1-4}$ alkoxy is optionally substituted with one or more deuterium or halogens. In some embodiments, $R^a$ is selected from the group consisting of hydrogen, hydroxy, halogen, cyano, $C_{1-3}$ alkyl and $C_{1-3}$ alkoxy, wherein the $C_{1-3}$ alkyl is optionally substituted with one or more halogens, and the $C_{1-3}$ alkoxy is optionally substituted with one or more deuterium or halogens.

In some embodiments, $R^a$ is selected from the group consisting of hydrogen, hydroxy, halogen, cyano and $C_{1-6}$ alkoxy, wherein the $C_{1-6}$ alkoxy is optionally substituted with one or more deuterium or halogens.

In some embodiments, $R^a$ is selected from the group consisting of hydrogen, hydroxy, halogen, cyano and $C_{1-4}$ alkoxy, wherein the $C_{1-4}$ alkoxy is optionally substituted with one or more deuterium or halogens. In some embodiments, $R^a$ is selected from the group consisting of hydrogen, hydroxy, halogen, cyano and $C_{1-4}$ alkoxy, wherein the $C_{1-4}$ alkoxy is optionally substituted with 3 deuterium, or one or more fluorine. In some embodiments, $R^a$ is selected from the group consisting of hydrogen, hydroxy, halogen, cyano and $C_{1-4}$ alkoxy, wherein the $C_{1-4}$ alkoxy is optionally substituted with 3 deuterium, or 1 or 2 fluorine.

In some embodiments, $R^a$ is selected from the group consisting of hydrogen, hydroxy, fluorine, cyano, methoxy, monofluorinemethoxy and difluorinemethoxy, wherein the methoxy is optionally substituted with 3 deuterium.

In some embodiments, $R^a$ is selected from the group consisting of hydrogen, hydroxy, fluorine, cyano, $CH_3O$—, $CD_3O$—, $CH_2FO$— and $CHF_2O$—.

In some embodiments, $R^a$ is selected from the group consisting of hydrogen, fluorine, $CH_3O$—, $CD_3O$— and $CHF_2O$—.

In some embodiments, $R^b$ is selected from the group consisting of hydrogen, $C_{1-4}$ alkyl and $C_{1-4}$ alkoxy.

In some embodiments, $R^b$ is selected from $C_{1-6}$ alkyl. In some embodiments, $R^b$ is selected from $C_{1-4}$ alkyl. In some embodiments, $R^b$ is selected from $C_{1-3}$ alkyl. In some embodiments, $R^b$ is selected from methyl.

In some embodiments, X is selected from the group consisting of CH, CF, C(CN) and $N(CH_3)$, and Y is selected from the group consisting of N, CH, C(O), C(OH), $C(OCH_3)$, $C(OCHF_2)$, $C(OCH_2F)$, CF and $C(OCD_3)$. In some embodiments, X is selected from CH, and Y is selected from the group consisting of C(OH), $C(OCH_3)$, $C(OCHF_2)$, $C(OCH_2F)$, CF and $C(OCD_3)$. In some embodiments, X is selected from CH, and Y is selected from N. In some embodiments, X is selected from $N(CH_3)$, and Y is selected from C(O). In some embodiments, X is selected from the group consisting of CF and C(CN), and Y is selected from the group consisting of CH and N.

In some embodiments, "------" is a double bond. In some embodiments, "------" is a single bond.

In some embodiments, $R^1$ and $R^2$ are each independently selected from the group consisting of $C_{1-6}$ alkyl, $NH(R^c)$—$C_{1-6}$ alkyl- and $N(R^c)(C_{1-6}$ alkyl)-$C_{1-6}$ alkyl-, or $R^1$, $R^2$ and the phosphorus atom to which they are both connected together form 5-10 membered heterocyclyl, wherein the 5-10 membered heterocyclyl is optionally substituted with one or more $R^c$.

In some embodiments, $R^1$ and $R^2$ are each independently selected from $C_{1-6}$ alkyl, or $R^1$, $R^2$ and the phosphorus atom to which they are both connected together form 5-10 membered heterocyclyl, wherein the 5-10 membered heterocyclyl is optionally substituted with one or more $R^c$.

In some embodiments, $R^1$ and $R^2$ are each independently selected from the group consisting of $C_{1-3}$ alkyl, $NH(R^c)$—$C_{1-3}$ alkyl- and $N(R^c)(C_{1-3}$ alkyl)-$C_{1-3}$ alkyl-.

In some embodiments, $R^1$ and $R^2$ are each independently selected from $C_{1-3}$ alkyl.

In some embodiments, $R^1$ and $R^2$ are each independently selected from the group consisting of methyl, ethyl, propyl and isopropyl.

In some embodiments, $R^1$ and $R^2$ are each independently selected from the group consisting of methyl and ethyl.

In some embodiments, $R^1$ and $R^2$ are each independently selected from methyl.

In some embodiments, $R^1$, $R^2$ and the phosphorus atom to which they are both connected together form 5-10 membered heterocyclyl, wherein the ring atoms of the 5-10 membered heterocyclyl optionally contain one or more heteroatoms selected from the group consisting of N, O and S atoms, and the 5-10 membered heterocyclyl is optionally substituted with one or more $R^c$.

In some embodiments, $R^1$, $R^2$ and the phosphorus atom to which they are both connected together form 5-10 membered heterocyclyl, wherein the ring atoms of the 5-10 membered heterocyclyl optionally contain one or more heteroatoms selected from the group consisting of N, O and S atoms, and the 5-10 membered heterocyclyl is optionally substituted with one or more $R^c$, and when the ring atoms contain an N atom, N is connected to $R^c$.

In some embodiments, $R^1$, $R^2$ and the phosphorus atom to which they are both connected together form 5-8 membered heterocyclyl, wherein the ring atoms of the 5-8 membered heterocyclyl optionally contain one heteroatom selected from the group consisting of N and O atoms, and when the ring atoms contain an N atom, N is connected to $R^c$.

In some embodiments, $R^1$, $R^2$ and the phosphorus atom to which they are both connected together form 5-8 membered heterocycloalkyl, wherein the ring atoms of the 5-8 membered heterocycloalkyl at least contain one N atom, and N is connected to $R^c$.

In some embodiments, $R^1$, $R^2$, and the phosphorus atom to which they are both connected together form 5 membered or 6 membered heterocycloalkyl, 9 membered or 10 membered spiro heterocycloalkyl and 9 membered or 10 membered fused heterocycloalkyl, wherein the 5 membered or 6 membered heterocycloalkyl, 9 membered or 10 membered spiro heterocycloalkyl, or 9 membered or 10 membered fused heterocycloalkyl is optionally substituted with one or more $R^c$.

In some embodiments, $R^1$, $R^2$, and the phosphorus atom to which they are both connected together form 5 membered or 6 membered heterocyclyl, wherein the 5 membered or 6 membered heterocyclyl is optionally substituted with one or more $R^c$.

In some embodiments, $R^1$, $R^2$ and the phosphorus atom to which they are both connected together form 5 membered or 6 membered heterocyclyl, wherein the ring atoms of the 5 membered or 6 membered heterocyclyl optionally contain one or more heteroatoms selected from the group consisting of N, O and S atoms, and when the ring atoms contain an N atom, N is connected to $R^c$. In some embodiments, $R^1$, $R^2$ and the phosphorus atom to which they are both connected together form 5 membered or 6 membered heterocyclyl, wherein the ring atoms of the 5 membered or 6 membered heterocyclyl optionally contain one heteroatom selected from the group consisting of N and O atoms, and when the ring atoms contain an N atom, N is connected to $R^c$.

In some embodiments, $R^1$, $R^2$ and the phosphorus atom to which they are both connected together form 6 membered heterocyclyl, wherein the ring atoms of the 6 membered heterocyclyl at least contain one N atom, and N is connected to $R^c$. In some embodiments, $R^1$, $R^2$ and the phosphorus atom to which they are both connected together form 6 membered heterocyclyl, wherein the ring atoms of the 6 membered heterocyclyl contain only one N atom, and N is connected to $R^c$.

In some embodiments, $R^1$, $R^2$, and the phosphorus atom to which they are both connected together form 6 membered heterocyclyl, wherein the ring atoms of the 6 membered heterocyclyl contain only one O atom.

In some embodiments, $R^1$, $R^2$ and the phosphorus atom to which they are both connected together form 5 membered or 6 membered heterocyclyl, and the ring atoms of the 5 membered or 6 membered heterocyclyl consist of carbon and phosphorus atoms.

In some embodiments, $R^1$, $R^2$ and the phosphorus atom to which they are both connected together form 6 membered heterocycloalkyl, wherein the ring atoms of the 6 membered heterocycloalkyl at least contain one N atom, and N is connected to $R^c$. In some embodiments, $R^1$, $R^2$ and the phosphorus atom to which they are both connected together form 6 membered heterocycloalkyl, wherein the ring atoms of the 6 membered heterocycloalkyl contain only one N atom, and N is connected to $R^c$. In some embodiments, $R^1$, $R^2$, and the phosphorus atom to which they are both connected together form 6 membered heterocycloalkyl, wherein the ring atoms of the 6 membered heterocycloalkyl contain only one O atom. In some embodiments, $R^1$, $R^2$ and the phosphorus atom to which they are both connected together form 5 membered or 6 membered heterocycloalkyl, and the ring atoms of the 5 membered or 6 membered heterocycloalkyl consist of carbon and phosphorus atoms.

In some embodiments, structural unit

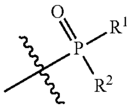

may be selected from the group consisting of structural units

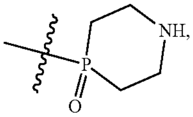
,

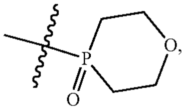
,

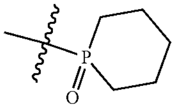
,

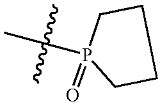
,

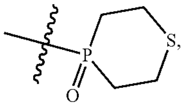
,

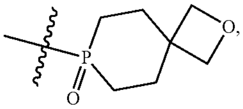
,

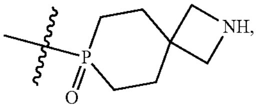
,

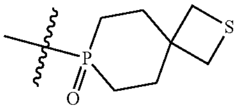
and

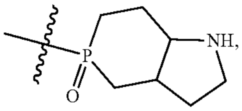
, wherein the structural unit

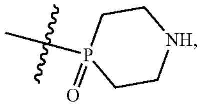

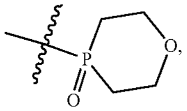

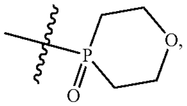

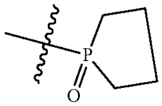
,

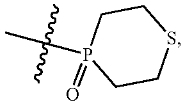

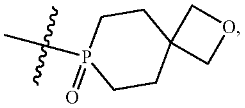

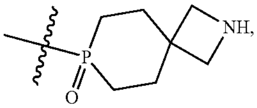

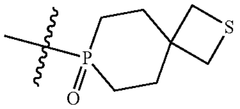
or

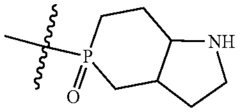

may be optionally substituted with one or more $R^c$.

In some embodiments, structural unit

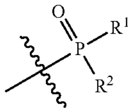

may be selected from the group consisting of structural units

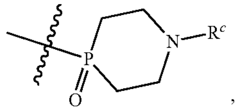
,
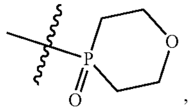
,
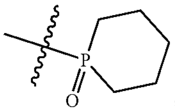
,
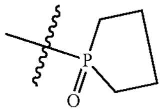
,
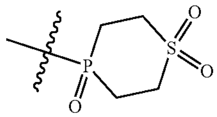
,
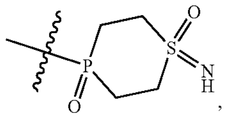
,

-continued

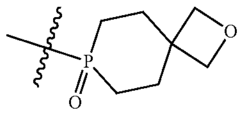
,
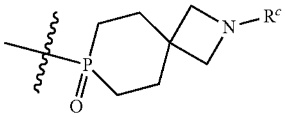
,
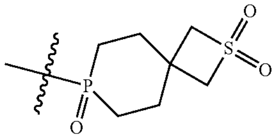
and
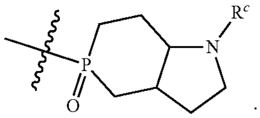
.

In some embodiments, structural unit

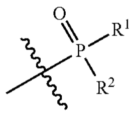

may be selected from the group consisting of structural units

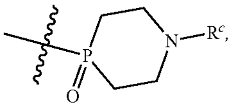

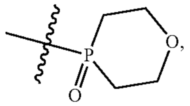

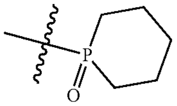
and
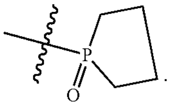
.

In some embodiments, structural unit

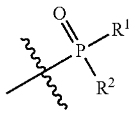

is structural unit

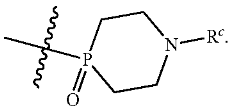

In some embodiments, $R^1$ and $R^2$ are each independently selected from the group consisting of methyl and ethyl, or structural unit

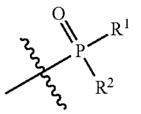

is selected from the group consisting of structural units

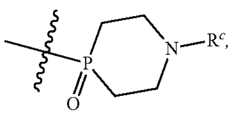

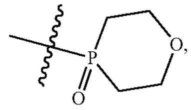

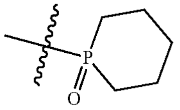

and

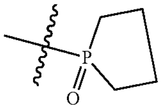

.

In some embodiments, $R^1$ and $R^2$ are each independently selected from methyl, or structural unit

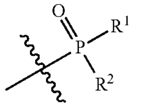

is structural unit

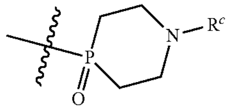

.

In some embodiments, each $R^c$ is independently selected from the group consisting of hydrogen, $C_{1-6}$ alkyl-, $C_{1-6}$ alkyl-C(O)—, $C_{1-6}$ alkyl OC(O)—, $C_{1-6}$ alkyl-O—$C_{1-6}$ alkyl-, $C_{1-6}$ alkyl-O—$C_{1-6}$ alkyl-C(O)—, amino-C(O)—, mono($C_{1-6}$ alkyl)amino-C(O)—, di($C_{1-6}$ alkyl)amino-C(O)—, amino-$C_{1-6}$ alkyl-C(O)—, mono($C_{1-6}$ alkyl)amino-$C_{1-6}$ alkyl-C(O)—, di($C_{1-6}$ alkyl)amino-$C_{1-6}$ alkyl-C(O)—, amino-C(O)—$C_{1-6}$ alkyl-, mono($C_{1-6}$ alkyl)amino-C(O)—$C_{1-6}$ alkyl-, di($C_{1-6}$ alkyl)amino-C(O)—$C_{1-6}$ alkyl-, 3-6 membered cycloalkyl-, 3-6 membered cycloalkyl-C(O)—, 3-6 membered cycloalkyl-$C_{1-6}$ alkyl-, $C_{6-10}$ aryl-$C_{1-6}$ alkyl-, and $C_{1-6}$ alkyl- substituted with one or more hydroxy.

In some embodiments, each $R^c$ is independently selected from the group consisting of hydrogen, O═, HN═, $C_{1-6}$ alkyl-N═, $C_{1-3}$ alkyl-, $C_{1-3}$ alkyl-C(O)—, $C_{1-3}$ alkyl-$S(O)_2$—, 3-6 membered cycloalkyl-$S(O)_2$—, $C_{1-3}$ alkyl OC(O)—, $C_{1-3}$ alkyl-O—$C_{1-3}$ alkyl-, $C_{1-3}$ alkyl-O—$C_{1-3}$ alkyl-C(O)—, amino-C(O)—, mono($C_{1-3}$ alkyl)amino-C(O)—, di($C_{1-3}$ alkyl)amino-C(O)—, amino-$C_{1-3}$ alkyl-C(O)—, mono($C_{1-3}$ alkyl)amino-$C_{1-3}$ alkyl-C(O)—, di($C_{1-3}$ alkyl)amino-$C_{1-3}$ alkyl-C(O)—, amino-C(O)—$C_{1-3}$ alkyl-, mono($C_{1-3}$ alkyl)amino-C(O)—$C_{1-3}$ alkyl-, di($C_{1-3}$ alkyl) amino-C(O)—$C_{1-3}$ alkyl-, 3-6 membered cycloalkyl-, 3-6 membered cycloalkyl-C(O)—, 3-6 membered cycloalkyl-$C_{1-3}$ alkyl-, 3-6 membered heterocycloalkyl-, 3-6 membered heterocycloalkyl-C(O)—, 3-6 membered heterocycloalkyl-$C_{1-3}$ alkyl-, phenyl-$C_{1-3}$ alkyl- and $C_{1-3}$ alkyl- substituted with one or more hydroxy or cyano, wherein the $R^c$ is optionally substituted with one or more halogens when it is not hydrogen and O═.

In some embodiments, each $R^c$ is independently selected from the group consisting of hydrogen, $C_{1-3}$ alkyl-, $C_{1-3}$ alkyl-C(O)—, $C_{1-3}$ alkyl-$S(O)_2$—, 3-6 membered cycloalkyl-$S(O)_2$—, $C_{1-3}$ alkyl OC(O)—, $C_{1-3}$ alkyl-O—$C_{1-3}$ alkyl-, $C_{1-3}$ alkyl-O—$C_{1-3}$ alkyl-C(O)—, amino-C(O)—, mono($C_{1-3}$ alkyl)amino-C(O)—, di($C_{1-3}$ alkyl)amino-C(O)—, amino-$C_{1-3}$ alkyl-C(O)—, mono($C_{1-3}$ alkyl)amino-$C_{1-3}$ alkyl-C(O)—, di($C_{1-3}$ alkyl)amino-$C_{1-3}$ alkyl-C(O)—, amino-C(O)—$C_{1-3}$ alkyl-, mono($C_{1-3}$ alkyl)amino-C(O)—$C_{1-3}$ alkyl-, di($C_{1-3}$ alkyl)amino-C(O)—$C_{1-3}$ alkyl-, 3-6 membered cycloalkyl-, 3-6 membered cycloalkyl-C(O)—, 3-6 membered cycloalkyl-$C_{1-3}$ alkyl-, 3-6 membered heterocycloalkyl-, 3-6 membered heterocycloalkyl-C(O)—, 3-6 membered heterocycloalkyl-$C_{1-3}$ alkyl-, phenyl-$C_{1-3}$ alkyl- and $C_{1-3}$ alkyl-substituted with one or more hydroxy or cyano, wherein the $R^c$ is optionally substituted with one or more halogens when it is not hydrogen.

In some embodiments, each $R^c$ is independently selected from the group consisting of hydrogen, $C_{1-3}$ alkyl-, $C_{1-3}$ alkyl-C(O)—, $C_{1-3}$ alkyl-$S(O)_2$—, 3-5 membered cycloalkyl-$S(O)_2$—, $C_{1-3}$ alkyl OC(O)—, $C_{1-3}$ alkyl-O—$C_{1-3}$ alkyl-, $C_{1-3}$ alkyl-O—$CH_2$—C(O)—, di($C_{1-3}$ alkyl)amino-C(O)—, di($C_{1-3}$ alkyl)amino-$CH_2$—C(O)—, di($C_{1-3}$ alkyl) amino-C(O)—$CH_2$—, 3-5 membered cycloalkyl-, 3-5 membered cycloalkyl-C(O)—, 3-5 membered cycloalkyl-$CH_2$—, 3-5 membered heterocycloalkyl-, phenyl-$CH_2$— and $C_{1-3}$ alkyl- substituted with one hydroxy or cyano, wherein the $R^c$ is optionally substituted with 1, 2 or 3 halogens when it is not hydrogen.

In some embodiments, each $R^c$ is independently selected from the group consisting of hydrogen, $C_{1-3}$ alkyl-, $C_{1-3}$ alkyl-C(O)—, $C_{1-3}$ alkyl-$S(O)_2$—, 3-5 membered cycloalkyl-$S(O)_2$—, $C_{1-3}$ alkyl OC(O)—, $C_{1-3}$ alkyl-O—$C_{1-3}$ alkyl-, $C_{1-3}$ alkyl-O—$CH_2$—C(O)—, di($C_{1-3}$ alkyl)amino-C(O)—, di($C_{1-3}$ alkyl)amino-$CH_2$—C(O)—, di($C_{1-3}$ alkyl) amino-C(O)—$CH_2$—, 3-5 membered cycloalkyl-, 3-5 membered cycloalkyl-C(O)—, 3-5 membered cycloalkyl-$CH_2$—, 3-5 membered heterocycloalkyl- and $C_{1-3}$ alkyl- substituted with one hydroxy or cyano, wherein the $R^c$ is optionally substituted with 1, 2 or 3 halogens when it is not hydrogen.

In some embodiments, each $R^c$ is independently selected from the group consisting of hydrogen, $C_{1-3}$ alkyl-, $C_{1-3}$ alkyl-C(O)—, $C_{1-3}$ alkyl OC(O)—, $C_{1-3}$ alkyl-O—$C_{1-3}$ alkyl-, $C_{1-3}$ alkyl-O—$CH_2$—C(O)—, di($C_{1-3}$ alkyl)amino-C(O)—, di($C_{1-3}$ alkyl)amino-$CH_2$—C(O)—, di($C_{1-3}$ alkyl) amino-C(O)—($CH_2$)—, 3-5 membered cycloalkyl-, 3-5 membered cycloalkyl-C(O)—, 3-5 membered cycloalkyl-$CH_2$—, phenyl-$CH_2$— and $C_{1-3}$ alkyl- substituted with one hydroxy.

In some embodiments each $R^c$ is independently selected from the group consisting of hydrogen, methyl, ethyl, isopropyl,

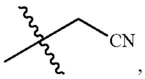 [SMILES: *CC#N]

, acetyl,

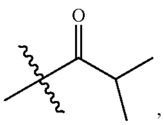 , 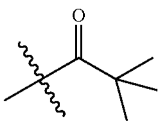 , 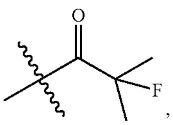 ,

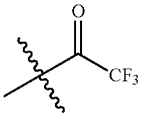 , 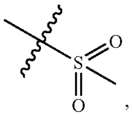 , 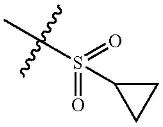 ,

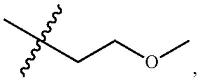 , 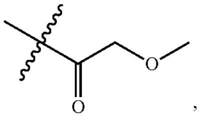 ,

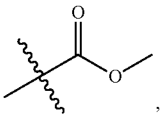 , 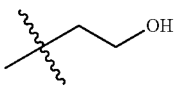 , 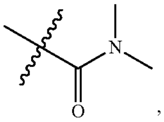 ,

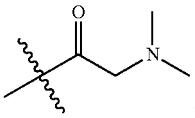 , 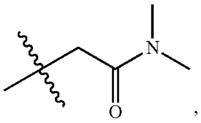 ,

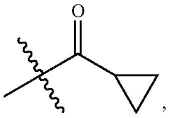 , 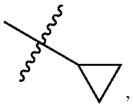 , 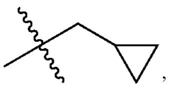 ,

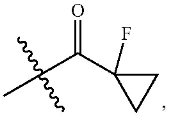 , 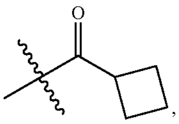 , 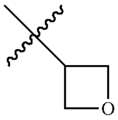 and

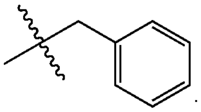 .

In some embodiments, each $R^c$ is independently selected from the group consisting of methyl, ethyl, isopropyl,

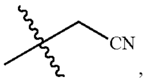 [SMILES: *CC#N] , acetyl,

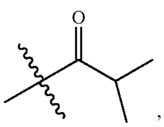 , 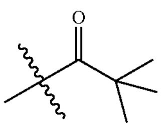 , 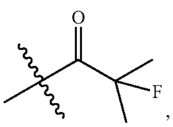 ,

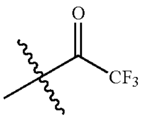 , 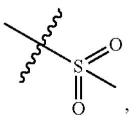 , 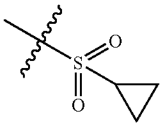 ,

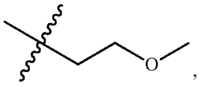 , 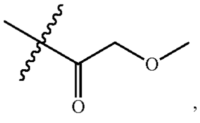 ,

-continued

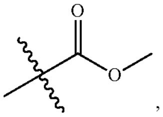 , 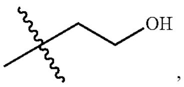 , 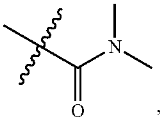 ,

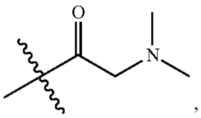 , 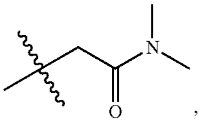 ,

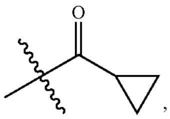 , 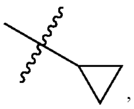 , 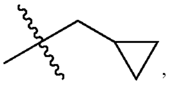 ,

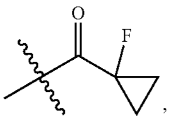 , 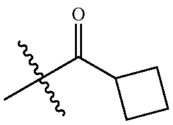 and

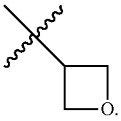 .

In some embodiments, ring A is selected from the group consisting of $C_{6-10}$ aryl, 5-10 membered heteroaryl, 8-12 membered benzocycloalkyl, 8-12 membered benzocycloalkenyl and 8-12 membered benzoheterocyclyl.

In some embodiments, ring A is selected from the group consisting of $C_{6-10}$ aryl, 5-10 membered heteroaryl, 8-12 membered benzocycloalkyl, 8-12 membered benzocycloalkenyl, 8-12 membered benzoheterocycloalkyl and 8-12 membered benzoheterocycloalkenyl.

In some embodiments, ring A is selected from the group consisting of $C_{6-10}$ aryl, 5-10 membered heteroaryl, 8-12 membered benzocycloalkyl and 8-12 membered benzocycloalkheterocycloalkyl.

In some embodiments, ring A is selected from the group consisting of $C_{6-10}$ aryl, 5-10 membered heteroaryl, 8-10 membered fused ring and 8-10 membered fused heterocyclic ring.

In some embodiments, ring A is selected from the group consisting of $C_{6-10}$ aryl, 5-10 membered heteroaryl, 8-10 membered benzocycloalkyl, 8-10 membered benzocycloalkenyl and 8-10 membered benzoheterocyclyl.

In some embodiments, ring A is selected from the group consisting of $C_{6-10}$ aryl, 5-10 membered heteroaryl, 8-10 membered benzocycloalkyl, 8-10 membered benzocycloalkenyl, 8-10 membered benzoheterocycloalkyl and 8-10 membered benzoheterocycloalkenyl.

In some embodiments, ring A is selected from the group consisting of $C_{6-10}$ aryl, 5-10 membered heteroaryl, 8-10 membered benzocycloalkyl and 8-10 membered benzoheterocycloalkyl.

In some embodiments, ring A is selected from the group consisting of phenyl, thienyl, 2,3-dihydro-1H-indenyl, 2,3-dihydrobenzofuranyl and benzofuranyl.

In some embodiments, ring A is selected from the group consisting of phenyl, thienyl and 2,3-dihydro-1H-indenyl.

In some embodiments, n is 0, 1 or 2; or, n is 1, 2 or 3.

In some embodiments, n is 0 or 1; or, n is 0 or 2; or, n is 0 or 3; or, n is 1 or 2; or, n is 1 or 3; or, n is 2 or 3. In some embodiments, n is 2.

In some embodiments, each $R^3$ is independently selected from the group consisting of amino, nitro, halogen, $C_{1-6}$ alkyl- and phenyl, wherein the $C_{1-6}$ alkyl- or phenyl is optionally substituted with one or more $R^d$.

In some embodiments, each $R^3$ is independently selected from the group consisting of amino, halogen, $C_{1-6}$ alkyl- and phenyl, wherein the $C_{1-6}$ alkyl- or phenyl is optionally substituted with one or more $R^d$.

In some embodiments, each $R^3$ is independently selected from the group consisting of amino, nitro, halogen, $C_{1-4}$ alkyl- and phenyl, wherein the $C_{1-4}$ alkyl- or phenyl is optionally substituted with one or more $R^d$.

In some embodiments, each $R^3$ is independently selected from the group consisting of amino, nitro, halogen, $C_{1-4}$ alkyl- and phenyl, wherein the $C_{1-4}$ alkyl- or phenyl is optionally substituted with 1, 2 or 3 $R^d$.

In some embodiments, $R^d$ is selected from the group consisting of hydroxy, halogen and $C_{1-3}$ alkyl-NH—$C_{1-3}$ alkyl-.

In some embodiments, $R^d$ is selected from the group consisting of hydroxy, fluorine and methyl-NH-methyl-.

In some embodiments, each $R^3$ is independently selected from the group consisting of amino, nitro, fluorine, methyl, trifluoromethyl, $—CF_2CH_2OH$, $—CHF_2$, $—CF_2CH_3$, $—CF_2C(CH_3)_2OH$ and

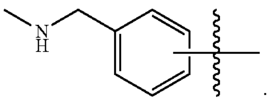

.

In some embodiments, each $R^3$ is independently selected from the group consisting of amino, fluorine, methyl, trifluoromethyl, $—CF_2CH_2OH$, $—CHF_2$, $—CF_2CH_3$, $—CF_2C(CH_3)_2OH$ and

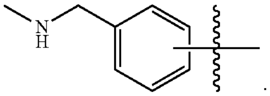

.

In some embodiments, each $R^3$ is independently selected from the group consisting of amino, nitro, fluorine, methyl and trifluoromethyl.

In some embodiments, structural unit

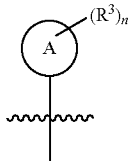

is selected from the group consisting of the group consisting of

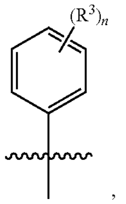

,

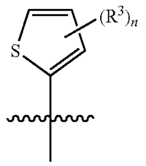

,

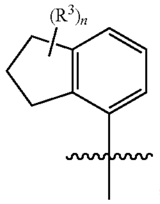

,

-continued

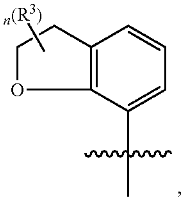

, and

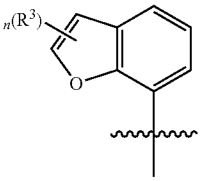

, further selected from the group consisting of

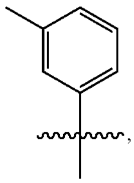

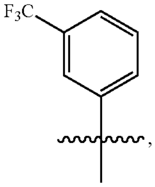

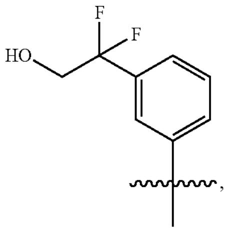

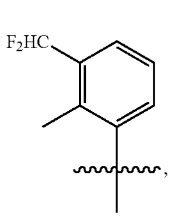

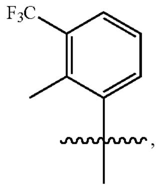

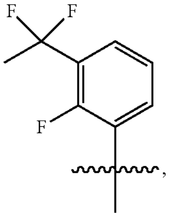

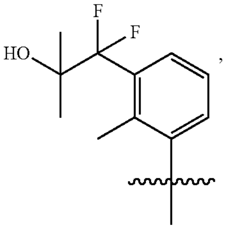

,

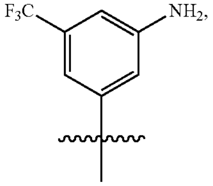

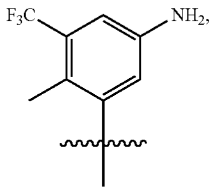

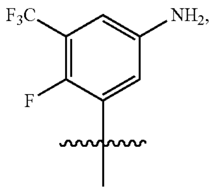

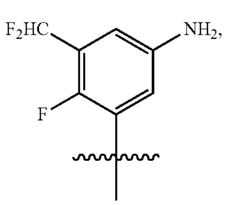

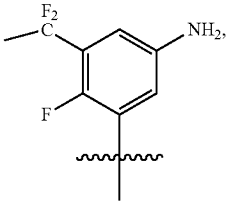

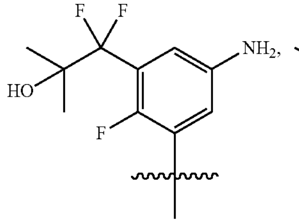

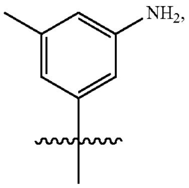

-continued

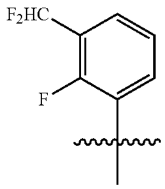, 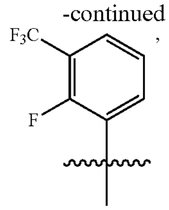, 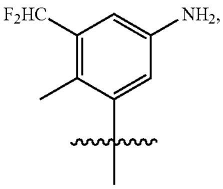

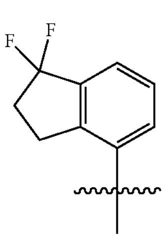, 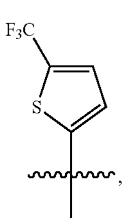, 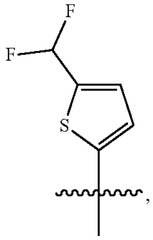,

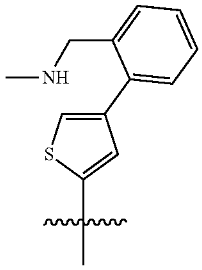, 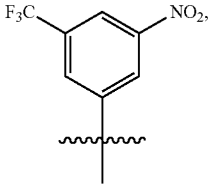

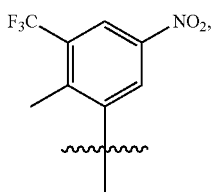 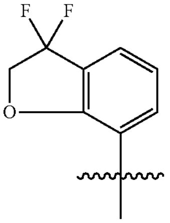 and

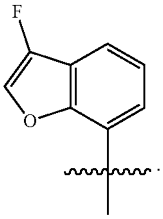.

In some embodiments, $R^4$ and $R^5$ are each independently selected from the group consisting of hydrogen, deuterium and $C_{1-3}$ alkyl, wherein the $C_{1-3}$ alkyl is optionally substituted with one or more halogens.

In some embodiments, $R^4$ is selected from $C_{1-3}$ alkyl, and $R^5$ is selected from the group consisting of hydrogen and deuterium, wherein the $C_{1-3}$ alkyl is optionally substituted with one or more halogens. In some embodiments, $R^4$ is selected from methyl, and $R^5$ is selected from the group consisting of hydrogen and deuterium, wherein the methyl is optionally substituted with one or more fluorine. In some embodiments, $R^4$ is selected from the group consisting of methyl and —$CH_2F$, and $R^5$ is selected from the group consisting of hydrogen and deuterium. In some embodiments, $R^4$ is selected from methyl, and $R^5$ is selected from hydrogen.

In some embodiments, $R^5$ is selected from $C_{1-3}$ alkyl, and $R^4$ is selected from the group consisting of hydrogen and deuterium, wherein the $C_{1-3}$ alkyl is optionally substituted with one or more halogens. In some embodiments, $R^5$ is selected from methyl, and $R^4$ is selected from the group consisting of hydrogen and deuterium, wherein the methyl is optionally substituted with one or more fluorine. In some embodiments, $R^5$ is selected from the group consisting of methyl and —$CH_2F$, and $R^4$ is selected from the group consisting of hydrogen and deuterium. In some embodiments, $R^5$ is selected from methyl, and $R^4$ is selected from hydrogen.

In some embodiments, $R^6$ is selected from the group consisting of hydrogen, halogen and $C_{1-3}$ alkyl, wherein the $C_{1-3}$ alkyl is optionally substituted with one or more halogens.

In some embodiments, $R^6$ is selected from the group consisting of hydrogen, fluorine, chlorine, bromine, methyl, ethyl, propyl and isopropyl, wherein the methyl, ethyl, propyl or isopropyl is optionally substituted with one or more halogens. In some embodiments, $R^6$ is selected from the group consisting of hydrogen, fluorine, chlorine and methyl, wherein the methyl is optionally substituted with 1, 2 or 3 fluorine. In some embodiments, $R^6$ is selected from the group consisting of hydrogen, chlorine, methyl and —$CH_2F$. In some embodiments, $R^6$ is selected from methyl.

In some embodiments, the heteroatom in the heterocyclyl, heteroaryl or heterocycloalkyl described herein is selected from the group consisting of N, O, S and P. In some embodiments, the heteroatom in the heterocyclyl, heteroaryl or heterocycloalkyl described herein is selected from the group consisting of N, O and P. In some embodiments, the heteroatom in the heterocyclyl, heteroaryl or heterocycloalkyl described herein is selected from the group consisting of N and P.

In another aspect, the present application provides a compound of formula (II), a stereoisomer thereof or a pharmaceutically acceptable salt thereof, (II)

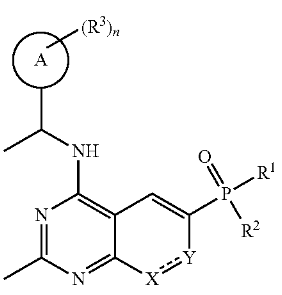

wherein,

X and Y are each independently selected from the group consisting of $CR^a$, C(O), N and $NR^b$;

"$\overline{\underline{-----}}$" represents a single bond or a double bond depending on X and Y;

$R^a$ is selected from the group consisting of hydrogen, hydroxy, halogen, $C_{1-6}$ alkyl and $C_{1-6}$ alkoxy, wherein the $C_{1-6}$ alkyl is optionally substituted with one or more halogens, and the $C_{1-6}$ alkoxy is optionally substituted with one or more deuterium or halogens;

$R^b$ is selected from the group consisting of hydrogen, $C_{1-6}$ alkyl and $C_{1-6}$ alkoxy;

$R^1$ and $R^2$ are each independently selected from the group consisting of $C_{1-6}$ alkyl, $NH(R^c)$—$C_{1-6}$ alkyl- and $N(R^c)(C_{1-6}$ alkyl)-$C_{1-6}$ alkyl-, or $R^1$, $R^2$ and the phosphorus atom to which they are both connected together form 5-8 membered heterocyclyl, wherein the ring atoms of the 5-8 membered heterocyclyl at least contain one N atom, and N is connected to $R^c$;

each $R^c$ is independently selected from the group consisting of hydrogen, $C_{1-6}$ alkyl-, $C_{1-6}$ alkyl-C(O)—, $C_{1-6}$ alkyl OC(O)—, $C_{1-6}$ alkyl-O—$C_{1-6}$ alkyl-, $C_{1-6}$ alkyl-O—$C_{1-6}$ alkyl-C(O)—, amino-C(O)—, mono($C_{1-6}$ alkyl)amino-C(O)—, di($C_{1-6}$ alkyl)amino-C(O)—, amino-$C_{1-6}$ alkyl-C(O)—, mono($C_{1-6}$ alkyl)amino-$C_{1-6}$ alkyl-C(O)—, di($C_{1-6}$ alkyl)amino-$C_{1-6}$ alkyl-C(O)—, amino-C(O)—$C_{1-6}$ alkyl-, mono($C_{1-6}$ alkyl)amino-C(O)—$C_{1-6}$ alkyl-, di($C_{1-6}$ alkyl)amino-C(O)—$C_{1-6}$ alkyl-, 3-6 membered cycloalkyl-, 3-6 membered cycloalkyl-C(O)—, 3-6 membered cycloalkyl-$C_{1-6}$ alkyl-, $C_{6-10}$ aryl-$C_{1-6}$ alkyl-, and $C_{1-6}$ alkyl- substituted with one or more hydroxy, wherein the $R^c$ is optionally substituted with one or more halogens when it is not hydrogen;

ring A is selected from the group consisting of $C_{6-10}$ aryl, 5-10 membered heteroaryl and 8-12 membered fused ring;

n is 0, 1, 2 or 3;

each $R^3$ is independently selected from the group consisting of amino, nitro, halogen, $C_{1-8}$ alkyl and 3-6 membered cycloalkyl, wherein the $C_{1-8}$ alkyl and 3-6 membered cycloalkyl are optionally substituted with one or more $R^d$.

$R^d$ is selected from the group consisting of hydroxy and halogen.

In some embodiments, in the compound of formula (II), $R^1$, $R^2$, $R^3$, X, Y, n, ring A and ------ are defined as above.

In some embodiments, X is selected from $CR^a$, and Y is selected from the group consisting of $CR^a$, C(O), N and $NR^b$. In some embodiments, X is selected from $CR^a$, and Y is selected from the group consisting of $CR^a$, C(O) and N. In some embodiments, X is selected from $CR^a$, and Y is selected from N.

In some embodiments, X and Y are both selected from $CR^a$. In some embodiments, X is selected from CH, and Y is selected from $CR^a$.

In some embodiments, $R^a$ is selected from the group consisting of hydrogen, halogen and $C_{1-4}$ alkoxy, wherein the $C_{1-4}$ alkoxy is optionally substituted with one or more deuterium or halogens. In some embodiments, $R^a$ is selected from the group consisting of hydrogen, halogen and $C_{1-4}$ alkoxy, wherein the $C_{1-4}$ alkoxy is optionally substituted with 3 deuterium, or one or more fluorine. In some embodiments, $R^a$ is selected from the group consisting of hydrogen, halogen and $C_{1-4}$ alkoxy, wherein the $C_{1-4}$ alkoxy is optionally substituted with 3 deuterium or 2 fluorine.

In some embodiments, $R^a$ is selected from the group consisting of hydrogen, fluorine, methoxy and difluorinemethoxy, wherein the methoxy is optionally substituted with 3 deuterium.

In some embodiments, $R^a$ is selected from the group consisting of hydrogen, fluorine, $CH_3O$—, $CD_3O$— and $CHF_2O$—.

In some embodiments, $R^b$ is selected from $C_{1-6}$ alkyl. In some embodiments, $R^b$ is selected from $C_{1-4}$ alkyl. In some embodiments, $R^b$ is selected from $C_{1-3}$ alkyl. In some embodiments, $R^b$ is selected from methyl.

In some embodiments, X is selected from the group consisting of CH and $N(CH_3)$, and Y is selected from the group consisting of N, C(O), $C(OCH_3)$, CF and $C(OCD_3)$. In some embodiments, X is selected from CH, and Y is selected from the group consisting of $C(OCH_3)$, CF and $C(OCD_3)$. In some embodiments, X is selected from CH, and Y is selected from N. In some embodiments, X is selected from $N(CH_3)$, and Y is selected from C(O).

In some embodiments, $R^1$ and $R^2$ are each independently selected from the group consisting of $C_{1-3}$ alkyl, $NH(R^c)$—$C_{1-3}$ alkyl- and $N(R^c)(C_{1-3}$ alkyl)-$C_{1-3}$ alkyl-.

In some embodiments, $R^1$ and $R^2$ are each independently selected from $C_{1-3}$ alkyl.

In some embodiments, $R^1$ and $R^2$ are each independently selected from methyl.

In some embodiments, $R^1$, $R^2$ and the phosphorus atom to which they are both connected together form 6 membered heterocyclyl, wherein the ring atoms of the 6 membered heterocyclyl at least contain one N atom, and N is connected to $R^c$. In some embodiments, $R^1$, $R^2$ and the phosphorus atom to which they are both connected together form 6 membered heterocyclyl, wherein the ring atoms of the 6 membered heterocyclyl contain only one N atom, and N is connected to $R^c$.

In some embodiments, $R^1$, $R^2$ and the phosphorus atom to which they are both connected together form 5-8 membered heterocycloalkyl, wherein the ring atoms of the 5-8 membered heterocycloalkyl at least contain one N atom, and N is connected to $R^c$. In some embodiments, $R^1$, $R^2$ and the phosphorus atom to which they are both connected together form 6 membered heterocycloalkyl, wherein the ring atoms of the 6 membered heterocycloalkyl at least contain one N atom, and N is connected to $R^c$. In some embodiments, $R^1$, $R^2$ and the phosphorus atom to which they are both connected together form 6 membered heterocycloalkyl, wherein the ring atoms of the 6 membered heterocycloalkyl contain only one N atom, and N is connected to $R^c$.

In some embodiments, structural unit

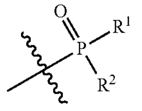

is selected from structural unit

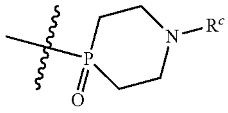

.

In some embodiments, $R^1$ and $R^2$ are each independently selected from methyl, or structural unit

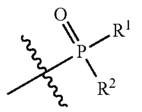

is selected from structural unit

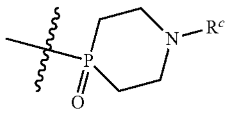

.

In some embodiments, each $R^c$ is independently selected from the group consisting of hydrogen, $C_{1-3}$ alkyl-, $C_{1-3}$ alkyl-C(O)—, $C_{1-3}$ alkyl OC(O)—, $C_{1-3}$ alkyl-O—$C_{1-3}$ alkyl-, $C_{1-3}$ alkyl-O—$C_{1-3}$ alkyl-C(O)—, amino-C(O)—, mono($C_{1-6}$ alkyl)amino-C(O)—, di($C_{1-3}$ alkyl)amino-C (O)—, amino-$C_{1-3}$ alkyl-C(O)—, mono($C_{1-3}$ alkyl)amino-$C_{1-3}$ alkyl-C(O)—, di($C_{1-3}$ alkyl)amino-$C_{1-3}$ alkyl-C(O)—, amino-C(O)—$C_{1-3}$ alkyl-, mono($C_{1-3}$ alkyl)amino-C(O)—$C_{1-3}$ alkyl-, di($C_{1-3}$ alkyl)amino-C(O)—$C_{1-3}$ alkyl-, 3-6 membered cycloalkyl-, 3-6 membered cycloalkyl-C(O)—, 3-6 membered cycloalkyl-$C_{1-3}$ alkyl-, phenyl-$C_{1-3}$ alkyl- and $C_{1-3}$ alkyl- substituted with one or more hydroxy.

In some embodiments, each $R^c$ is independently selected from the group consisting of hydrogen, $C_{1-3}$ alkyl, $C_{1-3}$ alkyl-C(O)—, $C_{1-3}$ alkyl OC(O)—, $C_{1-3}$ alkyl-O—$C_{1-3}$ alkyl-, $C_{1-3}$ alkyl-O—$CH_2$—C(O)—, di($C_{1-3}$ alkyl)amino-C (O)—, di($C_{1-3}$ alkyl)amino-$CH_2$—C(O)—, di($C_{1-3}$ alkyl) amino-C(O)—($CH_2$)—, 3-5 membered cycloalkyl, 3-5 membered cycloalkyl-C(O)—, 3-5 membered cycloalkyl-$CH_2$—, phenyl-$CH_2$— and $C_{1-3}$ alkyl substituted with one hydroxy.

In some embodiments, each $R^c$ is independently selected from the group consisting of methyl, ethyl, isopropyl, acetyl,

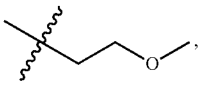,
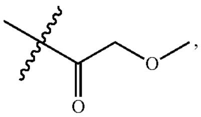,
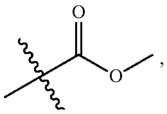,
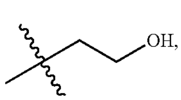
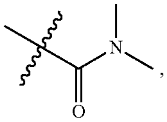,
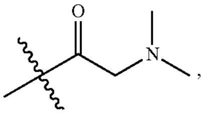,
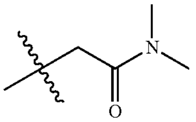,
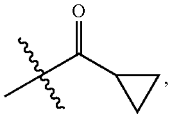,
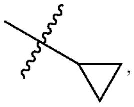,
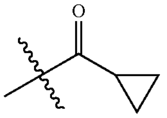 and
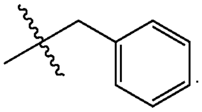.

In some embodiments, ring A is selected from the group consisting of $C_{6-10}$ aryl, 5-6 membered heteroaryl and 8-10 membered fused ring.

In some embodiments, ring A is selected from the group consisting of phenyl, thienyl and 2,3-dihydro-1H-indenyl.

In some embodiments, n is 0, 1 or 2; or, n is 1, 2 or 3.

In some embodiments, n is 0 or 1; or, n is 0 or 2; or, n is 0 or 3; or, n is 1 or 2; or, n is 1 or 3; or, n is 2 or 3. In some embodiments, n is 2.

In some embodiments, each $R^3$ is independently selected from the group consisting of amino, nitro, halogen and $C_{1-4}$ alkyl, wherein the $C_{1-4}$ alkyl is optionally substituted with 1, 2 or 3 $R^d$.

In some embodiments, $R^d$ is selected from the group consisting of hydroxy and fluorine.

In some embodiments, each $R^3$ is independently selected from the group consisting of amino, nitro, fluorine, methyl, trifluoromethyl, —$CF_2CH_2OH$, —$CHF_2$, —$CF_2CH_3$ and —$CF_2C(CH_3)_2OH$.

In some embodiments, structural unit

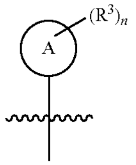

is selected from the group consisting of

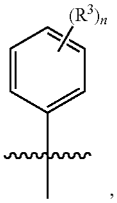,
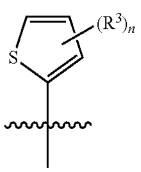 and
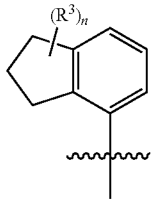, further selected from the group consisting of

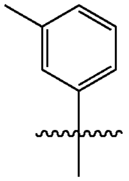,
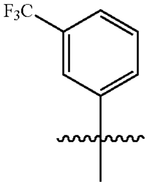,
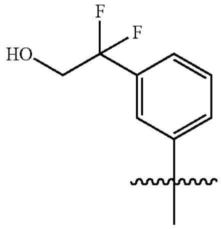,
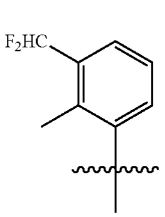,
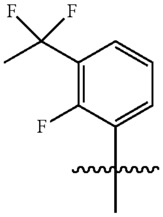,
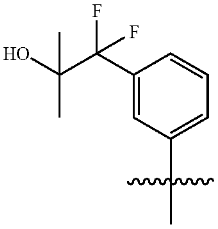,
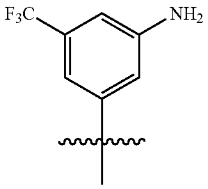,
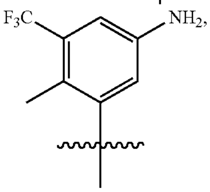
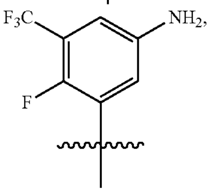
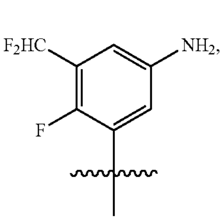
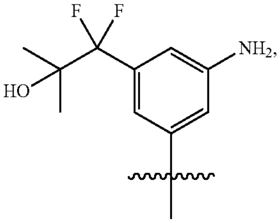

-continued

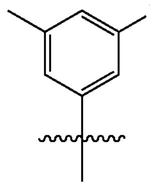

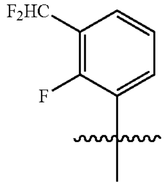

,

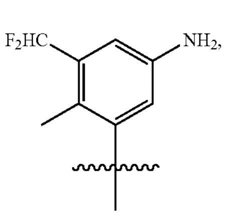

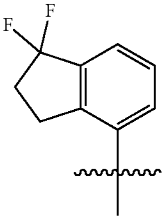

,

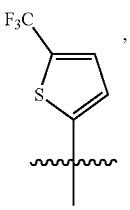

,

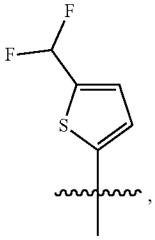

,

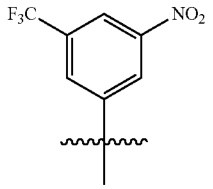

and

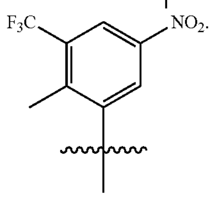

In some embodiments, the compound of formula (I) or formula (II), the stereoisomer thereof or the pharmaceutically acceptable salt thereof disclosed herein is selected from a compound of formula (III), a stereoisomer thereof or a pharmaceutically acceptable salt thereof, (III)

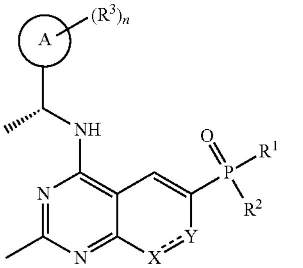

wherein $R^1$, $R^2$, $R^3$, X, Y, n, ring A and “------” are defined as above.

In some embodiments, in the compound of formula (I), the stereoisomer thereof or the pharmaceutically acceptable salt thereof disclosed herein, X and Y are each independently selected from the group consisting of $CR^a$ and N, for example, X and Y are both selected from $CR^a$, or X is $CR^a$ and Y is N;

$R^a$ is selected from the group consisting of hydrogen and $C_{1-4}$ alkoxy; preferably, $R^a$ is selected from the group consisting of hydrogen and methoxy;

“------” re resents a double bond;

$R^1$, $R^2$ and the phosphorus atom to which they are both connected together form 6 membered heterocyclyl, wherein the ring atoms of the 6 membered heterocyclyl at least contain one N atom or O atom, and when the ring atoms contain an N atom, N is connected to $R^c$ (preferably contain one N atom, and N is connected to $R^c$);

$R^c$ is selected from the group consisting of $C_{1-4}$ alkyl-$S(O)_2$— (preferably methylsulfonyl) and $C_{3-6}$ cycloalkyl-$S(O)_2$— (preferably cyclopropylsulfonyl);

ring A is selected from $C_{6-10}$ aryl, preferably $C_6$ aryl (i.e., phenyl);

n is 0, 1, 2 or 3, preferably 2;

each $R^3$ is independently selected from the group consisting of halogen (preferably F) and $C_{1-8}$ alkyl (preferably $C_{1-4}$ alkyl, and more preferably methyl or ethyl), wherein the $C_{1-8}$ alkyl is optionally substituted with one or more halogens (preferably F);

$R^4$ and $R^5$ are each independently selected from the group consisting of hydrogen and $C_{1-3}$ alkyl, wherein the $C_{1-3}$ alkyl is optionally substituted with one or more fluorine (preferably, $R^4$ is selected from hydrogen and $R^5$ is selected from methyl, or, $R^4$ is selected from methyl and $R^5$ is selected from hydrogen);

$R^6$ is selected from the group consisting of hydrogen, halogen and $C_{1-6}$ alkyl, wherein the $C_{1-6}$ alkyl is optionally substituted with one or more halogens, for example, $R^6$ may be selected from the group consisting of hydrogen, methyl, and methyl optionally substituted with one or more halogens (e.g., —$CH_2F$).

In some embodiments, in the compound of formula (II), the stereoisomer thereof or the pharmaceutically acceptable salt thereof disclosed herein, X and Y are each independently selected from the group consisting of $CR^a$ and N, for example, X and Y are both selected from $CR^a$, or X is $CR^a$ and Y is N;

$R^a$ is selected from the group consisting of hydrogen and $C_{1-4}$ alkoxy; preferably, $R^a$ is selected from the group consisting of hydrogen and methoxy; and more preferably, $R^a$ is selected from hydrogen;

“------” represents a double bond;

$R^1$, $R^2$ and the phosphorus atom to which they are both connected together form 6 membered heterocyclyl, wherein the ring atoms of the 6 membered heterocyclyl at least contain one N atom (preferably contain one N atom), and N is connected to $R^c$;

$R^c$ is selected from the group consisting of $C_{1-4}$ alkyl-$S(O)_2$— (preferably methylsulfonyl) and $C_{3-6}$ cycloalkyl-$S(O)_2$— (preferably cyclopropylsulfonyl);

ring A is selected from $C_{6-10}$ aryl, preferably $C_6$ aryl (i.e., phenyl);

n is 0, 1, 2 or 3, preferably 2;

each $R^3$ is independently selected from the group consisting of halogen (preferably F) and $C_{1-8}$ alkyl (preferably $C_{1-4}$ alkyl, and more preferably methyl or ethyl), wherein the $C_{1-8}$ alkyl is optionally substituted with one or more halogens (preferably F).

In some embodiments, the compound of formula (I) or formula (II), the stereoisomer thereof or the pharmaceutically acceptable salt thereof disclosed herein is selected from the group consisting of a compound of formula (III-1), a compound of formula (III-2), a compound of formula (III-3), a compound of formula (III-4), a compound of formula (III-5), a compound of formula (III-6), a compound of formula (III-7), a compound of formula (III-8) and a compound of formula (III-9), stereoisomers thereof or pharmaceutically acceptable salts thereof, (III-1)

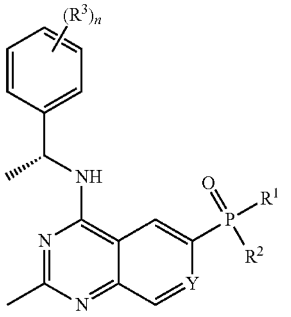

(III-2)

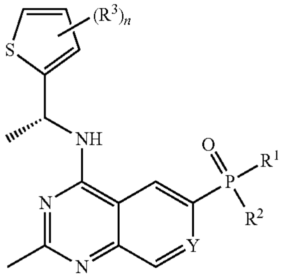

(III-3)

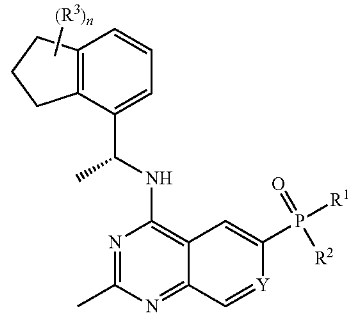

(III-4)

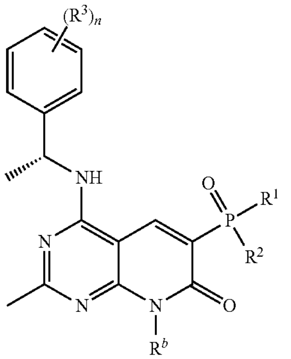

(III-5)

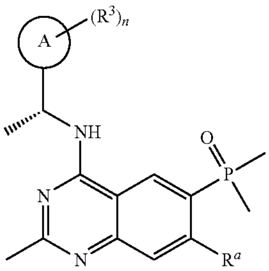

-continued (III-6)

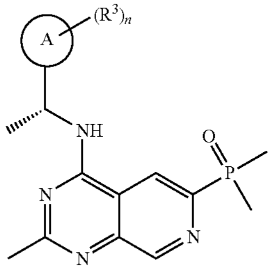

(III-7)

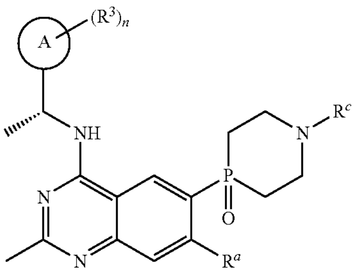

(III-8)

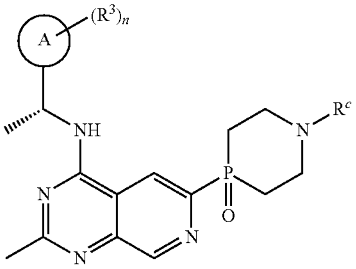

(III-9)

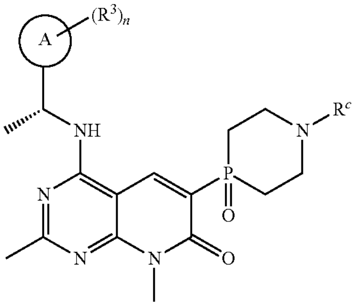

wherein $R^1$, $R^2$, $R^3$, Y, n, ring A, $R^a$, $R^b$ and $R^c$ are defined as above.

In some embodiments, the compound of formula (I) or formula (II), the stereoisomer thereof or the pharmaceutically acceptable salt thereof disclosed herein is selected from the group consisting of a compound of formula (IV), a compound of formula (V) and a compound of formula (VI), stereoisomers thereof or pharmaceutically acceptable salts thereof, (IV)

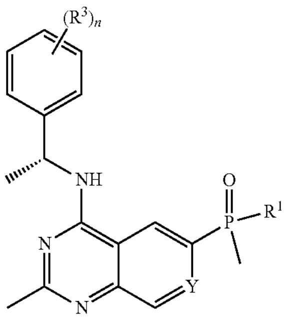

(V)

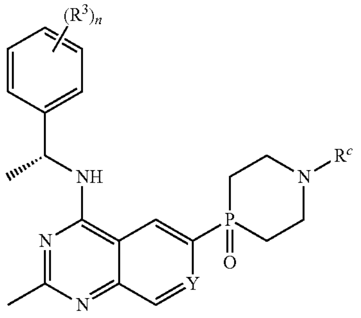

(VI)

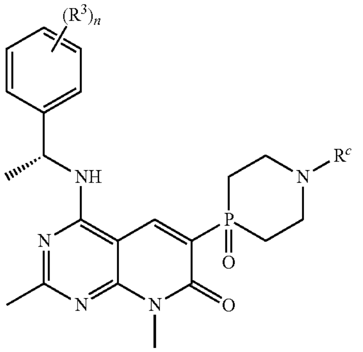

wherein $R^3$, Y, n, $R^b$ and $R^c$ are defined as above.

In some embodiments, the present application encompasses the variables defined above and embodiments thereof, as well as any combination thereof.

In some embodiments, the compound of formula (I) disclosed herein is selected from the following compounds, stereoisomers thereof or pharmaceutically acceptable salts thereof:

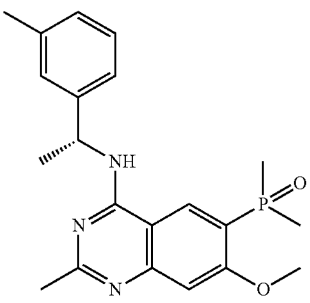

-continued

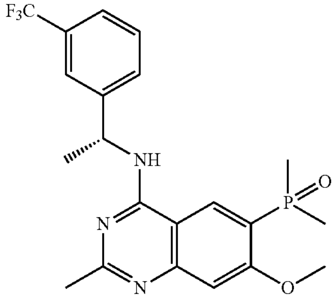

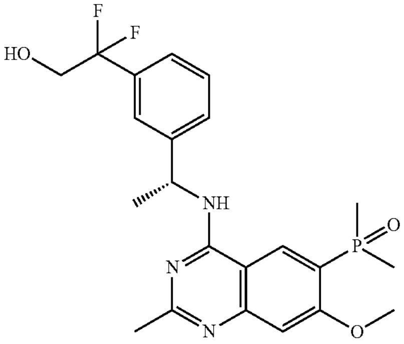

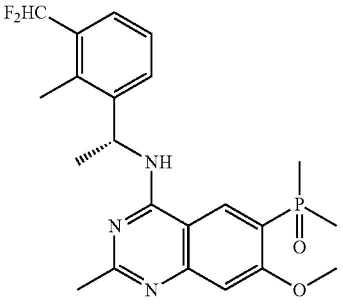

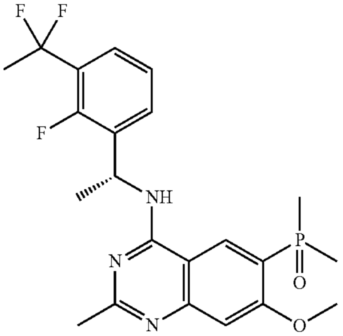

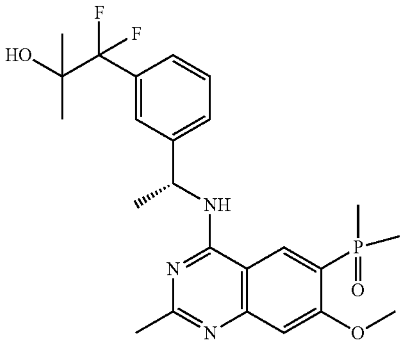

-continued
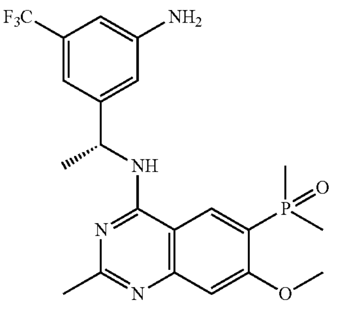
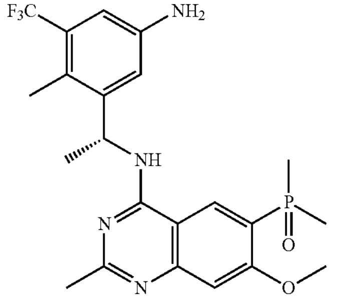
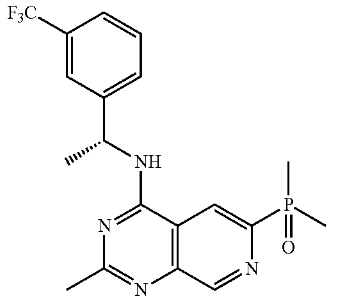
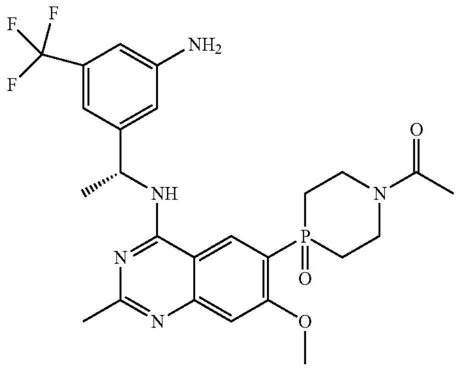
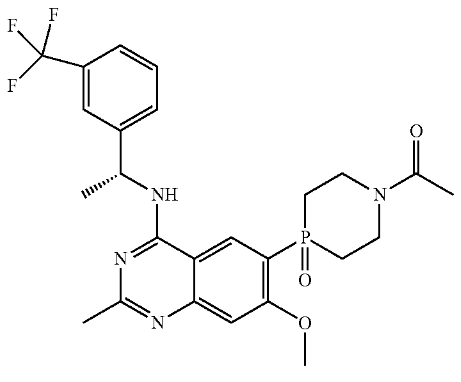
-continued
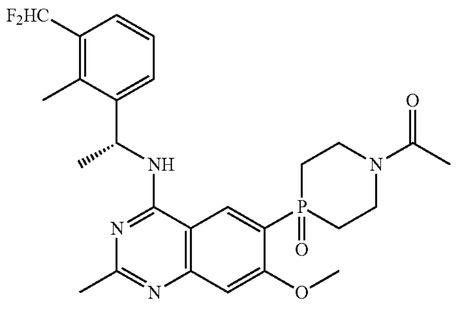
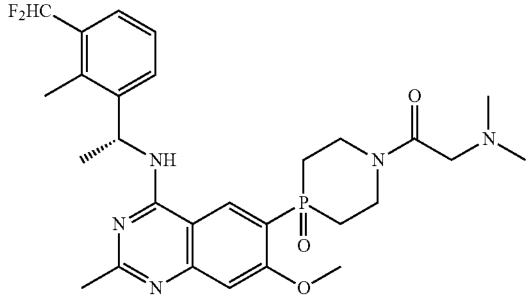
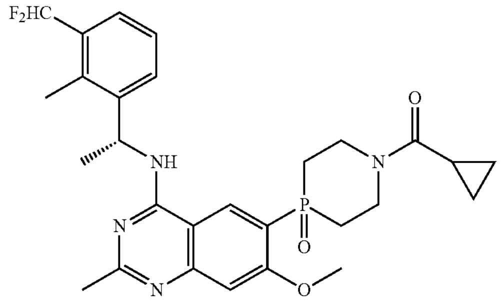
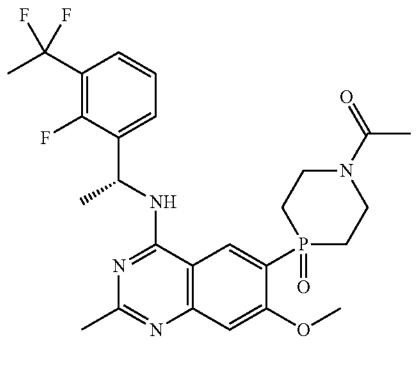
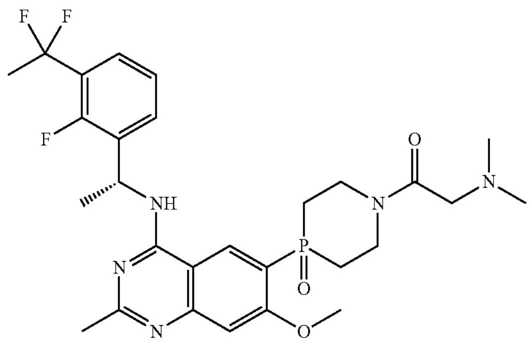

-continued
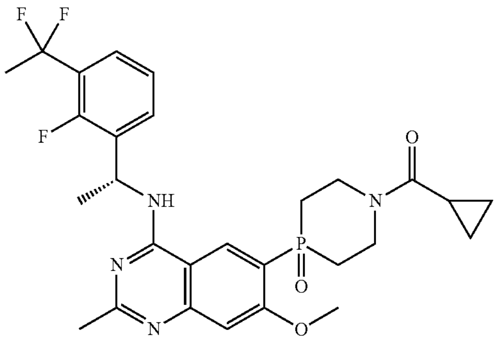
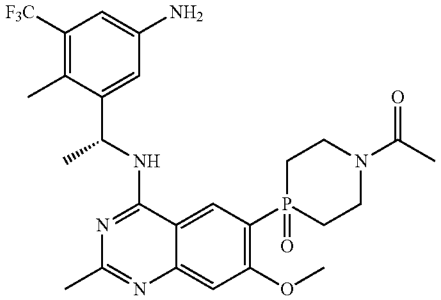
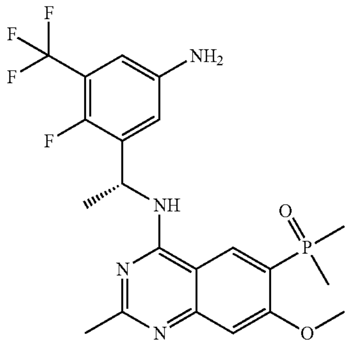
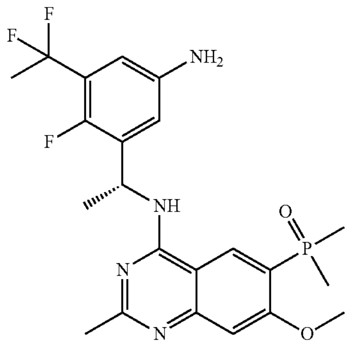
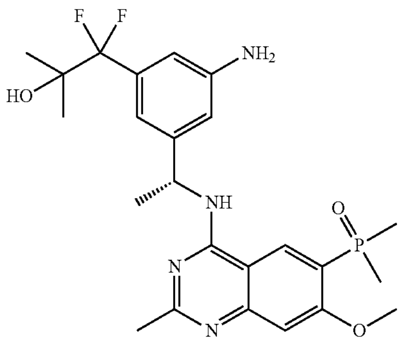
-continued
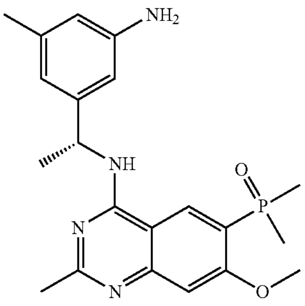
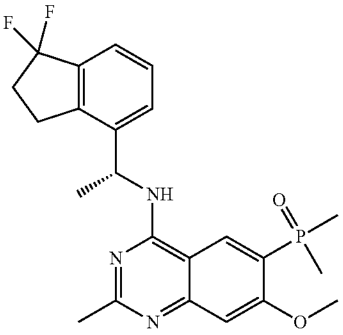
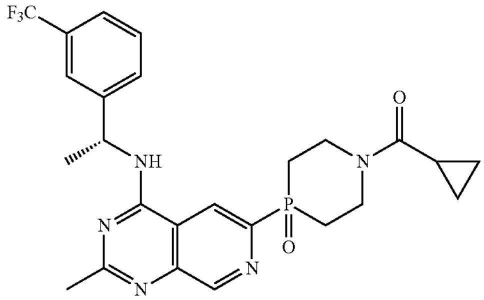
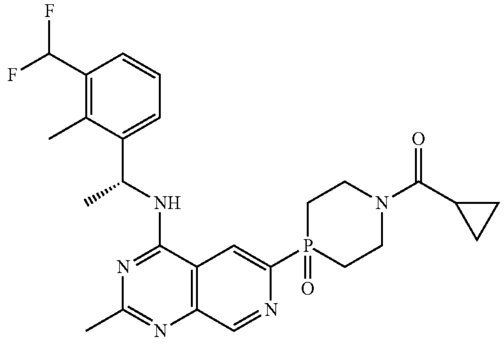
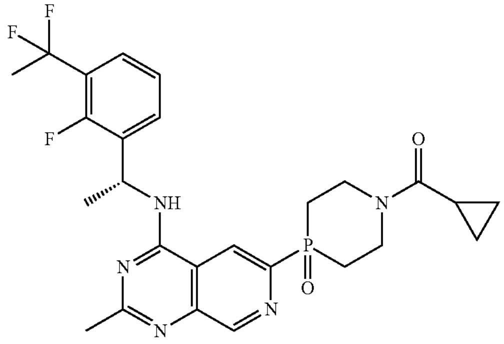

-continued
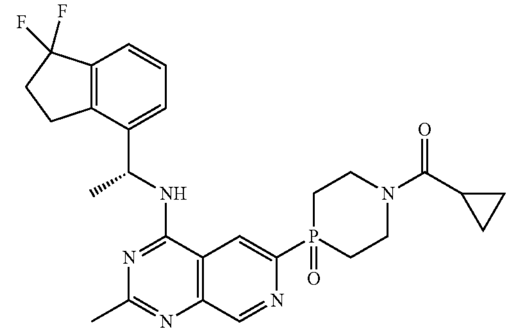
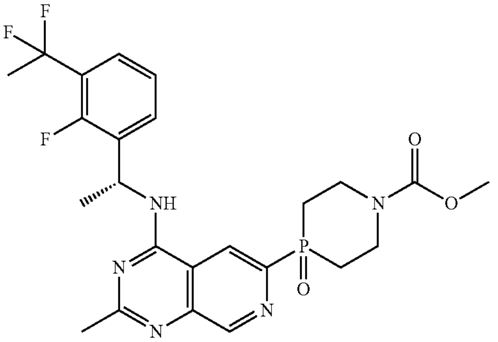
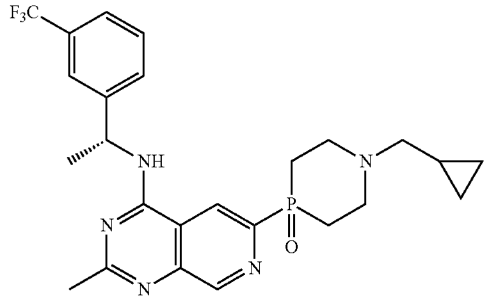
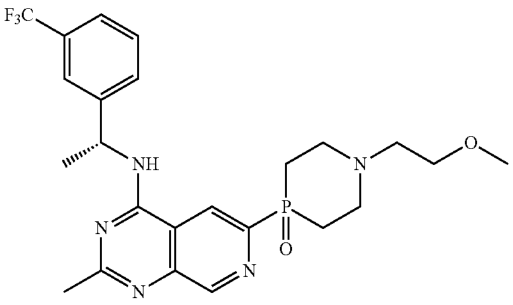
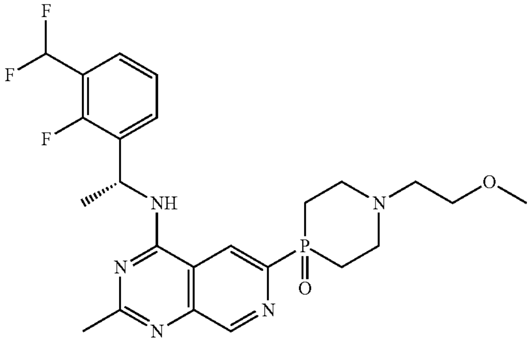
-continued
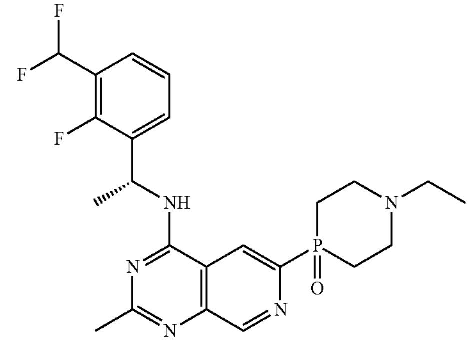
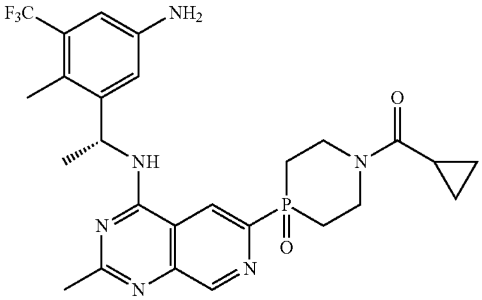
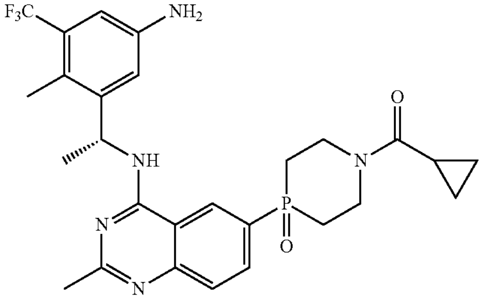
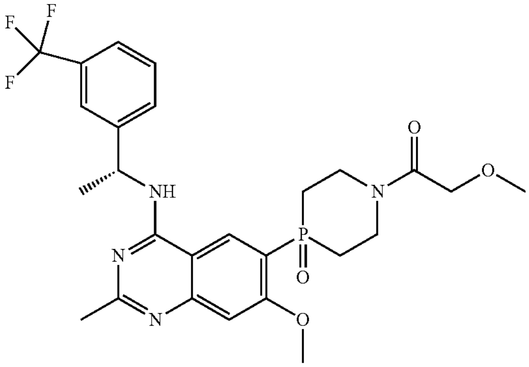
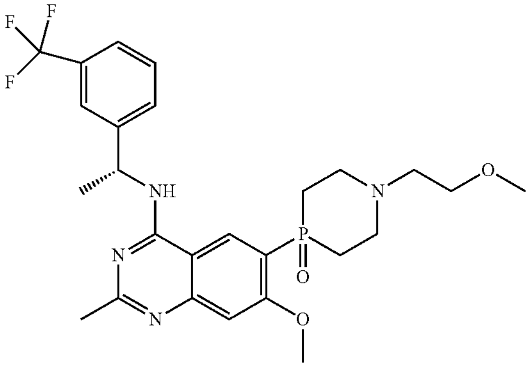

-continued
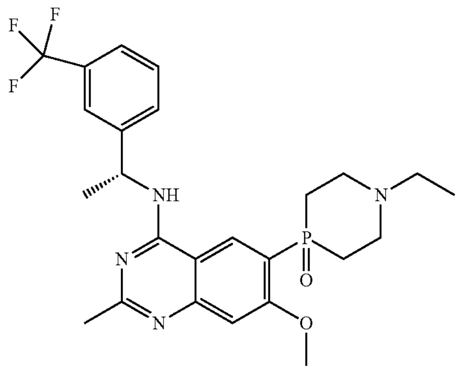
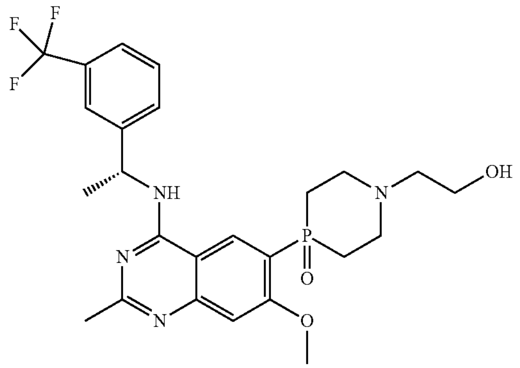
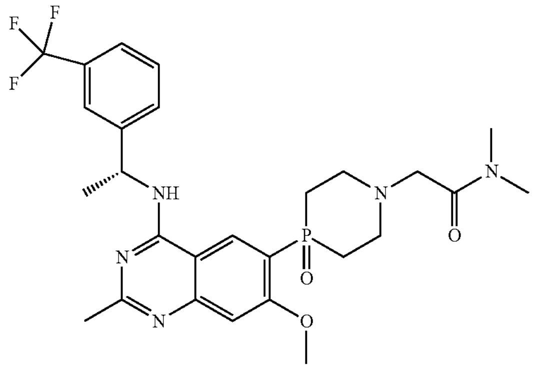
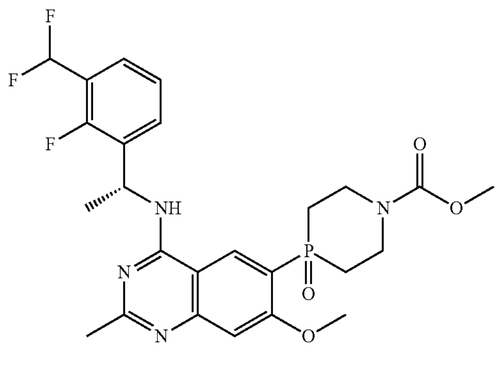
-continued
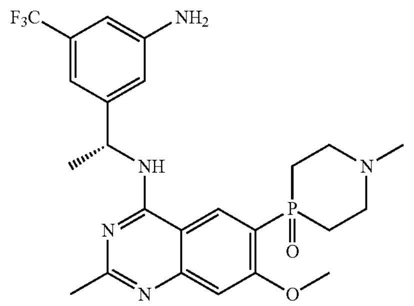
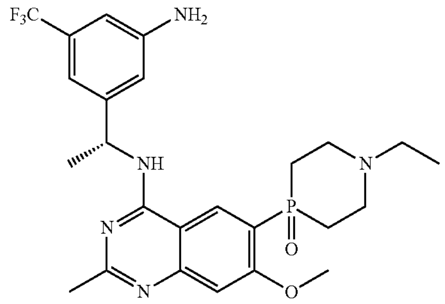
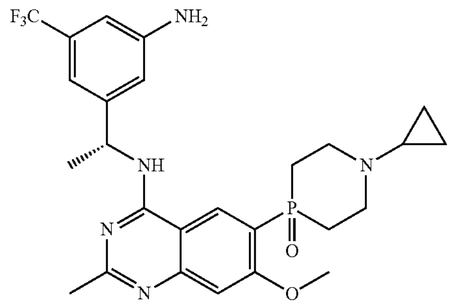
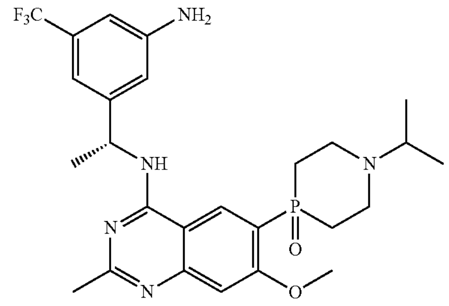
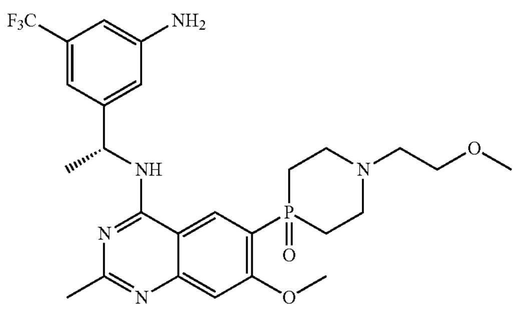

-continued
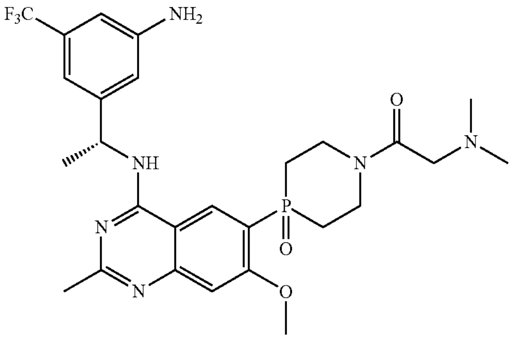
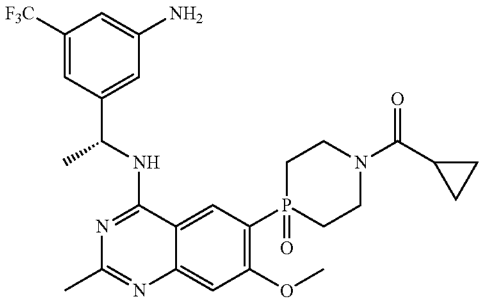
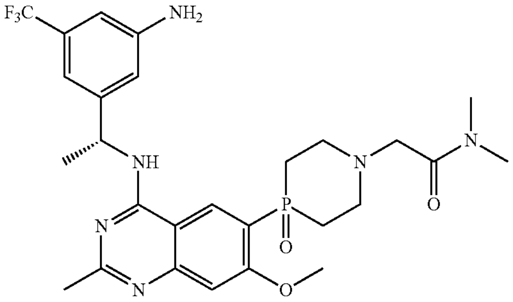
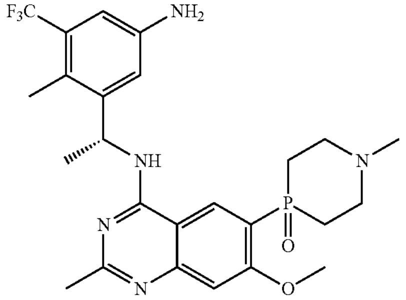
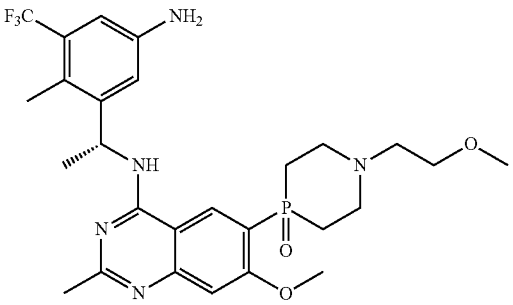
-continued
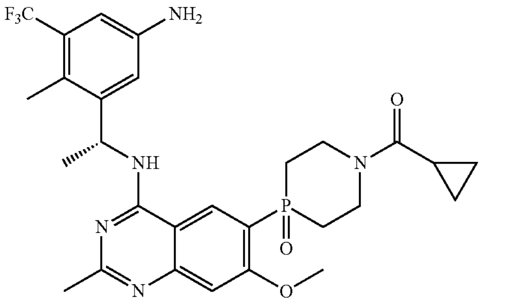
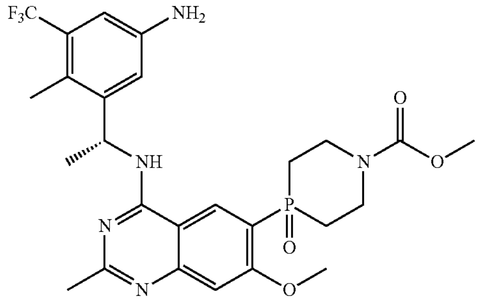
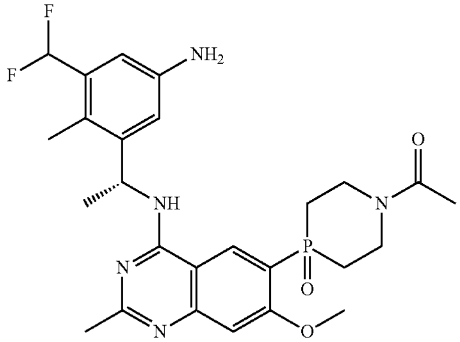
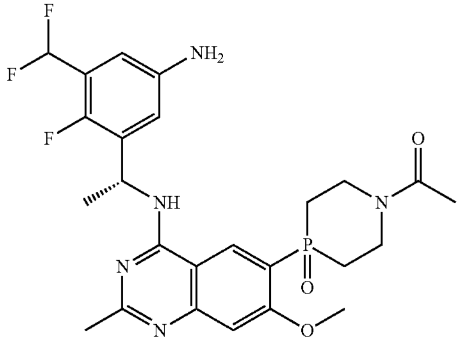
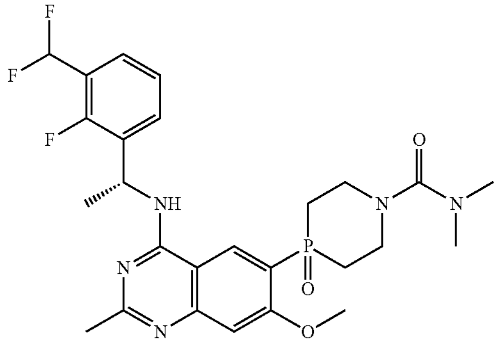

-continued
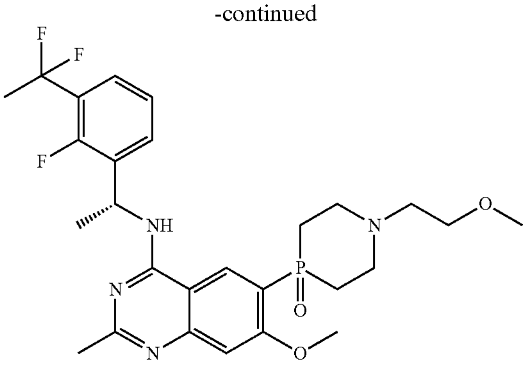
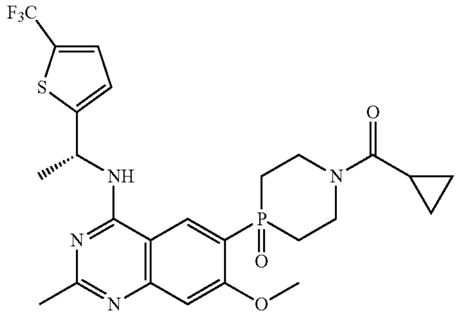
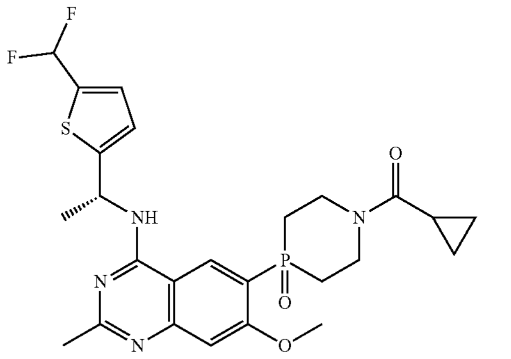
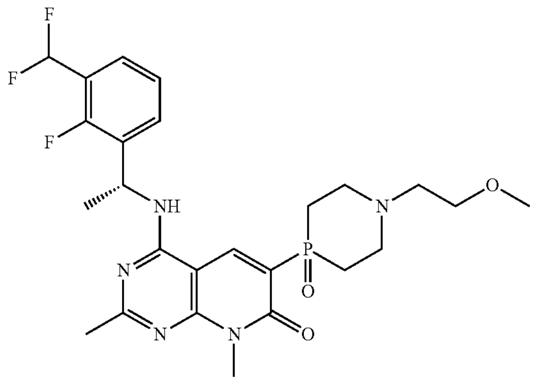
-continued
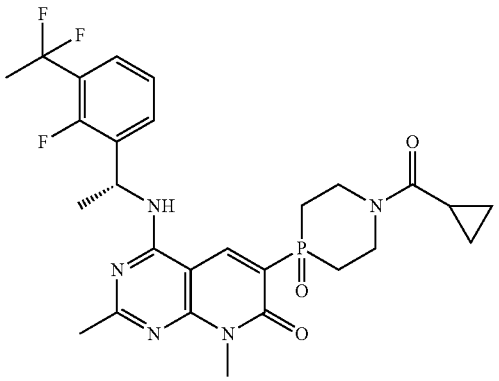
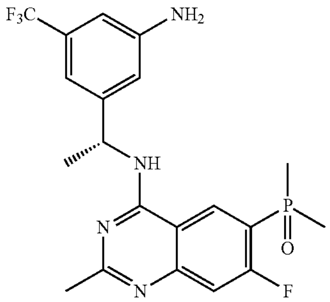
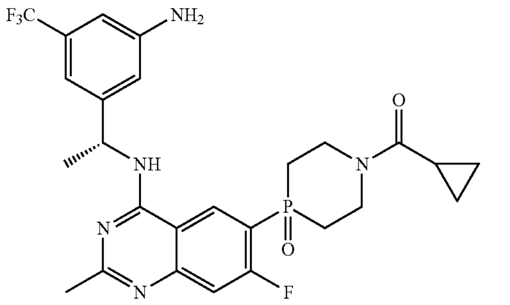
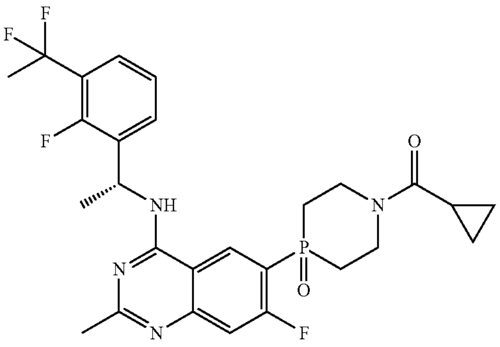
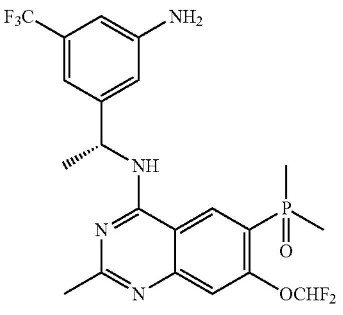

-continued
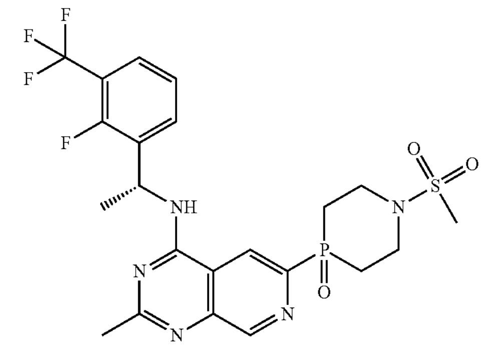
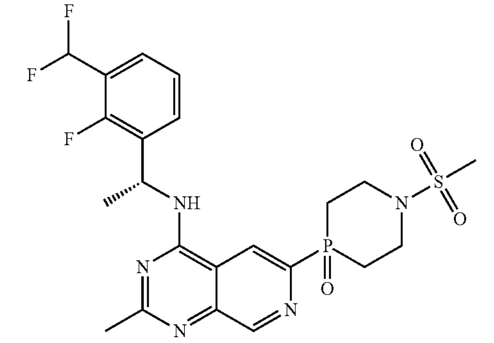
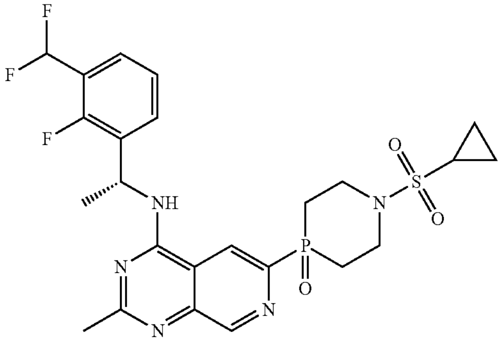
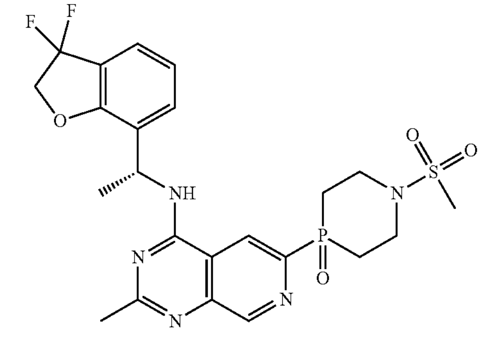
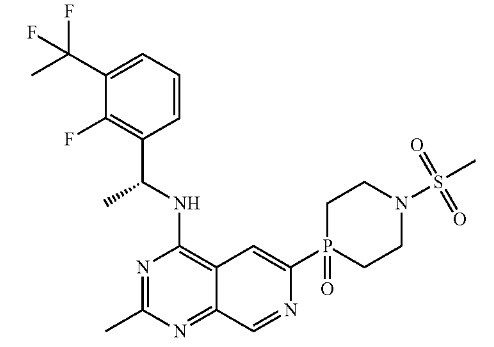
-continued
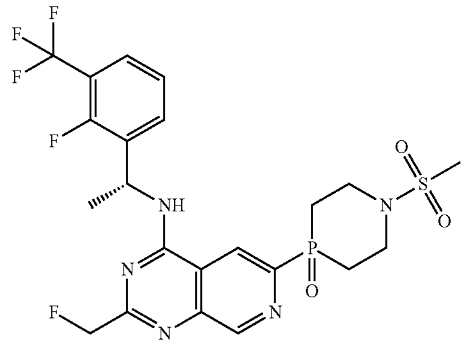
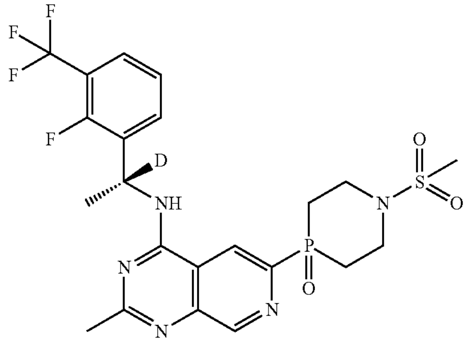
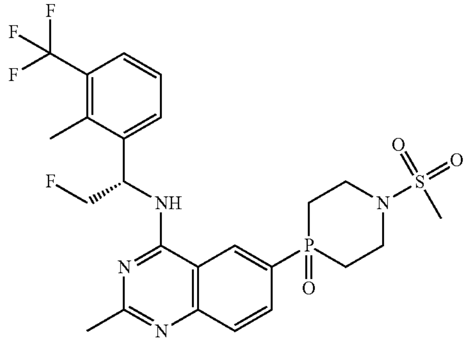
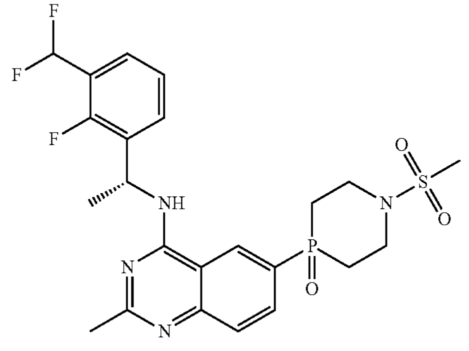
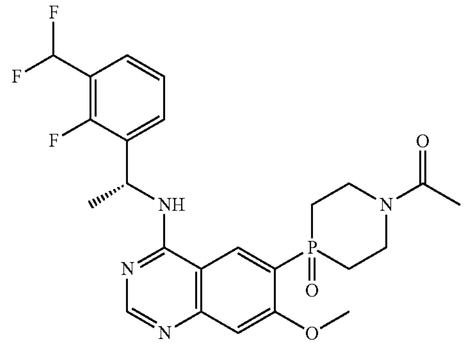

-continued
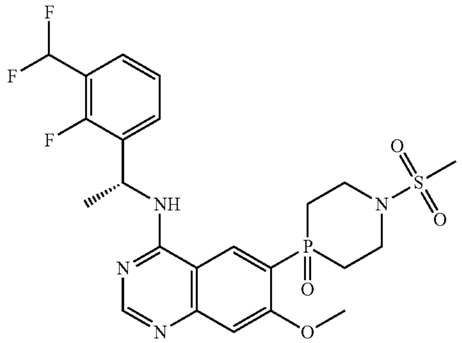
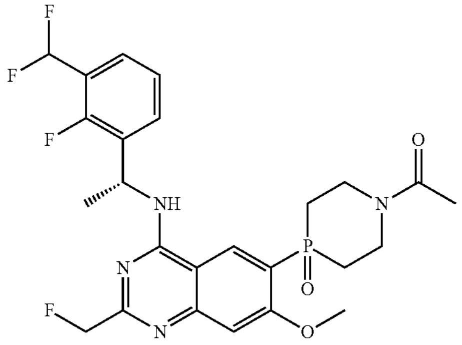
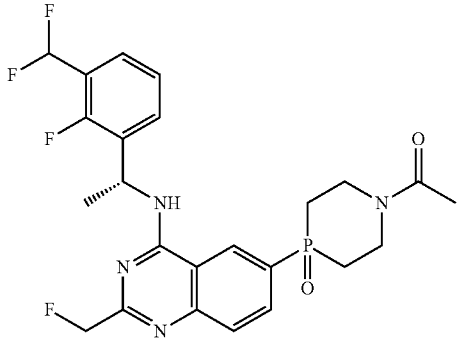
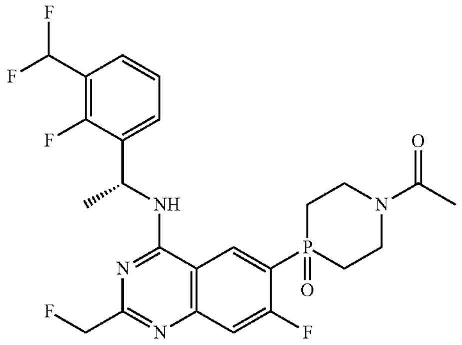
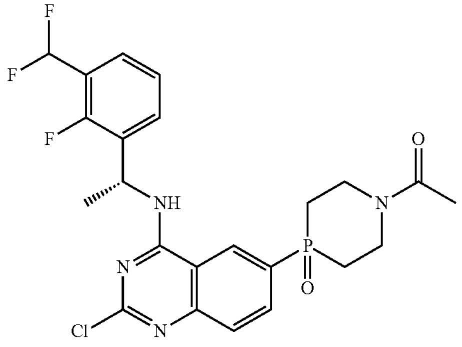
-continued
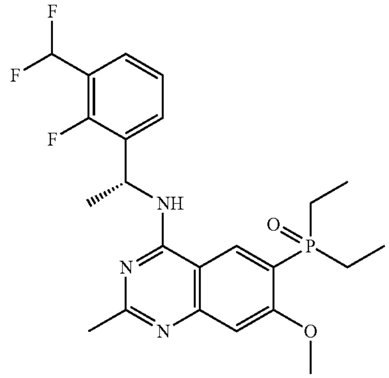
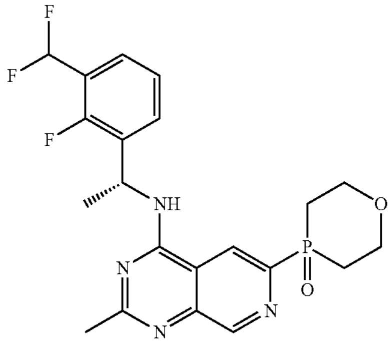
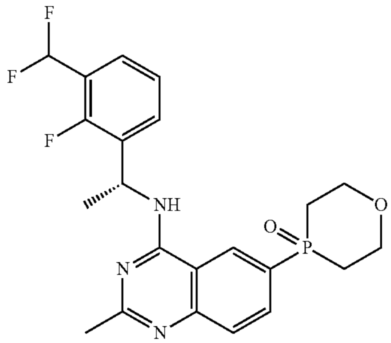
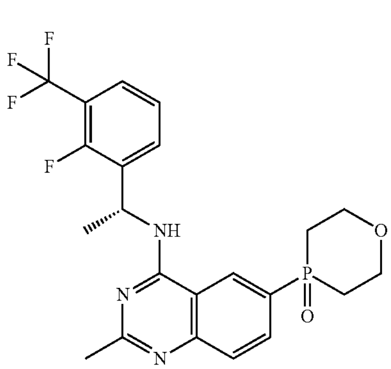

-continued
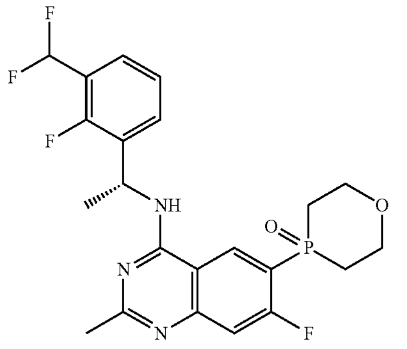
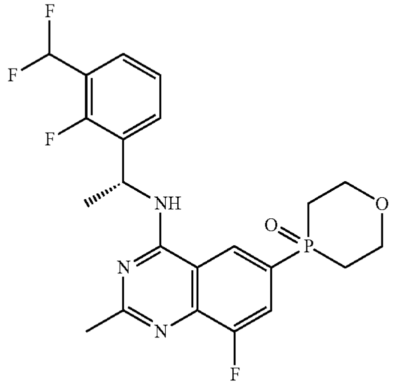
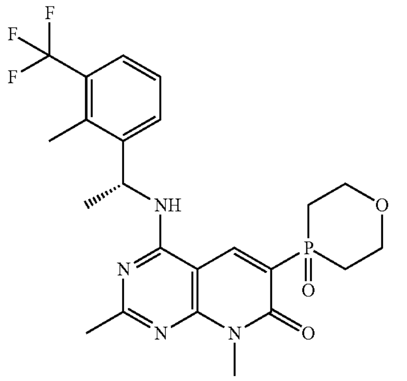
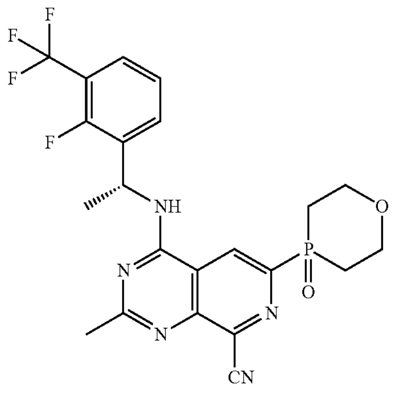
-continued
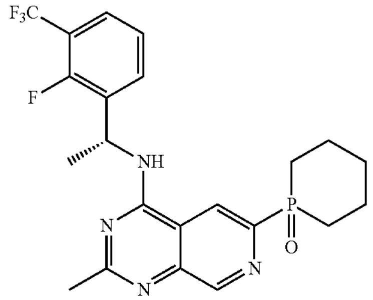
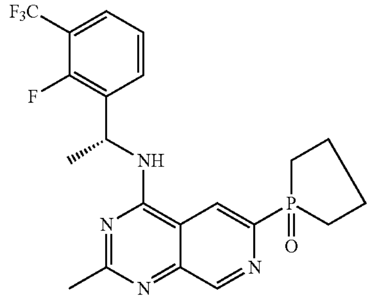
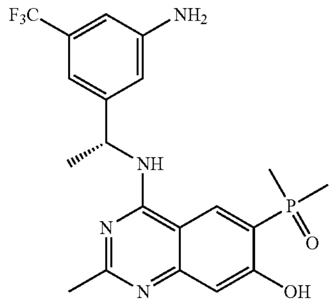
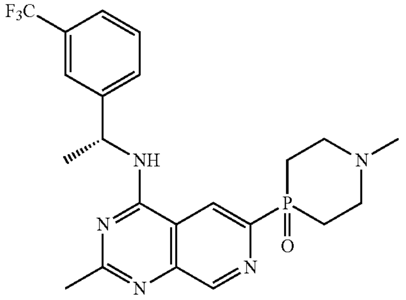
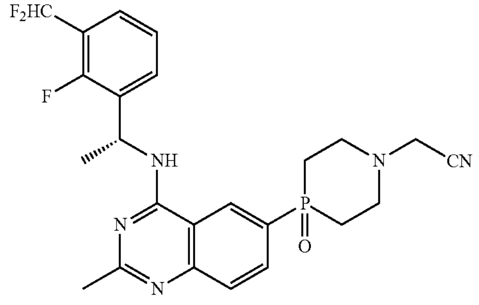

-continued
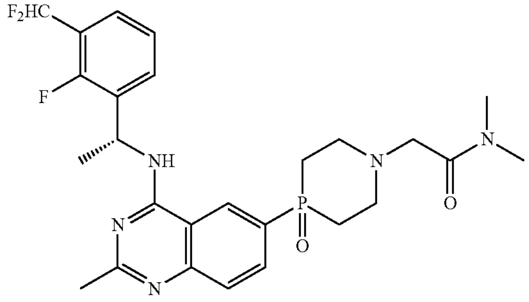
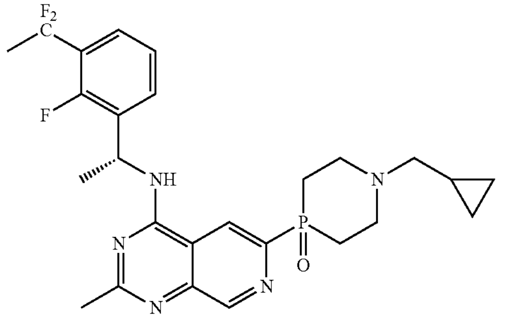
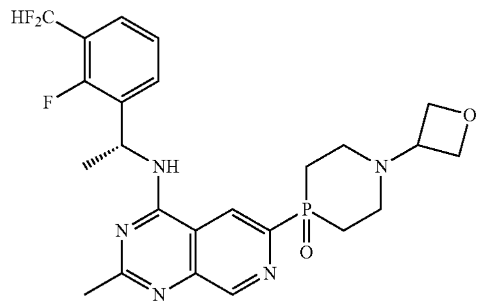
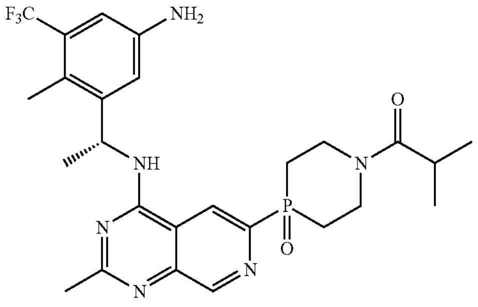
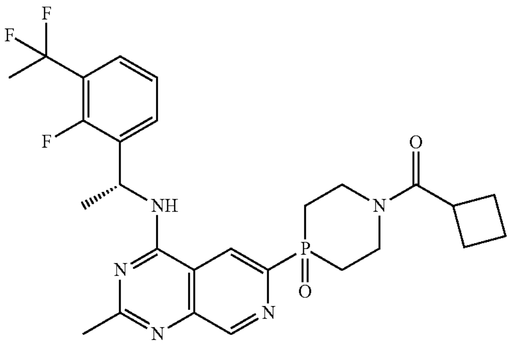
-continued
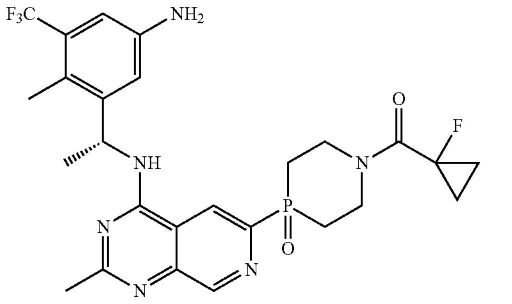
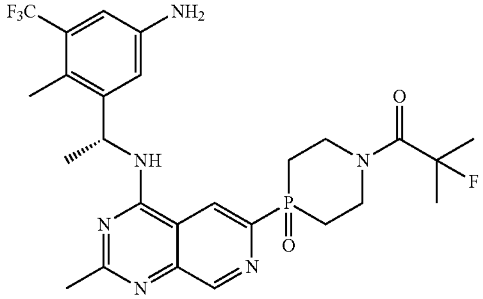
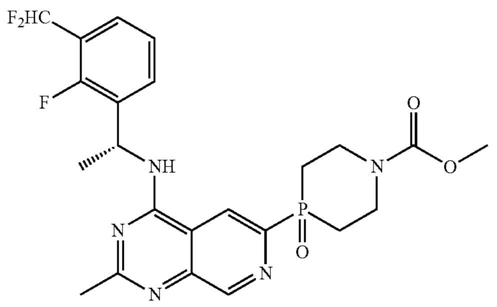
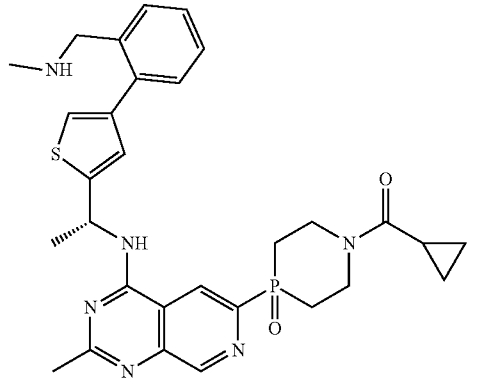
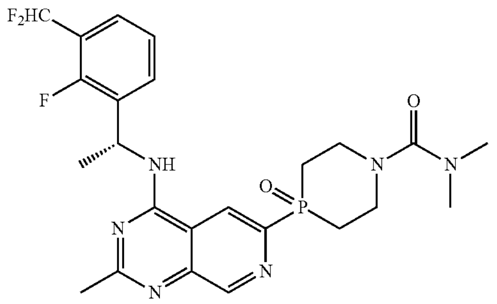

-continued
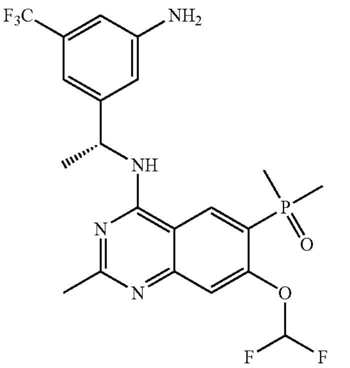
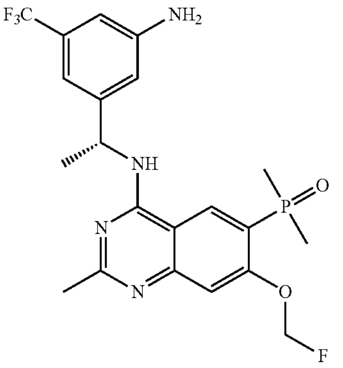
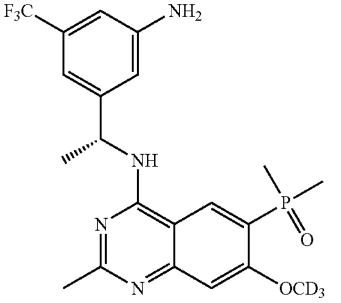
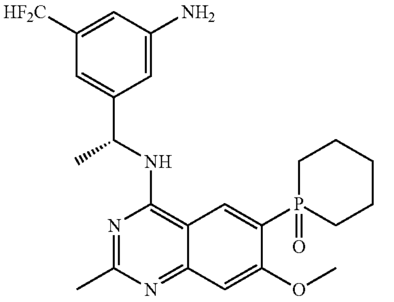
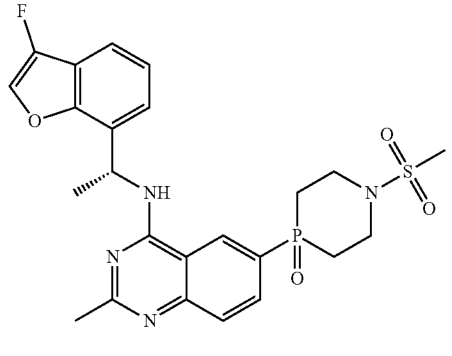
-continued
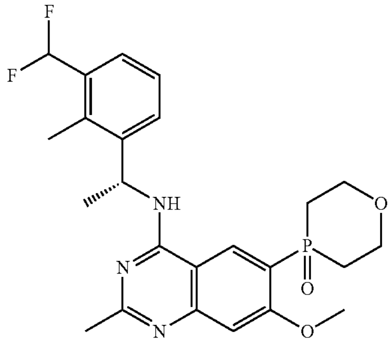
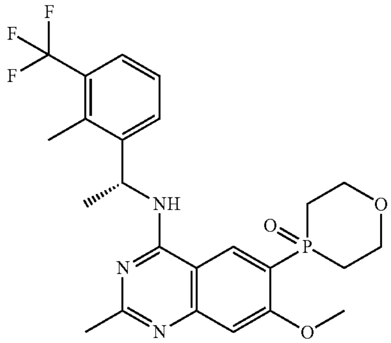
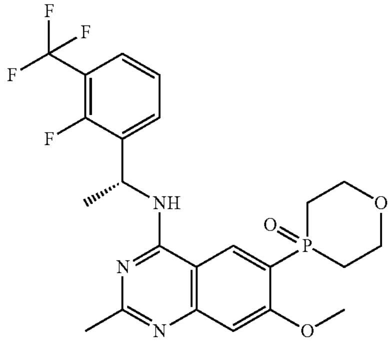
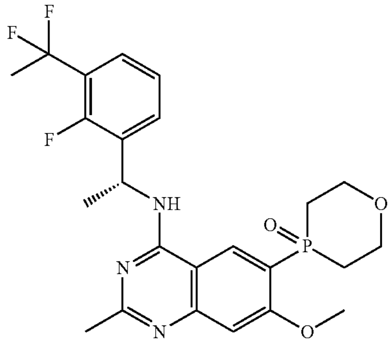
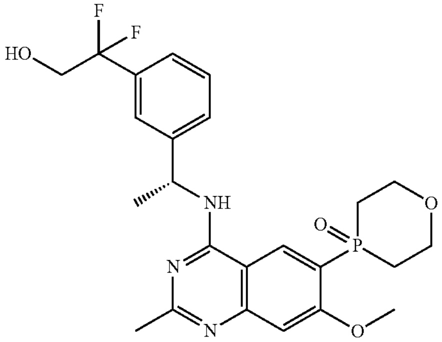

-continued
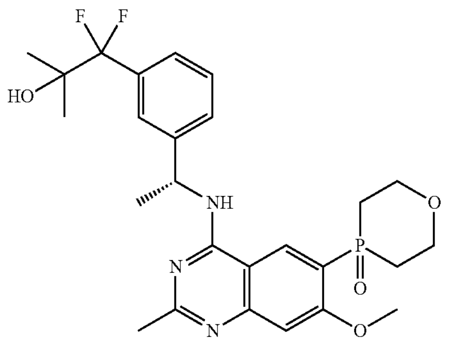
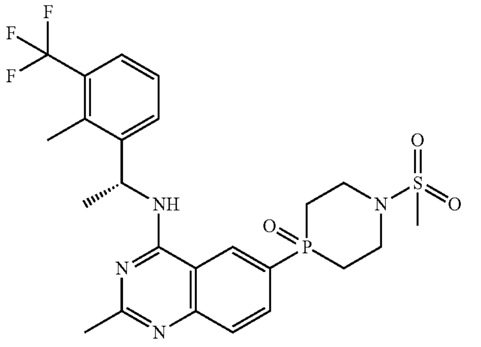
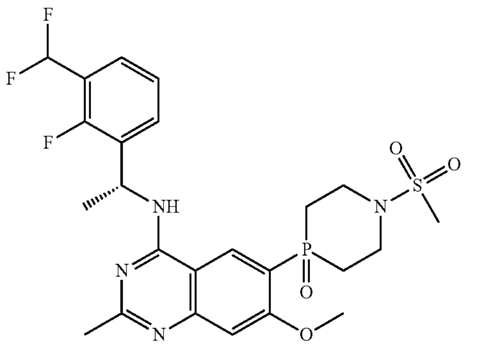
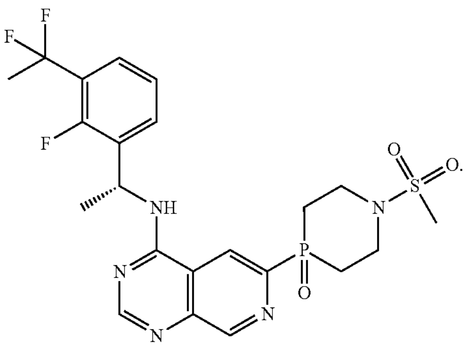
In some embodiments, the compound of formula (I) disclosed herein is selected from the following compounds, stereoisomers thereof or pharmaceutically acceptable salts thereof:
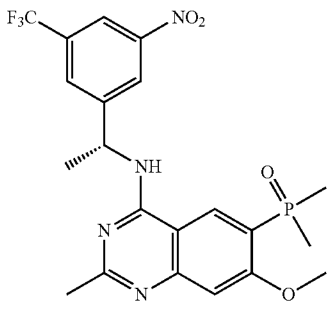
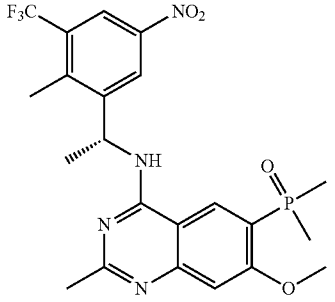
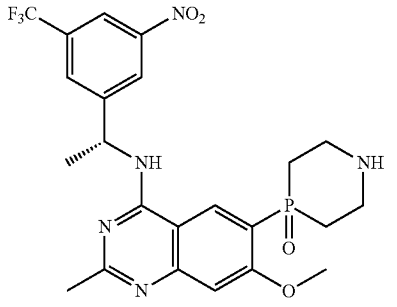
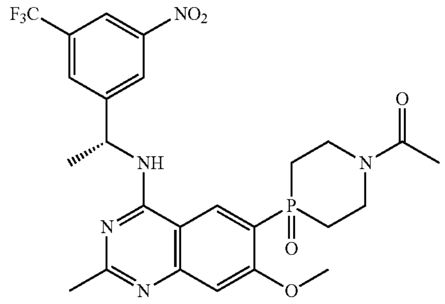
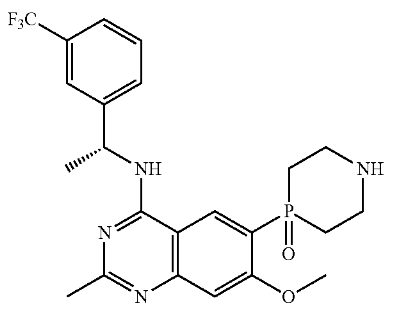

-continued
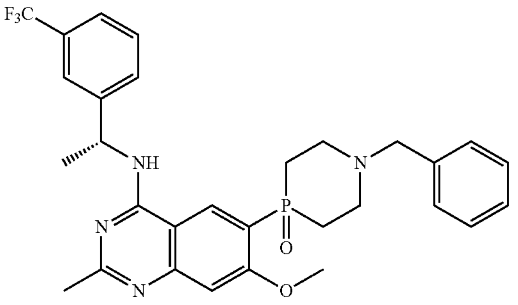
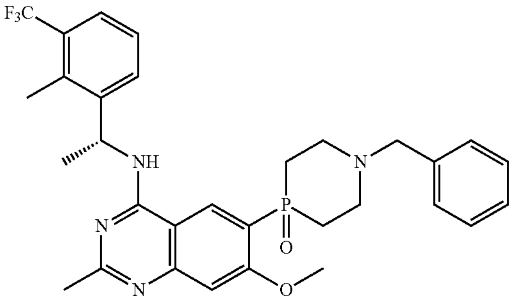
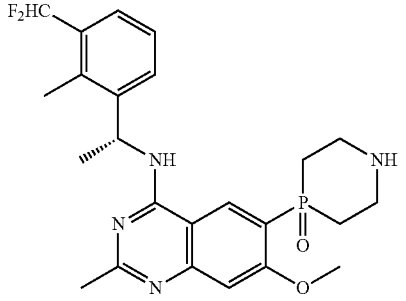
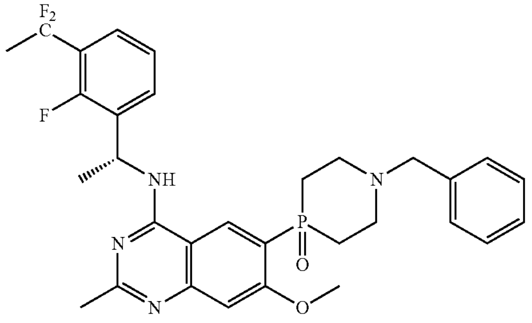
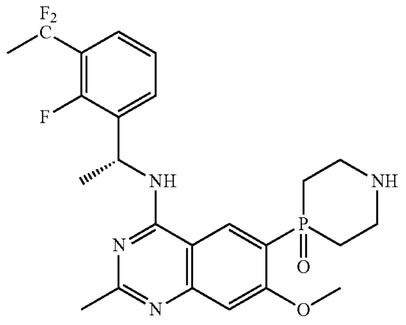
-continued
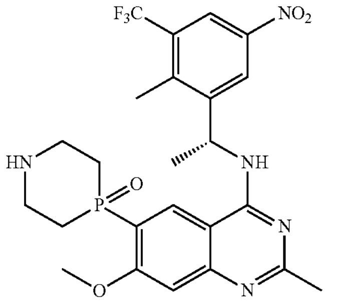
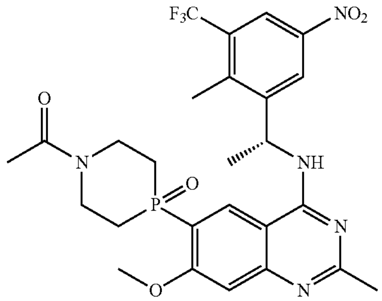
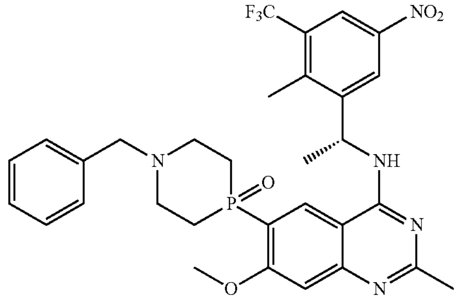
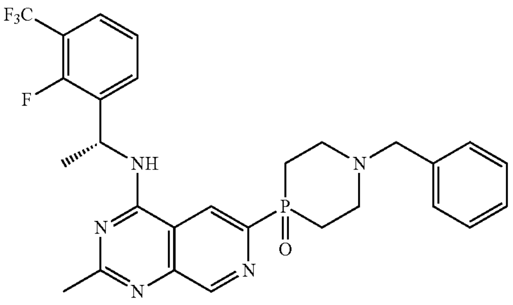
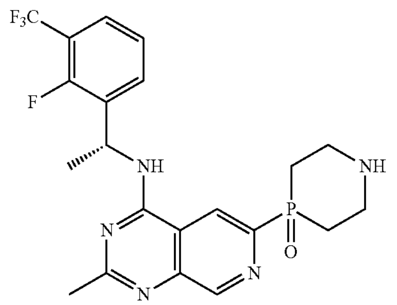

-continued
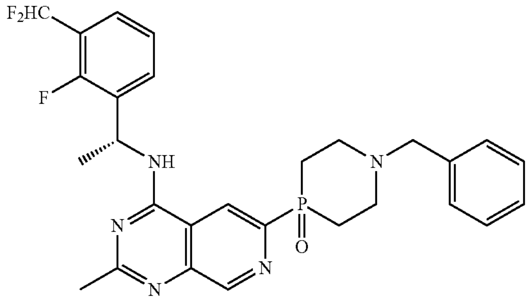
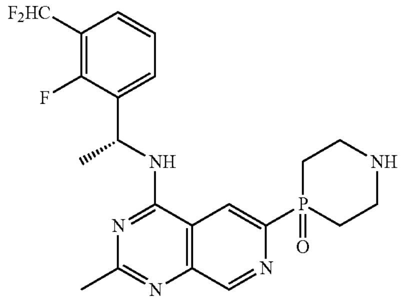
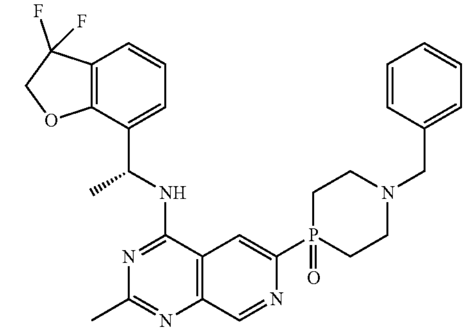
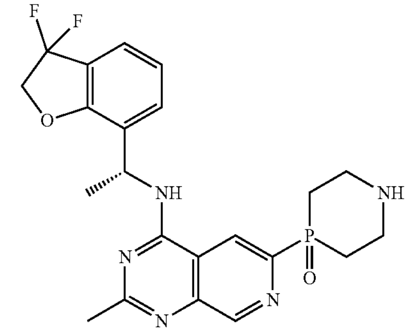
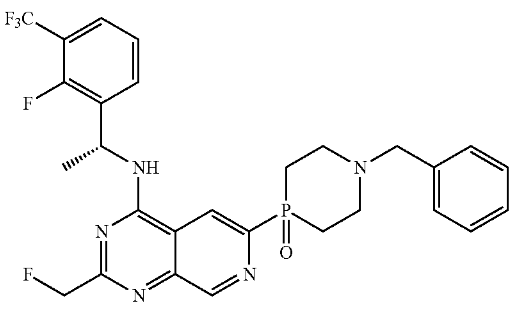
-continued
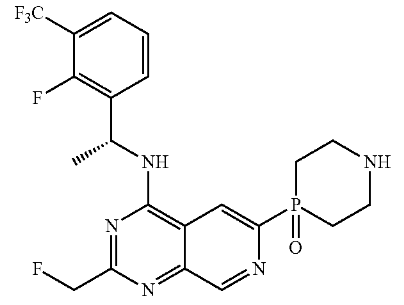
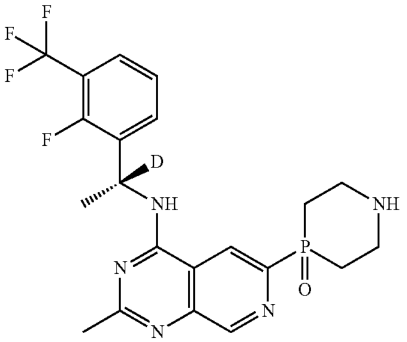
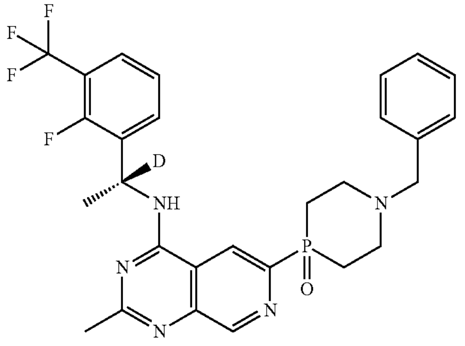
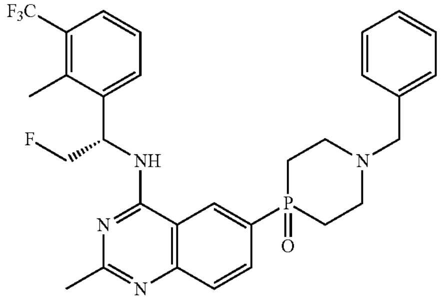
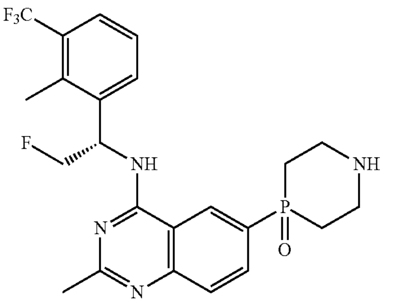

-continued
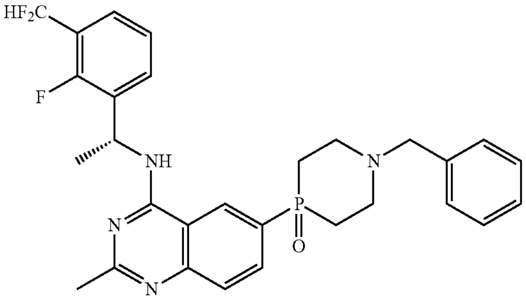
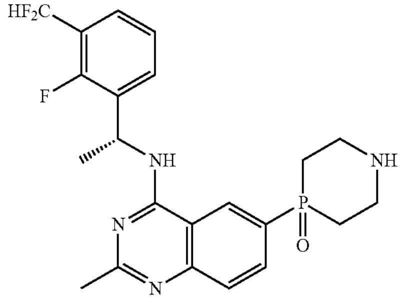
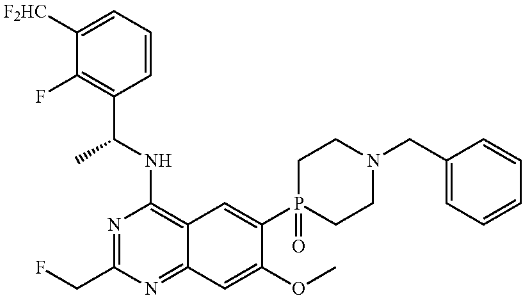
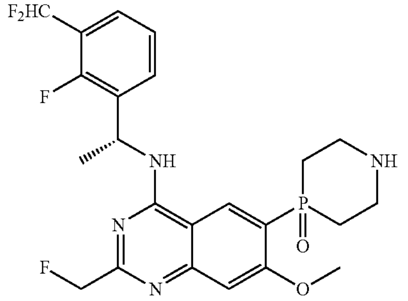
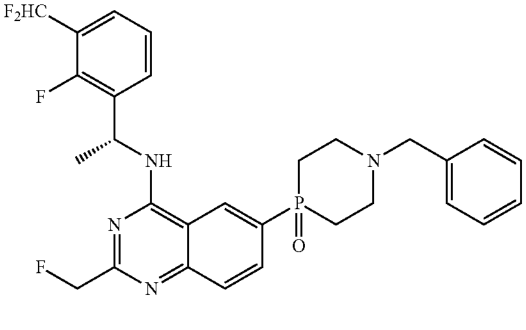
-continued
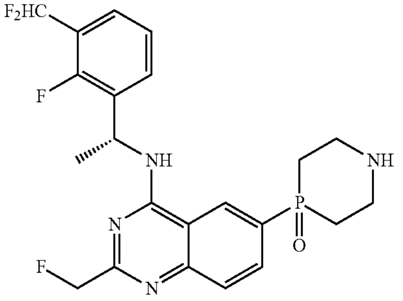
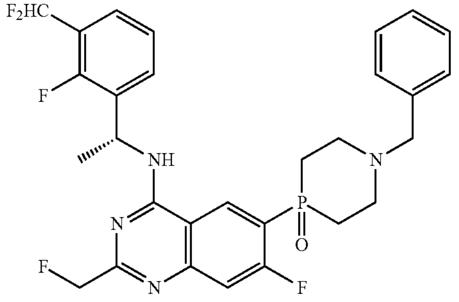
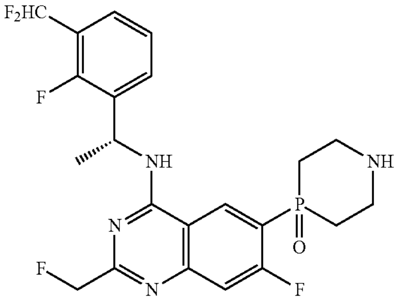
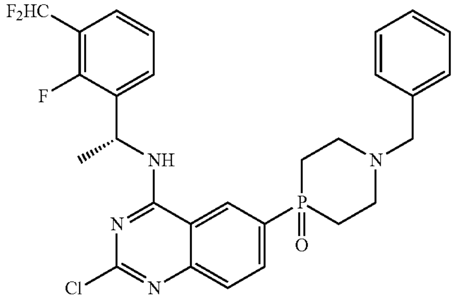
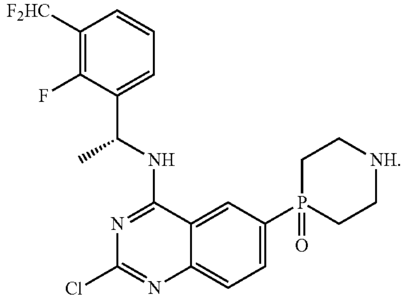
In another aspect, the present application provides a method for preparing a compound of formula (I), which comprises: reacting a compound of formula M3 with a compound of formula N3 to give the compound of formula (I),

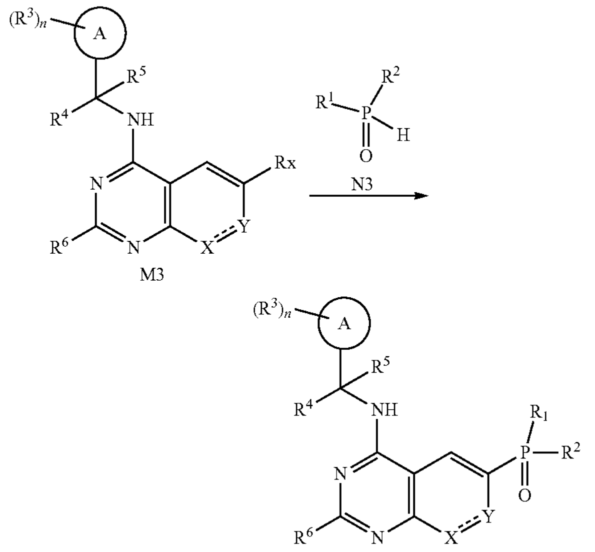

M3

(I)

wherein,

Rx is selected from the group consisting of chlorine, bromine and iodine;

$R^6$ is selected from $C_{1-6}$ alkyl optionally substituted with one or more halogens;

$R^1$, $R^2$, $R^3$, $R^4$, $R^5$, X, Y, n and ring A are defined as above.

In another aspect, the present application provides a method for preparing a compound of formula M3, which comprises:

step (i): reacting a compound of formula M1 with a compound of formula N1 under an acidic condition to give a compound of formula M2; and Step (ii): reacting the compound of formula M2 with a compound of formula N2 to give the compound of formula M3;

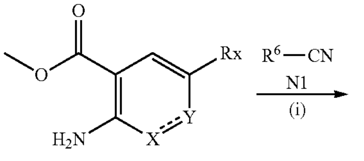

M1

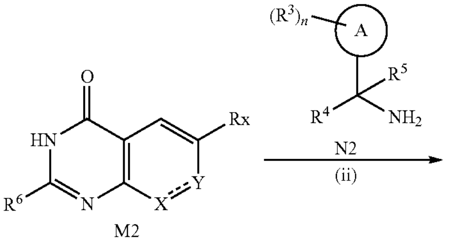

M2

-continued

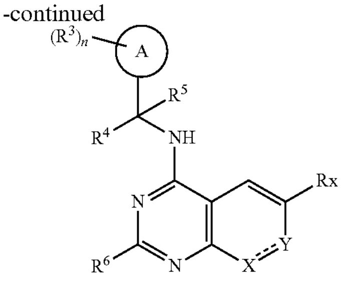

M3 wherein,

Rx is selected from the group consisting of chlorine, bromine and iodine;

$R^6$ is selected from $C_{1-6}$ alkyl optionally substituted with one or more halogens;

$R^3$, $R^4$, $R^5$, X, Y, n and ring A are defined as above.

In another aspect, the present application provides a method for preparing a compound of formula M3, which comprises:

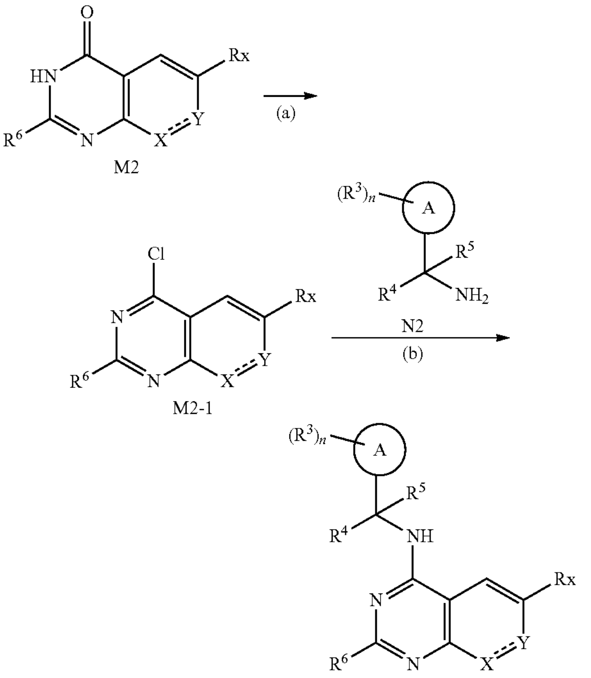

M2

M2-1

M3 step (a): reacting a compound of formula M2 with thionyl chloride to give a compound of formula M2-1, and step (b): performing substitution reaction on the compound of formula M2-1 and a compound of formula N2 under an alkaline condition to give the compound of formula M3, wherein, Rx is selected from the group consisting of chlorine, bromine and iodine;

$R^6$ is selected from $C_{1-6}$ alkyl optionally substituted with one or more halogens;

$R^3$, $R^4$, $R^5$, X, Y, n and ring A are defined as above.

In some embodiments, in the method for preparing a compound of formula (I), the compound of formula M3 is prepared using the method described above.

In another aspect, the present application provides a method for preparing a compound of formula (III-8), wherein the method comprises:

reacting a compound of formula M3-1 with 1-benzyl-1,4-azaphosphine-4-oxide to give a compound of formula M3-2, further removing benzyl protection to obtain a compound of formula M3-3, and finally performing substitution reaction to give the compound of formula (III-8),

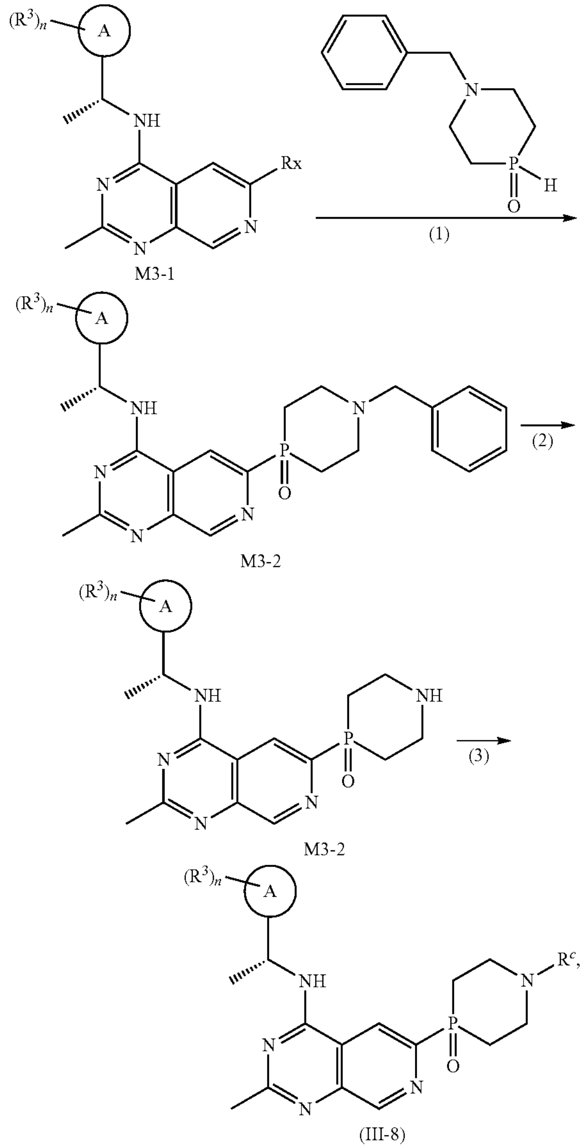

M3-1

M3-2

M3-2

(III-8)

wherein Rx is selected from the group consisting of chlorine, bromine and iodine;

$R^3$, $R^c$, n and Ring A are defined as above.

In some embodiments, the method for preparing a compound of formula (III-8) provided herein comprises:

step (1): reacting a compound of formula M3-1 with 1-benzyl-1,4-azaphosphine-4-oxide to give a compound of formula M3-2, step (2): reacting the compound of formula M3-2 to obtain a compound of formula M3-3, and step (3): reacting the compound of formula M3-3 to obtain the compound of formula (III-8), optionally, step (2) is performed in the presence of

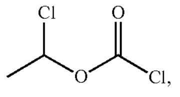

wherein,

Rx is selected from the group consisting of chlorine, bromine and iodine;

$R^6$ is selected from $C_{1-6}$ alkyl optionally substituted with one or more halogens;

$R^3$, $R^c$, n and Ring A are defined as above.

In another aspect, the present application further provides the following intermediate compounds, stereoisomers thereof or pharmaceutically acceptable salts thereof:

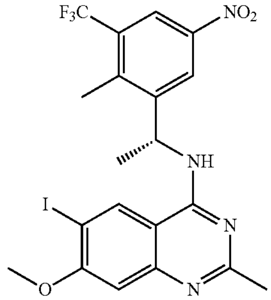

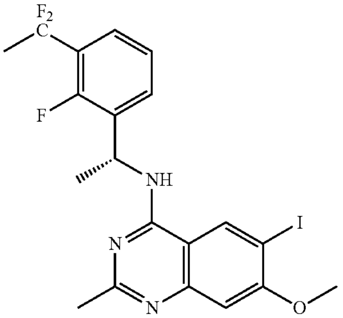

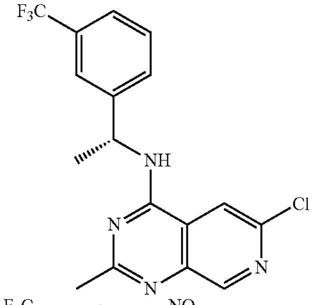

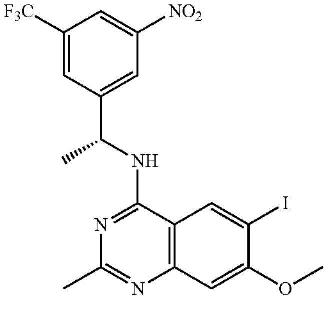

-continued
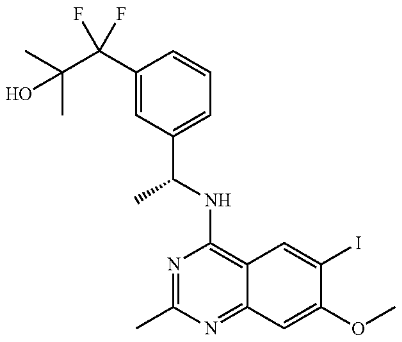
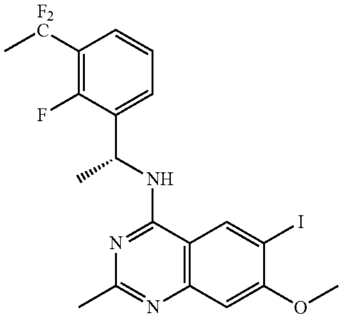
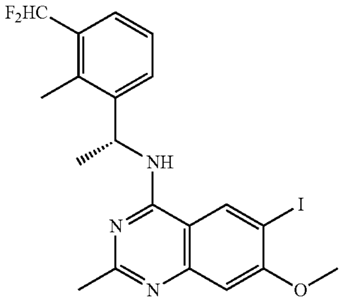
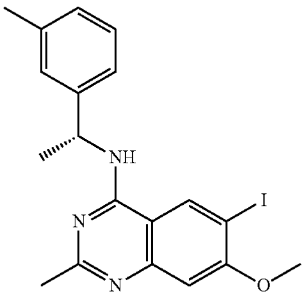
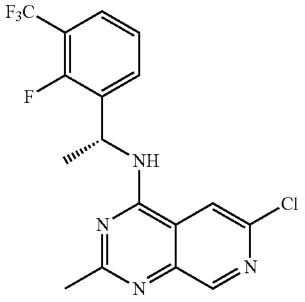
-continued
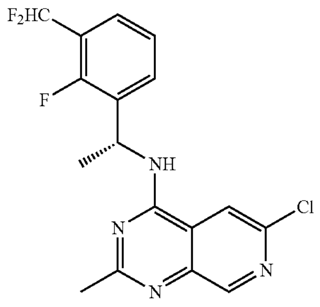
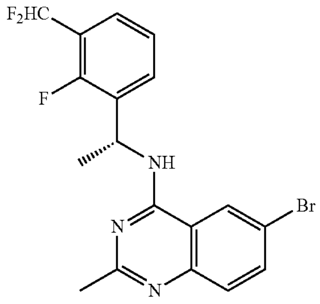
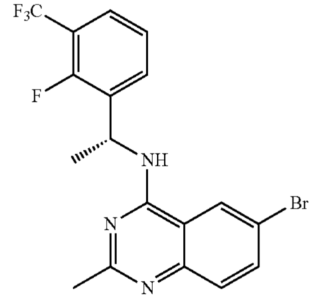
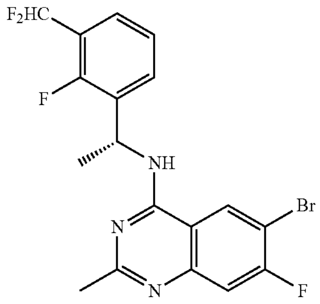
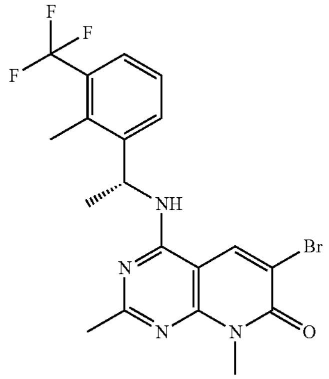

-continued

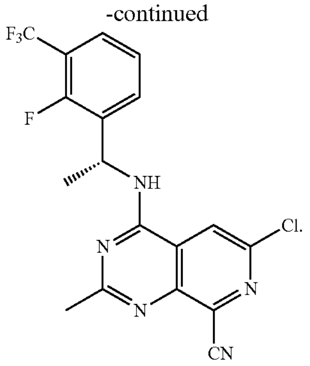

In another aspect, the present application provides a pharmaceutical composition comprising the compound, the stereoisomer thereof or the pharmaceutically acceptable salt thereof disclosed herein. In some embodiments, the pharmaceutical composition of the present application further comprises a pharmaceutically acceptable excipient.

In another aspect, the present application provides a method for treating or preventing a disease and/or disorder related to SOS1 or regulated by SOS1 in a mammal, wherein the method comprises administering to a mammal, preferably a human, in need of such treatment or prevention a therapeutically or prophylactically effective amount of the compound, the stereoisomer thereof or the pharmaceutically acceptable salt thereof, or the pharmaceutical composition thereof.

In another aspect, the present application provides use of the compound, the stereoisomer thereof or the pharmaceutically acceptable salt thereof, or the pharmaceutical composition thereof in preparing a medicament for treating or preventing a disease and/or disorder related to SOS1 or regulated by SOS1.

In another aspect, the present application provides use of the compound, the stereoisomer thereof or the pharmaceutically acceptable salt thereof, or the pharmaceutical composition thereof in treating or preventing a disease and/or disorder related to SOS1 or regulated by SOS1.

In another aspect, the present application provides the compound, the stereoisomer thereof or the pharmaceutically acceptable salt thereof, or the pharmaceutical composition thereof for use in treating or preventing a disease and/or disorder related to SOS1 or regulated by SOS1.

In some embodiments, the disease and/or disorder related to SOS1 or regulated by SOS1 is selected from a disease and/or disorder in which SOS1 interacts with RAS-family proteins.

In some embodiments, the disease and/or disorder related to SOS1 or regulated by SOS1 is selected from cancer, e.g., non-small cell lung cancer.

The compound of the present application has good inhibitory activity for KRAS-G12C/SOS1 protein binding, inhibitory activity for K562 cell proliferation, in vivo and in vitro pharmaceutical activity and good pharmacokinetic property.

Definitions

Unless otherwise stated, the following terms used herein shall have the following meanings. A certain term, unless otherwise specifically defined, should not be considered uncertain or unclear, but construed according to its common meaning in the field. When referring to a trade name, it is intended to refer to its corresponding commercial product or its active ingredient.

Chemical bond “ ” represents a single bone or a double bond depending on the groups connected to the two ends of the chemical bond. For example, chemical bond “ ” is a double bond when X and Y connected to the two ends of the chemical bond are $CR^a$ or N, respectively; chemical bond “ ” bond when one of X and Y connected to the two ends of the chemical bond is CO or $NR^a$. It will be understood those skilled in the art that the selection of X and Y does not violate the valence rules.

The term “substituted” means that any one or more hydrogen atoms on a specific atom are substituted by substituents, as long as the valence of the specific atom is normal and the resulting compound is stable. When the substituent is oxo (namely =O), it means that two hydrogen atoms are substituted, and oxo is not available on an aromatic group.

The term “optional” or “optionally” means that the subsequently described event or circumstance may, but not necessarily, occur. The description includes instances where the event or circumstance occurs and instances where the event or circumstance does not occur. For example, ethyl being “optionally” substituted with halogen means that the ethyl may be unsubstituted ($—CH_2CH_3$), monosubstituted (for example, $—CH_2CH_2F$), polysubstituted (for example, $—CHFCH_2F$ and $—CH_2CHF_2$) or fully substituted ($—CF_2CF_3$). It will be understood by those skilled in the art that for any groups comprising one or more substituents, any substitutions or substituting patterns which may not exist or cannot be synthesized spatially are not introduced.

$C_{m-n}$ used herein means that the portion has an integer number of carbon atoms in the given range. For example, “$C_{1-6}$” means that the group may have 1 carbon atom, 2 carbon atoms, 3 carbon atoms, 4 carbon atoms, 5 carbon atoms or 6 carbon atoms; “$C_{1-3}$” means that the group may have 1 carbon atom, 2 carbon atoms or 3 carbon atoms.

When any variable (e.g., R) occurs more than once in the constitution or structure of a compound, the variable is independently defined in each case. Therefore, for example, if a group is substituted with 2 R, the definition of each R is independent.

When a connecting group has a number of 0, for example, $—(CH_2)_0—$, it means that the connecting group is a covalent bond.

When a bond of a substituent is cross-linked to two atoms on a ring, the substituent can be bonded to any atom on the ring. For example, structural unit

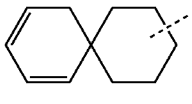

or

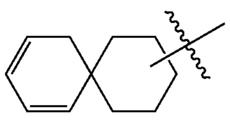

represents that substitution may occur at any one position of cyclohexyl or cyclohexadienyl.

The term “halo-” or “halogen” refers to fluorine, chlorine, bromine and iodine.

The term “hydroxy” refers to —OH group.

The term “amino” refers to $—NH_2$ group.

The term “nitro” refers to $—NO_2$ group.

The term “cyano” refers to —CN group.

The term “alkyl” refers to hydrocarbyl with a general formula of $C_nH_{2n+1}$. The alkyl can be linear or branched. For example, the term “$C_{1-6}$ alkyl” refers to alkyl containing 1 to 6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl and 2-methylpentyl). The alkyl moieties (namely alkyl) of alkoxy, alkylamino, dialkylamino, alkylsulfonyl and alkylthio are similarly defined as above.

The term "alkoxyl" refers to —O-alkyl.

The term "alkylamino" or "monoalkylamino" refers to —NH-alkyl.

The term "dialkylamino" refers to —N(alkyl)$_2$.

The term "cycloalkyl" refers to a carbon ring that is fully saturated and may exist as a single ring, a bridged ring, or a spiro ring. Unless otherwise specified, the carbon ring is generally a 3-10 membered ring. Non-limiting examples of cycloalkyl include, but are not limited to, cyclopropyl, cyclobutyl, cyclopentyl, cyclohexyl, norbornyl(bicyclo [2.2.1]heptyl), bicyclo[2.2.2]octyl, adamantyl, and the like.

The term "heterocyclyl" refers to a fully saturated or partially unsaturated (but not fully unsaturated heteroaromatic group) nonaromatic ring which may exist in the form of a monocyclic, bridged cyclic or spiro cyclic structure.

Unless otherwise specified, the heterocyclyl is usually a 3-12 membered ring containing 1-3 heteroatoms (preferably 1 or 2 heteroatoms) independently selected from the group consisting of sulfur, oxygen, phosphorus and/or nitrogen.

Non-limiting examples of heterocyclyl include, but are not limited to, oxiranyl, tetrahydrofuranyl, dihydrofuranyl, pyrrolidinyl, N-methylpyrrolidinyl, dihydropyrrolyl, piperidinyl, piperazinyl, pyrazolidinyl, 4H-pyranyl, morpholinyl, sulfomorpholinyl, tetrahydrothienyl

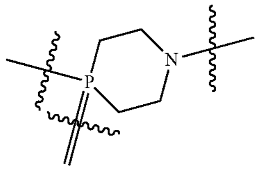 [SMILES: *N1CCP(*)(=*)CC1]

or the like.

The term "heterocycloalkyl" refers to a fully saturated cyclic group that may exist in the form of a monocyclic, bridged cyclic or spiro cyclic structure. Unless otherwise specified, the heterocycloalkyl is usually a 3-12 membered, 3-7 membered or 5-8 membered ring containing 1-3 heteroatoms (preferably 1 or 2 heteroatoms) independently selected from the group consisting of sulfur, oxygen, phosphorus and/or nitrogen. Examples of 3 membered heterocycloalkyl include, but are not limited to, oxiranyl, thietanyl and aziranyl. Non-limiting examples of 4 membered heterocycloalkyl include, but are not limited to, azetidinyl, oxetanyl and thietanyl. Examples of 5 membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl and tetrahydropyrazolyl. Examples of 6 membered heterocycloalkyl include, but are not limited to, piperidinyl, tetrahydropyranyl, tetrahydrothiopyranyl, morpholinyl piperazinyl, 1,4-oxathianyl, 1,4-dioxanyl, sulfomorpholinyl, 1,3-dithianyl, 1,4-dithianyl or

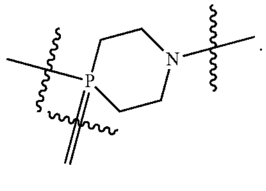 [SMILES: *N1CCP(*)(=*)CC1]

Examples of 7 membered heterocycloalkyl include, but are not limited to, azacycloheptanyl, oxacycloheptanyl and thiocycloheptanyl. Preferably, the heterocycloalkyl is a monocyclic heterocycloalkyl having 5 or 6 ring atoms.

The term "aryl" refers to an aromatic monocyclic or fused polycyclic group of carbon atoms with the conjugated pi-electron system. For example, aryl may have 6-20 carbon atoms, 6-14 carbon atoms or 6-12 carbon atoms. Non-limiting examples of aryl include, but are not limited to, phenyl, naphthyl, anthryl, 1,2,3,4-tetrahydronaphthalene and the like.

The term "heteroaryl" refers to a monocyclic or fused polycyclic system containing at least one ring atom selected from the group consisting of N, O and S, with the remaining ring atoms being C, and having at least one aromatic ring. Preferably, heteroaryl has a single 5-8 membered ring, or is a plurality of fused rings comprising 6-14 ring atoms, in particular 6-10 ring atoms. Non-limiting examples of heteroaryl include, but are not limited to, pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl and the like.

The term "fused ring" refers to a 7-20 membered all-carbon polycyclic ring in which two rings in the system share two adjacent carbon atoms, wherein at least one ring has a fully conjugated π-electron system, and it is not aromatic as a whole. According to the number of the formed rings, the fused ring may be bicyclic, tricyclic, tetracyclic or polycyclic fused ring, preferably bicyclic or tricyclic fused ring, and more preferably 6 membered/6 membered or 5 membered/6 membered bicyclic fused ring. Non-limiting examples of fused ring include:

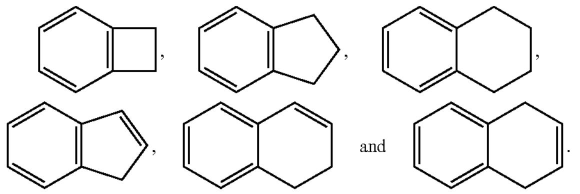

The term "spiro heterocycloalkyl" refers to a fully saturated 5-20 membered polycyclic ring in which monocyclic rings share one carbon atom (referred to as the spiro atom), wherein one or more ring atoms in the polycyclic ring is selected from heteroatoms (preferably 1 or 2 heteroatoms) of sulfur, silicon, phosphorus, oxygen and/or nitrogen, and the remaining ring atoms are carbon atoms. The spiro heterocycloalkyl is preferably a 6-14 membered polycyclic ring, and more preferably a 6-10 membered polycyclic ring. According to the number of spiro atoms shared among the rings, the spiro heterocyclic ring may be a monospiro heterocyclic ring, a bispiro heterocyclic ring or a polyspiro heterocyclic ring, preferably a monospiro heterocyclic ring or a bispiro heterocyclic ring, and more preferably a 4 membered/4 membered, 4 membered/5 membered, 4 membered/6 membered, 5 membered/5 membered or 5 membered/6 membered monospiro heterocyclic ring. Non-limiting examples of spiro heterocyclic ring include

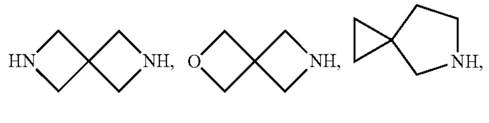

-continued

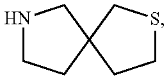, 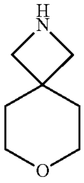, 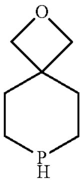, 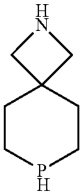, 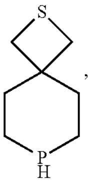, 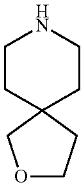 and 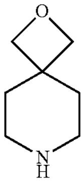.

The term "fused heterocycloalkyl" refers to a fully saturated polycyclic ring having 5 to 20 ring atoms, with two rings sharing 2 ring atoms, wherein one or more ring atoms in the polycyclic ring is selected from heteroatoms (preferably 1 or 2 heteroatoms) of sulfur, silicon, phosphorus, oxygen and/or nitrogen, and the remaining ring atoms are carbon atoms. The fused heterocycloalkyl is preferably a 6-14 membered polycyclic ring, and more preferably a 6-10 membered polycyclic ring. According to the number of the formed rings, the fused heterocycloalkyl may be bicyclic, tricyclic or polycyclic bridged heterocyclic ring, preferably bicyclic bridged heterocyclic ring. Non-limiting examples of fused heterocyclic ring include

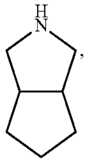, 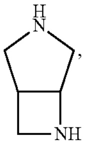, 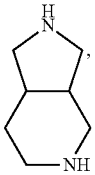, 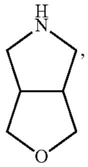, 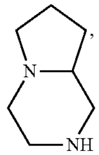, 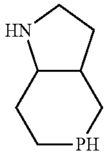 and 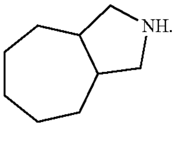

The term "benzocycloalkyl" refers to a phenyl ring fused to a cycloalkyl group (i.e., the phenyl ring and the cycloalkyl group share two adjacent carbon atoms). Non-limiting examples of benzocycloalkyl include:

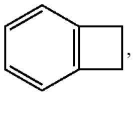, 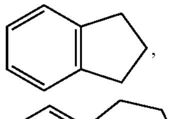, 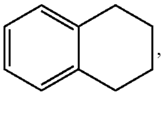, 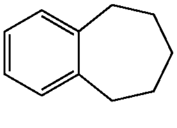

and the like.

The term "cycloalkenyl" refers to an unsaturated carbon ring that contains at least one carbon-carbon double bond and does not contain any carbon-carbon triple bond, and may exist as a monocyclic, bridged cyclic or spiro cyclic structure. Non-limiting examples of cycloalkenyl include: cyclopropenyl, cyclobutenyl, cyclopentenyl, cyclohexenyl and cyclohexadienyl.

The term "benzocycloalkenyl" refers to a phenyl ring fused to a cycloalkenyl group (i.e., the phenyl ring and the cycloalkenyl group share two adjacent carbon atoms). Non-limiting examples of benzocycloalkenyl include:

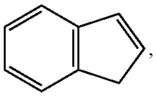, 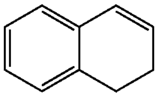 and 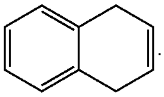.

The term "benzoheterocyclyl" refers to a phenyl ring fused to a heterocyclyl group (i.e., the phenyl ring and the heterocyclyl group share two adjacent carbon atoms). Non-limiting examples of benzoheterocyclyl include:

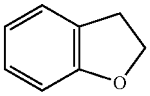, 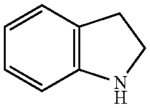, 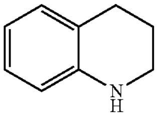, 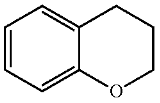, 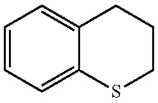, 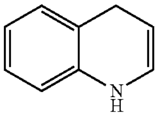, 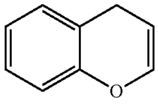 and 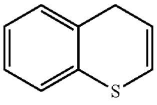.

The term "benzoheterocycloalkyl" refers to a phenyl ring fused to a heterocycloalkyl group (i.e., the phenyl ring and the heterocycloalkyl group share two adjacent carbon atoms). Non-limiting examples of benzoheterocycloalkyl include:

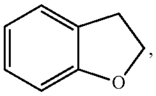, 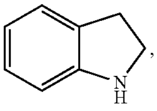, 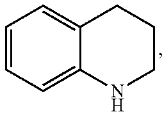, 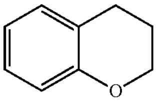 and 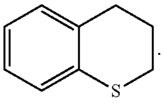.

The term "heterocycloalkenyl" refers to an unsaturated cyclic group that contains at least one carbon-carbon double bond or carbon-nitrogen double bond, and may exist as a monocyclic, bridged cyclic or spiro cyclic structure. Unless otherwise specified, the heterocyclic ring is usually a ring containing 1 to 3 heteroatoms (preferably 1 or 2 heteroatoms) independently selected from the group consisting of sulfur, oxygen, phosphorus and/or nitrogen. Non-limiting examples of heterocycloalkenyl include: 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 3-pyrrolinyl, 3,4-dihydro-2H-pyran, dihydrofuranyl, dihydrothienyl and thiopyranyl.

The term "benzoheterocycloalkenyl" refers to a phenyl ring fused to a heterocycloalkenyl group (i.e., the phenyl ring and the heterocycloalkenyl group share adjacent two carbon atoms). Non-limiting examples of benzoheterocycloalkenyl include:

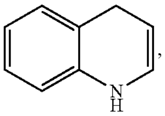,
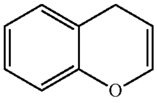
and
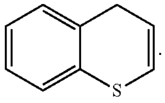.

The term "fused heterocyclic ring" refers to a 7-20 membered polycyclic ring in which two rings in the system share two adjacent atoms, wherein at least one ring atom is selected from the group consisting of N, O and S, with the remaining ring atoms being C, and at least one ring has a fully conjugated π-electron system, and it is not aromatic as a whole. According to the number of the formed rings, the fused heterocyclic ring may be bicyclic, tricyclic, tetracyclic or polycyclic fused ring, preferably bicyclic or tricyclic fused ring, and more preferably 6 membered/6 membered or 5 membered/6 membered bicyclic fused ring. Non-limiting examples of fused heterocyclic ring include:

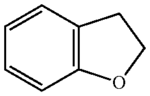
and
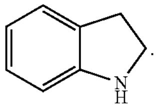.

The term "treating" or "treatment" means administering the compound or formulation described herein to ameliorate or eliminate a disease or one or more symptoms associated with the disease, and includes:

(i) inhibiting a disease or disease state, i.e., arresting its progression; and (ii) alleviating a disease or disease state, i.e., causing its regression.

The term "prevent" or "prevention" means administering the compound or formulation described herein to prevent a disease or one or more symptoms associated with the disease, and includes: preventing the occurrence of the disease or disease state in a mammal, particularly when such a mammal is predisposed to the disease state but has not yet been diagnosed with it.

The term "therapeutically or prophylactically effective amount" refers to an amount of the compound disclosed herein for (i) treating or preventing the specific disease, condition or disorder described herein; (ii) alleviating, ameliorating or eliminating one or more symptoms of the specific disease, condition or disorder described herein, or (iii) preventing or delaying onset of one or more symptoms of the specific disease, condition or disorder described herein. The amount of the compound of the present application composing the "therapeutically effective amount" varies dependently on the compound, the disease state and its severity, the route of administration, and the age of the mammal to be treated, but can be determined routinely by those skilled in the art in accordance with their knowledge and the present disclosure.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The term "pharmaceutical composition" refers to a mixture consisting of one or more of the compounds or the salts thereof disclosed herein and a pharmaceutically acceptable excipient. The pharmaceutical composition is intended to facilitate the administration of the compound to an organic entity.

The term "pharmaceutically acceptable excipients" refers to those which do not have a significant irritating effect on an organic entity and do not impair the biological activity and properties of the active compound. Suitable excipients are well known to those skilled in the art, for example carbohydrate, wax, water-soluble and/or water-swellable polymers, hydrophilic or hydrophobic material, gelatin, oil, solvent, or water.

The word "comprise" and variations thereof such as "comprises" or "comprising" will be understood in an open, non-exclusive sense, i.e., "including but not limited to".

Unless otherwise specified, terms in the singular shall be deemed to include the plural and vice versa. Unless otherwise specified, the word "a" or "an" refers to "at least one". Unless otherwise stated, use of "or" means "and/or".

The compound disclosed herein may demonstrate a specific geometric isomerism or stereoisomerism. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereoisomer enriched mixture, all of which are encompassed within the scope of the present invention. Substituents such as alkyl may have an additional asymmetric carbon atom. All these isomers and mixtures thereof are encompassed within the scope of the present invention.

Unless otherwise stated, "(D)" or "(+)" represents dextrorotation, "(L)" or "(−)" represents levorotation, and "(DL)" or "(±)" represents racemization.

Unless otherwise stated, the absolute configuration of a stereogenic center is represented by a wedged solid bond ( ) and a wedged dashed bond ( ), and the relative configuration of a stereogenic center is represented by a straight solid bond ( ) and a straight dashed bond ( ).

Optically active (R)- and (S)-isomers and D and L isomers can be prepared by chiral synthesis or chiral reagents or other conventional techniques. If one enantiomer of a certain compound disclosed herein is to be obtained, the desired pure enantiomer can be prepared by asymmetric synthesis or derivatization using a chiral additive, wherein the resulting diastereoisomeric mixture is separated and the auxiliary group is cleaved. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods in the art to give the pure enantiomer. Furthermore, the enantiomer and the diastereoisomer are generally isolated through chromatography using a chiral stationary phase, optionally in combination with chemical derivatization (e.g., carbamate generated from amines).

The present application also comprises isotopically labeled compounds which are identical to those recited herein but have one or more atoms replaced by an atom having an atomic mass or mass number different from the atomic mass or mass number usually found in nature. Examples of isotopes that can be incorporated into the compounds disclosed herein include isotopes of hydrogen, carbon, nitrogen, oxygen, phosphorus, sulfur, fluorine, iodine and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$.

Certain isotopically labeled compounds disclosed herein (e.g., those labeled with $^{3}H$ and $^{14}C$) can be used to analyze compounds and/or substrate tissue distribution. Tritium (i.e., $^{3}H$) and carbon-14 (i.e., $^{14}C$) isotopes are particularly preferred for their ease of preparation and detectability. Positron emitting isotopes, such as $^{15}O$, $^{13}N$, $^{11}C$ and $^{18}F$ can be used in positron emission tomography (PET) studies to determine substrate occupancy. Isotopically labeled compounds disclosed herein can generally be prepared by following procedures analogous to those disclosed in the schemes and/or examples below while substituting a non-isotopically labeled reagent with an isotopically-labeled reagent.

Furthermore, substitution with heavier isotopes such as deuterium (i.e., $^{2}H$ and D) may provide certain therapeutic advantages (e.g., increased in vivo half-life or reduced dosage) resulting from greater metabolic stability and hence may be preferred in some circumstances in which deuterium substitution may be partial or complete, wherein partial deuterium substitution refers to substitution of at least one hydrogen with at least one deuterium.

The pharmaceutical composition disclosed herein can be prepared by combining the compound disclosed herein with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere and aerosol.

Typical routes of administration of the compound or the pharmaceutically acceptable salt thereof or the pharmaceutical composition thereof of the present application include, but are not limited to, oral, rectal, local, inhalation, parenteral, sublingual, intravaginal, intranasal, intraocular, intraperitoneal, intramuscular, subcutaneous and intravenous administration.

The pharmaceutical composition disclosed herein can be manufactured using methods well known in the art, such as conventional mixing, dissolving, granulating, dragee-making, levigating, emulsifying, and lyophilizing.

In some embodiments, the pharmaceutical composition is in an oral form. For oral administration, the pharmaceutical composition can be formulated by mixing the active compounds with pharmaceutically acceptable excipients well known in the art. These excipients enable the compound disclosed herein to be formulated into tablets, pills, pastilles, dragees, capsules, liquids, gels, slurries, suspensions, etc. for oral administration to a patient.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents and the like.

The pharmaceutical compositions may also be suitable for parenteral administration, such as sterile solutions, suspensions or lyophilized products in suitable unit dosage forms.

In all of the administration methods of the compound of general formula I described herein, the daily dose administered is from 0.01 to 200 mg/kg body weight, given in individual or separated doses.

The compounds of the present application can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The chemical reactions of the embodiments disclosed herein are carried out in a proper solvent that must be suitable for the chemical changes in the present application and the reagents and materials required. In order to acquire the compounds disclosed herein, it is sometimes necessary for those skilled in the art to modify or select a synthesis procedure or a reaction scheme based on the existing embodiments.

An important consideration in synthesis route planning in the art is the selection of suitable protecting groups for reactive functional groups (e.g., amino in the present application). For example, reference may be made to *Greene's Protective Groups in Organic Synthesis* (4th Ed.) Hoboken, New Jersey: John Wiley & Sons, Inc. All references cited herein are incorporated by reference in their entirety.

All patents, patent applications and other identified publications are explicitly incorporated herein by reference for the purpose of description and disclosure. These publications are provided solely because they were disclosed prior to the filing date of the present application. All statements as to the dates of these documents or description as to the contents of these documents are based on the information available to the applicant and do not constitute any admission as to the correctness of the dates or the content of these documents. Moreover, in any country or region, any reference to these publications herein is not to be construed as an admission that the publications form part of the commonly recognized knowledge in the art.

In some embodiments, the compounds of the present application can be prepared by those skilled in the art of organic synthesis by reference to the following routes:

Route I:

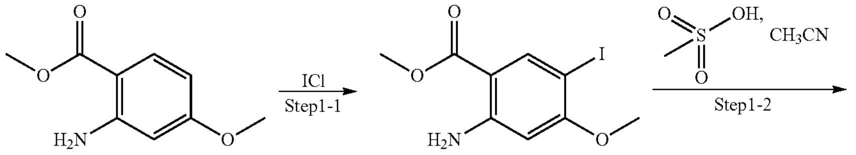

-continued
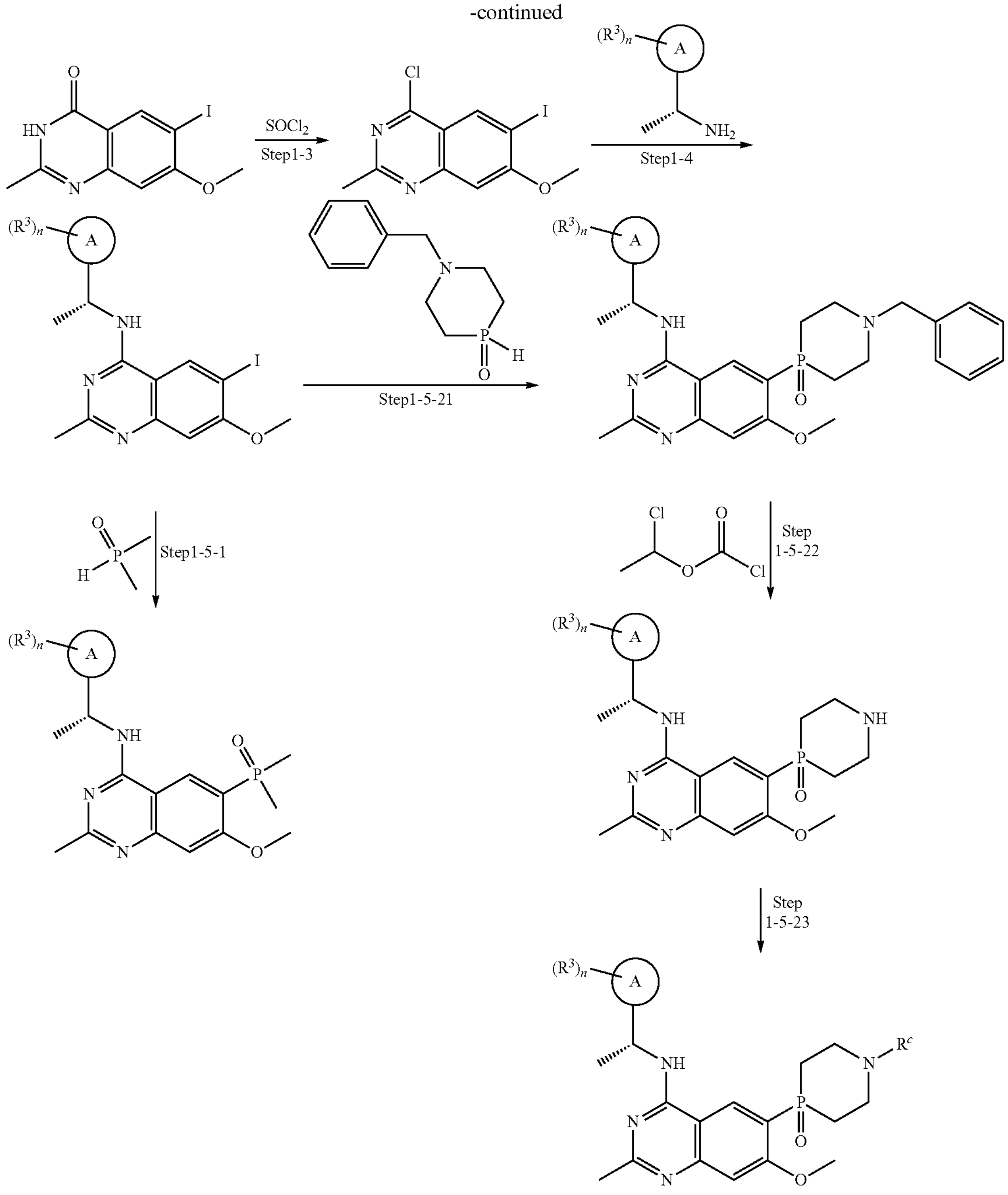
wherein,
ring A, $R^c$, $R^3$ and n are defined as above.
Route II:
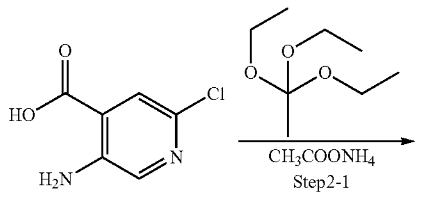
-continued
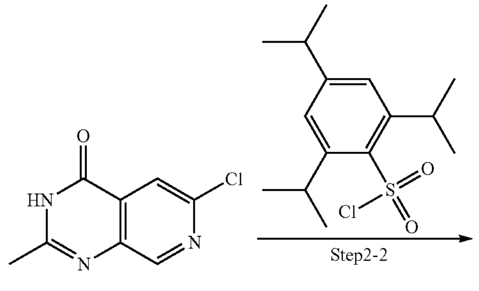

-continued

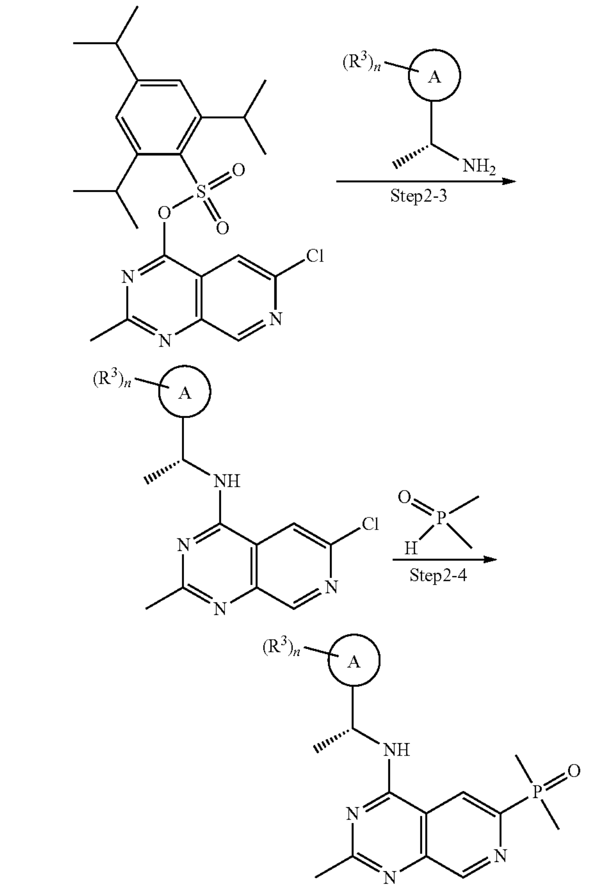

wherein, ring A, $R^3$ and n are defined as above.

Route III:

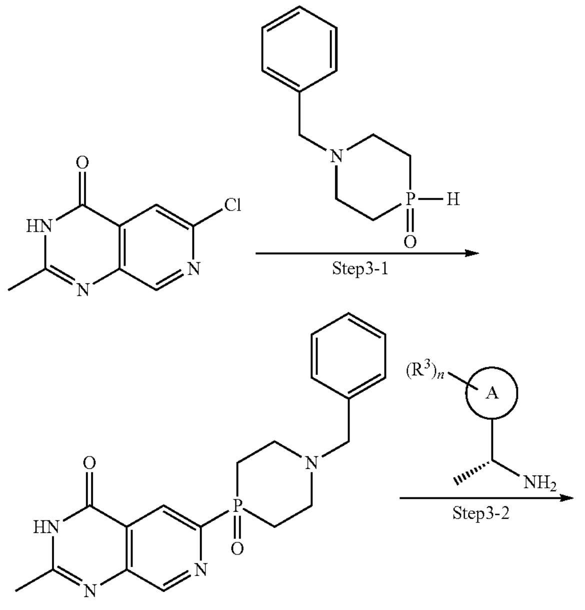

-continued

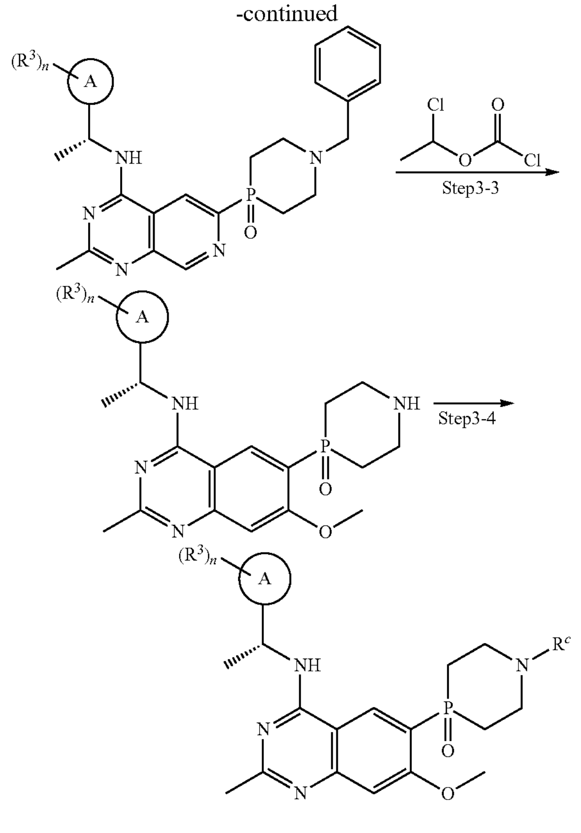

wherein, ring A, $R^3$ and n are defined as above.

The present application uses the following abbreviations:

PBS for fetal bovine serum; PBS for phosphate-buffered saline; PBST for phosphate-buffered saline with Tween;

BSA for bovine serum albumin; GAPDH for glyceraldehyde-3-phosphate dehydrogenase; DMSO for dimethyl sulfoxide; DTT for dithiothreitol; and HTRF for homogeneous time-resolved fluorescence.

DETAILED DESCRIPTION

For clarity, the present application is further described with the following examples, which are, however, not intended to limit the scope of the invention. It will be apparent to those skilled in the art that various changes and modifications can be made to the specific examples of the present invention without departing from the spirit and scope of the present invention. All reagents are commercially available and can be used without further purification.

Example 1: Preparation of Compound 1

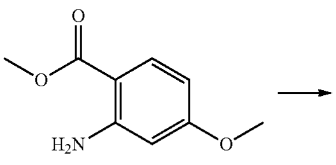

-continued

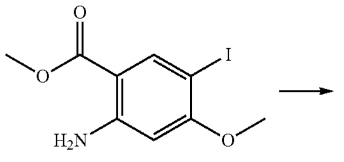

1-1

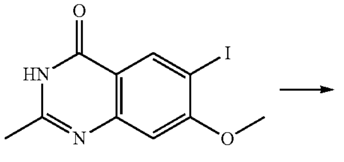

1-2

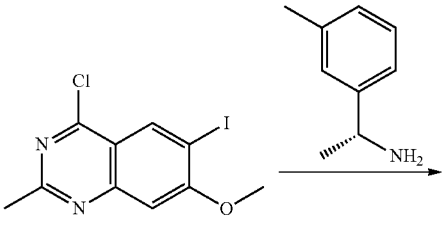

1-3

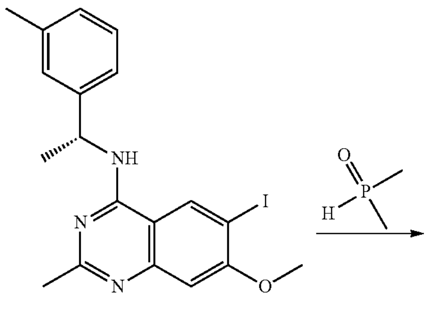

1-4

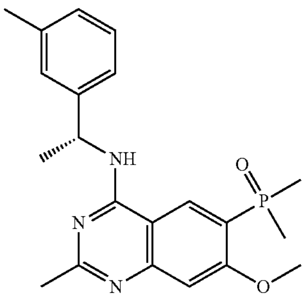

1

Step A: Preparation of Compound 1-1

Methyl 2-amino-4-methoxybenzoate (4 g) and anhydrous ethanol (16 mL) were added into a 250 mL three-necked flask. The mixture was added with water (28 mL) and concentrated hydrochloric acid (7 mL) under stirring at room temperature, cooled to 0° C. in an ice bath under mechanical stirring, and slowly added with a solution of iodine monochloride (3.58 g) in concentrated hydrochloric acid (2 mL). After the addition was completed, the reaction solution was transferred to a condition at room temperature and then stirred to react overnight at room temperature. The reaction solution was added with water (100 mL), vigorously stirred for 5 min, and filtered under vacuum. The filter cake was washed with water (20 mL). The solid was collected, and slurried with petroleum ether (50 mL) to obtain 6.45 g of compound 1-1.

MS (ESI, $[M+H]^+$): m/z=307.81.

$^1$H NMR (500 MHz, DMSO-$d_6$) δ 7.99 (s, 1H), 6.38 (s, 1H), 3.78 (s, 3H), 3.75 (s, 3H).

Step B: Preparation of Compound 1-2

The compound 1-1 (15 g) obtained in step A, acetonitrile (100 g) and methanesulfonic acid (37.6 g) were sequentially added to a 350 mL pressure-resistant flask. The reaction flask was placed in an oil bath at 120° C. and stirred to react for 6 h. The reaction was stopped, the reaction solution was concentrated to dryness under reduced pressure, and water (150 mL) was added to the residual solid. The mixture was vigorously stirred, added with 2.5 M aqueous sodium hydroxide solution to adjust the pH to alkalinity, and filtered under vacuum. The filter cake was washed with a large amount of water. The solid was collected, dried and subjected to silica gel column chromatography (petroleum ether:ethyl acetate=1:2) to obtain 5.9 g of compound 1-2.

MS (ESI, $[M+H]^+$): m/z=316.79.

$^1$H NMR (500 MHz, DMSO-$d_6$) δ 12.19 (s, 1H), 8.37 (s, 1H), 7.05 (s, 1H), 3.95 (s, 3H), 2.32 (s, 3H).

Step C: Preparation of Compound 1-3

The compound 1-2 (1 g) obtained in step B and chloroform (10 mL) were added to a 25 mL three-necked flask. The mixture was added with thionyl chloride (2.94 g) and two drops of N,N-dimethylformamide sequentially under stirring at room temperature. The reaction solution was heated to 70° C. and stirred to react for 3 h. The reaction solution was concentrated to dryness, and water (40 mL) and dichloromethane (50 mL) were added to the residue. The mixture was added dropwise with a saturated aqueous sodium bicarbonate solution under vigorous stirring and pH was adjusted to weak alkalinity. The reaction solution was separated, washed with saturated brine, dried over anhydrous sodium sulfate, and filtered under vacuum. The residue was concentrated and subjected to silica gel column chromatography (petroleum ether:ethyl acetate=90:10) to obtain 0.41 g of compound 1-3.

MS (ESI, $[M+H]^+$): m/z=334.77.

$^1$H NMR (500 MHz, DMSO-$d_6$) δ 8.42 (s, 1H), 7.18 (s, 1H), 3.98 (s, 3H), 2.50 (s, 3H).

Step D: Preparation of Compound 1-4

To a 25 mL single-neck flask were added the compound 1-3 (200 mg) obtained in step C, (R)-1-(m-tolyl)ethan-1-amine (98 mg), N,N-diisopropylethylamine (129 mg) and 1,4-dioxane (2 mL). The mixture was heated to 100° C. under nitrogen atmosphere and stirred to react for 5 h. The reaction was stopped, and the reaction solution was concentrated to dryness. The residue was dissolved in dichloromethane (20 mL), washed with a saturated aqueous sodium bicarbonate solution, 1 M hydrochloric acid and saturated brine, dried over anhydrous sodium sulfate and concentrated. The residue was subjected to silica gel column chromatography (petroleum ether:ethyl acetate=5:1) to obtain 160 mg of compound 1-4.

MS (ESI, $[M+H]^+$): m/z=434.00.

$^1$H NMR (500 MHz, DMSO-$d_6$) δ 8.88 (s, 1H), 8.29 (d, J=8.0 Hz, 1H), 7.28-7.16 (m, 3H), 7.05-7.03 (m, 2H), 5.58 (p, J=7.0 Hz, 1H), 3.92 (s, 3H), 2.36 (s, 3H), 2.29 (s, 3H), 1.54 (d, J=7.0 Hz, 3H).

Step E: Preparation of Compound 1

To a 15 mL pressure-resistant tube were added the compound 1-4 (0.09 g) obtained in step D, dimethyl phosphine oxide (0.017 g), triethylamine (0.032 g), 4,5-bis(diphenylphosphino)-9,9-dimethylxanthene (6.13 mg), tris(dibenzylideneacetone)dipalladium (4.85 mg) and 1,4-dioxane (2 mL). The reaction solution was heated to 120° C. in an oil bath under nitrogen protection and stirred to react for 2 h.

The reaction solution was cooled to room temperature and filtered under vacuum. The filtrate was concentrated to dryness, and the residue was purified by C18 column chromatography (120 g) (40% acetonitrile+60% water) to obtain 58.5 mg of compound 1.

HRMS (ESI, $[M+H]^+$): m/z=384.1855.

$^1H$ NMR (500 MHz, DMSO-$d_6$) δ 8.80 (d, J=8.0 Hz, 1H), 8.76 (d, J=13.6 Hz, 1H), 7.32 (s, 1H), 7.30 (d, J=7.8 Hz, 1H), 7.24 (t, J=7.5 Hz, 1H), 7.14 (d, J=4.7 Hz, 1H), 7.06 (d, J=7.3 Hz, 1H), 5.67 (p, J=7.1 Hz, 1H), 3.99 (s, 3H), 2.43 (s, 3H), 2.33 (s, 3H), 1.75 (s, 3H), 1.72 (s, 3H), 1.60 (d, J=7.1 Hz, 3H).

Example 2: Preparation of Compound 2

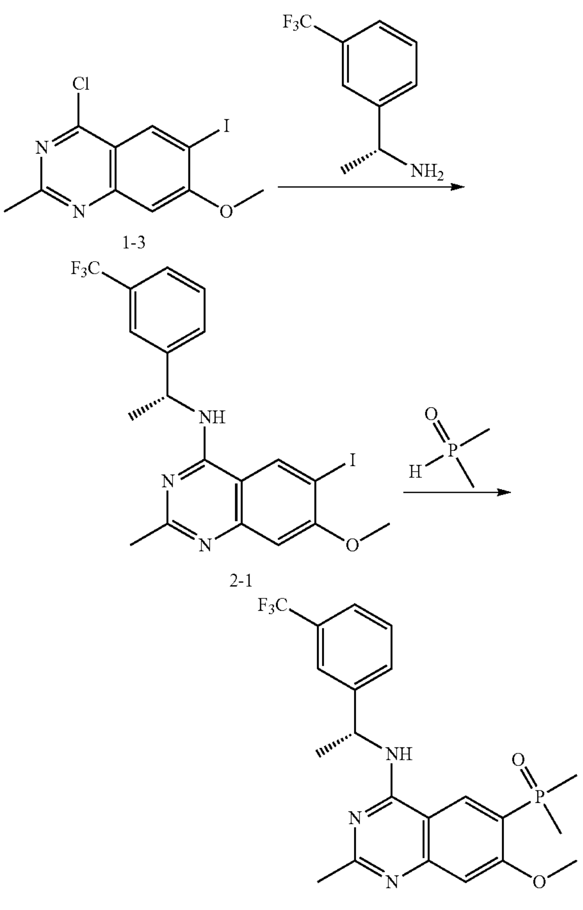

1-3

2-1

2

Step A: Preparation of Compound 2-1

Referring to the procedures of step D in Example 1, compound 2-1 was prepared by reacting the compound 1-3 with (R)-1-(3-(trifluoromethyl)phenyl)ethan-1-amine.

MS (ESI, $[M+H]^+$): m/z=487.94.

$^1H$ NMR (500 MHz, DMSO-$d_6$) δ 8.86 (s, 1H), 8.39 (d, J=7.6 Hz, 1H), 7.81 (s, 1H), 7.74 (t, J=7.9 Hz, 1H), 7.60-7.55 (m, 2H), 7.03 (d, J=8.3 Hz, 1H), 5.62 (p, J=7.1 Hz, 1H), 3.92 (s, 3H), 2.35 (s, 3H), 1.60 (d, J=7.1 Hz, 3H).

Step B: Preparation of Compound 2

Compound 2 was prepared referring to the procedures of step E in Example 1.

HRMS (ESI, $[M+H]^+$): m/z=438.1599.

$^1H$ NMR (500 MHz, DMSO-$d_6$) δ 8.88 (d, J=7.8 Hz, 1H), 8.76 (d, J=13.6 Hz, 1H), 7.91 (s, 1H), 7.82 (t, J=7.8 Hz, 1H), 7.65-7.57 (m, 2H), 7.15 (d, J=4.8 Hz, 1H), 5.70 (p, J=7.1 Hz, 1H), 3.99 (s, 3H), 2.42 (s, 3H), 1.76 (s, 3H), 1.73 (s, 3H), 1.66 (d, J=7.1 Hz, 3H).

Example 3: Preparation of Compound 3

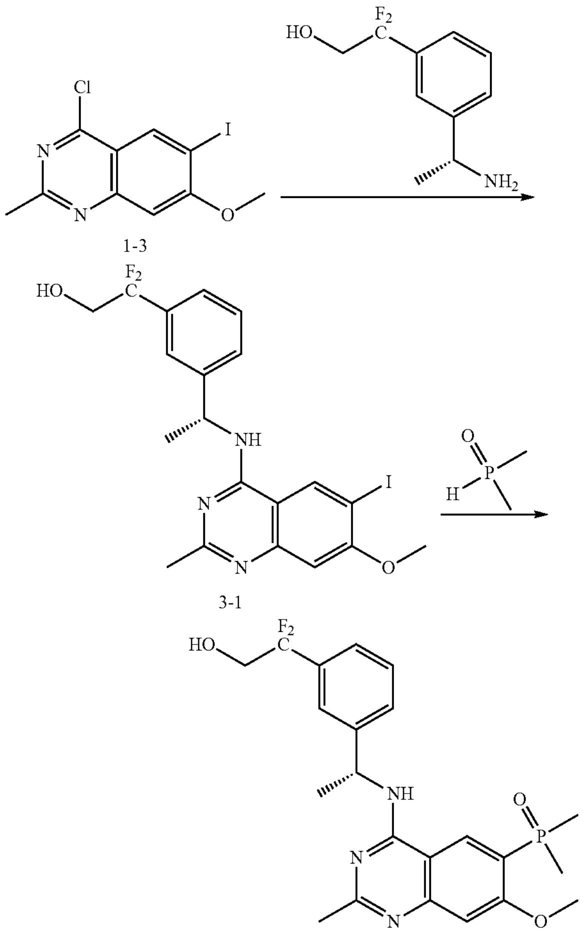

1-3

3-1

3

Step A: Preparation of Compound 3-1

Referring to the procedures of step D in Example 1, compound 3-1 was prepared by reacting the compound 1-3 with (R)-2-(3-(1-aminoethyl)phenyl)-2,2-difluorineethan-1-ol.

MS (ESI, $[M+H]^+$): m/z=499.95.

$^1H$ NMR (500 MHz, DMSO-$d_6$) δ 8.87 (s, 1H), 8.37 (d, J=7.8 Hz, 1H), 7.63 (s, 1H), 7.57 (d, J=7.7 Hz, 1H), 7.44 (t, J=7.7 Hz, 1H), 7.38 (d, J=7.7 Hz, 1H), 7.03 (s, 1H), 4.05-4.01 (m, 1H), 3.92 (s, 3H), 3.84 (td, J=14.2, 6.3 Hz, 2H), 2.36 (s, 3H), 1.58 (d, J=7.0 Hz, 3H).

Step B: Preparation of Compound 3

Compound 3 was prepared referring to the procedures of step E in Example 1.

HRMS (ESI, $[M+H]^+$): m/z=450.1728.

$^1H$ NMR (500 MHz, DMSO-$d_6$) δ 8.88 (d, J=7.9 Hz, 1H), 8.76 (d, J=13.6 Hz, 1H), 7.72 (s, 1H), 7.65 (d, J=7.6 Hz, 1H), 7.48 (t, J=7.7 Hz, 1H), 7.42 (d, J=7.7 Hz, 1H), 7.15 (d, J=4.7

Hz, 1H), 5.75-5.64 (m, 2H), 4.00 (s, 3H), 3.88 (td, J=14.1, 4.3 Hz, 2H), 2.44 (s, 3H), 1.76 (s, 3H), 1.73 (s, 3H), 1.65 (d, J=7.1 Hz, 3H).

Example 4: Preparation of Compound 4

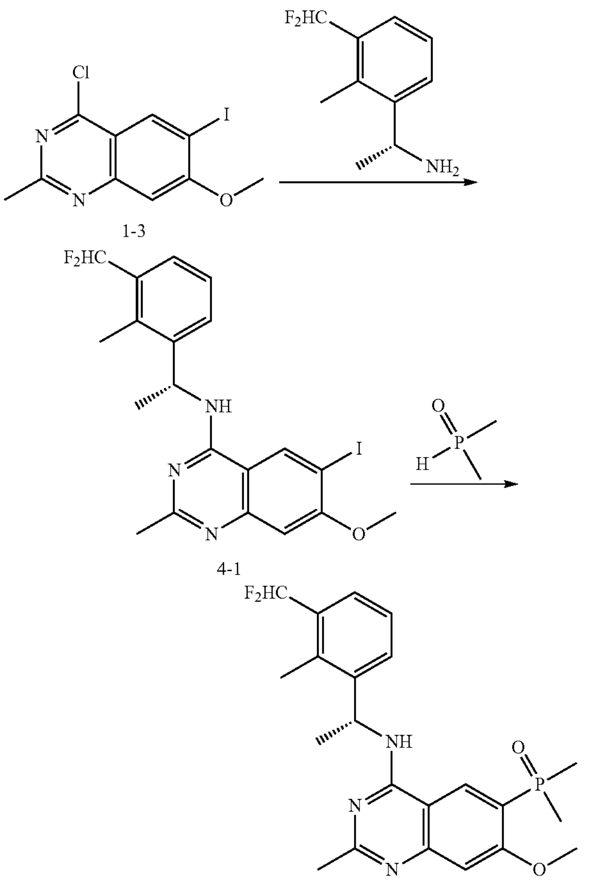

1-3

4-1

4

Step A: Preparation of Compound 4-1

Referring to the procedures of step D in Example 1, compound 4-1 was prepared by reacting the compound 1-3 with (R)-1-(3-(difluorinemethyl)-2-methylphenyl)ethan-1-amine.

MS (ESI, $[M+H]^+$): m/z=484.4.

$^1$H NMR (500 MHz, DMSO-$d_6$) δ 8.90 (s, 1H), 8.46 (d, J=7.3 Hz, 1H), 7.66 (d, J=7.7 Hz, 1H), 7.38 (d, J=7.5 Hz, 1H), 7.30 (dd, J=13.8, 6.1 Hz, 1H), 7.21 (s, 1H), 7.02 (s, 1H), 5.73 (p, J=7.0 Hz, 1H), 3.91 (s, 3H), 2.55 (s, 3H), 2.33 (s, 3H), 1.52 (d, J=7.0 Hz, 3H).

Step B: Preparation of Compound 4

Compound 4 was prepared referring to the procedures of step E in Example 1.

MS (ESI, $[M+H]^+$): m/z=434.17.

$^1$H NMR (500 MHz, $CDCl_3$) δ 8.41 (d, J=13.8 Hz, 1H), 7.54 (d, J=7.8 Hz, 1H), 7.43 (d, J=7.6 Hz, 1H), 7.28-7.27 (m, 1H), 7.12 (d, J=5.0 Hz, 1H), 6.83 (t, J=55.5 Hz, 1H), 6.32 (d, J=6.9 Hz, 1H), 5.85 (p, J=6.9 Hz, 1H), 3.96 (s, 3H), 2.54 (d, J=2.2 Hz, 6H), 1.79 (dd, J=13.9, 2.7 Hz, 6H), 1.60 (d, J=6.9 Hz, 3H).

Example 5: Preparation of Compound 5

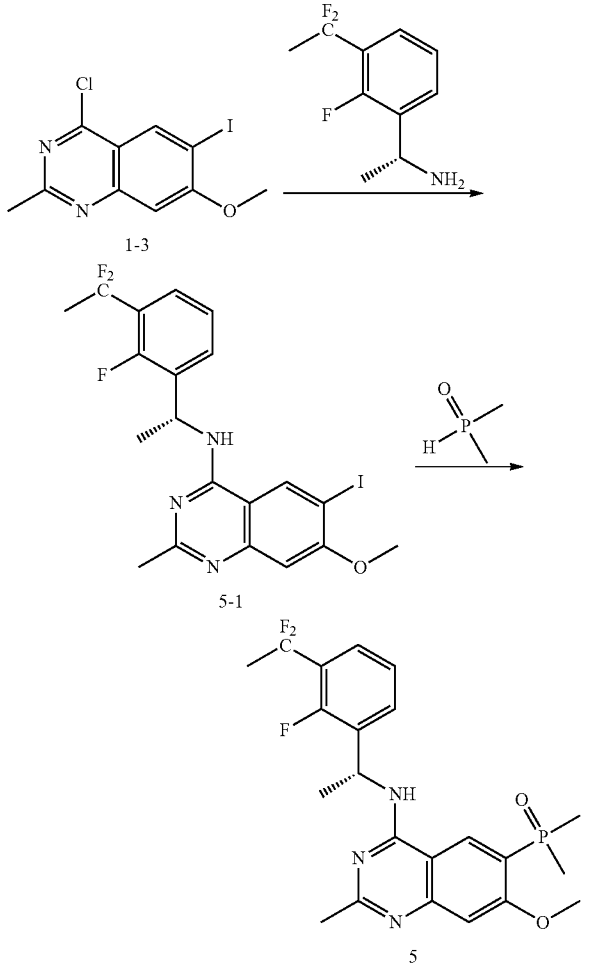

1-3

5-1

5

Step A: Preparation of Compound 5-1

Referring to the procedures of step D in Example 1, compound 5-1 was prepared by reacting the compound 1-3 with (R)-1-(3-(1,1-difluorineethyl)-2-fluorinephenyl)ethan-1-amine.

MS (ESI, $[M+H]^+$): m/z=502.25.

$^1$H NMR (500 MHz, $CDCl_3$) δ 8.14 (s, 1H), 7.50-7.41 (m, 2H), 7.14 (t, J=7.7 Hz, 1H), 7.06 (s, 1H), 5.88-5.68 (m, 2H), 3.96 (s, 3H), 2.52 (s, 3H), 2.02 (td, J=1.1, 18.6 Hz, 3H), 1.70 (s, 3H).

Step B: Preparation of Compound 5

Compound 5 was prepared referring to the procedures of step E in Example 1.

MS (ESI, $[M+H]^+$): m/z=452.5.

$^1$H NMR (500 MHz, $CDCl_3$) δ 8.48 (d, J=13.8 Hz, 1H), 7.51-7.46 (m, 1H), 7.43 (td, J=1.7, 7.5 Hz, 1H), 7.15-7.09 (m, 2H), 6.44 (d, J=7.2 Hz, 1H), 5.85 (p, J=7.0 Hz, 1H), 3.97 (s, 3H), 2.52 (s, 3H), 2.07-1.97 (m, 3H), 1.82 (s, 3H), 1.79 (s, 3H), 1.66 (d, J=7.0 Hz, 3H).

Example 6: Preparation of Compound 6
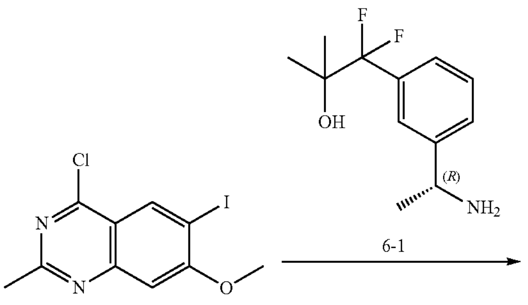
1-3
6-1
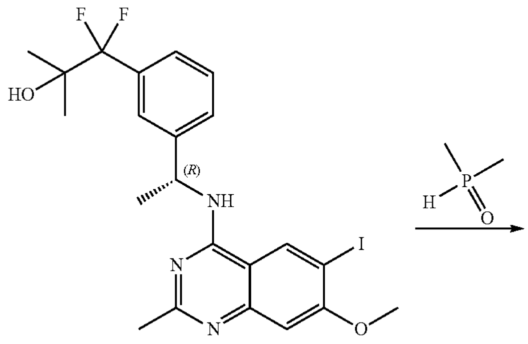
6-2
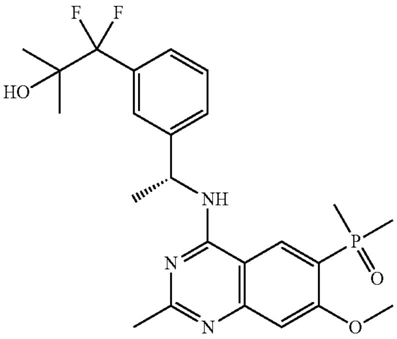
6
Step a: Preparation of Compound 6-1-1
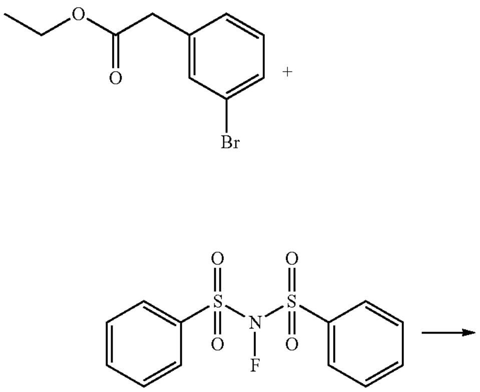
-continued
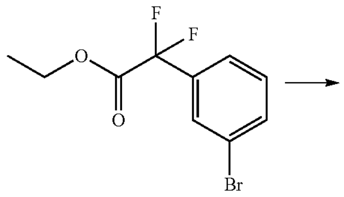
6-1-1
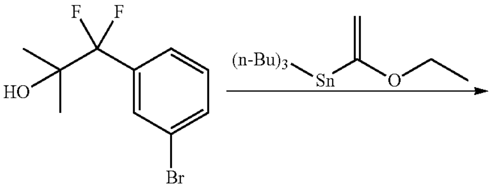
6-1-2
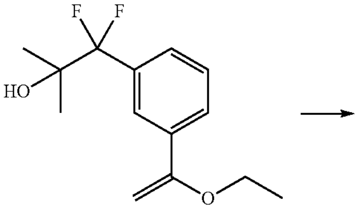
6-1-3
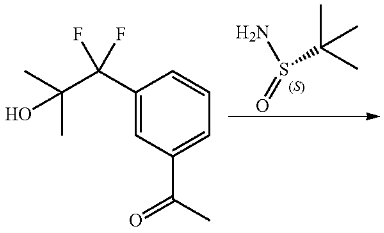
6-1-4
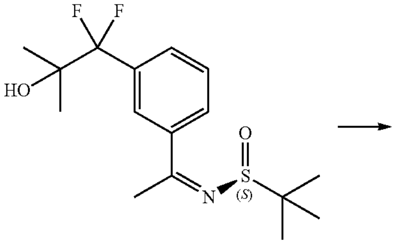
6-1-5
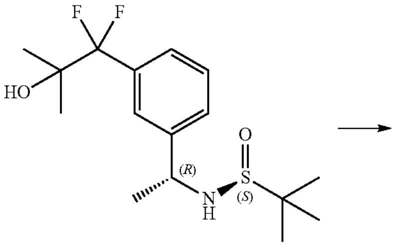
6-1-6

-continued

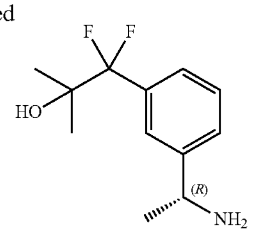

6-1

Ethyl 2-(3-bromophenyl)acetate (10 g) and anhydrous tetrahydrofuran (100 mL) were added to a 250 mL- three-necked flask. The mixture was cooled to −78° C. under nitrogen protection. Lithium bis(trimethylsilyl)amide (103 mL, 1 mol/L) was added dropwise to the reaction solution. The reaction solution was reacted for 30 min at −78° C.

Then, a solution of N-fluorine-N-(phenylsulfonyl)benzenesulfonamide (25.9 g) in anhydrous tetrahydrofuran (50 mL) was slowly added dropwise to the reaction system. After the addition was completed, the reaction system was warmed to room temperature and then stirred to react for 2 h. After the reaction was completed, the reaction solution was added with water (100 mL) and vigorously stirred, then extracted twice with ethyl acetate (100 mL), dried with rotary evaporator, and subjected to silica gel column chromatography (petroleum ether:ethyl acetate=97:3) to obtain 10.1 g of compound 6-1-1.

$^{19}$F-NMR (471 MHz, Methanol-$d_4$) δ −105.17-105.60 (m).

$^1$H-NMR (500 MHz, Methanol-$d_4$) δ 7.76-7.69 (m, 2H), 7.57 (m, 1H), 7.44 (m, 1H), 4.31 (m, 2H), 1.28 (t, J=7.1 Hz, 3H).

Step b: Preparation of Compound 6-1-2

The compound 6-1-1 (9 g) obtained in step a and anhydrous tetrahydrofuran (200 mL) were added into a 500 mL three-necked flask. The mixture was cooled to −78° C. under nitrogen protection. Methyl magnesium bromide (22 mL, 3 mol/L) was slowly added dropwise to the reaction solution. After the addition was completed was completed, the reaction solution was warmed to 0° C. and then stirred to react for 1 h. After the reaction was completed, the reaction solution was added with a saturated aqueous ammonium chloride solution (100 mL) and vigorously stirred, and then extracted twice with ethyl acetate (100 mL). The organic phases were combined, washed once with water (100 mL), dried over anhydrous sodium sulfate, and dried with rotary evaporator to obtain 7.0 g of compound 6-1-2.

Step c: Preparation of Compound 6-1-3

To a 250 mL three-necked flask were added the compound 6-1-2 (6.8 g) obtained in step b, 1,4-dioxane (150 mL), tributyl(1-ethoxyethylene tin (18.53 g), bis(triphenylphosphine)palladium(II) dichloride (1.811 g) and triethylamine (7.77 g). The mixture was heated to 100° C. in an oil bath under nitrogen protection and reacted for 3 h. The reaction solution was cooled and dried with rotary evaporator to obtain 20.0 g of compound 6-1-3.

MS (ESI, [M+H]$^+$): m/z=257.1.

Step d: Preparation of Compound 6-1-4

To a 250 mL single-neck flask were added the compound 6-1-3 (20 g) obtain in step c, tetrahydrofuran (20 mL) and diluted hydrochloric acid (19 mL, 4 mol/L). The mixture was reacted at room temperature for 2.5 h. After the reaction was completed, the reaction solution was added with water (200 mL) and vigorously stirred, then extracted once with ethyl acetate (100 mL), dried with rotary evaporator, and subjected to silica gel column chromatography (petroleum ether:ethyl acetate=3:1) to obtain 3.3 g of compound 6-1-4.

MS (ESI, [M+H]$^+$): m/z=229.1.

$^1$H NMR (500 MHz, DMSO-$d_6$) δ 8.14-8.04 (m, 1H), 8.02 (d, J=1.8 Hz, 1H), 7.79-7.69 (m, 1H), 7.63 (t, J=7.8 Hz, 1H), 2.62 (s, 3H), 1.18 (d, J=1.5 Hz, 6H).

Step e: Preparation of Compound 6-1-5

To a 100 mL three-necked flask were added the compound 6-1-4 (3 g) obtained in step d, tetrahydrofuran (30 mL), (S)-2-methylpropane-2-sulfinamide (2.390 g) and tetraethyl titanate (8.99 g). The mixture was heated to 80° C. in an oil bath under nitrogen protection and reacted for 4.5 h. After the reaction was completed, the reaction solution was added with water (50 mL), vigorously stirred, and filtered. The filter cake was washed three times with ethyl acetate (20 mL). The organic phase was separated, dried with rotary evaporator, and subjected to silica gel column chromatography (petroleum ether:ethyl acetate=10:1 to 5:1) to obtain 4.2 g of compound 6-1-5.

MS (ESI, [M+H]$^+$): m/z=332.2.

$^1$H NMR (500 MHz, Methanol-$d_4$) δ 8.13 (s, 1H), 8.05 (d, J=7.9 Hz, 1H), 7.75-7.650 (m, 1H), 7.55 (t, J=7.8 Hz, 1H), 2.79 (s, 3H), 1.32 (s, 9H), 1.28-1.23 (m, 6H).

Step f: Preparation of Compound 6-1-6

The compound 6-1-5 (4.2 g) obtained in step e and anhydrous tetrahydrofuran (40 mL) were added into a 100 mL three-necked flask. The reaction system was cooled to −78° C. and added dropwise with lithium tri-sec-butylborohydride (28.4 mL, 1 mol/L). The mixture was stirred to react for 2 h at −78° C. After the reaction was completed, the reaction solution was added with a saturated aqueous ammonium chloride solution (20 mL), vigorously stirred for 2 min, warmed to room temperature, and let stand to separate organic phase. The separated organic phase was dried with rotary evaporator and subjected to silica gel column chromatography (dichloromethane:methanol=98:2) to obtain 2.5 g of compound 6-1-6.

MS (ESI, [M+H]$^+$): m/z=334.0.

$^1$H NMR (500 MHz, Methanol-$d_4$) δ 7.53 (d, J=1.9 Hz, 1H), 7.47-7.35 (m, 3H), 4.59-4.49 (m, 1H), 1.55 (d, J=6.8 Hz, 3H), 1.24 (d, J=1.2 Hz, 6H), 1.20 (s, 9H).

Step g: Preparation of Compound 6-1

The compound 6-1-6 (2.3 g) obtained in step e and a solution of 1,4 dioxane in hydrochloric acid (8 mL, 4 mol/L) were added to a 100 mL single-neck flask. The mixture was reacted at room temperature for 2 h. After the reaction was completed, the reaction solution was dried with rotary evaporator to obtain 2.0 g of compound 6-1.

$^1$H NMR (500 MHz, Methanol-$d_4$) δ 7.63 (d, J=1.8 Hz, 1H), 7.63-7.53 (m, 2H), 7.54 (d, J=6.4 Hz, 1H), 4.58-4.48 (m, 1H), 1.66 (d, J=6.9 Hz, 3H), 1.26 (d, J=1.6 Hz, 6H).

Step B: Preparation of Compound 6-2

Referring to the procedures of step D in Example 1, compound 6-2 was prepared by reacting the compound 1-3 with the compound 6-1 obtained in step A.

MS (ESI, [M+H]$^+$): m/z=527.98.

Step C: Preparation of Compound 6

Compound 6 was prepared referring to the procedures of step E in Example 1.

MS (ESI, [M+H]$^+$): m/z=478.09.

$^1$H NMR (500 MHz, Methanol-$d_4$) δ 8.58 (d, J=14.0 Hz, 1H), 7.62 (s, 1H), 7.55 (t, J=4.2 Hz, 1H), 7.38 (d, J=4.8 Hz, 2H), 7.09 (d, J=5.0 Hz, 1H), 5.75-5.650 (m, 1H), 4.02 (s, 3H), 2.46 (s, 3H), 1.89-1.79 (m, 6H), 1.68 (d, J=7.0 Hz, 3H), 1.21 (s, 6H).

Example 7: Preparation of Compound 7

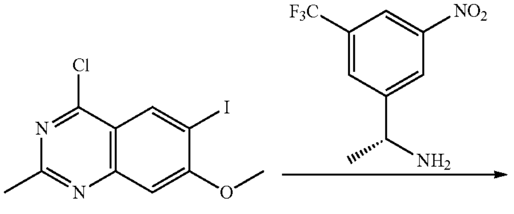

1-3

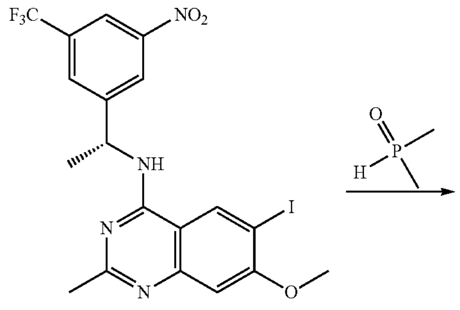

7-1

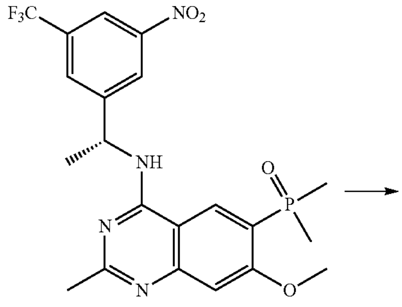

7-2

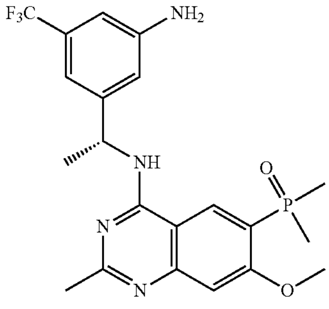

7

Step A: Preparation of Compound 7-1

Referring to the procedures of step D in Example 1, compound 7-1 was prepared by reacting the compound 1-3 with (R)-1-(3-nitro-5-(trifluoromethyl)phenyl)ethan-1-amine.

MS (ESI, $[M+H]^+$): m/z=532.89.

$^1$H NMR (500 MHz, DMSO-$d_6$) δ 8.82 (s, 1H), 8.61 (s, 1H), 8.48 (d, J=7.3 Hz, 1H), 8.33 (d, J=11.2 Hz, 2H), 7.04 (s, 1H), 5.65 (p, J=7.0 Hz, 1H), 3.92 (s, 3H), 2.34 (s, 3H), 1.65 (d, J=7.1 Hz, 3H).

Step B: Preparation of Compound 7-2

Compound 7-2 was prepared referring to the procedures of step E in Example 1.

MS (ESI, $[M+H]^+$): m/z=483.08.

$^1$H NMR (500 MHz, DMSO-$d_6$) δ 8.92 (d, J=7.6 Hz, 1H), 8.76-8.73 (m, 2H), 8.41-8.39 (m, 2H), 7.16 (d, J=4.7 Hz, 1H), 5.72 (p, J=7.1 Hz, 1H), 3.98 (d, J=9.8 Hz, 3H), 2.41 (s, 3H), 1.79-1.70 (m, 9H).

Step C: Preparation of Compound 7

To a 50 mL three-necked flask were added the compound 7-2 (100 mg) obtained in step B, tetrahydrofuran (15 mL) and water (5.00 mL). The mixture was added with ammonium chloride (444 mg) and zinc powder (203 mg) under stirring at room temperature. The reaction flask was stirred to react for 5 h at 70° C. in an oil bath. The reaction was stopped, the reaction solution was cooled to room temperature, added with saturated brine (15 mL), extracted with ethyl acetate (15 mL×2), dried over anhydrous sodium sulfate and concentrated. The residue was separated and purified by silica gel column chromatography (methanol: dichloromethane=7:93) to obtain 32 mg of compound 7.

HRMS (ESI, $[M+H]^+$): m/z=453.1675.

$^1$H NMR (500 MHz, $CDCl_3$) δ 8.55 (d, J=13.9 Hz, 1H), 7.14 (d, J=5.1 Hz, 1H), 7.08 (s, 1H), 6.90 (s, 1H), 6.78 (s, 1H), 6.69 (s, 1H), 5.62-5.59 (m, 1H), 3.97 (s, 3H), 2.56 (s, 3H), 1.79 (dd, J=13.8, 1.7 Hz, 6H), 1.61 (d, J=7.0 Hz, 3H).

Example 8: Preparation of Compound 8

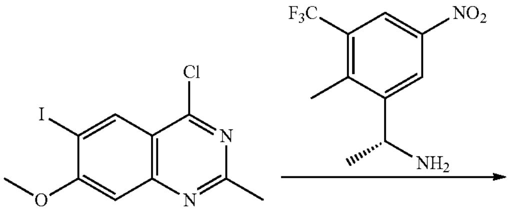

1-3

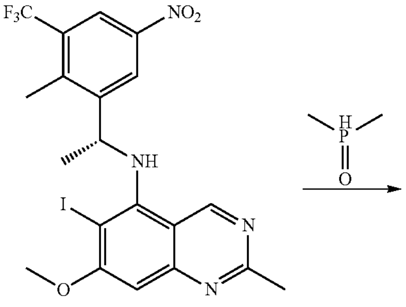

8-1

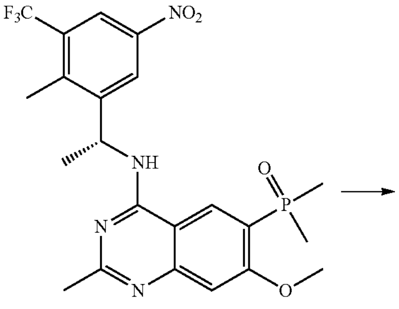

8-2

-continued

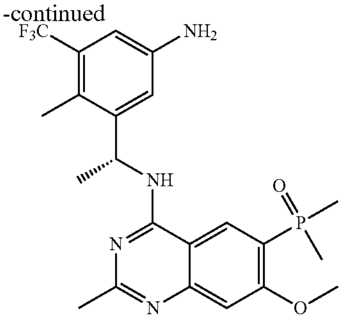

8

Step A: Preparation of Compound 8-1

Referring to the procedures of step D in Example 1, compound 8-1 was prepared by reacting the compound 1-3 with (R)-1-(2-methyl-5-nitro-3-(trifluoromethyl)phenyl) ethan-1-amine.

MS (ESI, $[M+H]^+$): m/z=546.88.

$^1H$ NMR (500 MHz, $CD_3OD$) δ 8.77 (s, 1H), 8.57 (d, J=2.3 Hz, 1H), 8.34 (d, J=2.3 Hz, 1H), 6.94 (s, 1H), 5.75 (q, J=7.0 Hz, 1H), 4.87 (s, 1H), 3.96 (s, 3H), 2.81 (s, 3H), 2.35 (s, 3H), 1.65 (d, J=7.1 Hz, 3H).

Step B: Preparation of Compound 8-2

Compound 8-2 was prepared referring to the procedures of step E in Example 1.

MS (ESI, $[M+H]^+$): m/z=497.08.

$^1H$ NMR (500 MHz, $CD_3OD$) δ 8.65 (d, J=14.0 Hz, 1H), 8.60 (d, J=2.3 Hz, 1H), 8.35 (d, J=2.3 Hz, 1H), 5.80 (q, J=7.0 Hz, 1H), 4.02 (s, 3H), 2.82 (s, 3H), 2.39 (s, 3H), 1.86 (d, J=14.0 Hz, 6H), 1.69 (d, J=7.0 Hz, 3H).

Step C: Preparation of Compound 8

To a 25 mL single-neck flask were sequentially added the compound 8-2 (0.16 g) obtained in step B, methanol (10 mL), water (2 mL) and tetrahydroxydiboron (0.231 g). The mixture was stirred for 10 min, added with a solution of sodium hydroxide (0.129 g) in water (2 mL) and stirred at room temperature overnight. The reaction solution was poured into water (20 mL), added with a saturated sodium bicarbonate solution to adjust the pH to 7-8, and added with ethyl acetate (10 mL) to separate the organic phase. The aqueous phase was extracted with ethyl acetate (10 mL×2). The organic phases were combined and washed with saturated brine (10 mL×2), dried over anhydrous sodium sulfate, filtered and concentrated to obtain 120 mg of compound 8.

MS (ESI, $[M+H]^+$): m/z=467.16.

$^1H$ NMR (500 MHz, $CD_3OD$) δ 8.61 (s, 1H), 7.08 (d, J=5.1 Hz, 1H), 7.04 (d, J=2.2 Hz, 1H), 6.90 (d, J=2.4 Hz, 1H), 5.75 (q, J=6.9 Hz, 1H), 4.86 (s, 3H), 4.01 (s, 3H), 2.45 (t, J=2.9 Hz, 6H), 1.84 (dd, J=14.0, 4.3 Hz, 6H), 1.59 (d, J=7.0 Hz, 3H).

Example 9: Preparation of Compound 9

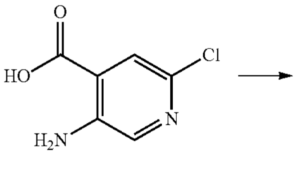

-continued

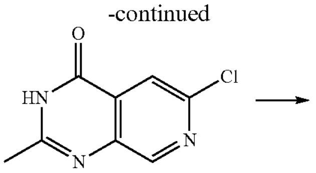

9-1

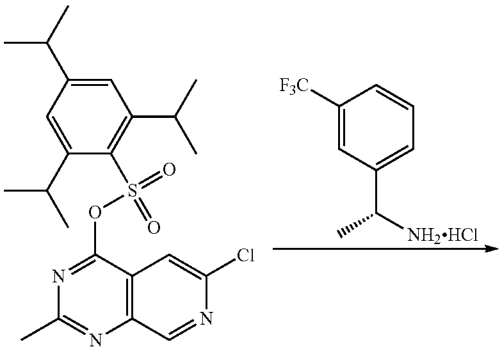

9-2

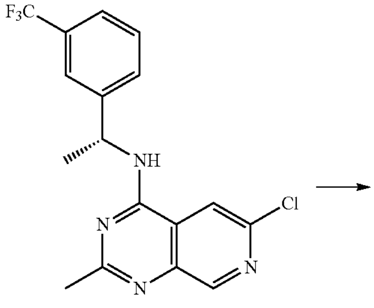

9-3

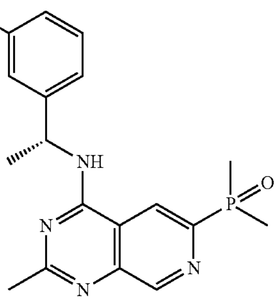

9

Step A: Preparation of Compound 9-1

To a 500 mL pressure-resistant flask were added 5-amino-2-chloroisonicotinic acid (15 g), ammonium acetate (67.0 g), triethyl orthoacetate (141 g) and methanol (100 mL). The mixture was stirred to react for 9 h at 125° C. in an oil bath. The reaction was stopped, and the reaction solution was cooled to room temperature and filtered under vacuum.

The filter cake was washed with ethyl acetate (50 mL), and the solid was collected and dried to obtain 8.1 g of compound 9-1.

MS (ESI, $[M-H]^-$): m/z=194.1.

$^1H$ NMR (500 MHz, DMSO-$d_6$) δ 8.79 (s, 1H), 7.90 (s, 1H), 2.38 (s, 3H).

Step B: Preparation of Compound 9-2

To a 250 mL single-neck flask were added the compound 9-1 (10 g) obtained in step A, 2,4,6-triisopropylbenzenesulfonyl chloride (18.58 g), triethylamine (15.52 g), 4-dimethylaminopyridine (0.625 g) and dichloromethane (100 mL). The mixture was stirred at room temperature overnight. The reaction was stopped, and the reaction solution was poured into water (50 mL) and separated. The organic phase was washed with saturated brine, dried over anhydrous sodium sulfate, filtered under vacuum and concentrated. The residue was separated and purified by silica gel column chromatography (petroleum ether:ethyl acetate=85:15) to obtain 9.7 g of compound 9-2.

Step C: Preparation of Compound 9-3

To a 25 mL single-neck flask were added the compound 9-2 (3 g) obtained in step B, (R)-1-(3-(trifluoromethyl)phenyl)ethan-1-amine hydrochloride (1.76 g), N,N-diisopropylethylamine (2.52 g) and 1,4-dioxane (20 mL). The mixture was stirred to react for 2 h at room temperature under nitrogen atmosphere. The reaction was stopped, and the reaction solution was poured into water (100 mL) and extracted with dichloromethane (30 mL×3). The organic phase was washed with saturated brine, dried over anhydrous sodium sulfate and concentrated. The residue was subjected to silica gel column chromatography (petroleum ether:ethyl acetate=85:15) to obtain 2.2 g of compound 9-3.

MS (ESI, $[M+H]^+$): m/z=367.26.

$^1H$ NMR (500 MHz, DMSO-$d_6$) δ 8.87-8.80 (m, 1H), 8.48 (s, 1H), 7.84 (s, 1H), 7.78-7.76 (t, J=6.6 Hz, 1H), 7.62-7.56 (m, 2H), 5.62 (p, J=7.1 Hz, 1H), 2.43 (s, 3H), 1.63 (d, J=7.1 Hz, 3H).

Step D: Preparation of Compound 9

Compound 9 was prepared referring to the procedures of step E in Example 1.

MS (ESI, $[M+H]^+$): m/z=409.4.

$^1H$ NMR (500 MHz, DMSO-$d_6$) δ 9.25 (d, J=7.6 Hz, 1H), 9.09 (s, 1H), 8.93 (d, J=6.4 Hz, 1H), 7.86 (s, 1H), 7.79 (d, J=7.3 Hz, 1H), 7.59 (dt, J=15.2, 7.7 Hz, 2H), 5.67 (p, J=7.0 Hz, 1H), 2.47 (s, 3H), 1.72 (d, J=13.5 Hz, 6H), 1.64 (d, J=7.1 Hz, 3H).

Example 10: Preparation of Compound 10

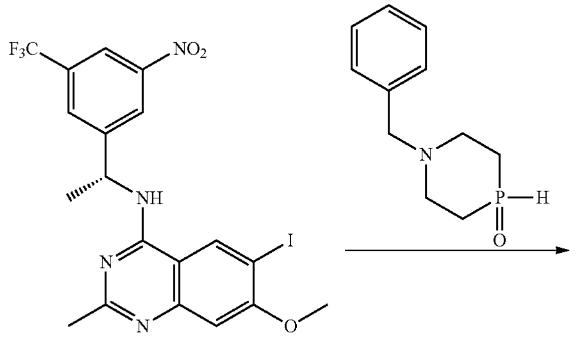

7-1

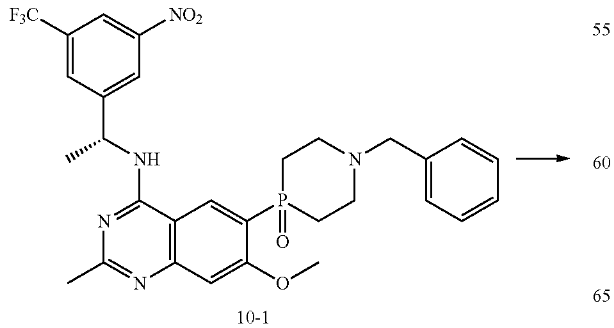

10-1

-continued

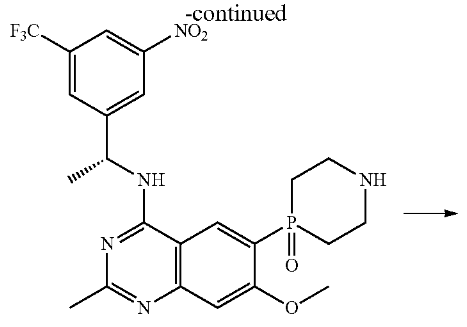

10-2

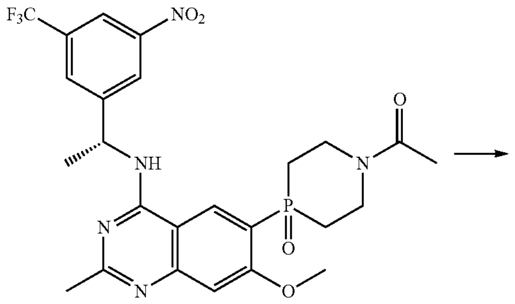

10-3

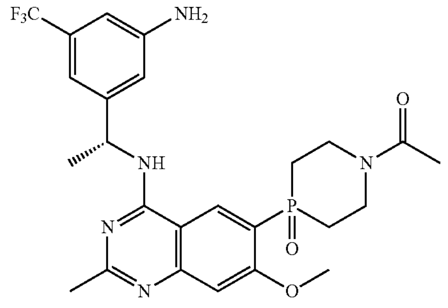

10

Step A: Preparation of Compound 10-1

To a 25 mL three-necked flask were added the compound 7-1 (1.1 g) obtained in step A in Example 7, 1-benzyl-1,4-azaphosphane 4-oxide (0.441 g), triethylamine (0.294 g), 4,5-bis(diphenylphosphino)-9,9-dimethylxanthene (0.113 g), tris(dibenzylideneacetone)dipalladium (0.090 g) and 1,4-dioxane (10 mL). The reaction solution was stirred to react for 1 h at 100° C. under nitrogen protection. The reaction solution was cooled to room temperature and filtered under vacuum. The filtrate was concentrated to dryness, and the residue was subjected to silica gel column chromatography (dichloromethane:methanol=95:5) to obtain 0.94 g of compound 10-1.

MS (ESI, $[M+H]^+$): m/z=614.40.

$^1H$ NMR (500 MHz, DMSO-$d_6$) δ 8.86 (d, J=7.5 Hz, 1H), 8.72-8.65 (m, 2H), 8.35-8.34 (m, 2H), 7.40-7.34 (m, 4H), 7.30-7.26 (m, 1H), 7.14 (d, J=4.7 Hz, 1H), 5.68 (p, J=7.1 Hz, 1H), 3.99 (s, 3H), 3.69 (s, 2H), 3.04-2.96 (m, 2H), 2.88-2.82 (m, 2H), 2.48-2.45 (m, 2H), 2.37 (s, 3H), 1.83-1.76 (m, 2H), 1.67 (d, J=7.1 Hz, 3H).

Step B: Preparation of Compound 10-2

The compound 10-1 (0.699 g) obtained in step A and 1,2-dichloroethane (10 mL) were added to a 25 mL three-necked flask. The mixture was stirred in an ice-water bath, added with 1-chloroethyl chloroformate (0.195 g) and refluxed for 2 h. The reaction solution was concentrated to dryness. The residue was added with methanol (5 mL), and the mixture was heated and stirred under reflux for 15 min. The reaction solution was concentrated to dryness, and the residue was subjected to silica gel column chromatography (dichloromethane:methanol=94:6) to obtain 348 mg of compound 10-2.

MS (ESI, $[M+H]^+$): m/z=524.07.

$^1$H NMR (500 MHz, DMSO-$d_6$) δ 8.85 (d, J=7.5 Hz, 1H), 8.71-8.65 (m, 2H), 8.35 (d, J=6.7 Hz, 2H), 7.12 (d, J=4.6 Hz, 1H), 5.68 (p, J=7.1 Hz, 1H), 3.96 (s, 3H), 3.20-3.06 (m, 4H), 2.42-2.30 (m, 5H), 1.80-1.70 (m, 2H), 1.68 (d, J=7.1 Hz, 3H).

Step C: Preparation of Compound 10-3

To a 10 mL single-neck flask were added the compound 10-2 (150 mg) obtained in step B, tetrahydrofuran (1 mL), triethylamine (87 mg) and acetic anhydride (32.2 mg). The reaction solution was stirred to react at room temperature for 1 h. The reaction solution was added with water (10 mL), stirred at room temperature for 5 min, extracted with dichloromethane (15 mL×2), dried over anhydrous sodium sulfate and concentrated. The residue was separated and purified by silica gel column chromatography (dichloromethane:methanol=96:4) to obtain 144 mg of compound 10-3.

MS (ESI, $[M+H]^+$): m/z=566.03.

$^1$H NMR (500 MHz, DMSO-$d_6$) δ 8.91 (dd, J=7.2, 5.3 Hz, 1H), 8.70 (dd, J=13.8, 5.1 Hz, 1H), 8.67 (s, 1H), 8.35 (d, J=6.1 Hz, 2H), 7.12 (d, J=4.8 Hz, 1H), 5.69-5.67 (m, 1H), 4.46 (dd, J=25.9, 13.2 Hz, 1H), 4.12-4.00 (m, 1H), 3.91 (s, 3H), 3.74-3.72 (m, 1H), 3.32-3.27 (m, 1H), 2.48-2.39 (m, 1H), 2.39-2.30 (m, 4H), 1.98- 1.79 (m, 2H), 1.68 (d, J=7.1 Hz, 3H).

Step D: Preparation of Compound 10

The compound 10-3 (114 mg) obtained in step C, tetrahydrofuran (1.5 mL) and ethanol (4.5 mL) were added to a 25 mL three-necked flask. The mixture was added with stannous chloride dihydrate (182 mg) under stirring at room temperature. The reaction flask was stirred to react for 1 h at 50° C. in an oil bath. The reaction was stopped, and the reaction solution was concentrated to dryness, and separated and purified by silica gel column chromatography (dichloromethane:methanol=94:6) to obtain 89 mg of compound 10.

HRMS (ESI, $[M+H]^+$): m/z=536.2073.

$^1$H NMR (500 MHz, DMSO-$d_6$) δ 8.76 (d, J=7.5 Hz, 1H), 8.68 (d, J=13.8 Hz, 1H), 7.12 (d, J=4.8 Hz, 1H), 6.91 (s, 1H), 6.86 (s, 1H), 6.70 (s, 1H), 5.61-5.50 (m, 3H), 4.45-4.30 (m, 1H), 4.04-3.96 (m, 1H), 3.91 (s, 3H), 3.77-3.67 (m, 1H), 3.40-3.35 (m, 1H), 2.48-2.29 (m, 5H), 2.12 (s, 3H), 2.03-1.81 (m, 2H), 1.55 (d, J=7.1 Hz, 3H).

Example 11: Preparation of Compound 11

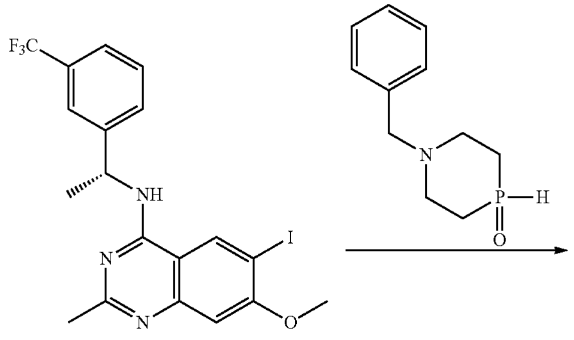

2-1

-continued

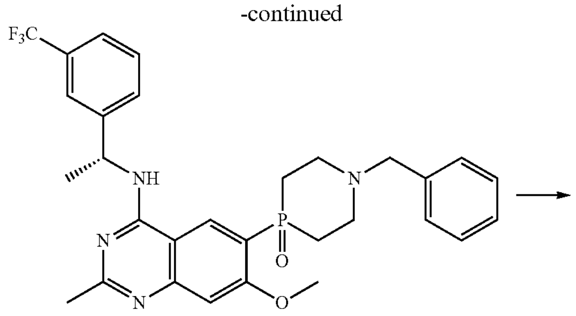

11-1

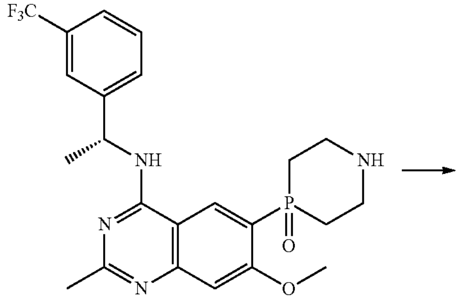

11-2

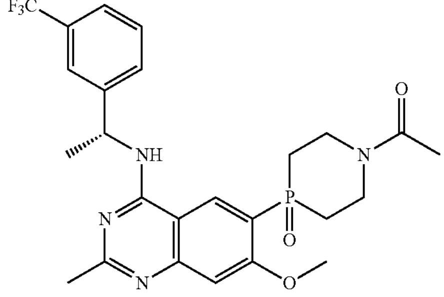

11

Step A: Preparation of Compound 11-1

Referring to the procedures of step A in Example 10, compound 11-1 was prepared using the compound 2-1 obtained in step A in Example 2.

HRMS (ESI, $[M+H]^+$): m/z=569.2283.

$^1$H NMR (500 MHz, DMSO-$d_6$) δ 8.78 (d, J=7.7 Hz, 1H), 8.69 (d, J=13.6 Hz, 1H), 7.84 (s, 1H), 7.77 (d, J=7.1 Hz, 1H), 7.59-7.54 (m, 2H), 7.39-7.34 (m, 4H), 7.31-7.24 (m, 1H), 7.13 (d, J=4.6 Hz, 1H), 5.66 (p, J=7.1 Hz, 1H), 3.99 (s, 3H), 3.67 (s, 2H), 3.00-2.92 (m, 2H), 2.85 (q, J=11.5 Hz, 2H), 2.48-2.45 (m, 2H), 2.38 (s, 3H), 1.82 (t, J=16.1 Hz, 2H), 1.62 (d, J=7.1 Hz, 3H).

Step B: Preparation of Compound 11-2

Compound 11-2 was prepared referring to the procedures of step B in Example 10.

HRMS (ESI, $[M+H]^+$): m/z=479.1814.

$^1$H NMR (500 MHz, DMSO-$d_6$) δ 8.80 (d, J=7.7 Hz, 1H), 8.68 (d, J=13.6 Hz, 1H), 7.84 (s, 1H), 7.78 (d, J=7.1 Hz, 1H), 7.60-7.55 (m, 2H), 7.11 (d, J=4.6 Hz, 1H), 5.67 (p, J=7.1 Hz, 1H), 3.96 (s, 3H), 3.17-3.06 (m, 4H), 2.43-2.34 (m, 5H), 1.79 (t, J=16.1 Hz, 2H), 1.62 (d, J=7.1 Hz, 3H).

Step C: Preparation of Compound 11

Compound 11 was prepared referring to the procedures of step C in Example 10.

HRMS (ESI, $[M+H]^+$): m/z=521.1961.

$^1$H NMR (500 MHz, DMSO-$d_6$) δ 8.83 (dd, J=7.6, 2.3 Hz, 1H), 8.70 (dd, J=13.8, 3.5 Hz, 1H), 7.84 (s, 1H), 7.77 (d,

J=6.7 Hz, 1H), 7.61-7.53 (m, 2H), 7.12 (d, J=4.8 Hz, 1H), 5.71-5.62 (m, 1H), 4.46-4.37 (m, 1H), 4.09-3.97 (m, 1H), 3.91 (s, 3H), 3.76-3.71 (m, 1H), 3.32-3.30 (m, 1H), 2.48-2.39 (m, 1H), 2.39-2.30 (m, 4H), 2.12 (s, 3H), 1.99-1.80 (m, 2H), 1.62 (d, J=7.1 Hz, 3H).

Example 12: Preparation of Compound 12

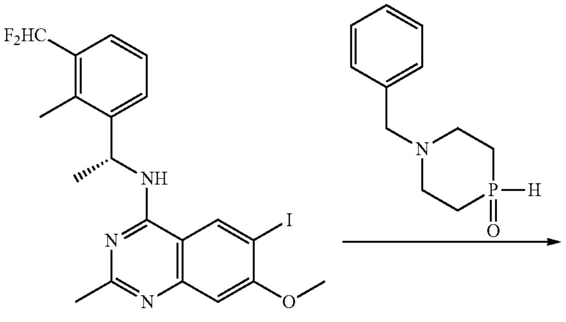

4-1

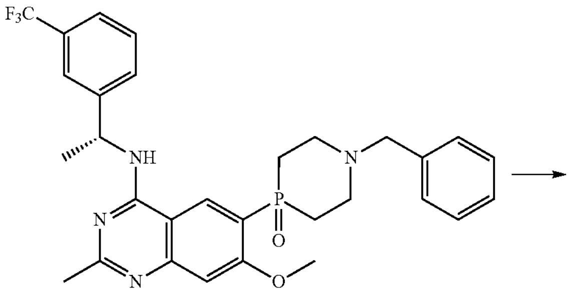

12-1

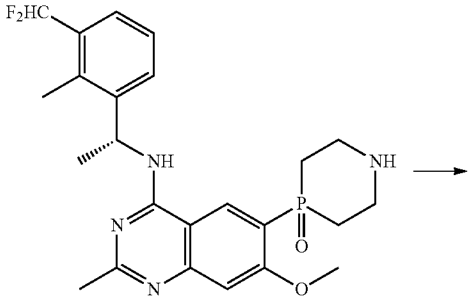

12-2

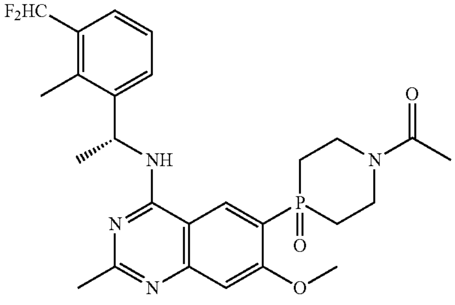

12

Step A: Preparation of Compound 12-1

Referring to the procedures of step A in Example 10, compound 12-1 was prepared using the compound 4-1 obtained in step A in Example 4.

MS (ESI, $[M+H]^+$): m/z=565.55.

$^1$H NMR (500 MHz, DMSO-$d_6$) δ 8.95 (s, 1H), 8.73 (d, J=13.6 Hz, 1H), 7.70 (d, J=7.8 Hz, 1H), 7.41-7.33 (m, 5H), 7.33-7.20 (m, 3H), 7.11 (d, J=4.7 Hz, 1H), 5.80-5.73 (m, 1H), 3.98 (s, 3H), 3.69 (s, 2H), 2.91 (dd, J=56.9, 16.5 Hz, 4H), 2.55 (s, 3H), 2.49-2.43 (m, 2H), 2.36 (s, 3H), 1.84 (s, 2H), 1.54 (d, J=7.0 Hz, 3H).

Step B: Preparation of Compound 12-2

Compound 12-2 was prepared referring to the procedures of step B in Example 10.

MS (ESI, $[M+H]^+$): m/z=475.18.

$^1$H NMR (500 MHz, DMSO-$d_6$) δ 8.86 (d, J=7.3 Hz, 1H), 8.70 (d, J=13.5 Hz, 1H), 7.71 (d, J=7.7 Hz, 1H), 7.38 (d, J=7.5 Hz, 1H), 7.34-7.18 (m, 2H), 7.13-7.06 (m, 1H), 5.76 (p, J=6.9 Hz, 1H), 3.95 (s, 3H), 3.17-3.06 (m, 4H), 2.55 (s, 3H), 2.43-2.36 (m, 2H), 2.35 (s, 3H), 1.77 (d, J=18.6 Hz, 2H), 1.54 (d, J=7.0 Hz, 3H).

Step C: Preparation of Compound 12

Compound 12 was prepared referring to the procedures of step C in Example 10.

MS (ESI, $[M+H]^+$): m/z=517.12.

$^1$H NMR (500 MHz, $CDCl_3$) δ 8.47 (d, J=14.1 Hz, 1H), 7.55 (d, J=7.5 Hz, 1H), 7.43 (d, J=7.6 Hz, 1H), 7.27 (s, 1H), 7.10 (d, J=5.3 Hz, 1H), 6.82 (t, J=55.5 Hz, 1H), 6.46-6.45 (m, 1H), 5.87-5.83 (m, 1H), 4.96-4.87 (m, 1H), 4.18-4.10 (m, 1H), 3.93 (s, 3H), 3.91-3.88 (m, 1H), 2.54 (d, J=5.1 Hz, 6H), 2.51-2.40 (m, 2H), 2.22 (s, 3H), 2.19-2.05 (m, 2H), 1.61 (d, J=6.8 Hz, 3H).

Example 13: Preparation of Compound 13

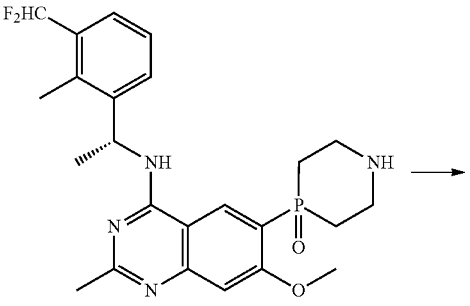

12-2

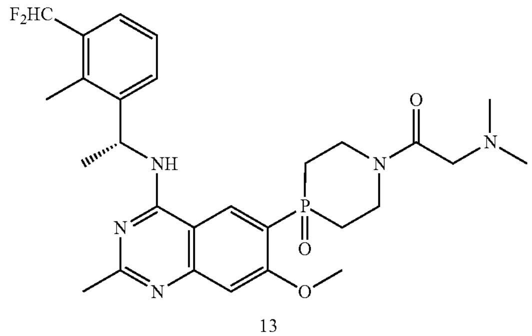

13

Referring to the procedures of step C in Example 10, compound 13 was prepared by reacting the compound 12-2 with N,N-dimethylglycine.

MS (ESI, $[M+H]^+$): m/z=560.11.

$^1$H NMR (500 MHz, $CDCl_3$) δ 8.53 (d, J=14.0 Hz, 1H), 7.59-7.53 (m, 1H), 7.43 (d, J=7.6 Hz, 1H), 7.30-7.23 (m, 1H), 7.09 (d, J=5.2 Hz, 1H), 6.83 (t, J=55.5 Hz, 1H), 6.61-6.56 (m, 1H), 5.89-5.82 (m, 1H), 4.99-4.91 (m, 1H), 4.52-4.44 (m, 1H), 3.90 (s, 3H), 3.83-3.77 (m, 1H), 3.38-3.35 (m, 1H), 3.10-3.07 (m, 1H), 2.60- 2.46 (m, 8H), 2.34 (s, 6H), 2.30-2.23 (m, 2H), 1.61 (d, J=6.9 Hz, 3H).

Example 14: Preparation of Compound 14

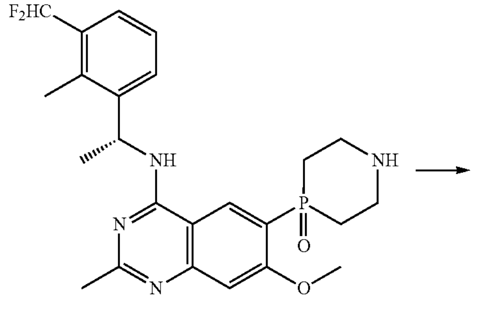

12-2

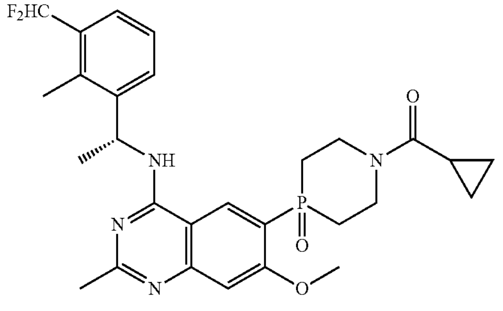

14

Referring to the procedures of step C in Example 10, compound 14 was prepared by reacting the compound 12-2 with cyclopropanecarboxylic acid.

MS (ESI, $[M+H]^+$): m/z=543.10.

$^1H$ NMR (500 MHz, $CDCl_3$) δ 8.47 (d, J=14.1 Hz, 1H), 7.55 (d, J=7.7 Hz, 1H), 7.43 (d, J=7.6 Hz, 1H), 7.30-7.23 (m, 1H), 7.09 (d, J=5.2 Hz, 1H), 6.83 (t, J=55.5 Hz, 1H), 6.47-6.42 (m, 1H), 5.89-5.81 (m, 1H), 4.92-4.84 (m, 1H), 4.62-4.47 (m, 1H), 4.02-3.93 (m, 1H), 3.91 (s, 3H), 2.61-2.48 (m, 8H), 2.06-1.89 (m, 3H), 1.61 (d, J=6.9 Hz, 3H), 1.11-1.02 (m, 4H).

Example 15: Preparation of Compound 15

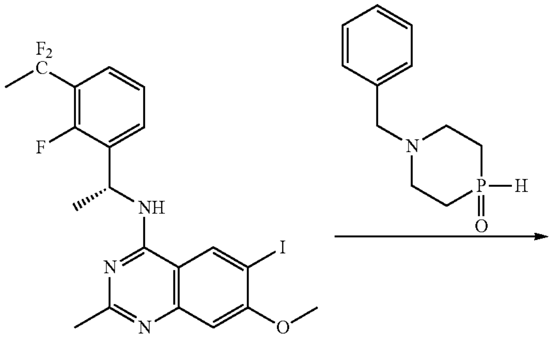

5-1

-continued

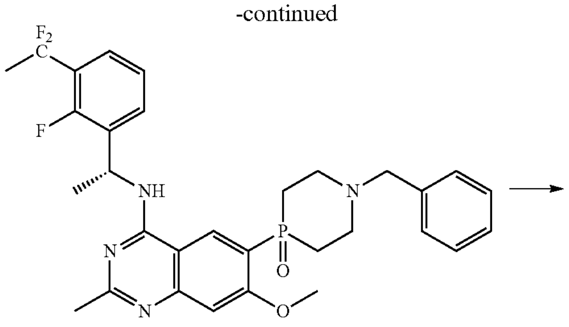

15-1

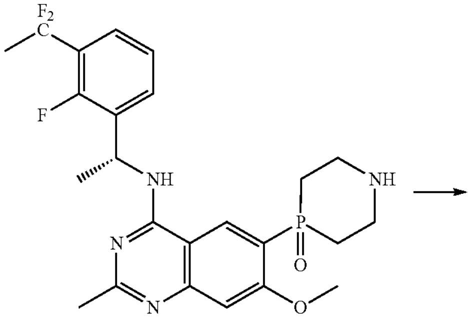

15-2

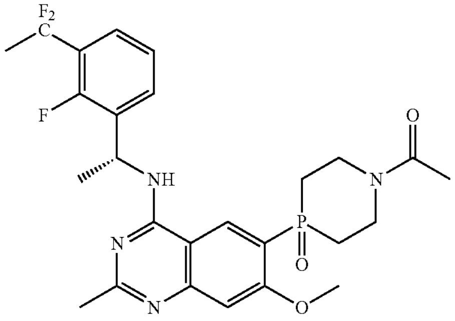

15

Step A: Preparation of Compound 15-1

Compound 15-1 was prepared referring to the procedures of step A in Example 10.

MS (ESI, $[M+H]^+$): m/z=583.1.

$^1H$ NMR (500 MHz, $CDCl_3$) δ 8.57 (dd, J=3.6, 13.9 Hz, 1H), 7.48 (d, J=6.4 Hz, 1H), 7.42 (t, J=7.4 Hz, 1H), 7.39-7.34 (m, 4H), 7.31-7.27 (m, 1H), 7.14-7.07 (m, 2H), 6.66 (d, J=7.6 Hz, 1H), 5.84 (p, J=7.1 Hz, 1H), 4.02 (d, J=1.3 Hz, 3H), 3.73-3.69 (m, 2H), 3.16 (dd, J=12.3, 29.5 Hz, 2H), 2.99 (dt, J=9.6, 19.6 Hz, 2H), 2.62 (td, J=6.0, 12.7, 13.2 Hz, 2H), 2.52 (s, 3H), 2.02 (t, J=18.6 Hz, 3H), 1.78 (ddt, J=2.9, 14.8, 20.3 Hz, 2H), 1.65 (d, J=7.0 Hz, 3H).

Step B: Preparation of Compound 15-2

Compound 15-2 was prepared referring to the procedures of step B in Example 10.

MS (ESI, $[M+H]^+$): m/z=493.08.

$^1H$ NMR (500 MHz, $CDCl_3$) δ 8.56 (d, J=13.9 Hz, 1H), 7.52-7.47 (m, 1H), 7.42 (t, J=7.4 Hz, 1H), 7.12 (t, J=7.0 Hz, 2H), 6.60 (s, 1H), 5.84 (p, J=7.0 Hz, 1H), 4.00 (s, 3H), 3.40 (ddd, J=3.2, 9.3, 21.8 Hz, 4H), 2.52 (s, 5H), 2.02 (t, J=18.6 Hz, 3H), 1.85 (ddt, J=2.8, 14.6, 20.0 Hz, 2H), 1.66 (d, J=7.0 Hz, 3H), 1.34-1.20 (m, 1H).

Step C: Preparation of Compound 15

Compound 15 was prepared referring to the procedures of step C in Example 10.

MS (ESI, [M+H]+): m/z=535.13.

$^1$H NMR (500 MHz, $CDCl_3$) δ 8.55 (dd, J=3.3, 14.2 Hz, 1H), 7.49 (q, J=6.8 Hz, 1H), 7.46-7.40 (m, 1H), 7.12 (dd, J=6.3, 11.4 Hz, 2H), 6.65 (dd, J=4.3, 7.3 Hz, 1H), 5.84 (pd, J=2.7, 6.7 Hz, 1H), 4.92 (dd, J=13.7, 28.7 Hz, 1H), 4.20-4.08 (m, 1H), 3.93 (s, 3H), 3.89 (dd, J=6.6, 13.9 Hz, 1H), 3.36 (td, J=6.6, 13.0 Hz, 1H), 2.52 (d, J=1.9 Hz, 3H), 2.45 (dp, J=4.7, 13.9 Hz, 1H), 2.23 (s, 4H), 2.02 (t, J=18.6 Hz, 3H), 1.97-1.82 (m, 2H), 1.67 (dd, J=1.7, 7.0 Hz, 3H).

Example 16: Preparation of Compound 16

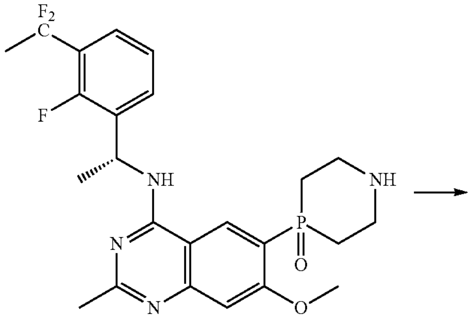

15-2

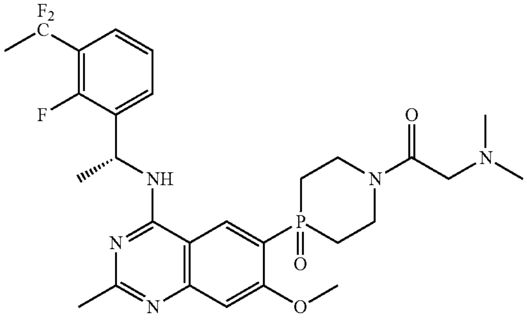

16

Referring to the procedures of step C in Example 10, compound 16 was prepared by reacting the compound 15-2 with N,N-dimethylglycine.

MS (ESI, [M+H]+): m/z=578.14.

$^1$H NMR (500 MHz, $CDCl_3$) δ 8.55 (dd, J=4.3, 14.2 Hz, 1H), 7.49 (q, J=7.5 Hz, 1H), 7.43 (t, J=7.4 Hz, 1H), 7.12 (d, J=5.4 Hz, 2H), 6.56 (d, J=6.6 Hz, 1H), 5.85 (td, J=3.3, 7.1 Hz, 1H), 4.96 (dd, J=13.6, 29.1 Hz, 1H), 4.48 (dd, J=14.0, 27.4 Hz, 1H), 3.91 (s, 3H), 3.81 (td, J=6.1, 13.3 Hz, 1H), 3.40-3.32 (m, 2H), 3.09 (d, J=13.2 Hz, 1H), 2.58-2.49 (m, 5H), 2.35 (s, 6H), 2.02 (t, J=18.6 Hz, 3H), 1.88 (q, J=12.4, 13.7 Hz, 2H), 1.67 (d, J=7.0 Hz, 3H).

Example 17: Preparation of Compound 17

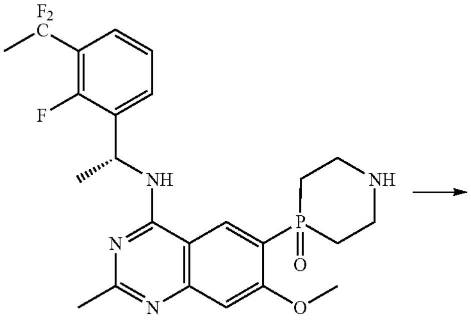

15-2

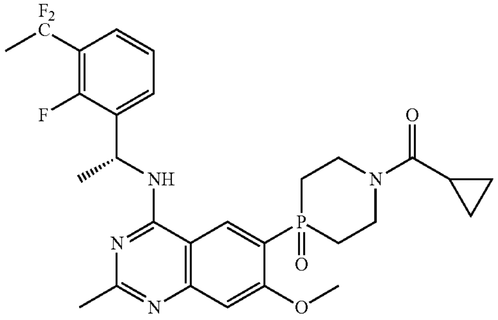

17

Referring to the procedures of step C in Example 10, compound 17 was prepared by reacting the compound 15-2 with cyclopropanecarboxylic acid.

MS (ESI, [M+H]+): m/z=561.11.

$^1$H NMR (500 MHz, $CDCl_3$) δ 8.56 (d, J=14.2 Hz, 1H), 7.58-7.38 (m, 2H), 7.18-7.06 (m, 2H), 6.63 (d, J=7.0 Hz, 1H), 5.85 (p, J=7.0 Hz, 1H), 4.88 (dd, J=13.2, 28.4 Hz, 1H), 4.54 (dd, J=15.2, 26.9 Hz, 1H), 3.96 (s, 1H), 3.92 (s, 3H), 2.61-2.54 (m, 2H), 2.52 (s, 3H), 2.03 (s, 2H), 1.86 (tt, J=4.5, 7.9 Hz, 2H), 1.67 (d, J=7.0 Hz, 3H), 1.32-1.21 (m, 2H), 1.11 (s, 1H), 1.02 (s, 1H), 0.93-0.77 (m, 3H).

Example 18: Preparation of Compound 18

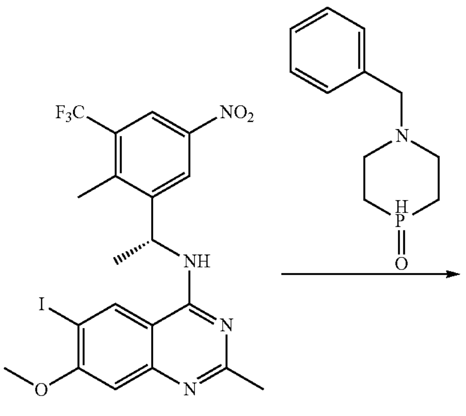

8-1

-continued

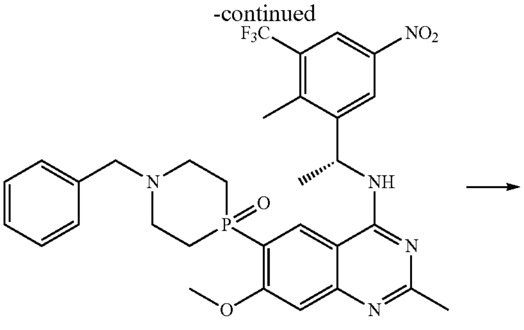

18-1

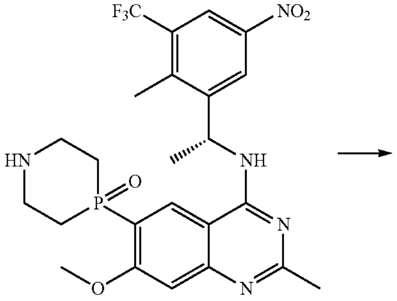

18-2

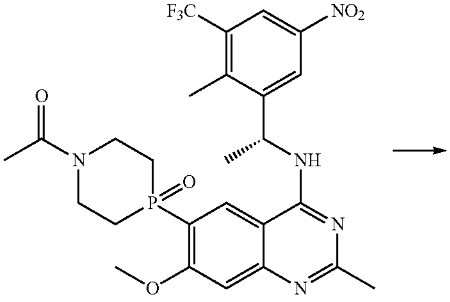

18-3

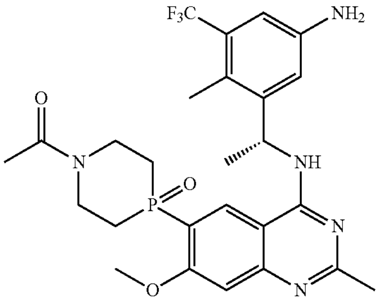

18

Step A: Preparation of Compound 18-1

Referring to the procedures of step A in Example 10, compound 18-1 was prepared using the compound 8-1 obtained in step A in Example 8.

MS (ESI, $[M+H]^+$): m/z=628.18.

$^1$H NMR (500 MHz, $CD_3OD$): δ 8.65 (d, J=14.0 Hz, 1H), 8.57 (d, J=2.3 Hz, 1H), 8.35 (d, J=2.2 Hz, 1H), 7.39 (d, J=7.2 Hz, 2H), 7.34 (dd, J=12.5, 4.8 Hz, 3H), 7.28 (d, J=7.2 Hz, 1H), 7.10 (d, J=4.8 Hz, 1H), 5.79 (q, J=7.0 Hz, 1H), 4.05 (s, 3H), 3.72 (s, 2H), 3.12 (dd, J=26.6, 12.6 Hz, 2H), 3.02-2.90 (m, 2H), 2.82 (s, 3H), 2.73-2.61 (m, 2H), 2.39 (s, 3H), 2.04 (t, J=15.7 Hz, 2H), 1.68 (d, J=7.0 Hz, 3H).

Step B: Preparation of Compound 18-2

Compound 18-2 was prepared referring to the procedures of step B in Example 10.

MS (ESI, $[M+H]^+$): m/z=538.09.

Step C: Preparation of Compound 18-3

Compound 18-3 was prepared referring to the procedures of step C in Example 10.

MS (ESI, $[M+H]^+$): m/z=580.07.

Step D: Preparation of Compound 18

Compound 18 was prepared referring to the procedures of step C in Example 8.

MS (ESI, $[M+H]^+$): m/z=550.09.

$^1$H NMR (500 MHz, $CD_3OD$): δ 8.62 (d, J=14.3 Hz, 1H), 7.08 (d, J=5.0 Hz, 1H), 7.03 (s, 1H), 6.90 (s, 1H), 5.76 (dt, J=6.8, 5.0 Hz, 1H), 4.86 (s, 3H), 4.70-4.54 (m, 1H), 4.25-4.12 (m, 1H), 3.99 (s, 3H), 3.87 (dd, J=23.5, 11.3 Hz, 1H), 3.50 (dd, J=23.2, 12.5 Hz, 1H), 2.65-2.52 (m, 2H), 2.44 (d, J=5.8 Hz, 6H), 2.23 (s, 3H), 2.16-1.99 (m, 2H), 1.59 (d, J=7.0 Hz, 3H).

Example 19: Preparation of Compound 19

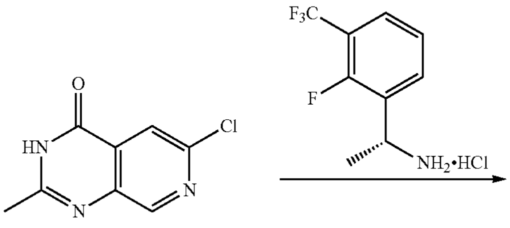

9-1

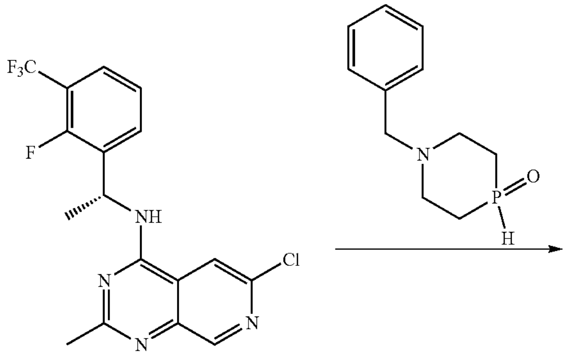

19-1

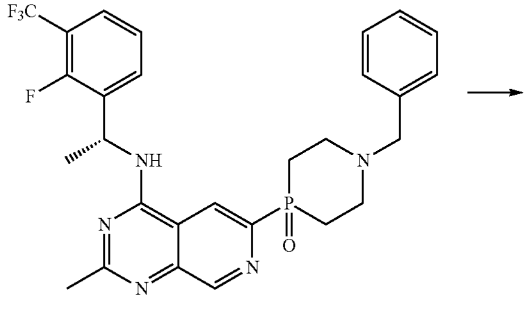

19-2

-continued

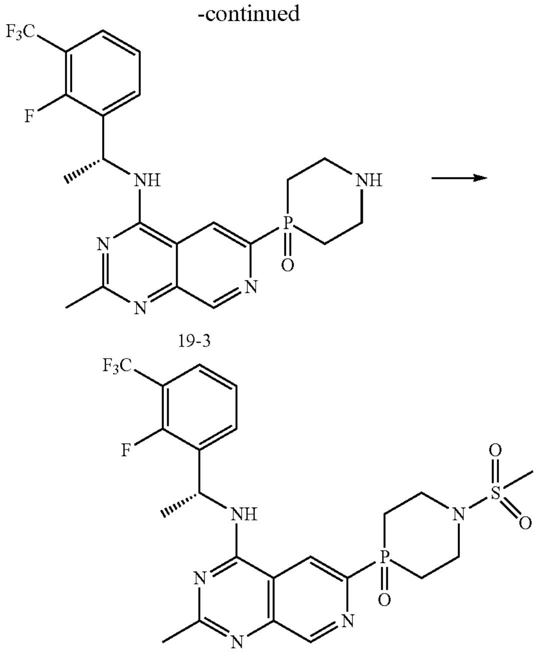

19-3

19

Step A: Preparation of Compound 19-1

To a 25 mL single-neck flask were sequentially added the compound 9-1 (0.13 g), N,N-dimethylformamide (1.3 mL), benzotriazol-1-yl-oxytripyrrolidinophosphonium hexafluorophosphate (0.45 g) and 1,8-diazabicycloundec-7-ene (0.152 g). The mixed solution was added dropwise with a mixed solution of (R)-1-(3-(trifluoromethyl)-2-fluorinephenyl)ethan-1-amine hydrochloride (0.178 g) and 1,8-diazabicycloundec-7-ene (0.152 g) in N,N-dimethylformamide (1.3 mL) under stirring at room temperature. After the addition was completed, the reaction solution was stirred at 50° C. overnight. After the reaction was completed, the reaction solution was poured into water (15 mL) and extracted with ethyl acetate (30 mL). The organic phases were combined and washed with saturated brine (10 mL), dried over anhydrous sodium sulfate, filtered and concentrated. The resulting crude product was separated and purified by silica gel column chromatography (petroleum ether: ethyl acetate=70:30) to obtain 0.14 g of compound 19-1.

MS (ESI, $[M+H]^+$): m/z=385.06.

$^1H$ NMR (500 MHz, DMSO-$d_6$) δ 8.91 (d, J=6.8 Hz, 1H), 8.84 (s, 1H), 8.53 (s, 1H), 7.82 (t, J=6.9 Hz, 1H), 7.66 (t, J=7.2 Hz, 1H), 7.37 (t, J=7.8 Hz, 1H), 5.72 (m, 1H), 2.38 (s, 3H), 1.63 (d, J=7.1 Hz, 3H).

Step B: Preparation of Compound 19-2

To a 10 mL microwave tube were added the compound 19-1 (0.14 g) obtained in step A, 1-benzyl-1,4-azaphosphine-4-oxide (0.075 g), N,N-diisopropylethylamine (0.070 g), 4,5-bis(diphenylphosphino)-9,9-dimethylxanthene (0.021 g, 0.036 mmol), tris(dibenzylideneacetone)dipalladium (0.017 g, 0.018 mmol) and N,N-dimethylformamide (3 mL).

After being purged with nitrogen, the reaction solution was heated to 165° C. under 150 W in the microwave reactor and reacted for 50 min. The reaction solution was filtered under vacuum, and the filtrate was poured into water (30 mL) and extracted by ethyl acetate (30 mL×2). The organic phase was washed with saturated brine, dried over anhydrous sodium sulfate and concentrated; and the residue was separated and purified by silica gel column chromatography (dichloromethane:methanol=97:3) to obtain 0.15 g of compound 19-2.

MS (ESI, $[M+H]^+$): m/z=558.16.

$^1H$ NMR (500 MHz, DMSO-$d_6$) δ 9.31 (d, J=6.9 Hz, 1H), 9.13 (s, 1H), 8.99 (d, J=6.4 Hz, 1H), 7.84 (t, J=7.0 Hz, 1H), 7.66 (t, J=7.1 Hz, 1H), 7.41-7.31 (m, 5H), 7.30-7.24 (m, 1H), 5.80-5.72 (m, 1H), 3.66 (s, 2H), 3.03-2.91 (m, 2H), 2.83 (q, J=12.0 Hz, 2H), 2.45-2.32 (m, 5H), 1.92 (t, J=14.6 Hz, 2H), 1.64 (d, J=7.1 Hz, 3H).

Step C: Preparation of Compound 19-3

The compound 19-2 (0.15 g) obtained in step B and 1,2-dichloroethane (14 mL) were added to a 50 mL single-neck flask. The mixture was added dropwise with 1-chloroethyl chloroformate (0.077 g) in an ice bath, and heated to reflux for 2.5 h. The reaction solution was concentrated to dryness, and the residue was added with methanol (5 mL) and heated to reflux for 30 min. The reaction solution was concentrated to dryness to obtain 0.16 g of compound 19-3.

MS (ESI, $[M+H]^+$): m/z=468.13.

$^1H$ NMR (500 MHz, DMSO-$d_6$) δ 11.11 (s, 1H), 9.75-9.44 (m, 2H), 9.38 (s, 1H), 8.04 (t, J=7.1 Hz, 1H), 7.72 (t, J=7.0 Hz, 1H), 7.50-7.27 (m, 2H), 5.96 (m, 1H), 3.56 (s, 2H), 3.38 (s, 2H), 2.83 (s, 2H), 2.53-2.41 (m, 4H), 1.74 (d, J=7.1 Hz, 3H).

Step D: Preparation of Compound 19

Methanesulfonyl chloride (0.043 g) was added dropwise to a solution of the compound 19-3 (0.16 g) obtained in step C and triethylamine (0.104 g) in tetrahydrofuran (3.2 mL) in an ice-water bath. After the addition was completed, the reaction solution was reacted for 2 h with the temperature maintained. The reaction solution was concentrated to dryness, added with water (10 mL), and extracted with dichloromethane (10 mL×3). The organic phase was dried over anhydrous sodium sulfate and concentrated; and the residue was separated and purified by C18 column chromatography (acetonitrile:water=40:60) to obtain 86 mg of compound 19.

HRMS (ESI, $[M+H]^+$): m/z=546.13611.

$^1H$ NMR (500 MHz, $CD_3OD$) δ 9.11 (d, J=0.8 Hz, 1H), 8.85 (dd, J=0.9, 6.8 Hz, 1H), 7.78-7.73 (m, 1H), 7.59-7.54 (m, 1H), 7.28 (t, J=7.8 Hz, 1H), 5.85 (q, J=7.1 Hz, 1H), 3.93 (m, 2H), 3.82-3.73 (m, 2H), 2.98 (s, 3H), 2.65 (m, 2H), 2.50 (s, 3H), 2.27-2.18 (m, 2H), 1.73 (d, J=7.1 Hz, 3H).

$^{31}P$ NMR (202 MHz, $CD_3OD$) δ 31.1.

Example 20: Preparation of Compound 20

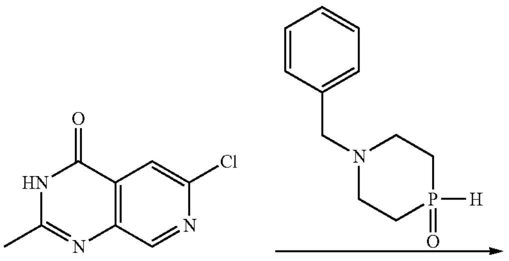

9-1

-continued

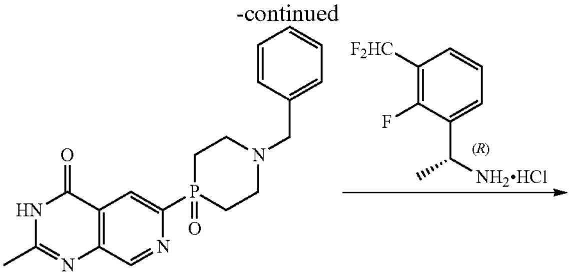

20-1

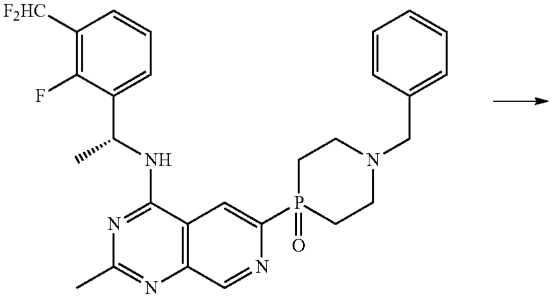

20-2

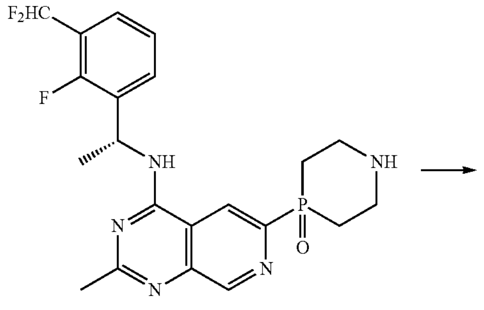

20-3

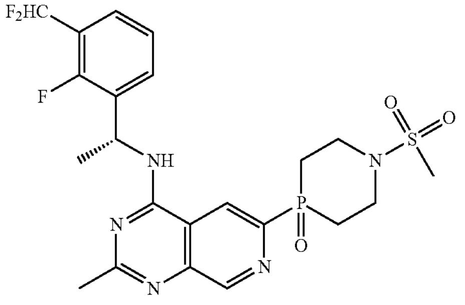

20

Step A: Preparation of Compound 20-1

Compound 20-1 was prepared referring to the procedures of step B in Example 19.

MS (ESI, $[M+H]^+$): m/z=369.09.

$^1$H NMR (500 MHz, DMSO-$d_6$) δ 12.80 (s, 1H), 9.14 (s, 1H), 8.42 (d, J=5.6 Hz, 1H), 7.37-7.29 (m, 5H), 3.63 (s, 2H), 2.95-2.76 (m, 4H), 2.44 (s, 3H), 2.41-2.31 (m, 2H), 1.94 (t, J=15.5 Hz, 2H).

Step B: Preparation of Compound 20-2

Referring to the procedures of step A in Example 19, compound 20-2 was prepared by reacting the compound 20-1 with (R)-1-(3-(difluorinemethyl)-2-fluorinephenyl) ethan-1-amine hydrochloride.

MS (ESI, $[M+H]^+$): m/z=540.16.

$^1$H NMR (500 MHz, $CDCl_3$) δ 9.18 (s, 1H), 8.78 (d, J=6.6 Hz, 1H), 7.48-7.42 (m, 2H), 7.38-7.31 (m, 5H), 7.13 (t, J=7.7 Hz, 1H), 6.89 (t, J=55.0 Hz, 1H), 5.78 (p, J=7.1 Hz, 1H), 3.67 (s, 2H), 3.05-3.00 (m, 4H), 2.57 (s, 4H), 2.05 (s, 3H), 1.68 (d, J=7.0 Hz, 3H).

Step C: Preparation of Compound 20-3

Compound 20-3 was prepared referring to the procedures of step C in Example 19.

MS (ESI, $[M+H]^+$): m/z=450.16.

Step D: Preparation of Compound 20

Compound 20 was prepared referring to the procedures of step D in Example 19.

HRMS (ESI, $[M+H]^+$): m/z=528.1443.

$^1$H NMR (500 MHz, DMSO-$d_6$) δ 9.40 (d, J=7.2 Hz, 1H), 9.11 (d, J=4.0 Hz, 2H), 7.75 (t, J=7.4 Hz, 1H), 7.52 (t, J=7.0 Hz, 1H), 7.36-7.30 (m, 1H), 7.30-7.13 (m, 1H), 5.82 (p, J=7.0 Hz, 1H), 3.76-3.64 (m, 4H), 3.34 (s, 2H), 3.02 (s, 3H), 2.44 (s, 3H), 2.10 (d, J=13.7 Hz, 2H), 1.65 (d, J=7.1 Hz, 3H).

Example 21: Preparation Compound 21

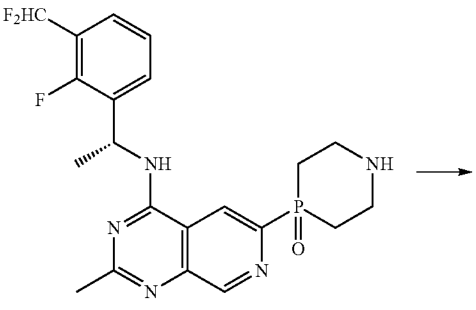

20-3

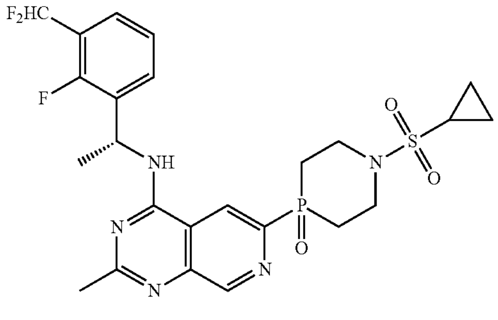

21

Cyclopropanesulfonyl chloride (0.13 g) was added dropwise to a solution of the compound 20-3 (0.1 g) and triethylamine (0.055 g) in dichloromethane (2 mL) in an ice-water bath. After the addition was completed, the reaction solution was reacted for 20 min with the temperature maintained. After the reaction was completed, the reaction solution was added with water (10 mL) and extracted with dichloromethane (15 mL). The organic phase was dried over anhydrous sodium sulfate and concentrated; and the residue was separated and purified by C18 column chromatography (acetonitrile:water=40:60) to obtain 49 mg of compound 21.

HRMS (ESI, $[M+H]^+$): m/z=554.1635.

$^1$H NMR (500 MHz, $CD_3OD$) δ 9.11 (s, 1H), 8.85 (dd, J=6.8, 0.9 Hz, 1H), 7.64 (t, J=7.4 Hz, 1H), 7.49 (t, J=7.1 Hz, 1H), 7.24 (t, J=7.7 Hz, 1H), 7.00 (m, 1H), 5.87 (q, J=7.1 Hz, 1H), 4.05-3.78 (m, 4H), 2.72-2.59 (m, 4H), 2.51 (s, 3H), 2.29-2.14 (m, 1H), 1.72 (d, J=7.1 Hz, 3H), 1.11 (m, 2H), 1.08 (dt, J=8.2, 2.2 Hz, 2H).

Example 22: Preparation of Compound 22

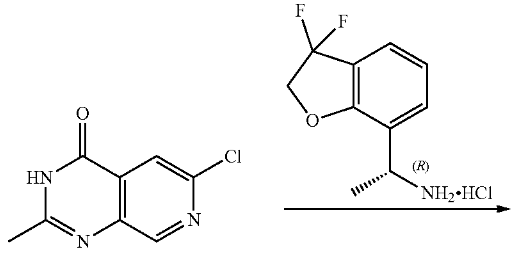

9-1

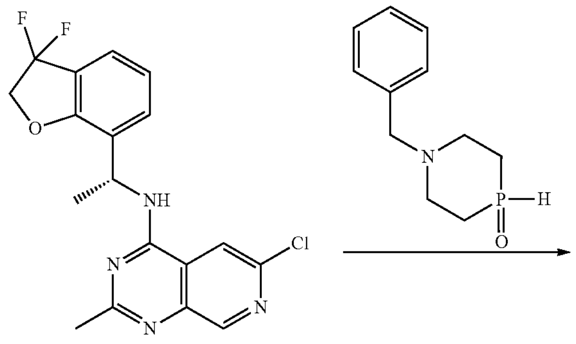

22-1

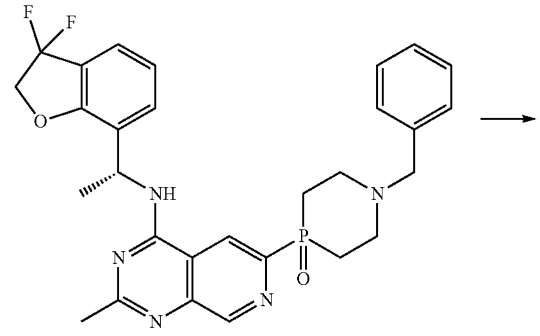

22-2

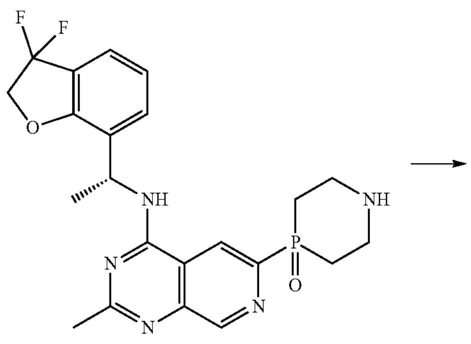

22-3

-continued

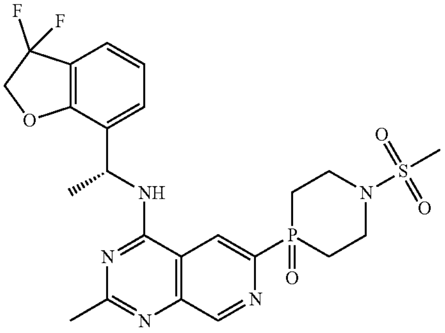

22

Step A: Preparation of Compound 22-1

Referring to the procedures of step A in Example 19, compound 22-1 was prepared by reacting the compound 9-1 with (R)-1-(3,3-difluorine-2,3-dihydrobenzofuran-7-yl) ethan-1-amine hydrochloride.

MS (ESI, $[M+H]^+$): m/z=377.10.

$^1$H NMR (500 MHz, Acetone-$d_6$) δ 8.81 (s, 1H), 8.26 (s, 1H), 7.66 (d, J=7.6 Hz, 1H), 7.48 (dd, J=7.6, 1.2 Hz, 1H), 7.08 (t, J=7.6 Hz, 1H), 5.80 (p, J=7.1 Hz, 1H), 4.81 (t, J=16.3 Hz, 2H), 2.46 (s, 3H), 1.69 (d, J=7.0 Hz, 3H).

Step B: Preparation of Compound 22-2

Compound 22-2 was prepared referring to the procedures of step B in Example 19.

MS (ESI, $[M+H]^+$): m/z=550.13.

$^1$H NMR (500 MHz, DMSO-$d_6$) δ 9.17 (d, J=7.4 Hz, 1H), 9.12 (d, J=0.8 Hz, 1H), 8.99 (d, J=6.4 Hz, 1H), 7.60 (d, J=7.5 Hz, 1H), 7.51 (dd, J=7.6, 1.4 Hz, 1H), 7.35 (d, J=6.0 Hz, 3H), 7.27 (s, 1H), 7.09 (dd, J=7.6 Hz, 1H), 5.74 (m, 1H), 4.87 (t, J=16.6 Hz, 2H), 3.65 (s, 3H), 2.99-2.79 (m, 4H), 2.44 (s, 3H), 2.43-2.34 (m, 2H), 1.93 (t, J=10.5 Hz, 2H), 1.60 (d, J=7.0 Hz, 3H).

Step C: Preparation of Compound 22-3

Compound 22-3 was prepared referring to the procedures of step C in Example 19.

MS (ESI, $[M+H]^+$): m/z=460.17.

Step D: Preparation of Compound 22

Compound 22 was prepared referring to the procedures of step D in Example 19.

HRMS (ESI, $[M+H]^+$): m/z=538.1596.

$^1$H NMR (500 MHz, $CD_3OD$) δ 9.10 (s, 1H), 8.82 (d, J=6.8 Hz, 1H), 7.55 (d, J=7.6 Hz, 1H), 7.47-7.40 (m, 1H), 7.05 (t, J=7.6 Hz, 1H), 5.80 (q, J=7.0 Hz, 1H), 4.72 (t, J=16.2 Hz, 2H), 3.97-3.72 (m, 4H), 2.97 (s, 3H), 2.65 (m, 2H), 2.52 (s, 3H), 2.32-2.16 (m, 2H), 1.70 (d, J=7.0 Hz, 3H).

$^{31}$P NMR (202 MHz, $CD_3OD$) δ 31.22.

Example 23: Preparation of Compound 23

23

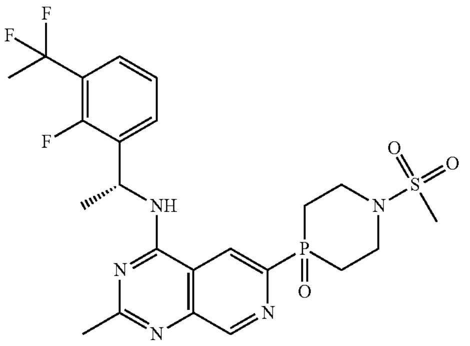

Referring to the preparation procedures of Example 19, (R)-1-(3-(trifluoromethyl)-2-fluorinephenyl)ethan-1-amine hydrochloride was replaced with (R)-1-(3-(1,1-difluorine-ethyl)-2-fluorinephenyl)ethan-1-amine hydrochloride to synthesize compound 23.

HRMS (ESI, $[M+H]^+$): m/z=542.1608.

$^1H$ NMR (500 MHz, DMSO-$d_6$) δ 9.18 (s, 1H), 8.64 (d, J=6.8 Hz, 1H), 7.45 (t, J=7.6 Hz, 2H), 7.13 (t, J=7.8 Hz, 1H), 6.91-6.90 (m, 1H), 5.82 (p, J=7.1 Hz, 1H), 4.07-4.01 (m, 2H), 3.83-3.77 (m, 2H), 2.93 (s, 3H), 2.65-2.58 (m, 5H), 2.20-2.14 (m, 2H), 2.00 (t, J=18.6 Hz, 3H), 1.70 (d, J=7.0 Hz, 3H).

Example 24: Preparation of Compound 24

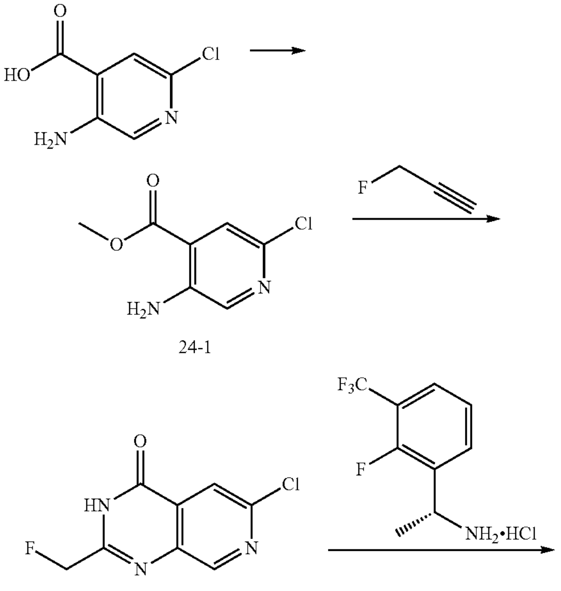

24-1

24-2

-continued

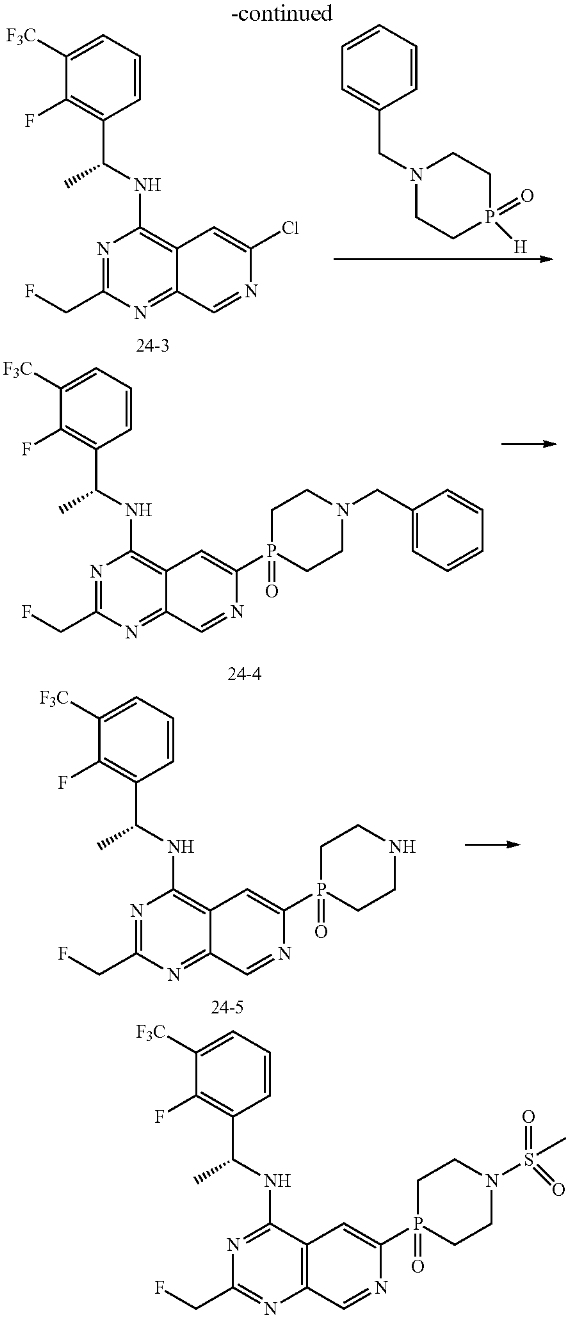

24-3

24-4

24-5

24

Step A: Preparation of compound 24-1

5-amino-2-chloropyridine-4-carboxylic acid (3 g) and methanol (11.14 g) were sequentially added to a 50 mL single-neck flask, and the mixture was stirred in an ice brine bath. The mixture was added dropwise with thionyl chloride (4.14 g) and two drops of N,N-dimethylformamide. After the addition was completed, the mixture was heated to 65° C. and reacted for 12 h. After the reaction was completed, the reaction solution was cooled to room temperature and concentrated to dryness under reduced pressure. The residue was dissolved in ethyl acetate (50 mL), added with a saturated sodium bicarbonate solution to adjust the pH to alkalinity and separated. The organic phase was washed with saturated brine, dried over anhydrous sodium sulfate, and concentrated to obtain 1.8 g of compound 24-1.

MS (ESI, $[M+H]^+$): m/z=186.97.

Step B: Preparation of Compound 24-2

The compound 24-1 (1.7 g) obtained in step A, fluorineacetonitrile (2.69 g) and methanesulfonic acid (7.0 g) were sequentially added to a 15 mL pressure-resistant flask. The reaction system was heated to 105° C. and stirred to react for 4 h. After the reaction was completed, the reaction solution was cooled to room temperature, added with water (5 mL), added with 4 M aqueous sodium hydroxide solution to adjust the pH to alkalinity, and extracted with dichloromethane (20 mL×5). The organic phase was dried over anhydrous sodium sulfate, filtered under vacuum and concentrated to dryness. The residue was separated and purified by silica gel column chromatography (dichloromethane:methanol=97:3) to obtain 0.43 g of compound 24-2.

MS (ESI, $[M+H]^+$): m/z=214.02.

$^1$H NMR (500 MHz, DMSO-$d_6$) δ 12.90 (br, 1H), 8.93 (s, 1H), 7.99 (s, 1H), 5.40 (s, 1H), 5.31 (s, 1H).

Step C: Preparation of Compound 24-3

Compound 24-3 was prepared referring to the procedures of step A in Example 19.

MS (ESI, $[M+H]^+$): m/z=403.06.

$^1$H NMR (500 MHz, DMSO-$d_6$) δ 9.13 (d, J=6.8 Hz, 1H), 8.96 (s, 1H), 8.60 (s, 1H), 7.84 (t, J=7.2 Hz, 1H), 7.67 (t, J=7.1 Hz, 1H), 7.37 (t, J=7.8 Hz, 1H), 5.74 (m, 1H), 5.26 (m, 2H), 1.64 (d, J=7.1 Hz, 3H).

Step D: Preparation of Compound 24-4

Compound 24-4 was prepared referring to the procedures of step B in Example 19.

MS (ESI, $[M+H]^+$): m/z=576.11.

$^1$H NMR (500 MHz, $CD_3OD$) δ 9.23 (s, 1H), 8.86 (d, J=6.5 Hz, 1H), 7.75 (t, J=7.2 Hz, 1H), 7.57 (t, J=7.1 Hz, 1H), 7.38 (d, J=7.3 Hz, 2H), 7.33 (t, J=7.5 Hz, 2H), 7.27 (m, 2H), 5.83 (q, J=7.1 Hz, 1H), 5.30 (m, 2H), 3.70 (s, 2H), 3.12-2.93 (m, 4H), 2.67-2.57 (m, 2H), 2.09 (t, J=15.5 Hz, 2H), 1.73 (d, J=7.1 Hz, 3H).

Step E: Preparation of Compound 24-5

Compound 24-5 was prepared referring to the procedures of step C in Example 19.

MS (ESI, $[M+H]^+$): m/z=486.11.

Step D: Preparation of Compound 24

Referring to the procedures of step D in Example 19, compound 24 was prepared by reacting the compound 24-5 with methanesulfonyl chloride.

HRMS (ESI, $[M+H]^+$): m/z=564.1277.

$^1$H NMR (500 MHz, $CD_3OD$) δ 9.24 (s, 1H), 8.90 (d, J=6.8 Hz, 1H), 7.76 (t, J=7.2 Hz, 1H), 7.58 (t, J=7.0 Hz, 1H), 7.29 (t, J=7.8 Hz, 1H), 5.83 (m, 1H), 5.30 (m, 2H), 4.01-3.88 (m, 2H), 3.82-3.74 (m, 2H), 2.98 (s, 3H), 2.69-2.62 (m, 2H), 2.27-2.20 (m, 2H), 1.74 (d, J=7.1 Hz, 3H).

Example 25: Preparation of Compound 25

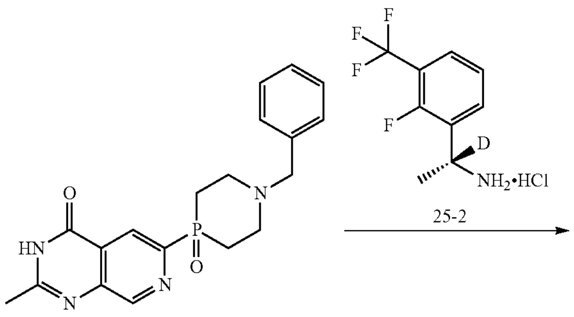

20-1

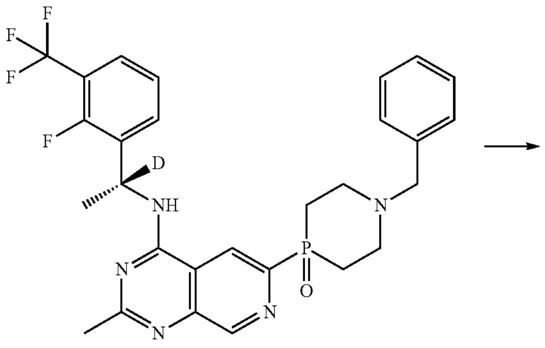

25-3

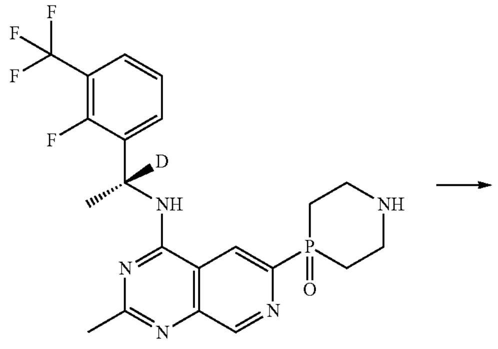

25-4

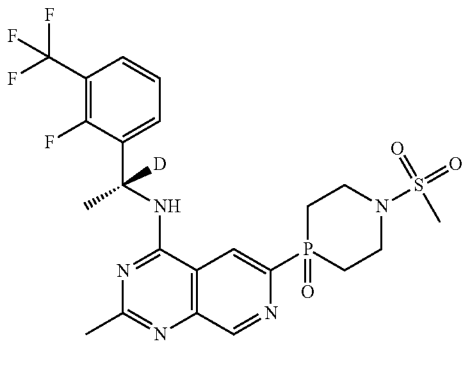

25

Step A: Preparation of Compound 25-2

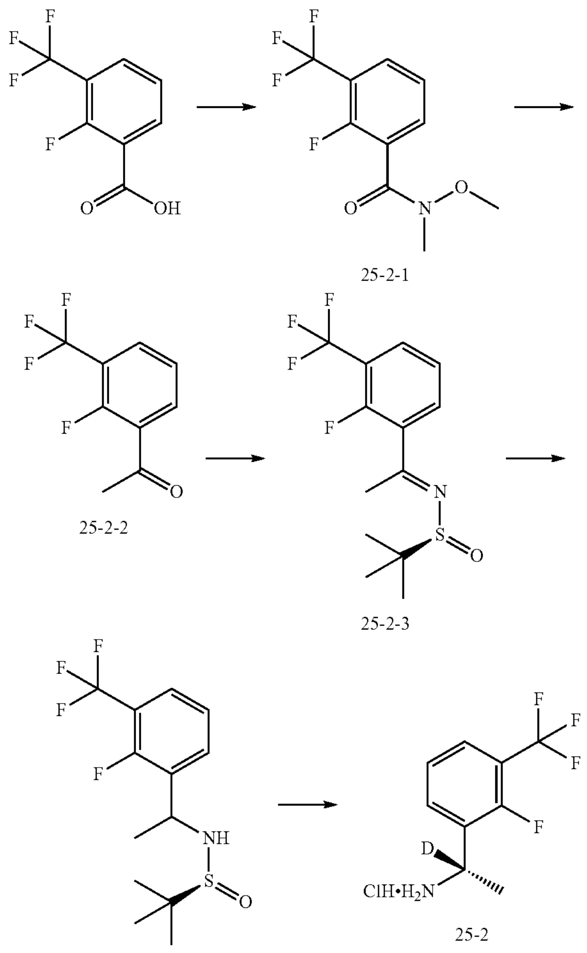

25-2-1

25-2-2

25-2-3

25-2-4

25-2

Step a: Preparation of Compound 25-2-1

To a 500 mL single-neck flask were added 2-fluorine-3-trifluoromethylbenzoic acid (15 g), N,N-dimethylformamide (100 mL), dimethylhydroxylamine hydrochloride (7.17 g), N,N-diisopropylethylamine (37.3 g) and 2-(7-azobenzotriazol)-N,N,N',N'-tetramethyluronium hexafluorophosphate (32.9 g). The mixture was stirred to react for 2.5 h at room temperature. The reaction was stopped, and the reaction solution was poured into water (500 mL) and extracted with ethyl acetate (200 mL). The organic phase was washed sequentially with water (200 mL) and saturated brine (100 mL), dried over anhydrous sodium sulfate and concentrated. The residue was separated and purified by silica gel column chromatography (petroleum ether:ethyl acetate=60:40) to obtain 17.4 g of compound 25-2-1.

MS (ESI, $[M+H]^+$): m/z=252.04.

$^1$H NMR (500 MHz, DMSO-$d_6$) δ 7.93-7.83 (m, 2H), 7.52 (t, J=7.8 Hz, 1H), 3.31 (s, 3H), 2.70 (s, 3H).

Step b: Preparation of Compound 25-2-2

A solution of 1 M methyl magnesium bromide in tetrahydrofuran (29.9 mL) was added dropwise to a stirred solution of the compound 25-2-1 (5 g) obtained in step a in extra dry tetrahydrofuran (50 mL) at 0° C. under nitrogen protection. After the addition was completed, the mixture was heated to 35° C. and stirred to react for 2 h. After the reaction was stopped, the reaction solution was slowly added with a saturated aqueous ammonium chloride solution (150 mL), stirred for 10 min at room temperature and left to stand for separation. The organic phase was taken and dried over anhydrous sodium sulfate, and concentrated to obtain 4 g of compound 25-2-2.

1H NMR (500 MHz, DMSO-$d_6$) δ 8.17-8.10 (m, 1H), 8.09-7.99 (m, 1H), 7.54 (t, J=7.8 Hz, 1H), 2.64 (d, J=4.1 Hz, 3H).

Step c: Preparation of Compound 25-2-3

To a 100 mL single-neck flask were added the compound 25-2-2 (4 g) obtained in step b, dry tetrahydrofuran (40 mL), (R)-(+)-tert-butylsulfinamide (2.352 g) and tetraethyl titanate (11.07 g). The mixture was heated to 80° C. and reacted for 3 h. After the reaction was stopped, the reaction solution was added with ice water (150 mL) and ethyl acetate (150 mL) under stirring at room temperature. The mixture was stirred for 5 min and filtered under vacuum; then the filtrate was separated. The organic phase was washed with saturated brine, dried over anhydrous sodium sulfate and concentrated to obtain 5.8 g of compound 25-2-3.

MS (ESI, $[M+H]^+$): m/z=309.97.

Step d: Preparation of Compound 25-2-4

The compound 25-2-3 (3 g) obtained in step c and tetrahydrofuran (30 mL) were sequentially added to a 250 mL three-necked flask. The mixture was cooled to −50° C. under nitrogen protection and added with sodium borodeuteride (0.731 g) in batches. After the addition was completed, the reaction solution was continuously stirred to react for 3 h with the temperature maintained. The reaction solution was added dropwise to heavy water (20 mL) to quench the reaction, and the resulting solution was extracted with ethyl acetate (30 mL×2). The organic phases were combined, dried over anhydrous sodium sulfate and concentrated; and the residue was separated and purified by silica gel column chromatography (petroleum ether:ethyl acetate=60:40) to obtain 0.62 g of compound 25-2-4.

MS (ESI, $[M+H]^+$): m/z=313.00.

$^1$H NMR (500 MHz, DMSO-$d_6$) δ 7.89 (t, J=7.2 Hz, 1H), 7.67 (t, J=7.2 Hz, 1H), 7.42 (t, J=7.8 Hz, 1H), 5.89 (s, 1H), 1-43 (s, 3H), 1.10 (s, 9H).

Step e: Preparation of Compound 25-2

The compound 25-2-4 (0.6 g) obtained in the step d, 1,4-dioxane (2 mL) and dioxane solution of 4 M hydrochloric acid (2.5 mL) were sequentially added to a 100 mL single-neck flask. The reaction solution was stirred to react for 2 h at room temperature and concentrated to dryness under reduced pressure; and the residue was slurried using methyl tert-butyl ether (5 mL) to obtain 0.38 g of compound 25-2.

MS (ESI, $[M-HCl+H]^+$): m/z=209.04.

$^1$H NMR (500 MHz, DMSO-$d_6$) δ 8.87 (s, 3H), 8.12 (t, J=7.2 Hz, 1H), 7.82 (t, J=7.3 Hz, 1H), 7.53 (t, J=7.8 Hz, 1H), 1.57 (s, 3H).

Step B: Preparation of Compound 25-3

Referring to the procedures of step A in Example 19, compound 25-3 was prepared by reacting the compound 25-2 prepared in step A above with the compound 20-1.

MS (ESI, $[M+H]^+$): m/z=559.14.

$^1$H NMR (500 MHz, DMSO-$d_6$) δ 9.30 (s, 1H), 9.13 (s, 1H), 8.99 (d, J=6.4 Hz, 1H), 7.84 (t, J=7.1 Hz, 1H), 7.65 (t, J=7.1 Hz, 1H), 7.40-7.31 (m, 5H), 7.30-7.24 (m, 1H), 3.66 (s, 2H), 3.05-2.92 (m, 2H), 2.83 (q, J=12.1 Hz, 2H), 2.45-2.35 (m, 5H), 1.92 (t, J=14.7 Hz, 2H), 1.64 (s, 3H).

Step C: Preparation of Compound 25-4

Compound 25-4 was prepared referring to the procedures of step C in Example 19.

MS (ESI, $[M+H]^+$): m/z=469.28.

Step D: Preparation of Compound 25

Referring to the procedures of step D in Example 19, compound 25 was prepared by reacting the compound 25-4 with methanesulfonyl chloride.

HRMS (ESI, $[M+H]^+$): m/z=547.1432.

$^1H$ NMR (500 MHz, $CD_3OD$) δ 9.11 (s, 1H), 8.85 (d, J=6.8 Hz, 1H), 7.75 (t, J=7.1 Hz, 1H), 7.57 (t, J=7.1 Hz, 1H), 7.28 (t, J=7.8 Hz, 1H), 4.00-3.86 (m, 2H), 3.81-3.74 (m, 2H), 2.98 (s, 3H), 2.68-2.62 (m, 2H), 2.50 (s, 3H), 2.23-2.20 (m, 2H), 1.72 (s, 3H).

Example 26: Preparation of Compound 26

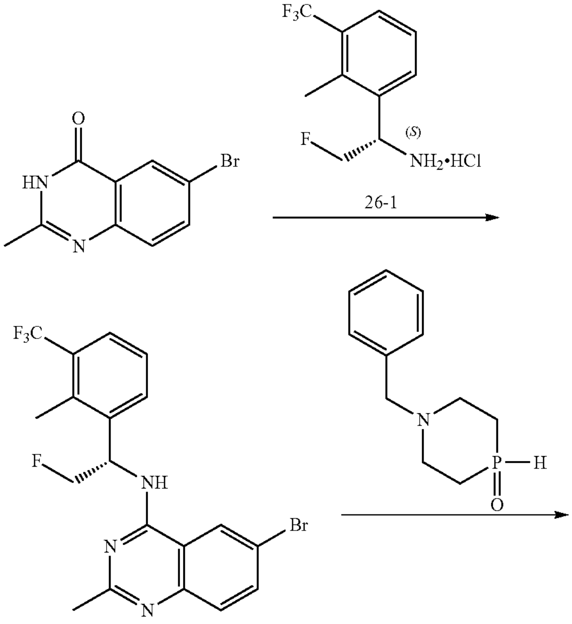

26-1

26-2

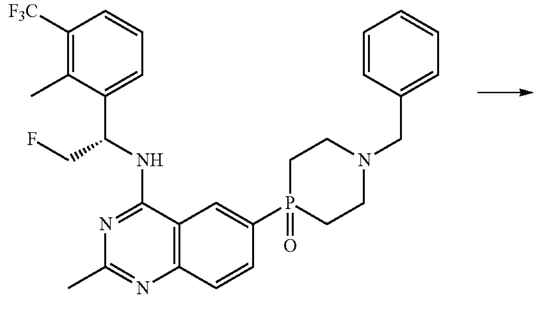

26-3

-continued

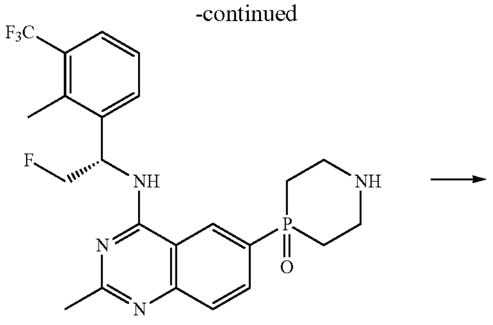

26-4

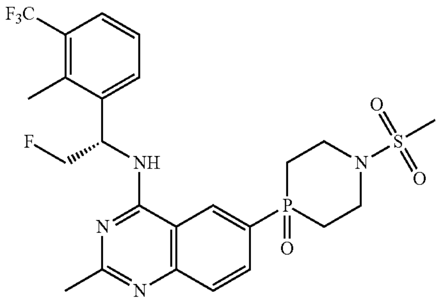

26

Step a: Preparation of Compound 26-1-1

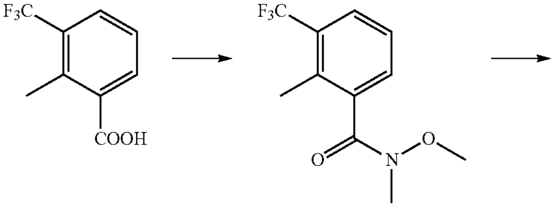

26-1-1

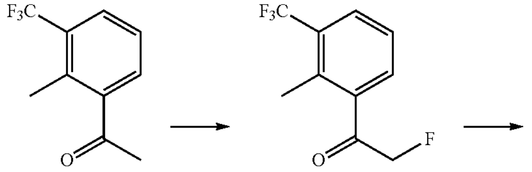

26-1-2

26-1-3

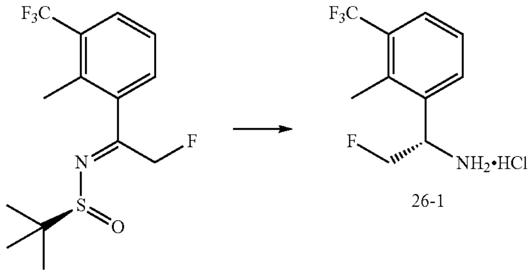

26-1-4

26-1

Referring to the procedures of step a in Example 25, compound 26-1-1 was prepared by replacing 2-fluorine-3-trifluoromethylbenzoic acid with 2-methyl-3-trifluoromethylbenzoic acid.

MS (ESI, $[M+H]^+$): m/z=248.07.

$^1H$ NMR (500 MHz, $CD_3OD$) δ 7.73 (d, J=7.9 Hz, 1H), 7.53 (d, J=7.6 Hz, 1H), 7.44 (t, J=8.0 Hz, 1H), 3.44 (s, 3H), 2.83 (s, 3H), 2.39 (s, 3H).

Step b: Preparation of Compound 26-1-2

Compound 26-1-2 was prepared referring to the procedures of step b in Example 25.

GCMS: $[M]^+$=202.

$^1H$ NMR (500 MHz, $CD_3OD$) δ 7.83 (d, J=7.8 Hz, 1H), 7.77 (dd, J=8.0, 1.2 Hz, 1H), 7.45 (t, J=7.8 Hz, 1H), 2.58 (s, 3H), 2.48 (q, J=1.8 Hz, 3H).

Step c: Preparation of Compound 26-1-3

A solution of 1 M lithium bis(trimethylsilyl)amide in tetrahydrofuran (17.68 mL) and dry tetrahydrofuran (50 mL) were sequentially added to a 100 mL three-necked flask. A solution of the compound 26-1-2 (2.75 g) obtained in step b in tetrahydrofuran (5 mL) was slowly added dropwise to the above reaction solution at −74° C. under nitrogen protection, and the mixture was stirred to react for 10 min at −74° C. Trimethylchlorosilane (1.921 g) was slowly added into the above reaction solution. After the addition was completed was completed after 2 min, the reaction solution was stirred to react for 1 h with the temperature maintained at −74° C., then warmed to the room temperature and continuously reacted for 20 min. After the reaction was completed, a saturated ammonium chloride solution (10 mL) was added to the reaction solution, and the mixture was vigorously stirred for 5 min. The reaction solution was extracted with ethyl acetate (10 mL×3). The organic phases were combined, dried over anhydrous sodium sulfate, filtered under vacuum and concentrated. The residue was dissolved in acetonitrile (50 mL), stirred at 0° C., added with an optional fluorine reagent (5.30 g), warm to room temperature and continuously stirred to react for 5 h. After the reaction was completed, the reaction solution was concentrated to dryness. The residue was added with water (20 mL) and extracted with ethyl acetate (40 mL×3). The organic phases were combined, dried over anhydrous sodium sulfate, filtered under vacuum and concentrated. The resulting residue was separated and purified by silica gel column chromatography (petroleum ether:ethyl acetate=91:10) to obtain 1.34 g of compound 26-1-3.

$^1H$ NMR (500 MHz, $CD_3OD$) δ 7.84 (dd, J=8.0, 1.2 Hz, 1H), 7.78 (d, J=7.8 Hz, 1H), 7.48 (t, J=7.9 Hz, 1H), 5.43 (d, J=46.9 Hz, 2H), 2.50 (q, J=1.8 Hz, 3H).

Step d: Preparation of Compound 26-1-4

Referring to the procedures of step c in Example 25, compound 26-1-4 was prepared by reacting the compound 26-1-3 obtained in step c above with S-tert-butylsulfinamide.

MS (ESI, $[M+H]^+$): m/z=324.10.

Step e: Preparation of Compound 26-1

The compound 26-1-4 (940 mg) obtained in step d and dry tetrahydrofuran (10 mL) were sequentially added to a 100 mL three-necked flask at −78° C. under nitrogen protection. A solution of 1 M lithium tri-sec-butylborohydride in tetrahydrofuran (51.0 mL) was slowly added into the above reaction solution. After the addition was completed, the mixture was stirred to react for 0.5 h −78° C. After the reaction was completed, the reaction solution was added dropwise to a saturated ammonium chloride solution (30 mL), vigorously stirred for 10 min, then warmed to room temperature, and extracted with ethyl acetate (50 mL×3). The organic phases were combined, dried over anhydrous sodium sulfate, filtered and concentrated; and the resulting residue was separated and purified by silica gel column chromatography (dichloromethane:methanol=98:2) to obtain 360 mg of a yellow oily liquid. To a 100 mL single-neck flask were sequentially added the yellow oily liquid obtained above, 1,4-dioxane (20 mL) and 1,4-dioxane solution of 4 M hydrogen chloride (0.857 mL). After the addition was completed, the mixture was stirred for 4 h at room temperature. The reaction solution was concentrated to dryness, and the residue was slurried with methyl tert-butyl ether (10 mL) to obtain 250 mg of compound 26-1.

MS (ESI, $[M+H]^+$): m/z=221.99.

$^1H$ NMR (500 MHz, $D_2O$) δ 7.83 (d, J=7.9 Hz, 1H), 7.66 (d, J=7.9 Hz, 1H), 7.52 (t, J=7.9 Hz, 1H), 5.22 (m, 1H), 4.90 (dd, J=10.8, 3.9 Hz, 1H), 4.86-4.81 (m, 1H), 2.53 (d, J=1.5 Hz, 3H).

Step B: Preparation of Compound 26-2

Referring to the procedures of step A in Example 19, compound 26-2 was prepared by replacing the compound 9-1 with 6-bromo-2-methyl-quinazolin-4(3H)-one.

MS (ESI, $[M+H+2]^+$): m/z=444.04.

Step C: Preparation of Compound 26-3

Compound 26-3 was prepared referring to the procedures of step B in Example 19.

MS (ESI, $[M+H]^+$): m/z=571.78.

Step D: Preparation of Compound 26-4

Compound 26-4 was prepared referring to the procedures of step C in Example 19.

MS (ESI, $[M+H]^+$): m/z=481.31.

Step E: Preparation of Compound 26

Compound 26 was prepared referring to the procedures of step D in Example 19.

HRMS (ESI, $[M+H]^+$) m/z=559.1558.

$^1H$ NMR (500 MHz, $CD_3OD$) δ 8.72 (dd, J=13.3, 1.7 Hz, 1H), 8.04 (ddd, J=10.2, 8.5, 1.7 Hz, 1H), 7.70 (dd, J=8.7, 2.5 Hz, 1H), 7.63 (d, J=7.8 Hz, 1H), 7.51 (d, J=7.9 Hz, 1H), 7.24 (t, J=7.9 Hz, 1H), 6.06 (m, 1H), 4.83 (dd, J=9.9, 7.9 Hz, 0.5H), 4.73-4.69 (m, 1H), 4.62 (dd, J=9.9, 4.8 Hz, 0.5H), 3.97 (m, 2H), 3.51 (q, J=11.8, 10.9 Hz, 2H), 2.88 (s, 3H), 2.61 (s, 3H), 2.53-2.43 (m, 2H), 2.40 (s, 3H), 2.23-2.10 (m, 2H).

$^{31}P$ NMR (202 MHz, $CD_3OD$) δ 32.62.

Example 27: Preparation of Compound 27

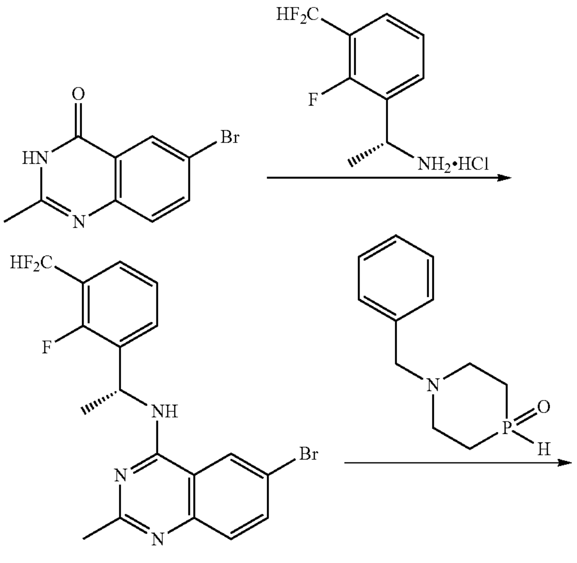

27-1

-continued

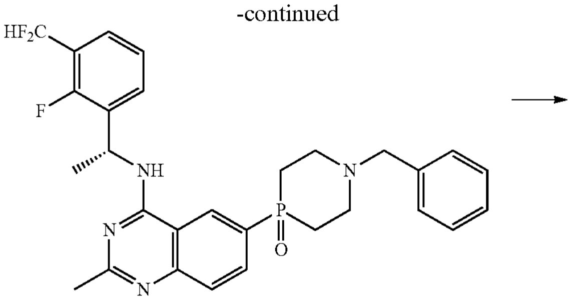

27-2

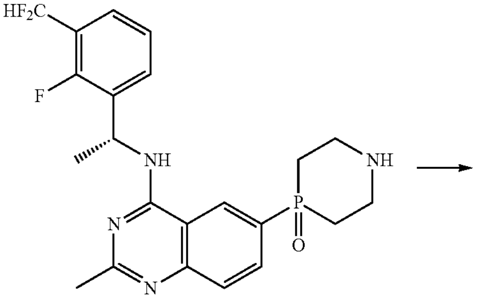

27-3

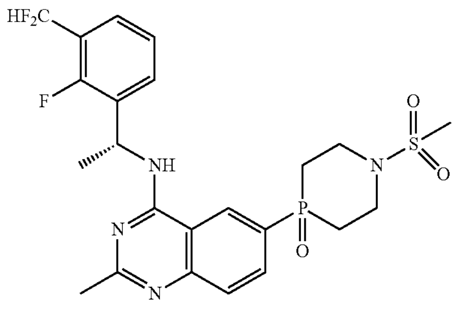

27

Step A: Preparation of Compound 27-1

Referring to the procedures of step A in Example 19, compound 27-1 was prepared by replacing the compound 9-1 with 6-bromo-2-methyl-quinazolin-4(3H)-one.

MS (ESI, $[M+H]^+$): m/z=410.05.

Step B: Preparation of Compound 27-2

Compound 27-2 was prepared referring to the procedures of step B in Example 19.

MS (ESI, $[M+H]^+$): m/z=539.15.

Step C: Preparation of Compound 27-3

Compound 27-3 was prepared referring to the procedures of step C in Example 19.

MS (ESI, $[M+H]^+$): m/z=449.15.

Step D: Preparation of Compound 27

Referring to the procedures of step D in Example 19, compound 27 was prepared by reacting the compound 27-3 with methanesulfonyl chloride.

HRMS (ESI, $[M+H]^+$): m/z=527.1489.

$^1$H NMR (500 MHz, $CD_3OD$) δ 8.80 (dd, J=13.2, 1.1 Hz, 1H), 8.20-8.04 (m, 1H), 7.78 (dd, J=8.6, 2.4 Hz, 1H), 7.63 (t, J=7.4 Hz, 1H), 7.48 (t, J=6.9 Hz, 1H), 7.23 (t, J=7.7 Hz, 1H), 7.01 (t, J=54.9 Hz, 1H), 5.87 (q, J=7.1 Hz, 1H), 4.05 (m, 2H), 3.62 (q, J=11.1 Hz, 2H), 3.00-2.96 (m, 3H), 2.63-2.53 (m, 2H), 2.49-2.44 (m, 3H), 2.25 (t, J=16.0 Hz, 2H), 1.72 (d, J=7.1 Hz, 3H).

Example 28: Preparation of Compound 28

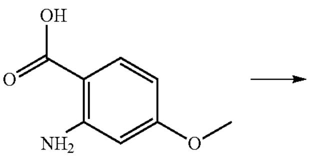

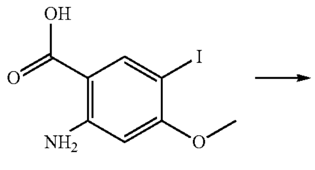

28-1

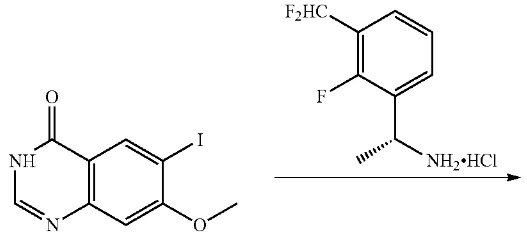

28-2

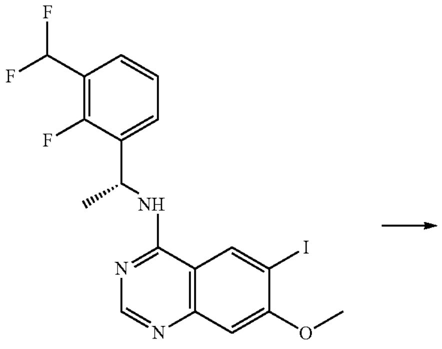

28-3

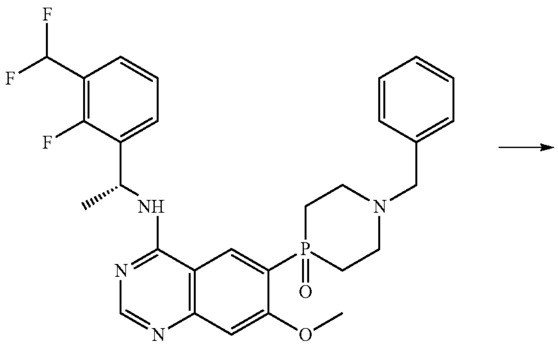

28-4

-continued

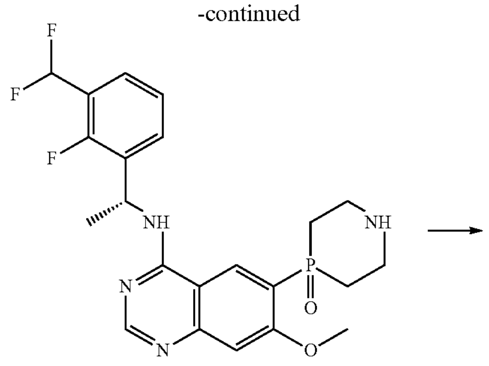

28-5

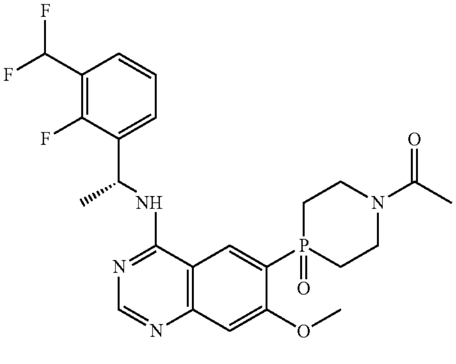

28

Step A: Preparation of Compound 28-1

To a 25 mL single-neck flask were sequentially added 2-amino-4-methoxybenzoic acid (1 g), ethylene glycol monomethyl ether (10 mL) and N-iodosuccinimide (1-48 g), and the mixture was stirred to react for 3 h at room temperature. The reaction was stopped, and a saturated sodium chloride solution (100 mL) was added to the reaction solution. The aqueous phase was extracted with ethyl acetate (100 mL×2), the organic phases were combined and concentrated, and the residue was separated by silica gel column chromatography (petroleum ether:ethyl acetate=3:2) to obtain 1.34 g of compound 28-1.

MS (ESI, $[M-H]^-$): m/z=291.79.

$^1$H NMR (500 MHz, DMSO-$d_6$) δ 7.98 (s, 1H), 6.35 (s, 1H), 3.78 (s, 3H), 2.57 (s, 2H).

Step B: Preparation of Compound 28-2

The compound 28-1 (1.3 g) obtained in step A above, 2-methoxyethanol (13 mL) and formamidine acetate (0.924 g) were sequentially added to a 50 mL single-neck flask, and the mixture was stirred to react for 2 h at 120° C. After the reaction was completed, the reaction solution was cooled to room temperature and filtered under vacuum; and the filter cake was washed with methanol (10 mL), collected and slurried with methanol (30 mL). The reaction solution was then filtered under vacuum; and the filter cake was collected and dried to obtain 0.95 g of compound 28-2. MS (ESI, $[M+H]^+$): m/z=302.81.

Step C: Preparation of Compound 28-3

To a 50 mL single-neck flask were sequentially added the compound 28-2 (0.5 g) obtained in step B above, N,N-dimethylformamide (10 mL) and 1H-benzotriazol-1-yl-oxytripyrrolidinyl hexafluorinephosphate (1.723 g). The mixture was added dropwise with a solution of 2,3,4,6,7,8,9,10-octahydropyrimidyl[1,2-a]azepine (0.756 g) and (R)-1-(3-(difluorinemethyl)-2-fluorinephenyl)ethan-1-amine hydrochloride (0.344 g) in N,N-dimethylformamide (10 mL) under stirring at room temperature. After the addition was completed, the reaction solution was stirred to react overnight at room temperature. The reaction was stopped, and the reaction solution was added with purified water (100 mL) and extracted with ethyl acetate (100 mL×2). The organic phases were combined and concentrated, and the residue was subjected to silica gel column chromatography (petroleum ether:ethyl acetate=5:1) to obtain 0.422 g of compound 28-3.

MS (ESI, $[M+H]^+$): m/z=473.97.

$^1$H NMR (500 MHz, DMSO-$d_6$) δ 9.01 (s, 1H), 8.51 (d, J=7.3 Hz, 1H), 8.36 (s, 1H), 7.65 (t, J=7.2 Hz, 1H), 7.50 (t, J=7.1 Hz, 1H), 7.37-7.12 (m, 2H), 7.10 (s, 1H), 5.81-5.71 (m, 1H), 3.96 (s, 3H), 1.59 (d, J=7.1 Hz, 3H).

Step D: Preparation of Compound 28-4

Referring to the procedures of step A in Example 10, compound 28-4 was prepared using the compound 28-3.

MS (ESI, $[M+H]^+$): m/z=555.14.

$^1$H NMR (500 MHz, DMSO-$d_6$) δ 8.94 (d, J=7.4 Hz, 1H), 8.81 (d, J=13.6 Hz, 1H), 8.39 (s, 1H), 7.67 (t, J=7.5 Hz, 1H), 7.50 (t, J=7.1 Hz, 1H), 7.39-7.34 (m, 4H), 7.31-7.12 (m, 4H), 5.86-5.76 (m, 1H), 4.02 (s, 3H), 3.70 (s, 2H), 3.08-2.82 (m, 4H), 2.51 (d, J=22.5 Hz, 4H), 1.60 (d, J=7.1 Hz, 3H).

Step E: Preparation of Compound 28-5

Acetonitrile (50 mL), ceric ammonium nitrate (2.471 g) and water (10 mL) were sequentially added to a 100 mL single-neck flask, and the mixture was stirred for 2 min until it was completely dissolved. The reaction solution was added with the compound 28-4 (0.5 g) obtained in step D above and stirred to react for 1 h at room temperature.

The reaction was stopped, and a saturated aqueous sodium bicarbonate solution was added to the reaction solution to quench the reaction. The reaction solution was extracted with dichloromethane (100 mL×2); and the organic phases were combined, washed sequentially with water (100 mL) and a saturated aqueous sodium chloride solution (100 mL), dried over anhydrous sodium sulfate and filtered under vacuum. The filtrate was concentrated, and the residue was subjected to silica gel column chromatography (dichloromethane:methanol=20:1) to obtain 0.208 g of compound 28-5.

MS (ESI, $[M+H]^+$): m/z=465.2

$^1$H NMR (500 MHz, DMSO-$d_6$) δ 8.93 (d, J=7.4 Hz, 1H), 8.79 (d, J=13.5 Hz, 1H), 8.38 (s, 1H), 7.68 (t, J=7.4 Hz, 1H), 7.50 (t, J=7.1 Hz, 1H), 7.36-7.12 (m, 3H), 5.86-5.76 (m, 1H), 3.99 (s, 3H), 3.16-3.06 (m, 4H), 2.44-2.34 (m, 2H), 1.84-1.74 (m, 2H), 1.61 (d, J=7.2 Hz, 3H), 1-40 (s, 1H).

Step E: Preparation of Compound 28

Referring to the procedures of step C in Example 10, compound 28 was prepared by reacting the compound 28-5 with acetic anhydride.

HRMS (ESI, $[M+H]^+$): m/z=507.1772.

$^1$H NMR (500 MHz, DMSO-$d_6$) δ 8.97 (d, J=7.3 Hz, 1H), 8.87-8.77 (m, 1H), 8.39 (d, J=1.7 Hz, 1H), 7.73-7.63 (m, 1H), 7.50 (t, J=7.1 Hz, 1H), 7.36-7.12 (m, 3H), 5.86-5.76 (m, 1H), 4.47-4.37 (m, 1H), 4.09-3.99 (m, 1H), 3.94 (s, 3H), 3.81-3.69 (m, 1H), 3.41-3.31 (m, 1H), 2.49-2.30 (m, 2H), 2.13 (s, 3H), 2.03-1.84 (m, 2H), 1.61 (d, J=7.1 Hz, 3H).

Example 29: Preparation of Compound 29

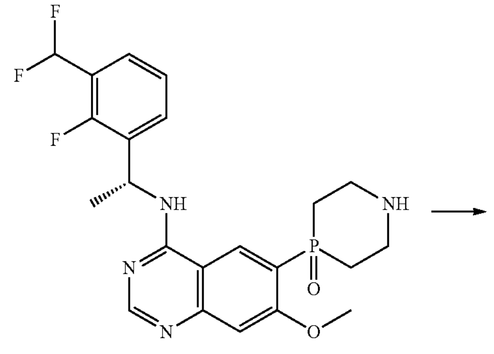

28-5

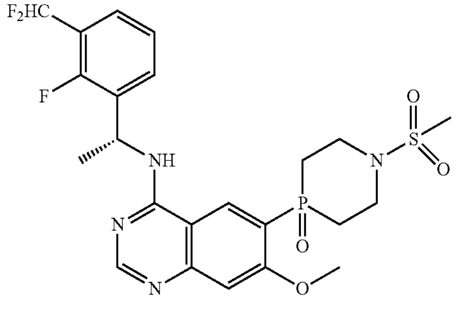

29

Step A: Preparation of Compound 29

Referring to the procedures of step D in Example 19, compound 29 was prepared by reacting the compound 28-5 with methanesulfonyl chloride.

HRMS (ESI, $[M+H]^+$): m/z=543.1441.

$^1H$ NMR (500 MHz, DMSO-$d_6$) δ 8.98 (d, J=7.4 Hz, 1H), 8.86 (d, J=14.0 Hz, 1H), 8.40 (s, 1H), 7.68 (t, J=7.3 Hz, 1H), 7.51 (t, J=7.1 Hz, 1H), 7.37-7.10 (m, 3H), 5.86-5.76 (m, 1H), 3.98 (s, 3H), 3.97-3.87 (m, 2H), 3.55-3.450 (m, 2H), 3.04 (s, 3H), 2.55 (d, J=13.7 Hz, 2H), 2.09-1.96 (m, 2H), 1.61 (d, J=7.1 Hz, 3H).

Example 30: Preparation of Compound 30

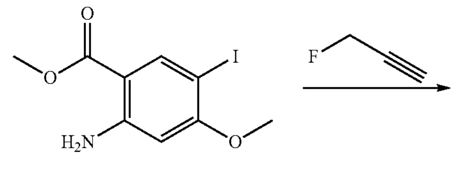

1-1

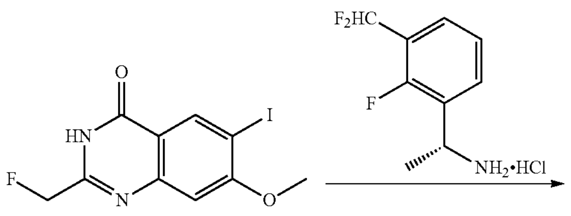

30-1

-continued

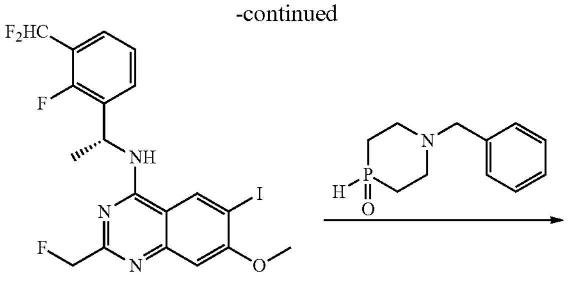

30-2

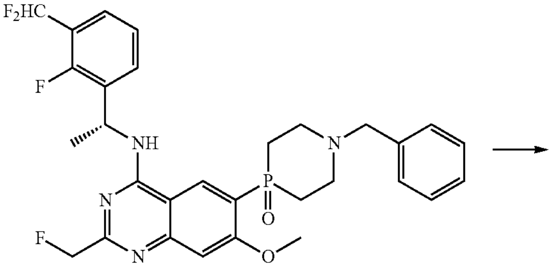

30-3

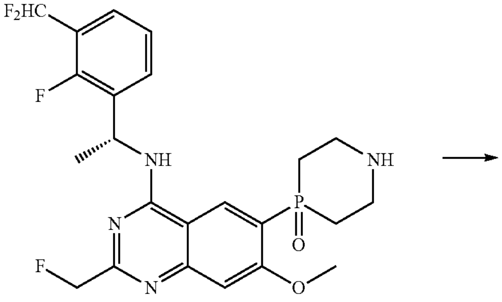

30-4

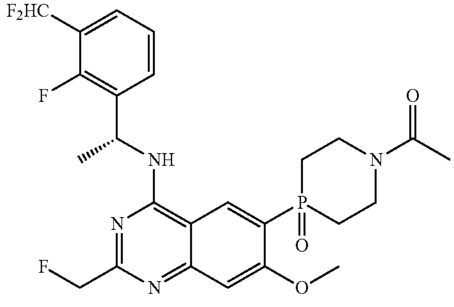

30

Step A: Preparation of Compound 30-1

The compound 1-1 (1 g), fluorineacetonitrile (1.923 g) and methanesulfonic acid (2.504 g) were sequentially added to a 15 mL pressure-resistant flask, and the reaction flask was placed in an oil bath at 120° C. and stirred to react for 4 h. The reaction was stopped, and the reaction solution was naturally cooled to room temperature. The reaction solution was concentrated, added with 4 M aqueous sodium hydroxide solution to directly adjust the pH to alkalinity, and filtered under vacuum. The filter cake was washed with a large amount of water. The solid was collected and dried to obtain 0.68 g of a compound 30-1.

MS (ESI, $[M+H]^+$): m/z=334.74.

Step B: Preparation of Compound 30-2

Referring to the procedures of step A in Example 19, compound 30-2 was prepared by replacing (R)-1-(3-(trifluoromethyl)-2-fluorinephenyl)ethan-1-amine hydrochloride with (R)-1-(3-(difluorinemethyl)-2-fluorinephenyl) ethan-1-amine hydrochloride.

MS (ESI, $[M+H]^+$): m/z=505.99.

$^1$H NMR (500 MHz, DMSO-$d_6$) δ 8.99 (s, 1H), 8.63 (d, J=7.3 Hz, 1H), 7.70 (t, J=7.3 Hz, 1H), 7.51 (t, J=6.9 Hz, 1H), 7.30 (t, J=7.7 Hz, 1H), 7.23 (t, J=54.4 Hz, 1H), 7.16 (s, 1H), 5.82-5.76 (m, 1H), 5.29-5.09 (m, 2H), 3.96 (s, 3H), 1.60 (d, J=7.1 Hz, 3H).

Step C: Preparation of Compound 30-3

Compound 30-3 was prepared referring to the procedures of step A in Example 10.

MS (ESI, $[M+H]^+$): m/z=587.20.

$^1$H NMR (500 MHz, DMSO-$d_6$) δ 9.06 (d, J=7.4 Hz, 1H), 8.80 (d, J=13.6 Hz, 1H), 7.72 (t, J=7.3 Hz, 1H), 7.50 (t, J=6.9 Hz, 1H), 7.40-7.34 (m, 4H), 7.32-7.25 (m, 3H), 7.23 (t, J=54.5 Hz, 1H), 5.82 (p, J=7.0 Hz, 1H), 5.32-5.13 (m, 2H), 4.02 (s, 3H), 3.69 (s, 2H), 3.03-2.95 (m, 2H), 2.86 (q, J=11.7 Hz, 2H), 2.50-2.47 (m, 2H), 1.85 (t, J=16.4 Hz, 2H), 1.62 (d, J=7.1 Hz, 3H).

Step D: Preparation of Compound 30-4

Compound 30-4 was prepared referring to the procedures of step B in Example 10.

MS (ESI, $[M+H]^+$) m/z=497.16.

Step E: Preparation of compound 30

Referring to the procedures of step C in Example 10, compound 30 was prepared by reacting the compound 30-4 with acetic anhydride.

HRMS (ESI, $[M+H]^+$): m/z=539.1835.

$^1$H NMR (500 MHz, $CD_3OD$) δ 8.69 (d, J=14.3 Hz, 1H), 7.63 (t, J=7.4 Hz, 1H), 7.47 (t, J=7.0 Hz, 1H), 7.26-7.24 (m, 2H), 7.00 (m, 1H), 5.83 (q, J=7.0 Hz, 1H), 5.24 (dt, J=48.0, 13.5 Hz, 2H), 4.67-4.59 (m, 1H), 4.24- 4.16 (m, 1H), 4.02 (s, 3H), 3.90-3.87 (m, 1H), 3.54-3.47 (m, 1H), 2.67-2.54 (m, 2H), 2.24 (s, 3H), 2.20-2.02 (m, 2H), 1.70 (d, J=7.1 Hz, 3H).

Example 31: Preparation of Compound 31

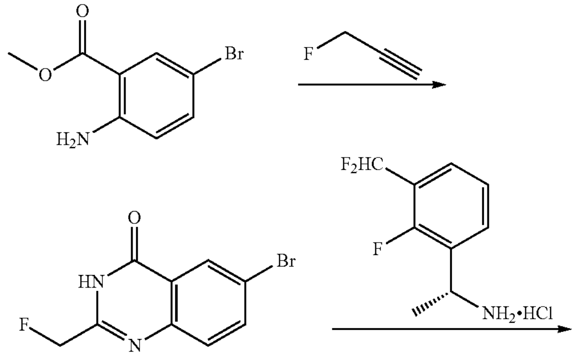

31-1

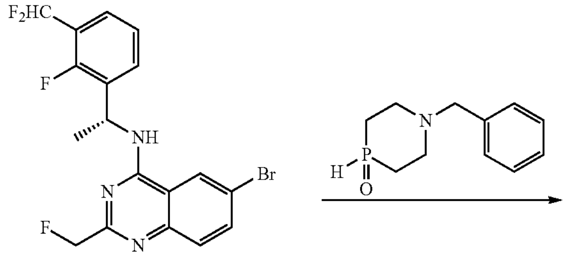

31-2

-continued

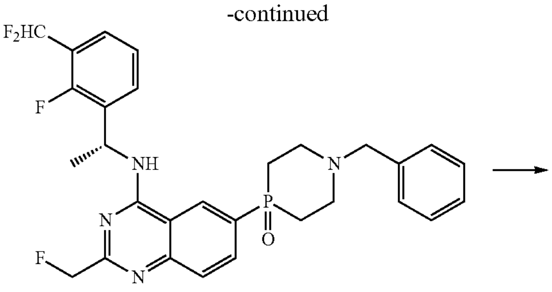

31-3

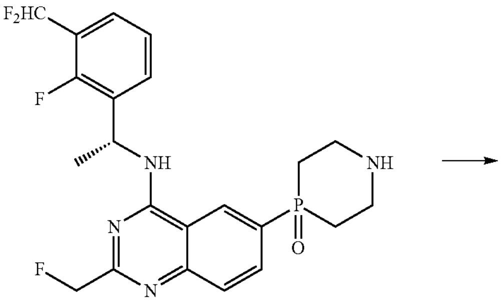

31-4

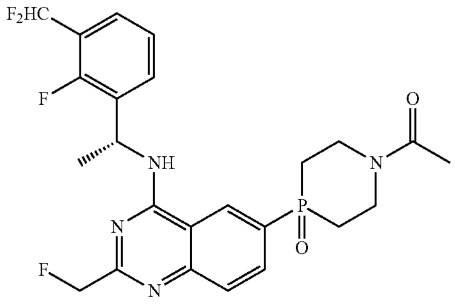

31

Step A: Preparation of Compound 31-1

Referring to the procedures of step B in Example 24, compound 31-1 was prepared by replacing the compound 24-1 with methyl 2-amino-5-bromobenzoate.

MS (ESI, $[M+H]^+$): m/z=256.94.

$^1$H NMR (500 MHz, DMSO-$d_6$) δ 12.74 (br, 1H), 8.20 (d, J=2.0 Hz, 1H), 7.99 (dd, J=8.7, 2.3 Hz, 1H), 7.65 (d, J=8.7 Hz, 1H), 5.36 (s, 1H), 5.26 (s, 1H).

Step B: Preparation of Compound 31-2

Compound 31-2 was prepared referring to the procedures of step A in Example 19.

MS (ESI, $[M+H]^+$): m/z=428.03.

$^1$H NMR (500 MHz, DMSO-$d_6$) δ 8.79 (t, J=4.9 Hz, 2H), 7.93 (dd, J=8.9, 1.9 Hz, 1H), 7.70 (t, J=7.8 Hz, 1H), 7.66 (d, J=8.9 Hz, 1H), 7.51 (t, J=6.9 Hz, 1H), 7.30 (t, J=7.7 Hz, 1H), 7.23 (t, J=54.4 Hz, 1H), 5.83-5.75 (m, 1H), 5.33-5.13 (m, 2H), 1.62 (d, J=7.0 Hz, 3H).

Step C: Preparation of Compound 31-3

Compound 31-3 was prepared referring to the procedures of step B in Example 19.

MS (ESI, $[M+H]^+$): m/z=557.13.

$^1$H NMR (500 MHz, DMSO-$d_6$) δ 9.08 (d, J=7.2 Hz, 1H), 8.90 (d, J=12.2 Hz, 1H), 8.14 (t, J=9.0 Hz, 1H), 7.81 (dd, J=8.5, 1.8 Hz, 1H), 7.71 (t, J=7.3 Hz, 1H), 7.51 (t, J=6.9 Hz, 1H), 7.37-7.34 (m, 4H), 7.31-7.25 (m, 2H), 7.23 (m, 1H), 5.83 (m, 1H), 5.25 (m, 2H), 3.66 (s, 2H), 3.02-2.88 (m, 2H), 2.85-2.78 (m, 2H), 2.42-2.35 (m, 2H), 1.99 (t, J=15.6 Hz, 2H), 1.65 (d, J=7.1 Hz, 3H).

Step D: Preparation of Compound 31-4

Compound 31-4 was prepared referring to the procedures of step B in Example 10.

MS (ESI, $[M+H]^+$): m/z=467.20.

Step E: Preparation of Compound 31

Referring to the procedures of step E in Example 30, compound 31 was prepared by reacting the compound 31-4 with acetic anhydride.

HRMS (ESI, $[M+H]^+$): m/z=509.1730.

$^1$H NMR (500 MHz, $CD_3OD$) δ 8.81 (d, J=13.1 Hz, 1H), 8.22-8.11 (m, 1H), 7.91 (dd, J=8.6, 2.4 Hz, 1H), 7.64 (t, J=7.3 Hz, 1H), 7.48 (t, J=7.0 Hz, 1H), 7.24 (t, J=7.7 Hz, 1H), 7.00 (t, J=54.9 Hz, 1H), 5.85 (q, J=7.0 Hz, 1H), 5.27 (td, J=47.5, 13.5 Hz, 2H), 4.61-4.47 (m, 1H), 4.18-4.09 (m, 1H), 3.96-3.89 (m, 1H), 3.62 (dd, J=22.6, 10.9 Hz, 1H), 2.57-2.41 (m, 2H), 2.29-2.11 (m, 5H), 1.72 (d, J=7.1 Hz, 3H).

$^{31}$P NMR (202 MHz, $CD_3OD$) δ 34.37.

Example 32: Preparation of Compound 32

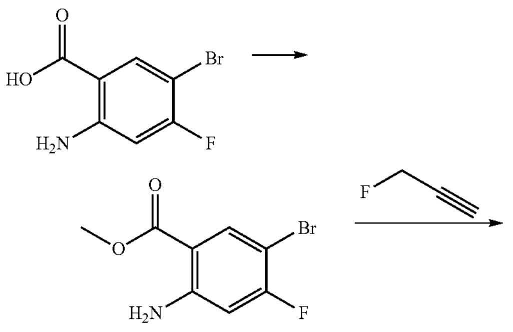

32-1

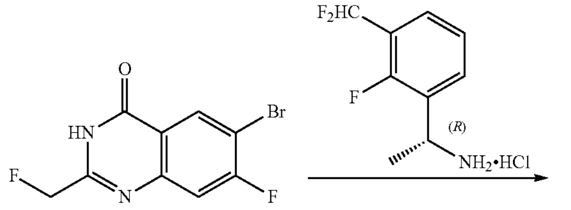

32-2

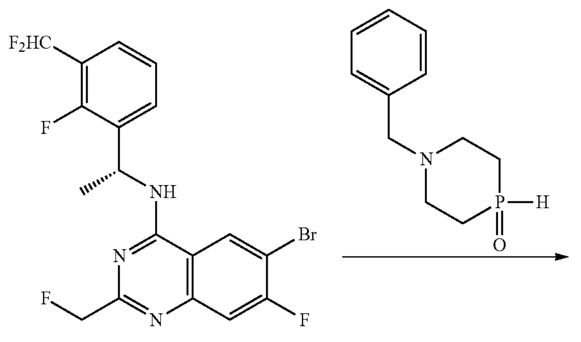

32-3

-continued

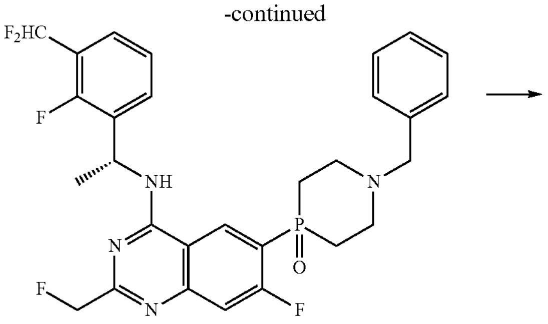

32-4

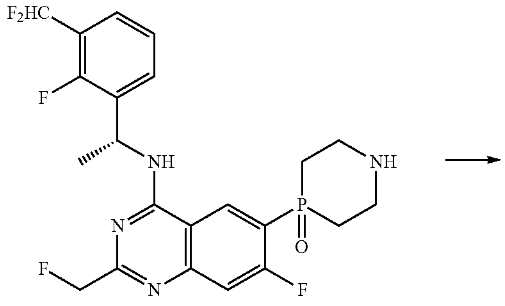

32-5

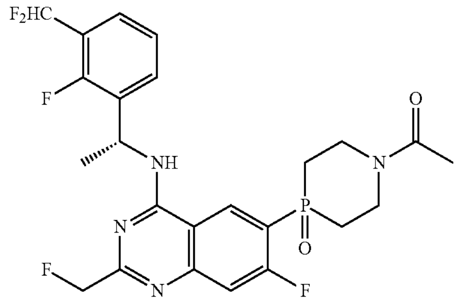

32

Step A: Preparation of Compound 32-1

Referring to the procedures of step A in Example 24, compound 32-1 was prepared by replacing 5-amino-2-chloropyridine-4-carboxylic acid with 2-amino-5-bromo-4-fluorinebenzoic acid.

MS (ESI, $[M+H]^+$): m/z=249.05.

$^1$H NMR (500 MHz, DMSO-$d_6$) δ 7.90 (d, J=8.1 Hz, 1H), 7.01 (s, 2H), 6.72 (d, J=11.5 Hz, 1H), 3.79 (s, 3H).

Step B: Preparation of Compound 32-2

Compound 32-2 was prepared referring to the procedures of step B in Example 24.

$^1$H NMR (500 MHz, DMSO-$d_6$) δ 12.78 (s, 1H), 8.35 (d, J=7.6 Hz, 1H), 7.69 (d, J=9.7 Hz, 1H), 5.36 (s, 1H), 5.27 (s, 1H).

Step C: Preparation of Compound 32-3

Compound 32-3 was prepared referring to the procedures of step A in Example 19.

MS (ESI, $[M+H+2]^+$): m/z=448.02.

$^1$H NMR (500 MHz, DMSO-$d_6$) δ 8.98 (d, J=7.5 Hz, 1H), 8.85 (d, J=7.2 Hz, 1H), 7.70 (dd, J=7.5 Hz, 1H), 7.65 (d, J=9.9 Hz, 1H), 7.52 (dd, J=7.1 Hz, 1H), 7.35-7.10 (m, 2H), 5.78 (p, J=7.1 Hz, 1H), 5.33-5.11 (m, 2H), 1.62 (d, J=7.1 Hz, 3H).

Step D: Preparation of Compound 32-4

Compound 32-4 was prepared referring to the procedures of step B in Example 19.

MS (ESI, $[M+H]^+$): m/z=575.11.

$^1$H NMR (500 MHz, $CD_3OD$) δ 8.70-8.64 (m, 1H), 7.52 (dd, J=7.9 Hz, 1H), 7.37 (m, 2H), 7.28-7.24 (m, 2H), 7.21 (dd, J=7.5 Hz, 2H), 7.17-7.10 (m, 2H), 6.88 (t, J=54.9 Hz, 1H), 5.72 (q, J=7.0 Hz, 1H), 5.14 (m, 2H), 3.58 (s, 2H), 3.05-2.79 (m, 4H), 2.44 (m, 2H), 2.10 m, 2H), 1.60 (d, J=7.1 Hz, 3H).

Step E: Preparation of Compound 32-5

Compound 32-5 was prepared referring to the procedures of step C in Example 19.

MS (ESI, $[M+H]^+$): m/z=485.15.

Step F: Compound 32 was Prepared Referring to the Procedures of Step C in Example 10.

HRMS (ESI, $[M+H]^+$): m/z=527.1646.

$^1$H NMR (500 MHz, $CD_3OD$) δ 8.80 (dd, J=13.5, 6.7 Hz, 1H), 7.64 (t, J=7.5 Hz, 1H), 7.49 (m, 2H), 7.24 (t, J=7.7 Hz, 1H), 6.99 (t, J=54.9 Hz, 1H), 5.84 (q, J=7.1 Hz, 1H), 5.25 (m, 2H), 4.64-4.11 (m, 2H), 4.00-3.57 (m, 2H), 2.59-2.43 (m, 2H), 2.38-2.24 (m, 2H), 2.22 (s, 3H), 1.72 (d, J=7.2 Hz. 3H).

$^{31}$P NMR (202 MHz, $CD_3OD$) δ 31.37.

Example 33: Preparation of Compound 33

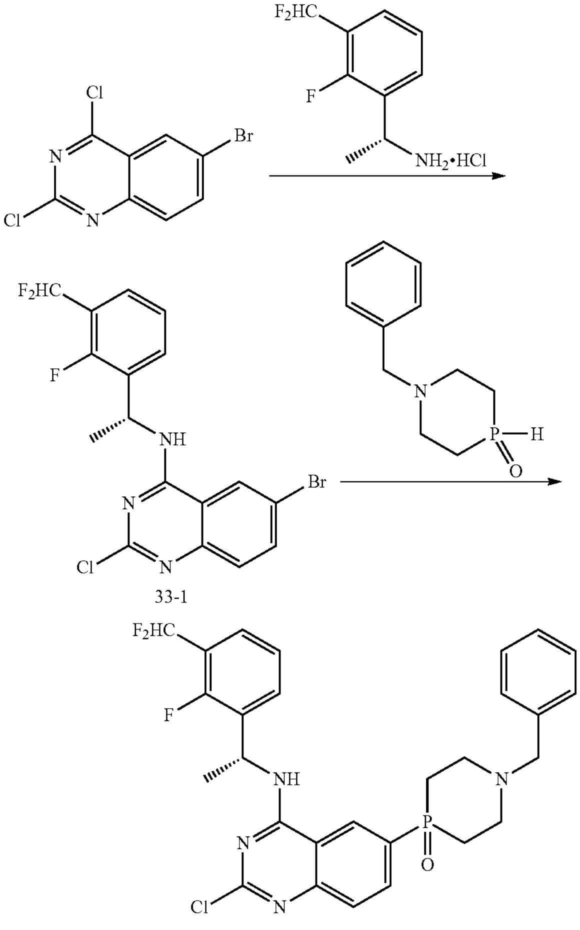

33-1

33-2

-continued

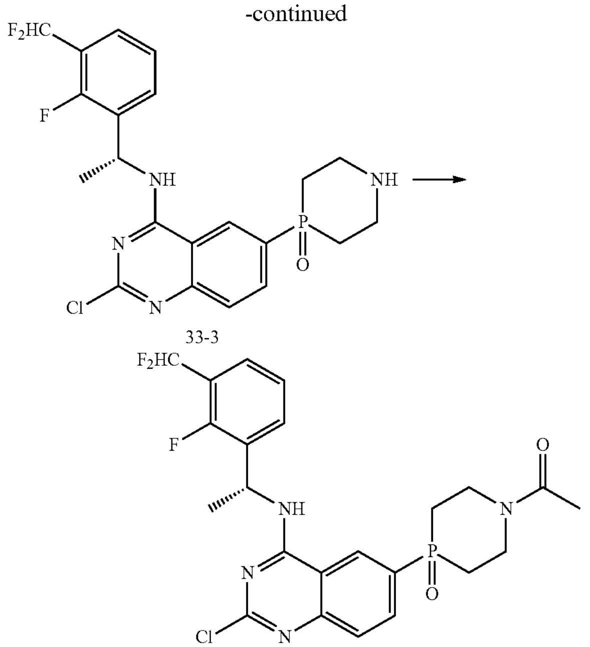

33-3

33

Step A: Preparation of Compound 33-1

To a 25 mL single-neck flask were added 6-bromo-2,4-dichloroquinazoline (0.5 g), (R)-1-(3-(difluorinemethyl)-2-fluorinephenyl)ethan-1-amine hydrochloride (0.447 g), N,N-diisopropylethylamine (0.689 g) and acetonitrile (3 mL), and the reaction solution was stirred to react for 2 h at room temperature. After the reaction was completed, the reaction solution was concentrated to dryness, and the residue was separated and purified by silica gel column chromatography (petroleum ether:ethyl acetate=80:20) to obtain 0.7 g of compound 33-1.

MS (ESI, $[M+H+2]^+$): m/z=432.00.

$^1$H NMR (500 MHz, DMSO-$d_6$) δ 9.10 (d, J=7.3 Hz, 1H), 8.81 (d, J=2.1 Hz, 1H), 7.96 (dd, J=8.8, 2.1 Hz, 1H), 7.70 (t, J=7.5 Hz, 1H), 7.58 (d, J=8.9 Hz, 1H), 7.54 (t, J=7.1 Hz, 1H), 7.37-7.32 (m, 1H), 7.32-7.07 (m, 1H), 5.70 (m, 1H), 1.62 (d, J=7.0 Hz, 3H).

Step B: Preparation of Compound 33-2

To a 25 mL single-neck flask were added the compound 33-1 obtained in step A (0.5 g), 1-benzyl-1,4-azaphosphane 4-oxide (0.267 g), 4,5-bis(diphenylphosphino)-9,9-dimethylxanthene (0.134 g), tris(dibenzylideneacetone)dipalladium (0.106 g), N,N-diisopropylethylamine (0.225 g) and 1,4-dioxane (10 mL).

The reaction solution was heated to 70° C. in an oil bath under nitrogen protection and stirred to react for 2 h. The reaction solution was cooled to room temperature and filtered under vacuum. The filtrate was concentrated to dryness, and the residue was separated and purified by silica gel column chromatography (dichloromethane:methanol=95:5) to obtain 0.5 g of compound 33-2.

MS (ESI, $[M+H]^+$): m/z=559.09.

$^1$H NMR (500 MHz, DMSO-$d_6$) δ 9.41 (d, J=7.3 Hz, 1H), 8.92 (d, J=12.1 Hz, 1H), 8.27 (br, 1H), 8.17 (t, J=9.1 Hz, 1H), 7.77-7.68 (m, 2H), 7.55 (t, J=7.2 Hz, 1H), 7.39-7.34 (m, 4H), 7.33 (d, J=7.9 Hz, 1H), 7.29 (dd, J=6.0, 2.9 Hz, 1H), 5.82-5.69 (m, 1H), 3.62 (dt, J=6.6, 3.3 Hz, 1H), 3.15 (m, 1H), 3.03-2.86 (m, 2H), 2.81 (q, J=11.8 Hz, 2H), 2.43-2.31 (m, 2H), 1.98 (t, J=15.7 Hz, 2H), 1.66 (d, J=7.0 Hz, 3H).

Step C: Preparation of Compound 33-3

To a 100 mL single-neck flask were added the compound 33-2 (0.18 g) obtained in step B, ceric ammonium nitrate (0.883 g), acetonitrile (20 mL) and water (4 mL), and the reaction solution was stirred to react for 1 h at room temperature. The reaction solution was added with a saturated aqueous sodium bicarbonate solution to quench the reaction and extracted with dichloromethane (30 mL×3). The organic phase was washed sequentially with water and saturated aqueous sodium chloride, dried over anhydrous sodium sulfate and filtered under vacuum. The filtrate was concentrated to dryness to obtain 0.3 g of crude compound 33-3, which was directly used in the next step.

MS (ESI, [M+H]+): m/z=469.12.

Step D: Preparation of Compound 33

Referring to the procedures of step C in Example 10, compound 33 was prepared by reacting the compound 33-3 with acetic anhydride.

HRMS (ESI, $[M+H]^+$): m/z=511.1277.

$^1H$ NMR (500 MHz, $CDCl_3$) δ 8.79 (d, J=13.0 Hz, 1H), 7.81 (q, J=6.2, 5.6 Hz, 2H), 7.65-7.41 (m, 3H), 7.17 (q, J=7.5 Hz, 1H), 6.88 (td, J=55.0, 3.0 Hz, 1H), 5.79 (t, J=7.1 Hz, 1H), 4.76-4.54 (m, 1H), 4.14-3.84 (m, 2H), 3.58 (q, J=12.0 Hz, 1H), 2.33-2.24 (m, 1H), 2.20 (d, J=8.8 Hz, 3H), 2.09 (s, 3H), 1.71 (t, J=6.0 Hz, 3H). $^{31}P$ NMR (202 MHz, $CDCl_3$) δ 29.70.

Example 34: Preparation of Compound 34

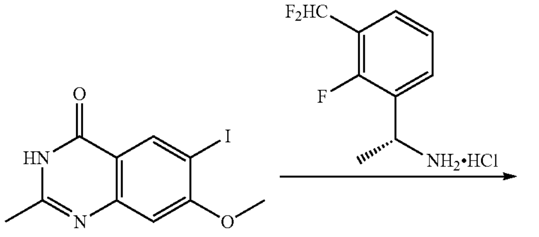

1-2

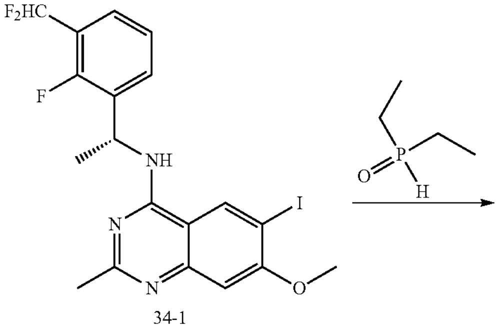

34-1

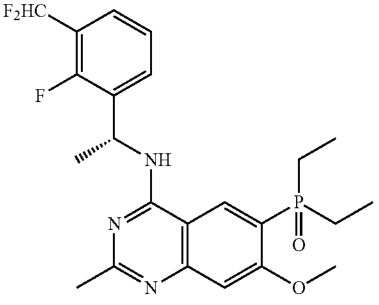

34

Step A: Preparation of Compound 34-1

Referring to the procedures of step A in Example 19, Compound 34-1 was prepared by reacting (R)-1-(3-(difluorinemethyl)-2-fluorinephenyl)ethan-1-amine hydrochloride replaced by (R)-1-(3-(trifluoromethyl)-2-fluorinephenyl)ethan-1-amine hydrochloride with the compound 1-2.

MS (ESI, $[M+H]^+$): m/z=488.02.

Step B: Preparation of Compound 34

To a 5 mL microwave tube were added the compound 34-1 (0.075 g) obtained in step A, diethylphosphine oxide (0.016 g), N,N-diisopropylethylamine (0.04 g), 4,5-bis(diphenylphosphino)-9,9-dimethylxanthene (8.9 mg), tris(dibenzylideneacetone)dipalladium (7.05 mg) and N,N-dimethylformamide (3 mL). After the addition was completed, the reaction solution was heated to 170° C. under 150 W in the microwave reactor after being purged with nitrogen and reacted for 35 min. After the reaction was completed, the sample was taken. The reaction solution was filtered under vacuum through celite, and the filtrate was poured into water (30 mL) and extracted with ethyl acetate. The organic phase was washed with saturated brine, dried over anhydrous sodium sulfate and concentrated; and the residue was separated and purified with silica gel column chromatography (dichloromethane:methanol=97:3) to obtain 29 mg of compound 34.

HRMS (ESI, $[M+H]^+$): m/z=466.1886.

$^1H$ NMR (500 MHz, $CD_3OD$) δ 8.59 (d, J=13.0 Hz, 1H), 7.64 (t, J=7.3 Hz, 1H), 7.48 (t, J=7.1 Hz, 1H), 7.24 (t, J=7.7 Hz, 1H), 7.13-6.88 (m, 2H), 5.87 (q, J=7.1 Hz, 1H), 4.00 (s, 3H), 2.44 (s, 3H), 2.13 (m, 4H), 1.69 (d, J=7.1 Hz, 3H), 1.07 (m, 6H). $^{31}P$ NMR (202 MHz, $CD_3OD$) δ 49.9.

Example 35: Preparation of Compound 35

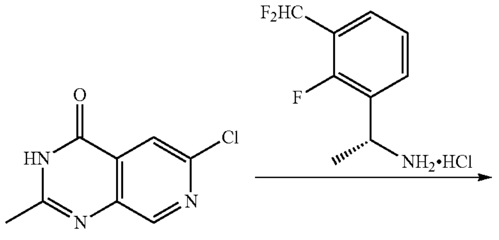

9-1

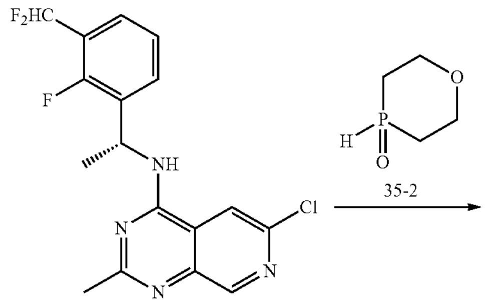

35-2

35-1

-continued

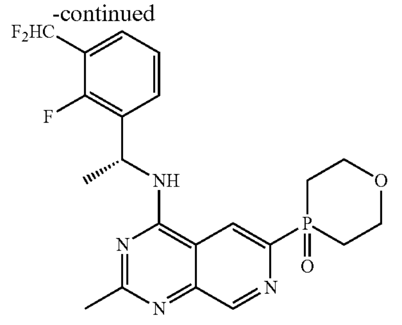

35

Step A: Preparation of Compound 35-1

Referring to the procedures of step A in Example 19, Compound 35-1 was prepared by reacting (R)-1-(3-(difluorinemethyl)-2-fluorinephenyl)ethan-1-amine hydrochloride replaced by (R)-1-(3-(trifluoromethyl)-2-fluorinephenyl) ethan-1-amine hydrochloride with the compound 9-1.

MS (ESI, $[M+H]^+$): m/z=367.05.

$^1$H NMR (500 MHz, $CD_3OD$) δ 8.76 (s, 1H), 8.33 (s, 1H), 7.60 (t, J=7.3 Hz, 1H), 7.48 (t, J=6.9 Hz, 1H), 7.24 (t, J=7.7 Hz, 1H), 7.01 (t, J=54.9 Hz, 1H), 5.80 (q, J=7.1 Hz, 1H), 2.46 (s, 3H), 1.69 (d, J=7.1 Hz, 3H).

Step B: Preparation of Compound 35-2

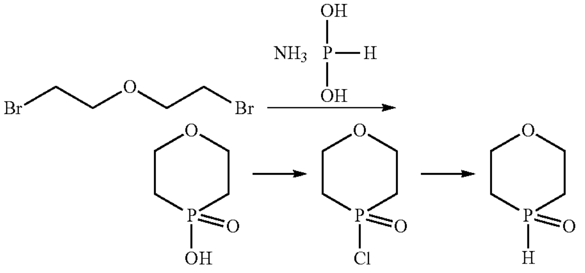

35-2-1 35-2-2 35-2

Step a: Preparation of Compound 35-2-1

Ammonium hypophosphite (28 g, 337 mmol) was added to a 500 mL three-necked flask, and hexamethyldisilazane (109 g) was added dropwise thereto. After the addition was completed, the reaction solution was heated to 120° C. under nitrogen protection and stirred to react for 4 h. The reaction flask was added dropwise with bis(2-bromoethyl)ether (78 g) and continuously reacted for 4 h with keeping the temperature maintained. The reaction solution was stirred in an ice-water bath to reduce the temperature and added dropwise with anhydrous ethanol (150 mL). After the addition was completed, the reaction solution was heated to reflux and reacted for 1 h. The reaction was stopped, and the reaction solution was cooled to room temperature and filtered under vacuum. The filter cake was washed with dichloromethane, and the filtrate was concentrated to obtain 42.4 g of crude compound 35-2-1.

GCMS: $[M]^+$=136.

Step b: Preparation of Compound 35-2-2

The compound 35-2-1 (1 g) obtained in step a and dichloromethane (20 mL) were added to a 25 mL three-necked flask. The mixture was cooled to below 0° C. in an ice-salt bath under nitrogen protection and added dropwise with oxalyl chloride (1.578 g). After the addition was completed, the mixture was stirred overnight at room temperature.

The reaction solution was concentrated to dryness, and the residue was dissolved in toluene (10 mL) and concentrated to dryness to obtain 1.8 g of crude compound 35-2-2, which was used in the next step without purification.

Step c: Preparation of Compound 35-2

A solution of 1 M diisobutylaluminum hydride in toluene (6.48 mL) was slowly added to a stirred solution of the compound 35-2-2 (1.8 g) obtained in step b in dichloromethane (15 mL) at −70° C. under nitrogen protection, and the mixture was stirred at for 2 h −70° C. After the reaction was completed, methanol (3 mL) was added to the reaction solution at −70° C. and stirred to react for 5 min. The reaction solution was transferred to an ice-water bath and continuously stirred until the temperature of the reaction solution increased to 0° C., added with 10 vol % aqueous acetic acid solution (10 mL), and stirred for 10 min at room temperature. The resulting solution was subjected to separation, the aqueous phase was extracted with dichloromethane (20 mL×5), and the organic phases were combined, dried over anhydrous sodium sulfate and concentrated to obtain 1.7 g of crude compound 35-2, which was used in the next step without purification.

Step C: Preparation of Compound 35

Referring to the procedures of step B in Example 19, compound 35 was prepared by reacting the compound 35-1 with the compound 35-2.

HRMS (ESI, $[M+H]^+$): m/z=451.1510.

$^1$H NMR (500 MHz, $CD_3OD$) δ 9.12 (s, 1H), 8.83 (d, J=6.8 Hz, 1H), 7.63 (t, J=7.3 Hz, 1H), 7.49 (t, J=7.0 Hz, 1H), 7.24 (t, J=7.7 Hz, 1H), 7.00 (t, J=54.9 Hz, 1H), 5.87 (q, J=7.1 Hz, 1H), 4.23-4.02 (m, 4H), 2.65 (dt, J=15.6, 7.4 Hz, 2H), 2.51 (s, 3H), 2.22-2.08 (m, 2H), 1.72 (d, J=7.1 Hz, 3H). $^{31}$P NMR (202 MHz, $CD_3OD$) δ 30.08.

Example 36: Preparation of Compound 36

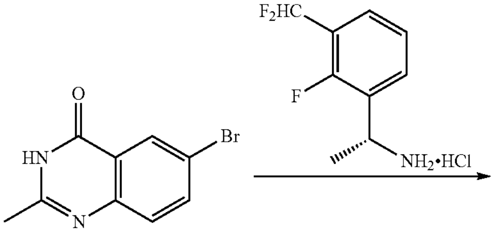

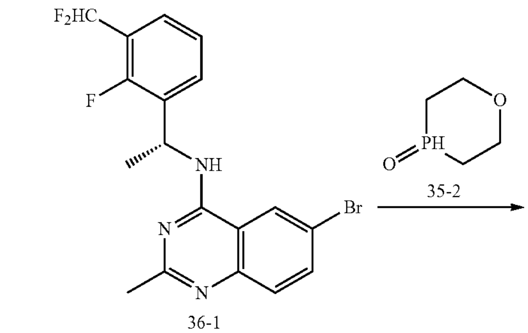

36-1

-continued

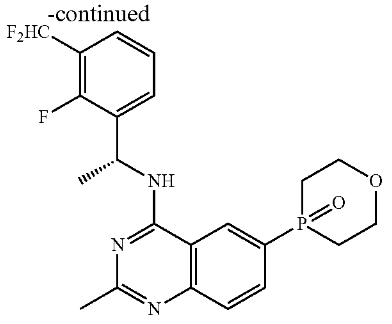

36

Step A: Preparation of Compound 36-1

Referring to the procedures of step A in Example 19, compound 36-1 was prepared by replacing (R)-1-(3-(trifluoromethyl)-2-fluorinephenyl)ethan-1-amine hydrochloride with (R)-1-(3-(difluorinemethyl)-2-fluorinephenyl) ethan-1-amine hydrochloride.

MS (ESI, $[M+H]^+$): m/z=411.96.

$^1$H NMR (500 MHz, DMSO-$d_6$) δ 9.50 (s, 1H), 8.75 (d, J=2.2 Hz, 1H), 7.96 (s, 1H), 7.87 (dd, J=8.9, 2.1 Hz, 1H), 7.72-7.68 (m, 1H), 7.56-7.53 (m, 1H), 7.36-7.11 (m, 2H), 5.79 (m, 1H), 2.37 (s, 3H), 1.61 (d, J=7.0 Hz, 3H).

Step B: Preparation of compound 36

Compound 36 was prepared referring to the procedures of step B in Example 19.

HRMS (ESI, $[M+H]^+$): m/z=450.1552.

$^1$H NMR (500 MHz, $CD_3OD$) δ 8.69 (dd, J=13.1, 1.7 Hz, 1H), 8.02 (m, 1H), 7.68 (dd, J=8.6, 2.5 Hz, 1H), 7.53 (t, J=7.4 Hz, 1H), 7.38 (t, J=7.1 Hz, 1H), 7.14 (t, J=7.7 Hz, 1H), 6.91 (t, J=54.9 Hz, 1H), 5.78 (q, J=7.1 Hz, 1H), 4.13-3.94 (m, 4H), 2.50 (m, 2H), 2.36 (s, 3H), 2.11-1.96 (m, 2H), 1.62 (d, J=7.1 Hz, 3H).

$^{31}$P NMR (202 MHz, $CD_3OD$) δ 31.65.

Example 37: Preparation of Compound 37

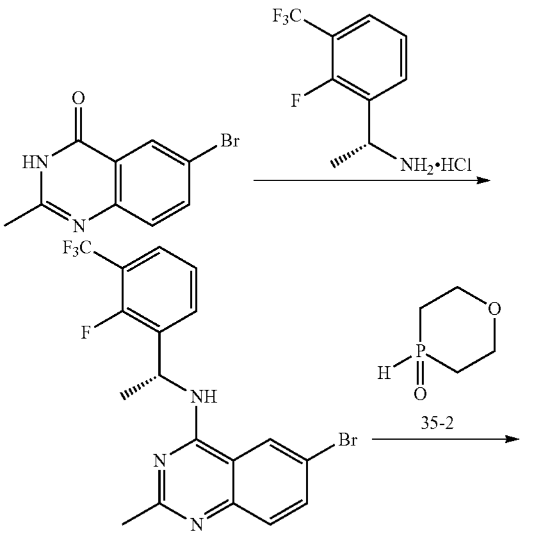

37-1

-continued

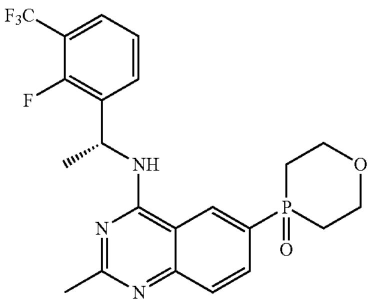

37

Step A: Preparation of Compound 37-1

Referring to the procedures of step A in Example 19, compound 37-1 was prepared by reacting (R)-1-(3-(trifluoromethyl)-2-fluorinephenyl)ethan-1-amine hydrochloride with 6-bromo-2-methylquinazolin-4(3H)-one.

MS (ESI, $[M+H]^+$): m/z=428.08.

Step B: Preparation of Compound 37

Referring to the procedures of step B in Example 19, compound 37 was prepared by reacting the compound 37-1 with the compound 35-2.

HRMS (ESI, $[M+H]^+$): m/z=468.1479.

$^1$H NMR (500 MHz, $CD_3OD$) δ 8.80 (dd, J=13.1, 1.4 Hz, 1H), 8.13 (m, 1H), 7.79 (dd, J=8.6, 2.5 Hz, 1H), 7.74 (t, J=7.0 Hz, 1H), 7.56 (t, J=6.9 Hz, 1H), 7.27 (t, J=7.8 Hz, 1H), 5.86 (q, J=7.1 Hz, 1H), 4.26-4.01 (m, 4H), 2.61 (m, 2H), 2.45 (s, 3H), 2.14 (t, J=16.1 Hz, 2H), 1.73 (d, J=7.1 Hz, 3H).

$^{31}$P NMR (202 MHz, $CD_3OD$) δ 31.62.

Example 38: Preparation of Compound 38

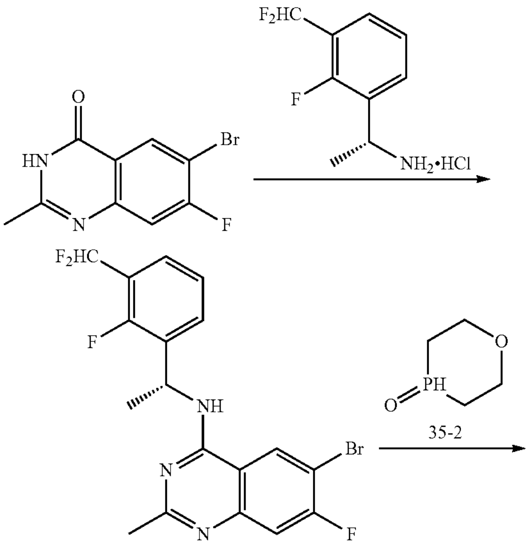

38-1

-continued

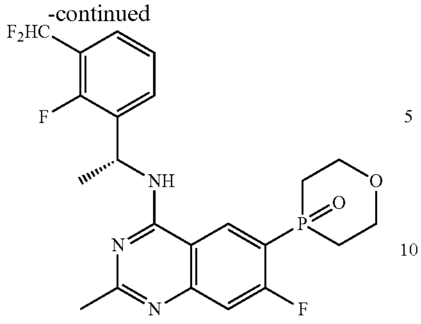

38

Step A: Preparation of Compound 38-1

Referring to the procedures of step A in Example 19, compound 38-1 was prepared by reacting (R)-1-(3-(difluoromethyl)-2-fluorinephenyl)ethan-1-amine hydrochloride with 6-bromo-7-fluorine-2-methyl quinazolin-4(3H)-one.

MS (ESI, $[M+H]^+$): m/z=428.05.

$^1H$ NMR (500 MHz, DMSO-$d_6$) δ 8.91 (d, J=7.5 Hz, 1H), 8.63 (d, J=7.1 Hz, 1H), 7.68 (t, J=7.3 Hz, 1H), 7.51 (t, J=7.8 Hz, 2H), 7.37-7.18 (m, 2H), 5.78 (m, 1H), 2.34 (s, 3H), 1.60 (d, J=7.1 Hz, 3H).

Step B: Preparation of Compound 38

Compound 38 was prepared referring to the procedures of step B in Example 19.

HRMS (ESI, $[M+H]^+$): m/z=468.1463.

$^1H$ NMR (500 MHz, $CD_3OD$) δ 8.66 (dd, J=13.5, 6.7 Hz, 1H), 7.53 (t, J=7.5 Hz, 1H), 7.38 (t, J=7.1 Hz, 1H), 7.26 (dd, J=11.4, 4.4 Hz, 1H), 7.14 (t, J=7.7 Hz, 1H), 6.90 (t, J=54.9 Hz, 1H), 5.77 (q, J=7.1 Hz, 1H), 4.04 (m, 4H), 2.52 (m, 2H), 2.35 (s, 3H), 2.22-2.02 (m, 2H), 1.61 (d, J=7.1 Hz, 3H).

$^{31}P$ NMR (202 MHz, $CD_3OD$) δ 28.87.

Example 39: Preparation of Compound 39

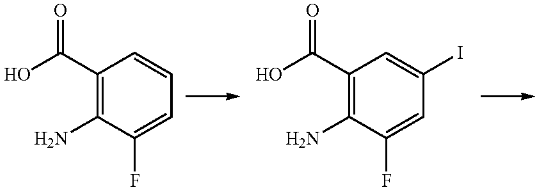

39-1

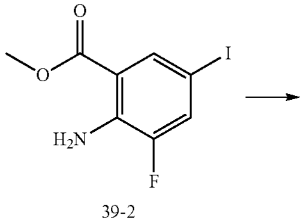

39-2

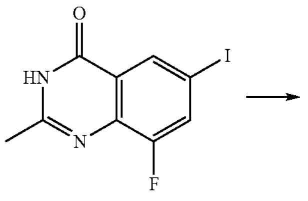

39-3

-continued

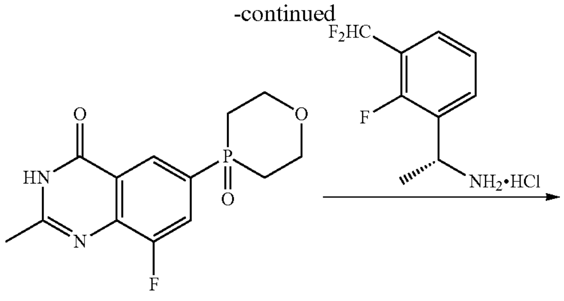

39-4

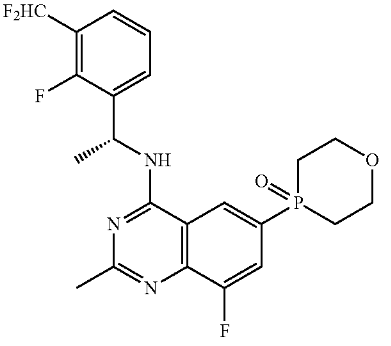

39

Step A: Preparation of Compound 39-1

2-amino-3-fluorinebenzoic acid (10 g) and methylene chloride (170 mL) were sequentially added to a 500 mL single-neck flask, and the mixture was stirred at room temperature and added with N-iodosuccinimide (14.50 g). After the addition was completed, the reaction solution was stirred overnight at room temperature. After the reaction was completed, the reaction solution was filtered under vacuum, and the filter cake was slurried with dichloromethane (50 mL), filtered and dried to obtain 12.9 g of compound 39-1.

$^1H$ NMR (500 MHz, DMSO-$d_6$) δ 7.81-7.80 (m, 1H), 7.57 (dd, J=10.8, 2.0 Hz, 1H).

Step B: Preparation of Compound 39-2

Compound 39-2 was prepared referring to the procedures of step A in Example 24.

$^1H$ NMR (500 MHz, DMSO-$d_6$) δ 7.84-7.79 (m, 1H), 7.61-7.59 (m, 1H), 6.69 (s, 2H), 3.82 (s, 3H).

Step C: Preparation of Compound 39-3

Compound 39-3 was prepared referring to the procedures of step B in Example 1.

MS (ESI, $[M+H]^+$): m/z=304.75.

Step D: Preparation of Compound 39-4

Compound 39-4 was prepared referring to the procedures of step E in Example 1.

MS (ESI, [M+H]+): m/z=297.04.

$^1H$ NMR (500 MHz, DMSO-$d_6$) δ 12.64 (br, 1H), 8.30 (dd, J=11.7, 1.3 Hz, 1H), 8.09 (m, 1H), 4.06-3.83 (m, 4H), 2.49-2.39 (m, 5H), 2.02-1.95 (m, 2H).

Step E: Preparation of Compound 39

Compound 39 was prepared referring to the procedures of step A in Example 19.

HRMS (ESI, $[M+H]^+$): m/z=468.1466.

$^1H$ NMR (500 MHz, $CD_3OD$) δ 8.50 (d, J=12.9 Hz, 1H), 7.81 (t, J=10.6 Hz, 1H), 7.53 (t, J=7.3 Hz, 1H), 7.39 (t, J=7.0 Hz, 1H), 7.14 (t, J=7.7 Hz, 1H), 6.91 (t, J=54.9 Hz, 1H), 5.77 (q, J=7.1 Hz, 1H), 4.14-3.91 (m, 4H), 2.50 (m, 2H), 2.39 (s, 3H), 2.04 (t, J=16.5 Hz, 2H), 1.62 (d, J=7.1 Hz, 3H).

$^{31}P$ NMR (202 MHz, $CD_3OD$) δ 31.53.

Example 40: Preparation of Compound 40

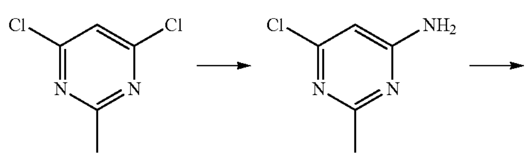

40-1

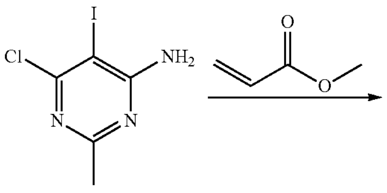

40-2

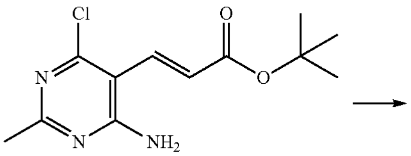

40-3

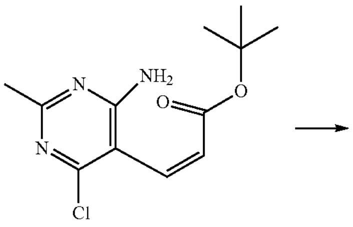

40-4

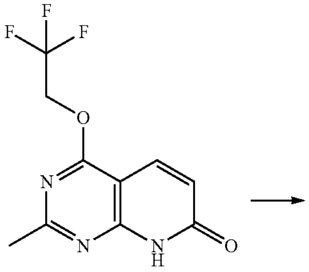

40-5

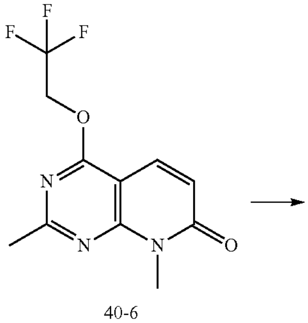

40-6

-continued

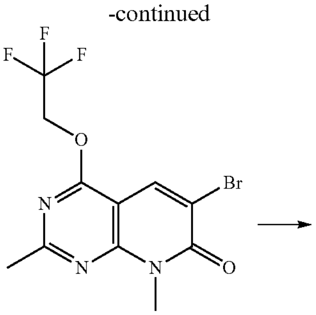

40-7

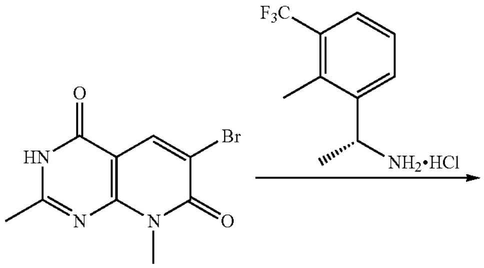

40-8

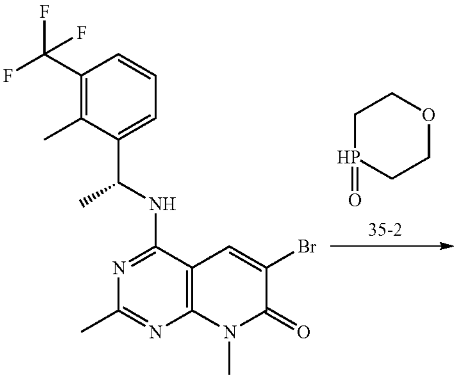

40-9

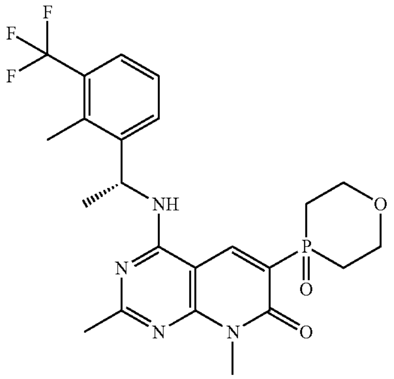

40

Step A: Preparation of Compound 40-1

4,6-dichloro-2-methylpyrimidine (16.3 g) and ammonium hydroxide (80 mL) were sequentially added to a 350 mL pressure-resistant reaction flask; and after the flask was sealed, the mixture was heated to 90° C. and reacted overnight. The reaction was stopped, the reaction solution was cooled to room temperature and filtered, and the filter cake was collected and dried under reduced pressure to obtain 14 g of compound 40-1.

MS (ESI, $[M+H]^+$): m/z=143.93.

Step B: Preparation of Compound 40-2

The compound 40-1 (2 g) obtained in step A and methanol (20 mL) were sequentially added to a 100 mL three-necked flask. The mixture was cooled to 0° C. in an ice-salt bath and added dropwise with a solution of iodine monochloride (15.58 g) in methanol (20 mL). After the addition was completed, the mixture was stirred overnight at room temperature. After the reaction was completed, the reaction solution was poured into water (100 mL), then added with a saturated sodium sulfite solution (200 mL), added with 2 M sodium hydroxide solution to adjust the pH to 6-7, and extracted with ethyl acetate (100 mL×3). The organic phases were combined, washed with saturated brine (100 mL), dried over anhydrous sodium sulfate and concentrated under reduced pressure to obtain 3.3 g of compound 40-2.

MS (ESI, $[M+H]^+$): m/z=269.86.

$^1$H NMR (500 MHz, DMSO-$d_6$) δ 7.28 (d, 2H), 2.29 (s, 3H).

Step C: Preparation of Compound 40-3

To a 250 mL single-neck flask were sequentially added the compound 40-2 (2.8 g) obtained in step B, N,N-dimethylformamide (28 mL), tert-butyl acrylate (1.598 g), triethylamine (2.103 g), palladium acetate (0.058 g) and Tri(o-tolyl)phosphine (0.158 g). After being purged with nitrogen three times, the mixture was heated to 100° C. under nitrogen protection and reacted for 8 h. After the reaction was completed, the reaction solution was cooled to room temperature, poured into water (100 mL) and extracted with ethyl acetate (80 mL×3). The organic phases were combined, washed with saturated brine (60 mL), dried over anhydrous sodium sulfate, filtered and concentrated. The resulting crude product was separated and purified by silica gel column chromatography (petroleum ether:ethyl acetate=70:30) to obtain 1.7 g of compound 40-3.

MS (ESI, $[M+H]^+$): m/z=270.38.

$^1$H NMR (500 MHz, DMSO-$d_6$) δ 7.45-7.40 (m, 3H), 6.34 (d, J=16.4 Hz, 1H), 2.31 (s, 3H), 1-48 (s, 9H).

Step D: Preparation of Compound 40-4

The compound 40-3 (0.4 g) obtained in step C and acetonitrile (8 mL) were sequentially added to a 25 mL reaction flask, and the reaction flask was placed under a light with a wavelength of 365 nm and stirred for 4 h at room temperature. The reaction was stopped, the reaction solution was filtered, and the filter cake was collected to obtain 0.22 g of compound 40-4.

MS (ESI, $[M+H]^+$): m/z=270.08.

$^1$H NMR (500 MHz, DMSO-$d_6$) δ 6.88 (s, 2H), 6.70 (d, J=11.6 Hz, 1H), 6.05 (d, J=11.6 Hz, 1H), 2.30 (s, 3H), 1.29 (s, 9H).

Step E: Preparation of Compound 40-5

To a 250 mL reaction flask were sequentially added the compound 40-4 (2.8 g) obtained in step D, trifluoroethanol (1.038 g) and potassium tert-butoxide (2.56 g), and the mixture was heated to 80° C. and reacted for 2 h. After the reaction was completed, the reaction solution was cooled to room temperature, poured into a saturated ammonium chloride solution (30 mL) and extracted with ethyl acetate (50 mL×3). The organic phases were combined, washed with saturated brine (50 mL), dried over anhydrous sodium sulfate, filtered and concentrated; and the resulting residue was added with methyl tert-butyl ether (20 mL) and slurried to obtain 2.2 g of compound 40-5.

MS (ESI, $[M+H]^+$): m/z=260.05.

$^1$H NMR (500 MHz, DMSO-$d_6$) δ 12.46 (s, 1H), 7.86 (d, J=9.6 Hz, 1H), 6.51 (d, J=9.6 Hz, 1H), 5.19 (q, J=8.9 Hz, 2H), 2.55 (s, 3H).

Step F: Preparation of Compound 40-6

The compound 40-5 (2 g) obtained in step E and N,N-dimethylformamide (20 mL) were sequentially added to a 250 mL single-neck flask. The mixture was cooled to below 5° C. in an ice-water bath and added with sodium hydride (0.370 g). After the addition was completed, the reaction solution was stirred for 5 min at room temperature and then added dropwise with methyl iodide (1.314 g) under an ice-water bath. After the addition was completed, the reaction solution was naturally heating to room temperature and stirred for 2 h. After the reaction was completed, the reaction solution was poured into ice water (20 mL) and extracted with ethyl acetate (30 mL×3). The organic phases were combined, washed with saturated brine (30 mL), dried over anhydrous sodium sulfate, filtered and concentrated; and the resulting crude product was separated and purified by silica gel column chromatography (petroleum ether:ethyl acetate=70:30) to obtain 1.7 g of compound 40-6.

MS (ESI, $[M+H]^+$): m/z=274.03.

$^1$H NMR (500 MHz, DMSO-$d_6$) δ 7.90 (d, J=9.6 Hz, 1H), 6.64 (d, J=9.6 Hz, 1H), 5.21 (q, J=8.9 Hz, 2H), 3.60 (s, 3H), 2.62 (s, 3H).

Step G: Preparation of Compound 40-7

The compound 40-6 (0.65 g) obtained in step F and a 48% aqueous hydrobromic acid solution (8 mL) were sequentially added to a 100 mL single-neck flask. The mixture was stirred at room temperature and added with sodium bromate (1.077 g) in batches. After the addition was completed, the reaction flask was transferred into an oil bath at 60° C. and stirred for 2 h. After the reaction was completed, the reaction solution was poured into ice water (10 mL), then added with a saturated sodium sulfite solution (30 mL), stirred vigorously for 5 min, added with a saturated sodium bicarbonate solution to adjust the pH to 6-7, and extracted with ethyl acetate (50 mL×3).

The organic phases were combined, washed with saturated brine (30 mL), dried over anhydrous sodium sulfate, filtered and concentrated; and the resulting crude product was separated and purified by silica gel column chromatography (petroleum ether:ethyl acetate=80:20) to obtain 0.7 g of compound 40-7.

MS (ESI, $[M+H]^+$): m/z=351.92.

$^1$H NMR (500 MHz, DMSO-$d_6$) δ 8.31 (s, 1H), 5.23 (q, J=8.9 Hz, 2H), 3.68 (s, 3H), 2.62 (s, 3H).

Step H: Preparation of Compound 40-8

The compound 40-7 (0.7 g) obtained in step G and a 48% aqueous hydrobromic acid solution (7 mL) were sequentially added to a 100 mL single-neck flask, and after the addition was completed, the mixture was heated to 100° C. and reacted for 2.5 h. After the reaction was completed, the reaction solution was cooled to room temperature, poured into ice water (100 mL), added with a saturated sodium bicarbonate solution to adjust the pH to 6-7 and filtered. The filter cake was collected and dried to obtain 0.537 g of compound 40-8.

MS (ESI, $[M+H+2]^+$): m/z=271.96.

$^1$H NMR (500 MHz, DMSO-$d_6$) δ 12.90 (s, 1H), 8.24 (s, 1H), 3.63 (s, 3H), 2.41 (s, 3H).

Step I: Preparation of Compound 40-9

Compound 40-9 was prepared referring to the procedures of step A in Example 19.

$^1$H NMR (500 MHz, DMSO-$d_6$) δ 8.93 (s, 1H), 8.44 (d, J=6.9 Hz, 1H), 7.73 (d, J=7.8 Hz, 1H), 7.54 (d, J=7.6 Hz, 1H), 7.36 (t, J=7.8 Hz, 1H), 5.64 (p, J=6.9 Hz, 1H), 3.57 (s, 3H), 2.59 (s, 3H), 2.31 (s, 3H), 1.52 (d, J=7.0 Hz, 3H).

Step J: Preparation of Compound 40

Referring to the procedures of step B in Example 19, compound 40 was prepared by reacting the compound 40-9 with the compound 35-2 obtained in step c in Example 35.

HRMS (ESI, $[M+H]^+$): m/z=495.1768.

$^1H$ NMR (500 MHz, $CD_3OD$) δ 8.78 (d, J=14.5 Hz, 1H), 7.68 (d, J=7.8 Hz, 1H), 7.52 (d, J=7.8 Hz, 1H), 7.29 (t, J=7.8 Hz, 1H), 5.79 (q, J=7.0 Hz, 1H), 4.19 (m, 2H), 4.07 (q, J=11.3 Hz, 2H), 3.64 (s, 3H), 2.81 (m, 2H), 2.62 (s, 3H), 2.41 (s, 3H), 1.87 (t, J=16.8 Hz, 2H), 1.60 (d, J=7.0 Hz, 3H).

Example 41: Preparation of Compound 41

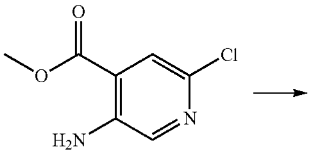

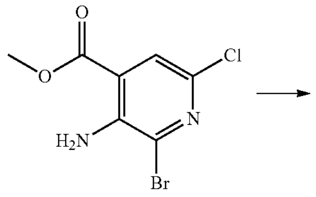

41-1

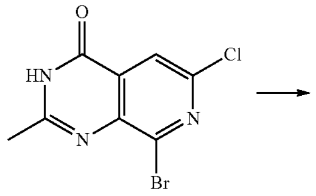

41-2

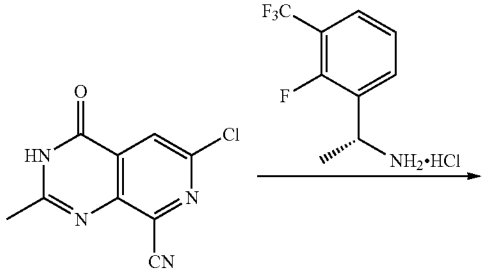

41-3

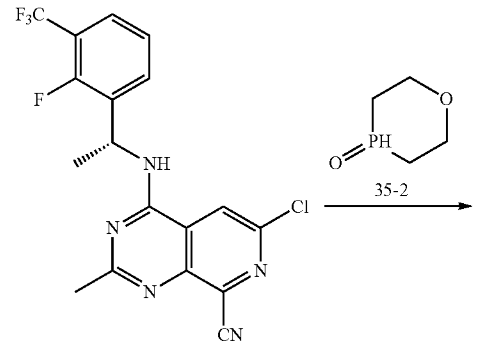

41-4

-continued

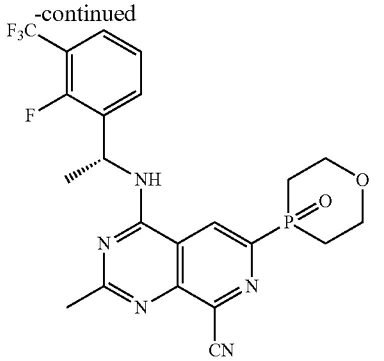

41

Step A: Preparation of Compound 41-1

To a 100 mL single-neck flask were sequentially added methyl 5-amino-2-chloroisonicotinate (2 g), N,N-dimethylformamide (20 mL) and N-bromosuccinimide (1.9 g), and the reaction solution was heated to 80° C. and reacted for 3 h. After the reaction was completed, the reaction solution was poured into water (200 mL) and extracted with methyl tert-butyl ether (50 mL×3). The organic phase was dried over anhydrous sodium sulfate and concentrated; and the residue was separated and purified by silica gel column chromatography (petroleum ether:ethyl acetate=80:20) to obtain 2.6 g of compound 41-1.

MS (ESI, $[M+H+2]^+$): m/z=266.87.

$^1H$ NMR (500 MHz, DMSO-$d_6$) δ 7.63 (s, 1H), 6.78 (s, 2H), 3.88 (s, 3H).

Step B: Preparation of Compound 41-2

To a 35 mL microwave tube were sequentially added the compound 41-1 (1.1 g) obtained in step A, acetonitrile (3.40 g) and methanesulfonic acid (3.98 g), and the tube was stirred at room temperature for 10 min, placed in a microwave reactor, heated to 120° C. at 50 W and reacted for 2 h. After the reaction was completed, the obtained sample solution was concentrated to dryness under reduced pressure, diluted with water (20 mL), added with a 15% aqueous sodium hydroxide solution to adjust the pH to alkalinity and filtered under vacuum to obtain 0.8 g of compound 41-2.

MS (ESI, $[M-H]^-$): m/z=273.89.

$^1H$ NMR (500 MHz, $CD_3OD$) δ 7.94 (s, 1H), 2.48 (s, 3H).

Step C: Preparation of Compound 41-3

The compound 41-2 (0.2 g) obtained in step B and N,N-dimethylformamide (2 mL) were sequentially added to a 5 mL microwave tube, and the mixture was added with zinc cyanide (39.4 mg) and tetrakis(triphenylphosphine) palladium (78 mg). After being purged with nitrogen three times, the reaction solution was heated to 110° C. under 50 W in the microwave reactor and reacted for 1 h. After the reaction was completed, the reaction solution was poured into water (20 mL) and extracted with ethyl acetate (20 mL×3). The organic phase was dried over anhydrous sodium sulfate and concentrated; and the residue was separated and purified by silica gel column chromatography (dichloromethane:methanol=80:20) to obtain 136 mg of compound 41-3.

MS (ESI, $[M-H]^-$): m/z=218.95.

$^1H$ NMR (500 MHz, $CD_3OD$) δ 7.97 (s, J=7.2 Hz, 1H), 2.51 (s, 3H).

Step D: Preparation of Compound 41-4

Compound 41-4 was prepared referring to the procedures of step A in Example 19.

MS (ESI, [M+H]+): m/z=410.12.

Step E: Preparation of Compound 41

Referring to the procedures of step B in Example 19, compound 41 was prepared by reacting the compound 41-1 prepared in step D above with the compound 35-2.

HRMS (ESI, $[M+H]^+$): m/z=494.1365.

$^1H$ NMR (500 MHz, $CD_3OD$) δ 8.97 (d, J=6.1 Hz, 1H), 7.71-7.62 (m, 1H), 7.51-7.45 (m, 1H), 7.19 (t, J=7.8 Hz, 1H), 5.73 (q, J=7.1 Hz, 1H), 4.15-3.94 (m, 4H), 2.54 (m, 2H), 2.42 (s, 3H), 2.08 (m, 2H), 1.64 (d, J=7.1 Hz, 3H).

$^{31}P$ NMR (202 MHz, $CD_3OD$) δ 29.64.

Example 42: Preparation of Compound 42

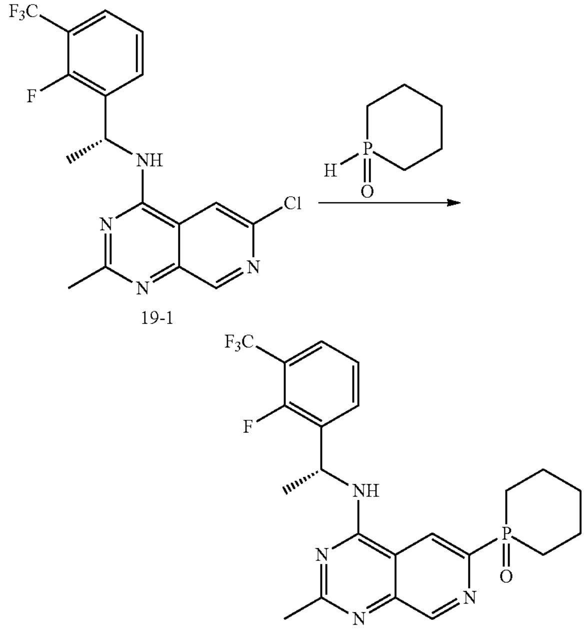

19-1

42

Step A: Preparation of Compound 42

Referring to the procedures of step B in Example 19, compound 42 was prepared by reacting the compound 19-1 with 1-phosphorinane oxide.

HRMS (ESI, $[M+H]^+$): m/z=467.1620.

$^1H$ NMR (500 MHz, $CD_3OD$) δ 9.10 (s, 1H), 8.81-8.78 (m, 1H), 7.75 (t, J=6.9 Hz, 1H), 7.57 (t, J=7.0 Hz, 1H), 7.28 (t, J=7.8 Hz, 1H), 5.85 (q, J=7.1 Hz, 1H), 2.50 (s, 3H), 2.47-2.39 (m, 2H), 2.13-1.94 (m, 6H), 1.85-1.79 (m, 1H), 1.73 (d, J=7.1 Hz, 3H), 1.66-1.59 (m, 1H).

Example 43: Preparation of Compound 43

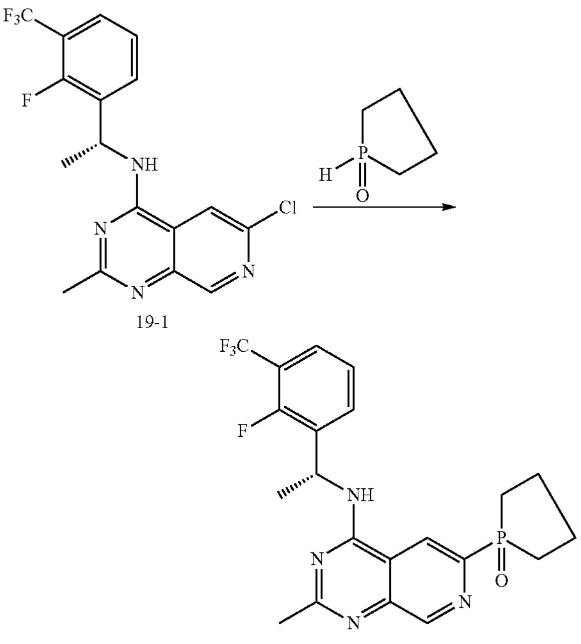

19-1

43

Step A: Preparation of Compound 43

Referring to the procedures of step B in Example 19, compound 43 was prepared by reacting the compound 19-1 with 1-phospholane oxide.

HRMS (ESI, $[M+H]^+$): m/z=453.1594.

$^1H$ NMR (500 MHz, $CD_3OD$) δ 9.09 (s, 1H), 8.81 (dd, J=6.5, 0.7 Hz, 1H), 7.75 (t, J=6.9 Hz, 1H), 7.57 (t, J=7.1 Hz, 1H), 7.28 (t, J=7.8 Hz, 1H), 5.85 (q, J=7.1 Hz, 1H), 2.50 (s, 3H), 2.33-2.29 (m, 2H), 2.20-2.10 (m, 4H), 2.02-1.94 (m, 2H), 1.72 (d, J=7.1 Hz, 3H).

The following Examples 44 to 47 (Table 1) can refer to the procedures in Example 1, and specifically, compounds 44 to 47 were prepared by replacing methyl 2-amino-4-methoxybenzoate with the following fragments 1-1, replacing (R)-1-(m-tolyl)ethan-1-amine with the following fragments 1-2, and finally referring to the procedures of step C in Example 7.

TABLE 1

| Examples | Fragments 1-1 | Fragments 1-2 | Compound | $[M + H]^+$ | $^1H$ NMR |
|---|---|---|---|---|---|
| 44 | 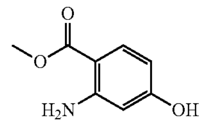 | 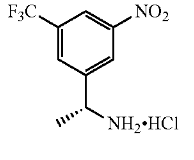 | 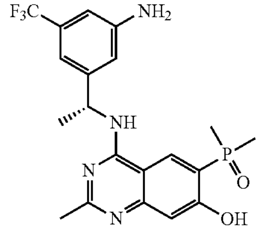 [SMILES: Cc1nc(N[C@H](C)c2cc(N)cc(C(F)(F)F)c2)c2cc(P(C)(C)=O)c(O)cc2n1] | 439.1505 | $^1H$ NMR (500 MHz, $CD_3OD$) δ 8.51 (d, J = 14.3 Hz, 1H), 6.97 (q, J = 1.8 Hz, 2H), 6.81 (t, J = 2.0 Hz, 1H), 6.71 (d, J = 5.0 Hz, 1H), 5.68 (q, J = 7.0 Hz, 1H), 2.50 (s, 3H), 1.85 (dd, J = 1.4, 14.1 Hz, 6H), 1.65 (d, J = 7.0 Hz, 3H). |

TABLE 1-continued

| Examples | Fragments 1-1 | Fragments 1-2 | Compound | [M + H]$^+$ | $^1$H NMR |
|---|---|---|---|---|---|
| 45 | 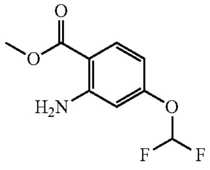 | 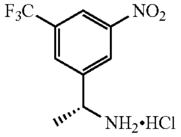 | 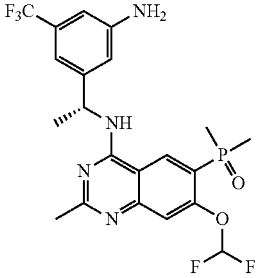 [SMILES: Cc1nc(N[C@H](C)c2cc(N)cc(C(F)(F)F)c2)c2cc(P(C)(C)=O)c(OC(F)F)cc2n1] | 489.1469 | $^1$H NMR (500 MHz, $CD_3OD$) δ 8.72 (d, J = 13.6 Hz, 1H), 7.41-7.12 (t, J = 70 Hz 1H), 7.31 (d, J = 4.6 Hz, 1H), 6.98 (dd, J = 2.6, 4.6 Hz, 2H), 6.81 (s, 1H), 5.63 (q, J = 7.1 Hz, 1H), 2.50 (s, 3H), 1.89 (dd, J = 1.3, 13.9 Hz, 6H), 1.65 (d, J = 7.1 Hz, 3H). |
| 46 | 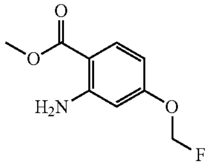 | 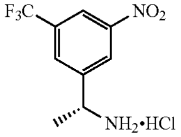 | 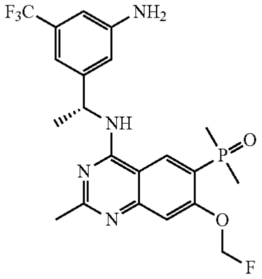 [SMILES: Cc1nc(N[C@H](C)c2cc(N)cc(C(F)(F)F)c2)c2cc(P(C)(C)=O)c(OCF)cc2n1] | 471.1556 | $^1$H NMR (500 MHz, $CD_3OD$) δ 8.66 (d, J = 13.7 Hz, 1H), 7.34 (d, J = 4.8 Hz, 1H), 6.99 (d, J = 5.9 Hz, 2H), 6.81 (s, 1H), 6.06 (s, 1H), 5.96 (s, 1H), 5.63 (m, 1H), 2.50 (s, 3H), 1.89 (d, J = 13.8 Hz, 6H), 1.65 (d, J = 7.1 Hz, 3H). |
| 47 | 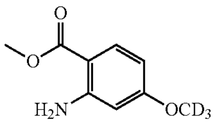 | 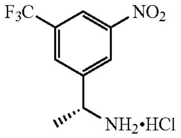 | 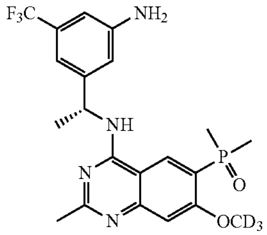 | 456.1854 | $^1$H NMR (500 MHz, DMSO) δ 8.78 (d, J = 7.9 Hz, 1H), 8.72 (d, J = 13.6 Hz, 1H), 7.10 (d, J = 4.8 Hz, 1H), 6.93 (s, 1H), 6.87 (t, J = 1.8 Hz, 1H), 6.70 (t, J = 1.9 Hz, 1H), 5.54 (s, 1H), 2.39 (s, 3H), 1.69 (dd, J = 2.4, 13.8 Hz, 6H), 1.55 (d, J = 7.1 Hz, 3H). |

The following intermediates (Table 2-1) were prepared by referring to the procedures in Example 19, and specifically, intermediate compounds 2a-1 to 2a-6 were prepared by replacing (R)-1-(3-(trifluoromethyl)-2-fluorinephenyl) ethan-1-amine hydrochloride with the following fragments a and reacting the fragments a with the corresponding fragment b.

TABLE 2-1

| No. | Fragments a | Fragments b | Intermediates |
|---|---|---|---|
| 2a-1 | 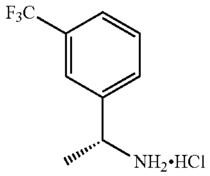 | 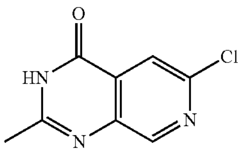 | 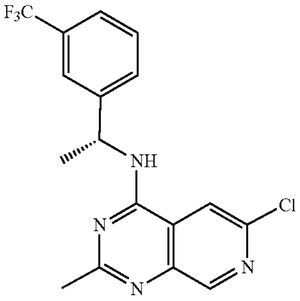 [SMILES: Cc1nc(N[C@H](C)c2cccc(C(F)(F)F)c2)c2cc(Cl)ncc2n1] |

TABLE 2-1-continued
| No. | Fragments a | Fragments b | Intermediates |
| --- | --- | --- | --- |
| 2a-2 | 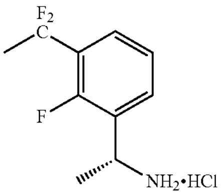 | 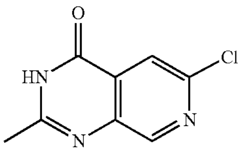 | 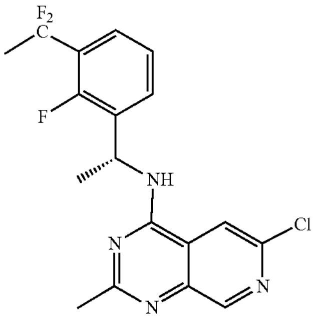 [SMILES: Cc1nc(N[C@H](C)c2cccc(C(C)(F)F)c2F)c2cc(Cl)ncc2n1] |
| 2a-3 | 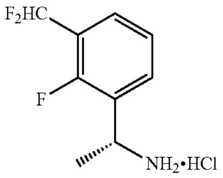 | 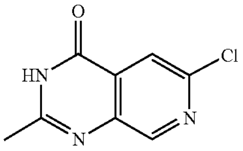 | 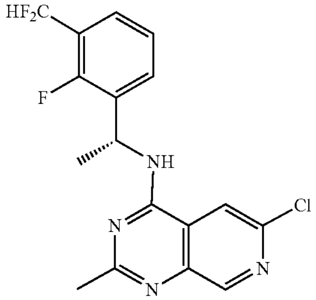 |
| 2a-4 | 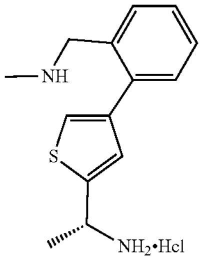 | 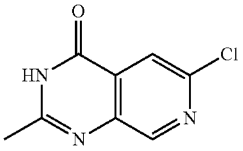 | 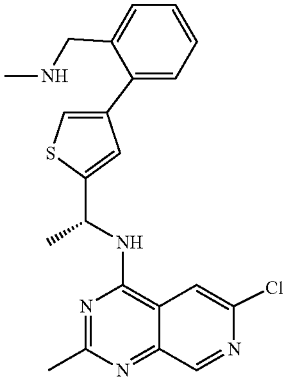 [SMILES: CNCc1ccccc1-c1csc([C@@H](C)Nc2nc(C)nc3cnc(Cl)cc23)c1] |
| 2a-5 | 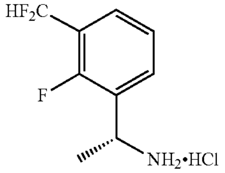 | 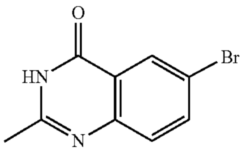 | 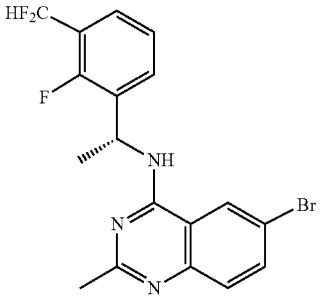 |

TABLE 2-1-continued

| No. | Fragments a | Fragments b | Intermediates |
| --- | --- | --- | --- |
| 2a-6 | 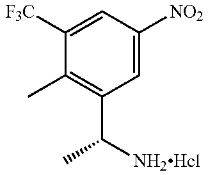 | 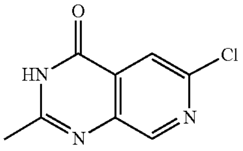 | 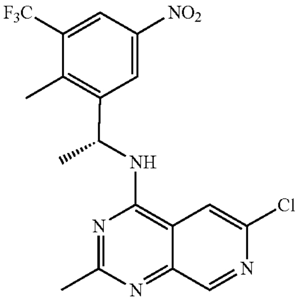 [SMILES: Cc1nc(N[C@H](C)c2cc([N+](=O)[O-])cc(C(F)(F)F)c2C)c2cc(Cl)ncc2n1] |

Examples 48 to 60 (Table 2) can refer to the procedures in Example 10, and specifically, compounds 48 to 60 were prepared by replacing the compound 7-1 with the prepared intermediates 2a-1 to 2a-6, and replacing acetic anhydride with the following fragments 2 for performing substitution, reductive amination or condensation reaction.

TABLE 2

| Examples | Intermediates | Fragments 2 | Compound | $[M + H]^+$ | $^1H$ NMR |
| --- | --- | --- | --- | --- | --- |
| 48 | 2a-1 | 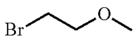 | 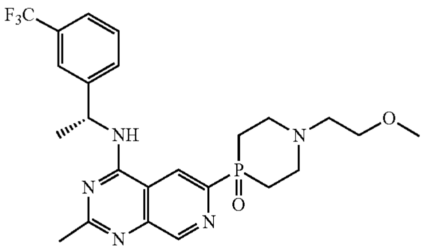 [SMILES: COCCN1CCP(=O)(c2cc3c(N[C@H](C)c4cccc(C(F)(F)F)c4)nc(C)nc3cn2)CC1] | 508.2092 | $^1H$ NMR (500 MHz, DMSO-$d_6$) δ 9.22 (d, J = 7.6 Hz, 1H), 9.11 (s, 1H), 8.94 (d, J = 6.4 Hz, 1H), 7.85 (s, 1H), 7.78 (d, J = 7.4 Hz, 1H), 7.62-7.56 (m, 2H), 5.67 (p, J = 7.1 Hz, 1H), 3.46 (t, J = 5.7 Hz, 2H), 3.25 (s, 3H), 3.06-2.87 (m, 4H), 2.67 (t, J = 5.6 Hz, 2H), 2.47 (s, 3H), 2.42-2.32 (m, 2H), 1.88 (t, J = 15.8 Hz, 2H), 1.64 (d, J = 7.1 Hz, 3H). |
| 49 | 2a-1 | Formaldehyde | 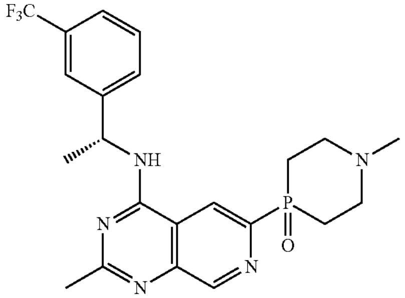 [SMILES: Cc1nc(N[C@H](C)c2cccc(C(F)(F)F)c2)c2cc(P3(=O)CCN(C)CC3)ncc2n1] | 464.1841 | $^1H$ NMR (500 MHz, DMSO-$d_6$) δ 9.22 (d, J = 7.6 Hz, 1H), 9.11 (s, 1H), 8.95 (d, J = 6.4 Hz, 1H), 7.85 (s, 1H), 7.78 (d, J = 7.3 Hz, 1H), 7.62-7.56 (m, 2H), 5.67 (p, J = 7.1 Hz, 1H), 2.91-2.80 (m, 2H), 2.78-2.72 (m, 2H), 2.47 (s, 3H), 2.44-2.33 (m, 2H), 2.29 (s, 3H), 1.95-1.88 (m, 2H), 1.65 (d, J = 7.1 Hz, 3H). |
| 50 | 2a-2 | 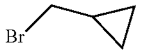 | 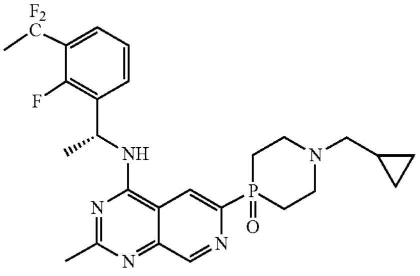 [SMILES: Cc1nc(N[C@H](C)c2cccc(C(C)(F)F)c2F)c2cc(P3(=O)CCN(CC4CC4)CC3)ncc2n1] | 518.2300 | $^1H$ NMR (500 MHz, $CD_3OD$) δ 9.11 (s, 1H), 8.82 (dd, J = 6.7, 0.6 Hz, 1H), 7.58 (t, J = 6.8 Hz, 1H), 7.44 (dd, J = 10.6, 4.3 Hz, 1H), 7.19 (t, J = 7.8 Hz, 1H), 5.87 (q, J = 7.0 Hz, 1H), 3.25-3.04 (m, 4H), 2.68-2.58 (m, 2H), 2.51 (s, 3H), 2.47 (d, J = 6.6 Hz, 2H), 2.15-2.09 (m, 2H), 1.99 (t, J = 18.6 Hz, 3H), 1.71 (d, J = 7.1 Hz, 3H), 0.98-0.91 (m, 1H), 0.60-0.54 (m, 2H), 0.18 (q, J = 4.6 Hz, 2H). |

TABLE 2-continued

| Examples | Intermediates | Fragments 2 | Compound | [M + H]$^+$ | $^1$H NMR |
|---|---|---|---|---|---|
| 51 | 2a-3 | 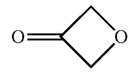 | 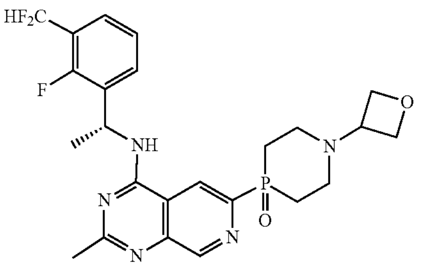 | 506.13 | $^1$H NMR (500 MHz, $CD_3OD$) δ 9.11 (d, J = 3.0 Hz, 1H), 8.89-8.78 (m, 1H), 7.63 (t, J = 7.5 Hz, 1H), 7.49 (t, J = 7.2 Hz, 1H), 7.24 (t, J = 7.7 Hz, 1H), 7.00 (t, J = 54.8 Hz, 1H), 5.87 (q, J = 7.1 Hz, 1H), 4.70 (t, J = 6.6 Hz, 2H), 4.61 (t, J = 6.2 Hz, 2H), 3.72 (m, 1H), 2.83 (m, 4H), 2.63 (d, J = 11.9 Hz, 2H), 2.51 (s, 3H), 2.15 (d, J = 17.0 Hz, 2H), 1.72 (m, 3H). |
| 52 | 2a-2 | 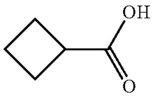 | 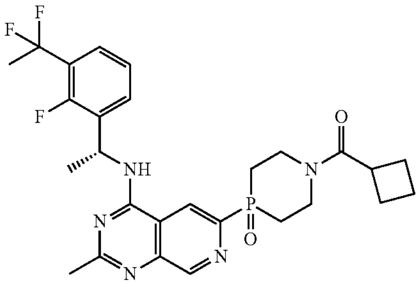 [SMILES: Cc1nc(N[C@H](C)c2cccc(C(C)(F)F)c2F)c2cc(P3(=O)CCN(C(=O)C4CCC4)CC3)ncc2n1] | 546.2257 | $^1$H NMR (500 MHz, DMSO-$d_6$) δ 9.28 (d, J = 7.1 Hz, 1H), 9.10 (s, 1H), 9.02 (d, J = 6.5 Hz, 1H), 7.67 (t, J = 7.1 Hz, 1H), 7.45 (t, J = 7.0 Hz, 1H), 7.26 (t, J = 7.8 Hz, 1H), 5.80 (p, J = 6.8 Hz, 1H), 4.04 (dd, J = 20.9, 11.5 Hz, 1H), 3.87-3.69 (m, 3H), 3.46 (p, J = 8.5 Hz, 1H), 2.43 (s, 3H), 2.40-2.18 (m, 4H), 2.18-2.09 (m, 2H), 2.08-1.88 (m, 6H), 1.81-1.72 (m, 1H), 1.63 (d, J = 7.1 Hz, 3H). |
| 53 | 2a-3 | Oxalyl chloride and sodium methoxide | 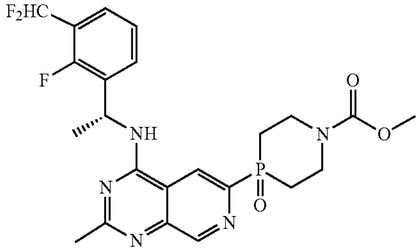 [SMILES: COC(=O)N1CCP(=O)(c2cc3c(N[C@H](C)c4cccc(C(F)F)c4F)nc(C)nc3cn2)CC1] | 508.1716 | $^1$H NMR (500 MHz, $CD_3OD$) δ 9.09 (s, 1H), 8.84 (d, J = 6.7 Hz, 1H), 7.64 (t, J = 7.4 Hz, 1H), 7.49 (t, J = 7.2 Hz, 1H), 7.24 (t, J = 7.7 Hz, 1H), 7.00 (t, J = 54.8 Hz, 1H), 5.86 (q, J = 7.1 Hz, 1H), 4.07-3.98 (m, 2H), 3.91 (s, 2H), 3.77 (s, 3H), 2.55 (m, 2H), 2.51 (s, 3H), 2.15-2.06 (m, 2H), 1.72 (d, J = 7.1 Hz, 3H). |
| 54 | 2a-4 | 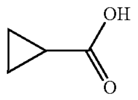 | 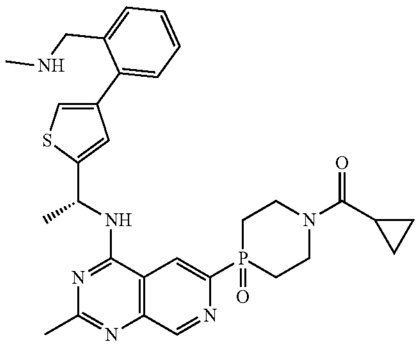 [SMILES: CNCc1ccccc1-c1csc([C@@H](C)Nc2nc(C)nc3cnc(P4(=O)CCN(C(=O)C5CC5)CC4)cc23)c1] | 575.2341 | $^1$H NMR (500 MHz, $CD_3OD$) δ 9.14 (s, 1H), 8.79-8.77 (m, 1H), 7.52-7.49 (m, 1H), 7.42-7.35 (m, 3H), 7.27 (d, J = 1.5 Hz, 1H), 7.20 (t, J = 1.2 Hz, 1H), 6.12-6.07 (m, 1H), 4.33-4.20 (m, 2H), 4.12 (s, 1H), 4.06 (s, 2H), 3.98 (s, 1H), 2.64 (s, 3H), 2.51 (s, 1H), 2.46 (s, 3H), 2.17-2.20 (m, 1H), 2.08 (m, 2H), 1.83 (d, J = 7.0 Hz, 3H), 0.94 m, 2H), 0.88 (m, 3H). |
| 55 | 2a-3 | 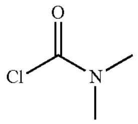 | 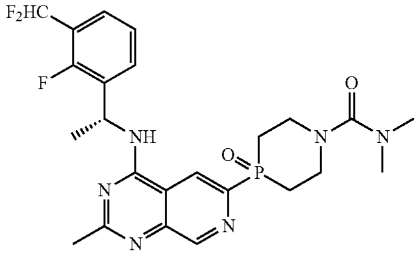 [SMILES: Cc1nc(N[C@H](C)c2cccc(C(F)F)c2F)c2cc(P3(=O)CCN(C(=O)N(C)C)CC3)ncc2n1] | 521.2061 | $^1$H NMR (500 MHz, $CD_3OD$) δ 9.10 (s, 1H), 8.84 (dd, J = 6.7, 0.9 Hz, 1H), 7.64 (t, J = 7.5 Hz, 1H), 7.49 (t, J = 7.1 Hz, 1H), 7.24 (t, J = 7.8 Hz, 1H), 7.00 (t, J = 54.9 Hz, 1H), 5.87 (m, 1H), 3.75 (m, 4H), 2.90 (s, 6H), 2.61 (h, J = 6.6 Hz, 2H), 2.51 (s, 3H), 2.22-2.05 (m, 2H), 1.72 (d, J = 7.1 Hz, 3H). |

TABLE 2-continued

| Examples | Intermediates | Fragments 2 | Compound | [M + H]$^+$ | $^1$H NMR |
|---|---|---|---|---|---|
| 56 | 2a-5 | 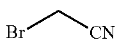 | 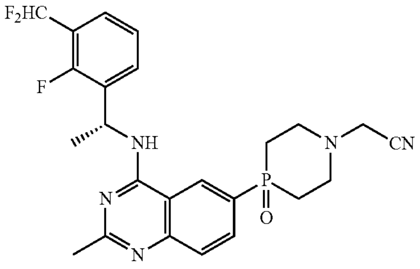 [SMILES: Cc1nc(N[C@H](C)c2cccc(C(F)F)c2F)c2cc(P3(=O)CCN(CC#N)CC3)ccc2n1] | 488.17 | $^1$H NMR (500 MHz, DMSO-$d_6$) δ 8.89-8.81 (m, 2H), 8.07 (t, J = 9.1 Hz, 1H), 7.73-7.67 (m, 2H), 7.51 (t, J = 6.9 Hz, 1H), 7.30 (t, J = 7.7 Hz, 1H), 7.25 (t, J = 54.4 Hz, 1H), 5.83 (p, J = 7.0 Hz, 1H), 3.89 (s, 2H), 3.07-2.91 (m, 4H), 2.47-2.35 (m, 5H), 2.06 (t, J = 16.1 Hz, 2H), 1.65 (d, J = 7.1 Hz, 3H). |
| 57 | 2a-5 | 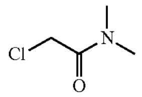 | 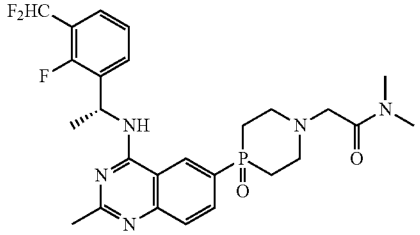 [SMILES: Cc1nc(N[C@H](C)c2cccc(C(F)F)c2F)c2cc(P3(=O)CCN(CC(=O)N(C)C)CC3)ccc2n1] | 534.15 | $^1$H NMR (500 MHz, DMSO-$d_6$) δ 8.89-8.81 (m, 2H), 8.06 (t, J = 9.0 Hz, 1H), 7.73-7.67 (m, 2H), 7.51 (t, J = 6.9 Hz, 1H), 7.30 (t, J = 7.7 Hz, 1H), 7.25 (t, J = 54.4 Hz, 1H), 5.83 (p, J = 7.0 Hz, 1H), 3.37 (s, 2H), 3.08-2.92 (m, 7H), 2.82 (s, 3H), 2.43-2.33 (m, 5H), 1.97 (t, J = 15.8 Hz, 2H), 1.65 (d, J = 7.1 Hz, 3H). |
| 58 | 2a-6 | 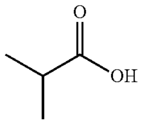 | 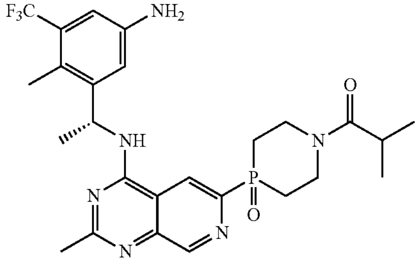 [SMILES: Cc1nc(N[C@H](C)c2cc(N)cc(C(F)(F)F)c2C)c2cc(P3(=O)CCN(C(=O)C(C)C)CC3)ncc2n1] | 549.2364 | $^1$H NMR (500 MHz, $CD_3OD$) δ 9.09 (s, 1H), 8.85 (d, J = 6.7 Hz, 1H), 7.02 (s, 1H), 6.91 (d, J = 2.4 Hz, 1H), 5.76 (q, J = 7.0 Hz, 1H), 4.19-3.94 (m, 4H), 3.05 (p, J = 6.7 Hz, 1H), 2.60 (d, J = 10.0 Hz, 1H), 2.52 (s, 3H), 2.50 (s, 1H), 2.45 (s, 3H), 2.13 (s, 2H), 1.62 (d, J = 6.9 Hz, 3H), 1.16 (t, J = 6.6 Hz, 6H). |
| 59 | 2a-6 | 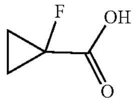 | 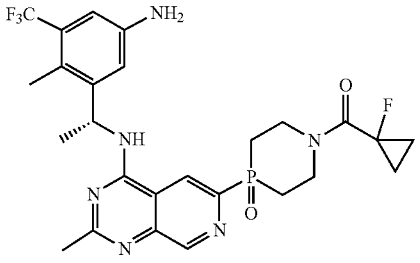 [SMILES: Cc1nc(N[C@H](C)c2cc(N)cc(C(F)(F)F)c2C)c2cc(P3(=O)CCN(C(=O)C4(F)CC4)CC3)ncc2n1] | 565.2111 | $^1$H NMR (500 MHz, $CD_3OD$) δ 9.10 (s, 1H), 8.87-8.84 (m, 1H), 7.02 (d, J = 2.2 Hz, 1H), 6.91 (d, J = 2.4 Hz, 1H), 5.76 (q, J = 6.9 Hz, 1H), 4.46-4.03 (m, 4H), 2.67-2.56 (m, 2H), 2.52 (s, 3H), 2.45 (s, 3H), 2.25-2.14 (m, 2H), 1.62 (d, J = 7.0 Hz, 3H), 1.36-1.30 (m, 4H). |
| 60 | 2a-6 | 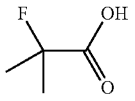 | 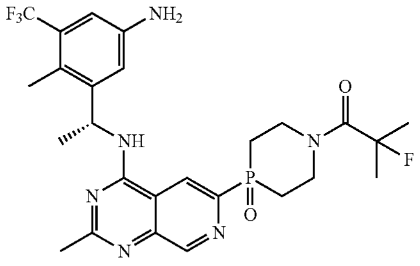 [SMILES: Cc1nc(N[C@H](C)c2cc(N)cc(C(F)(F)F)c2C)c2cc(P3(=O)CCN(C(=O)C(C)(C)F)CC3)ncc2n1] | 567.2259 | $^1$H NMR (500 MHz, $CD_3OD$) δ 9.09 (s, 1H), 8.85 (dd, J = 6.8, 0.6 Hz, 1H), 7.02 (d, J = 2.2 Hz, 1H), 6.91 (d, J = 2.4 Hz, 1H), 5.76 (q, J = 7.0 Hz, 1H), 4.36-4.15 (m, 4H), 2.67-2.55 (m, 2H), 2.52 (s, 3H), 2.45 (s, 3H), 2.21-2.12(m, 2H), 1.68 (s, 3H), 1.63 (s, 3H), 1.62 (d, J = 7.0 Hz, 3H). |

The following intermediates (Table 3-1) were prepared by referring to the procedures of step A in Example 9, and specifically, the following intermediate compounds 3a-1 to 3a-2 were prepared by replacing 5-amino-2-chiloroisonicotinic acid with the following fragments 2a.

TABLE 3-1

| No. | Fragments 2a | Intermediates |
|---|---|---|
| 3a-1 | 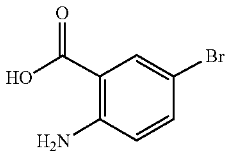 [SMILES: Nc1ccc(Br)cc1C(=O)O] | 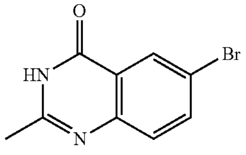 |

TABLE 3-1-continued

| No. | Fragments 2a | Intermediates |
|---|---|---|
| 3a-2 | 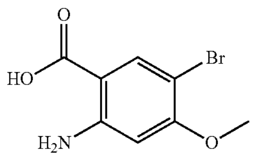 | 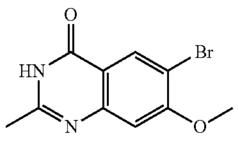 |

The following Examples 61 to 64 (Table 3) were prepared by referring to the procedures in Example 19, and specifically, compounds 61 to 64 were prepared by replacing (R)-1-(3-(trifluoromethyl)-2-fluorinephenyl)ethan-1-amine hydrochloride with the following fragments 3-1, and replacing the compound 9-1 with the prepared intermediate compounds.

TABLE 3

| Examples | Fragments 3-1 | Intermediates | Compound | $[M + H]^+$ | $^1H$ NMR |
|---|---|---|---|---|---|
| 61 | 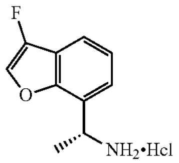 | 3a-1 | 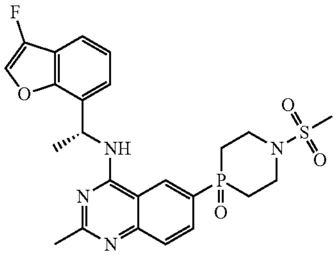 [SMILES: Cc1nc(N[C@H](C)c2cccc3c(F)coc23)c2cc(P3(=O)CCN(S(C)(=O)=O)CC3)ccc2n1] | 517.1467 | $^1H$ NMR (500 MHz, $CD_3OD$) δ 8.68 (dd, J = 13.2, 1.6 Hz, 1H), 8.01 (m, 1H), 7.77 (d, J = 4.4 Hz, 1H), 7.66 (dd, J = 8.6, 2.5 Hz, 1H), 7.39 (dd, J = 7.8, 1.2 Hz, 1H), 7.33 (d, J = 7.4 Hz, 1H), 7.15 (t, J = 7.5 Hz, 1H), 6.03 (q, J = 7.1 Hz, 1H), 4.02-3.86 (m, 2H), 3.50 (qd, J = 12.8, 11.9, 2.2 Hz, 2H), 2.86 (d, J = 0.9 Hz, 3H), 2.47 (m, 2H), 2.34 (s, 3H), 2.13 (m, 2H), 1.69 (d, J = 7.0 Hz, 3H). |
| 62 | 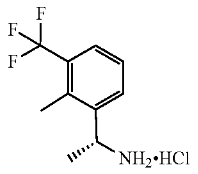 | 3a-1 | 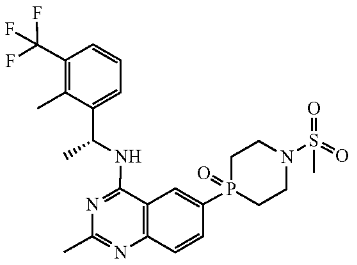 [SMILES: Cc1nc(N[C@H](C)c2cccc(C(F)(F)F)c2C)c2cc(P3(=O)CCN(S(C)(=O)=O)CC3)ccc2n1] | 541.1584 | $^1H$ NMR (500 MHz, $CD_3OD$) δ 8.68 (dd, J = 13.2, 1.8 Hz, 1H), 8.01 (m, 1H), 7.66 (dd, J = 8.6, 2.6 Hz, 1H), 7.61 (d, J = 7.8 Hz, 1H), 7.42 (dd, J = 7.9, 1.2 Hz, 1H), 7.18 (t, J = 7.9 Hz, 1H), 5.74 (q, J = 7.0 Hz, 1H), 3.95 (m, 2H), 3.68-3.38 (m, 2H), 2.87 (s, 3H), 2.55 (d, J = 1.6 Hz, 3H), 2.47 (m, 2H), 2.35 (s, 3H), 2.14 (m, 2H), 1.55 (d, J = 7.0 Hz, 3H). |
| 63 | 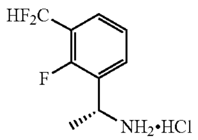 | 3a-2 | 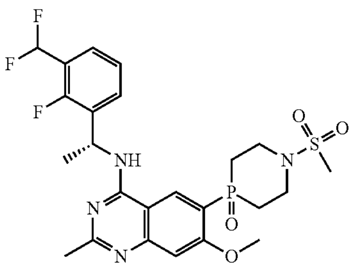 [SMILES: COc1cc2nc(C)nc(N[C@H](C)c3cccc(C(F)F)c3F)c2cc1P1(=O)CCN(S(C)(=O)=O)CC1] | 557.1597 | $^1H$ NMR (500 MHz, $CD_3OD$) δ 8.65 (d, J = 14.4 Hz, 1H), 7.62 (t, J = 7.3 Hz, 1H), 7.47 (t, J = 7.0 Hz, 1H), 7.23 (t, J = 7.7 Hz, 1H), 7.11-6.89 (m, 2H), 5.86 (m, 1H), 4.12 (dd, J = 26.7, 13.4 Hz, 2H), 4.03 (s, 3H), 3.66-3.52 (m, 2H), 2.99 (s, 3H), 2.79-2.64 (m, 2H), 2.43 (s, 3H), 2.12 (dd, J = 18.2, 15.7 Hz, 2H), 1.69 (d, J = 7.1 Hz, 3H). |

TABLE 3-continued

| Examples | Fragments 3-1 | Intermediates | Compound | [M + H]+ | $^1$H NMR |
|---|---|---|---|---|---|
| 64 | 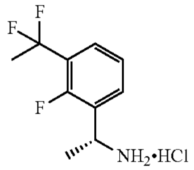 | 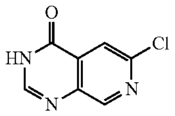 [SMILES: O=c1[nH]cnc2cnc(Cl)cc12] | 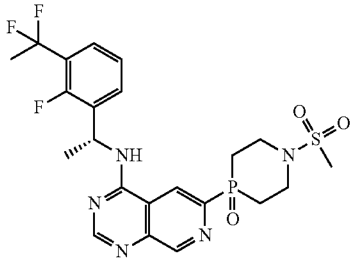 [SMILES: C[C@@H](Nc1ncnc2cnc(P3(=O)CCN(S(C)(=O)=O)CC3)cc12)c1cccc(C(C)(F)F)c1F] | 528.07 | $^1$H NMR (500 MHz, Chloroform-d) δ 9.17 (s, 1H), 8.98 (d, J = 6.6 Hz, 1H), 8.66 (s, 1H), 7.76 (d, J = 7.5 Hz, 1H), 7.38-7.28 (m, 2H), 6.99 (t, J = 7.8 Hz, 1H), 5.81-5.71 (m, 1H), 3.9-3.8 (m, 2H), 3.75-3.65 (m, 1H), 2.84 (s, 3H), 2.60 (dm, 2H), 2.27-2.13 (m, 2H), 1.87 (t, J = 18.6 Hz, 3H), 1.60 (d, J = 7.0 Hz, 3H), 1.20 (d, J = 15.0 Hz, 1H). |

The following Example 65 (Table 4) can refer to the procedures in Example 35, and specifically, compound 65 was prepared by replacing the compound 9-1 with the intermediate 3a-2, replacing (R)-1-(3-(trifluoromethyl)-2-fluorophenyl)ethan-1-amine hydrochloride with the corresponding fragments 4-1, replacing the compound 35-2 with the corresponding fragments 4-2 for reaction and finally referring to the procedures of step C in Example 7.

The following Examples 66 to 71 (Table 4) can refer to the procedures in Example 35, and specifically, compounds 66 to 71 were prepared by replacing the compound 9-1 with the intermediate 3a-2, replacing (R)-1-(3-(trifluoromethyl)-2-fluorophenyl)ethan-1-amine hydrochloride with the following fragments 4-1, and replacing the compound 35-2 with the following fragments 4-2.

TABLE 4

| Examples | Fragments 4-1 | Fragments 4-2 | Compound | [M + H]+ | $^1$H NMR |
|---|---|---|---|---|---|
| 65 | 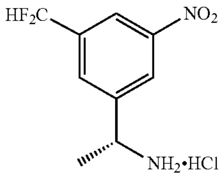 | 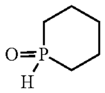 | 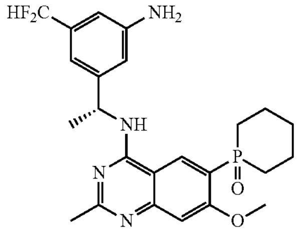 | 475.2131 | $^1$H NMR (500 MHz, $CD_3OD$) δ 8.56 (d, J = 13.8 Hz, 1H), 7.09 (d, J = 4.8 Hz, 1H), 6.91 (d, J = 1.7 Hz, 2H), 6.73 (s, 1H), 6.58 (t, J = 56.6 Hz, 1H), 5.64 (m, 1H), 4.02 (s, 3H), 2.49 (s, 3H), 2.40 (m, 2H), 2.08-1.96 (m, 6H), 1.89-1.83 (m, 1H), 1.63 (d, J = 7.0 Hz, 3H), 1.54 (dd, J = 8.5, 14.6 Hz, 1H). |
| 66 | 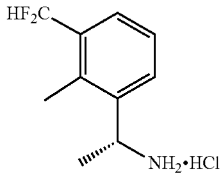 | 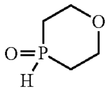 | 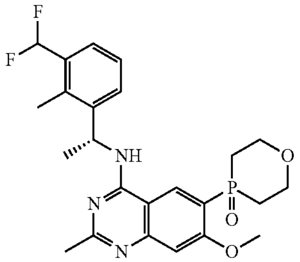 [SMILES: COc1cc2nc(C)nc(N[C@H](C)c3cccc(C(F)F)c3C)c2cc1P1(=O)CCOCC1] | 476.1908 | $^1$H NMR (500 MHz, $CD_3OD$) δ 8.60 (d, J = 14.3 Hz, 1H), 7.61 (d, J = 7.8 Hz, 1H), 7.39 (d, J = 7.7 Hz, 1H), 7.25 (t, J = 7.8 Hz, 1H), 7.10 (d, J = 5.0 Hz, 1H), 6.95 (t, J = 55.3 Hz, 1H), 5.86 (q, J = 7.0 Hz, 1H), 4.23-4.06 (m, 4H), 4.03 (s, 3H), 2.70 (m, 2H), 2.56 (d, J = 1.3 Hz, 3H), 2.45 (s, 3H), 2.03 (m, 2H), 1.63 (d, J = 7.0 Hz, 3H). |
| 67 | 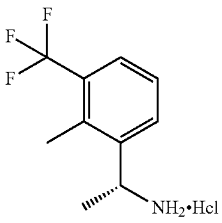 | 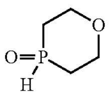 | 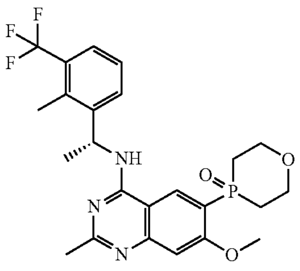 [SMILES: COc1cc2nc(C)nc(N[C@H](C)c3cccc(C(F)(F)F)c3C)c2cc1P1(=O)CCOCC1] | 494.1816 | $^1$H NMR (500 MHz, $CD_3OD$) δ 8.62 (d, J = 14.3 Hz, 1H), 7.71 (d, J = 7.8 Hz, 1H), 7.55-7.49 (m, 1H), 7.29 (t, J = 7.9 Hz, 1H), 7.10 (d, J = 4.9 Hz, 1H), 5.83 (q, J = 7.0 Hz, 1H), 4.25-4.07 (m, 4H), 4.03 (s, 3H), 2.70 (td, J = 11.0, 10.6, 5.3 Hz, 2H), 2.64 (d, J = 1.7 Hz, 3H), 2.43 (s, 3H), 2.04 (m, 2H), 1.63 (d, J = 7.0 Hz, 3H). |

TABLE 4-continued

| Examples | Fragments 4-1 | Fragments 4-2 | Compound | [M + H]+ | 1H NMR |
|---|---|---|---|---|---|
| 68 | 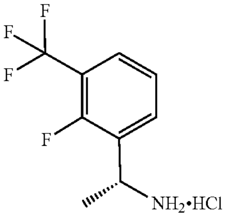 | 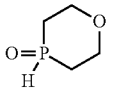 | 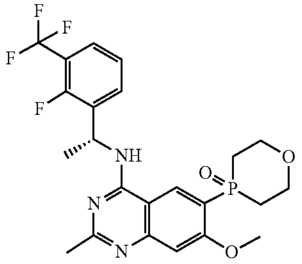 [SMILES: COc1cc2nc(C)nc(N[C@H](C)c3cccc(C(F)(F)F)c3F)c2cc1P1(=O)CCOCC1] | 498.1566 | $^1$H NMR (500 MHz, $CD_3OD$) δ 8.64 (d, J = 14.3 Hz, 1H), 7.73 (t, J = 7.0 Hz, 1H), 7.55 (t, J = 7.1 Hz, 1H), 7.27 (t, J = 7.8 Hz, 1H), 7.12 (d, J = 5.0 Hz, 1H), 5.84 (q, J = 7.1 Hz, 1H), 4.27-4.07 (m, 4H), 4.04 (s, 3H), 2.75-2.68 (m, 2H), 2.42 (s, 3H), 2.13-1.99 (m, 2H), 1.70 (d, J = 7.1 Hz, 3H). |
| 69 | 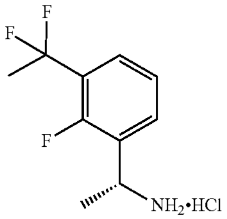 | 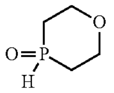 | 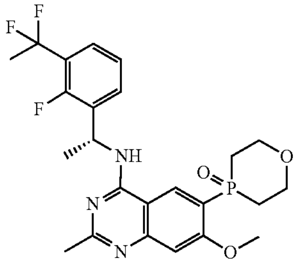 [SMILES: COc1cc2nc(C)nc(N[C@H](C)c3cccc(C(C)(F)F)c3F)c2cc1P1(=O)CCOCC1] | 494.1815 | $^1$H NMR (500 MHz, $CD_3OD$) δ 8.63 (d, J = 14.3 Hz, 1H), 7.59-7.54 (m, 1H), 7.42 (td, J = 1.7, 7.4 Hz, 1H), 7.17 (t, J = 7.8 Hz, 1H), 7.11 (d, J = 5.0 Hz, 1H), 5.86 (q, J = 7.1 Hz, 1H), 4.22-4.08 (m, 4H), 4.04 (s, 3H), 2.71 (m, 2H), 2.43 (s, 3H), 2.02 (m, 5H), 1.68 (d, J = 7.1 Hz, 3H). |
| 70 | 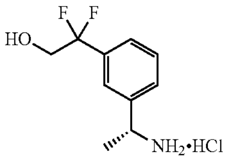 | 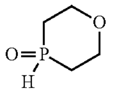 | 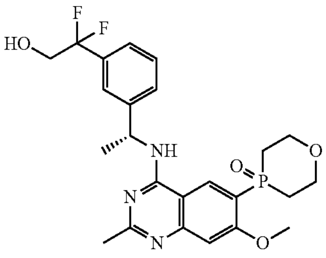 [SMILES: COc1cc2nc(C)nc(N[C@H](C)c3cccc(C(F)(F)CO)c3)c2cc1P1(=O)CCOCC1] | 492.1862 | $^1$H NMR (500 MHz, $CD_3OD$) δ 8.59 (d, J = 14.3 Hz, 1H), 7.65 (s, 1H), 7.58 (d, J = 7.1 Hz, 1H), 7.43-7.39 (m, 2H), 7.11 (d, J = 5.0 Hz, 1H), 5.73 (q, J = 7.0 Hz, 1H), 4.22-4.08 (m, 4H), 4.04 (s, 3H), 3.87 (t, J = 13.5 Hz, 2H), 2.74-2.64 (m, 2H), 2.48 (s, 3H), 2.07-2.00 (m, 2H), 1.68 (d, J = 7.1 Hz, 3H). |
| 71 | 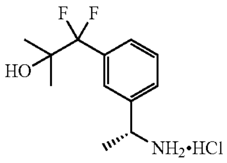 | 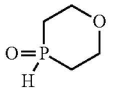 | 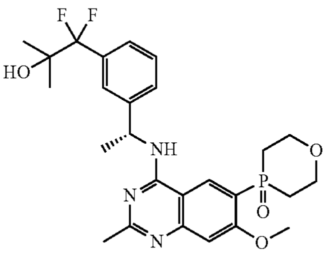 [SMILES: COc1cc2nc(C)nc(N[C@H](C)c3cccc(C(F)(F)C(C)(C)O)c3)c2cc1P1(=O)CCOCC1] | 520.2179 | $^1$H NMR (500 MHz, $CD_3OD$) δ 8.59 (d, J = 14.3 Hz, 1H), 7.61 (s, 1H), 7.58-7.52 (m, 1H), 7.42-7.33 (m, 2H), 7.11 (d, J = 5.0 Hz, 1H), 5.71 (m, 1H), 4.2-4.07 (m, 4H), 4.04 (s, 3H), 2.73-2.66 (m, 2H), 2.46 (s, 3H), 2.09-2.01 (m, 2H), 1.68 (d, J = 7.1 Hz, 3H), 1.20 (s, 6H). |

Test Example 1 Inhibition Test of In Vitro Cell Level Phosphorylation Activity

1.1 Test Reagents and Instruments

1.1.1 Test Reagents

| Name | Manufacturer/source | Catalog number/test number |
|---|---|---|
| RPMI medium | Hyclone | SH30809.01 |
| FBS | Gibco | 10099-141 |
| PBS | Sangon Biotech | B040100-0005 |
| Tween-20 | Sinopharm Chemical Reagent Co., Ltd. | 30189328 |
| BSA | SIGMA | B2064 |
| 4% polyoxymethylene | BBI | E672002-0500 |
| Methanol | Merk | 103726 |

-continued

| Name | Manufacturer/source | Catalog number/test number |
|---|---|---|
| Anti-rabbit IgG (H + L), F(ab')2 Fragment (Alexa Fluor ® 647 Conjugate) | Biodragon | 4414S |
| Anti-rabbit IgG (H + L) (Dylight ™ 800 4x PEG Conjugate) | CST | 5151 |
| Phospho-p44/42 MAPK (Erk1/2) (Thr202/Tyr204) Antibody | CST | 9101S |
| GAPDH(2B8) Mouse mAb | Biodragon | B1030 |
| 384-well clear-bottom microplate | Nunc | 142761 |
| PS/polymer substrate | | |

1.1.2 Instruments

| Name | Manufacturer | Model |
|---|---|---|
| Cell incubator | Thermo | 371 |
| Fluorescent inverted microscope | NOVEL | XD-202 |
| Ultra clean bench | AIRTECH | BCM-1000A |
| Centrifuge | Sigma | 3K15 |
| Porous shaker | Vortex | Gentus3 |
| Microplate centrifuge | ALLSHENG | Mini-P25 |
| Full-automatic cell counter | Nexcelom | Cellometer Auto T4 |
| Ultra microsyringe | Tecan | D300E |
| Sapphire ™ dual-mode multi-spectral laser imaging system | Azure Biosystems | Sapphire RGBNIR |
| Pipette | Raining | 0.5-10 μL |
| Pipette | Raining | 2-20 μL |
| Pipette | Thermo | 10-100 μL |
| Pipette | Thermo | 20-200 μL |
| Pipette | Thermo | 100-1000 μL |
| Electric pipette | Thermo | 9501 |
| Electric pipette | Eppendorf | 8-channel, 5-100 |

1.2 Test Method for In Vitro Cell Level Phosphorylation Activity

A dish of H358 human non-small cell lung cancer cells (Nanjing Cobioer Biosciences Co., Ltd.) in logarithmic growth phase and good cell condition were added to a centrifuge tube and centrifuged at 1000 rpm for 5 min in a low speed benchtop centrifuge. The supernatant was discarded, and 5 mL of a plating medium containing 5% FBS was added using a pipette for cell resuspension. The cell suspension was loaded on a cell counter for counting, and diluted with the plating medium to adjust the cell density to $1.5\times10^5$ cells/mL. The cells were seeded on a black clear-bottom 384-well plate at 40 μL/well using a multi-channel pipette, and cultured overnight in a cell incubator at 37° C., 5% $CO_2$ and saturated humidity. The compound was loaded using a Tecan D300e ultra microsyringe. The medium was discarded after 1 h, 40 μL, of 4% polyoxymethylene was added to each well, and the plate was incubated for 20 min at room temperature and washed with PBS. 40 μL of methanol was added to each well, and the plate was incubated for 10 min at room temperature and washed with PBST. 20 μL of 5% BSA blocking buffer was added to each well, and the blocking buffer was discarded after the plate was blocked for 1 h at room temperature. 20 μL of the primary antibody mixed solution was added to each well, wherein Rabbit anti-pERK was diluted at 1:1000 (final concentration) and mouse anti-GAPDH was diluted at 1:5000 (final concentration), and the plate was incubated overnight at 4° C. and washed with PBST. 20 μL of the secondary antibody mixed solution was added to each well, wherein goat anti rabbit 800 and goat anti mouse 647 were both diluted at 1:1000 (final concentration), and the plate was incubated in the dark at room temperature for 45 min and washed with PBST. Readings were scanned by Azure Biosystems, $EC_{50}$ values were calculated and analyzed using the four-parameter logistic model with the logarithm of the compound concentration as the abscissa and the phosphorylation inhibition rate as the ordinate, and the results are shown in Table 5.

TABLE 5

| Examples | $EC_{50}$ (nM) |
|---|---|
| 12 | 103 |
| 14 | 108 |

TABLE 5-continued

| Examples | $EC_{50}$ (nM) |
|---|---|
| 15 | 148 |
| 17 | 82 |
| 18 | 71 |

Test Example 2 Guanine Nucleotide Exchange Test

This test quantitatively investigates the ability of SOS to mediate KRAS activation. KRAS G12C with a His tag was added to the system, anti-His antibody labeled with lanthanide Eu was combined with the system, then auxiliary protein SOS1cat and GTP analogue EDA-GTP-DY-647P1 with fluorophore were added thereto, the GTP analogue with fluorophore was loaded on KRAS G12C with the assistance of the auxiliary protein, and then energy resonance transfer occurred between Anti-6HS-Cryptate (FRET donor) and EDA-GTP-DY-647P1 (FRET acceptor).

However, after pretreatment with SOS1 inhibitor compounds, the ability of SOS1 to bind and mediate KRAS activation was weakened, and the ability of FRET between donor and acceptor was weakened.

2.1 Test Reagents and Instruments 2.1.1 Test Reagents

| Name | Manufacturer/source | Catalog number/test number |
|---|---|---|
| His-KRAS G12C | In-house manufacture | TQB3822PP01a |
| SOS1cat | In-house manufacture | TQB3822PP02 |
| Anti-6HIS-Cryptate | Cisbio | 61HISKLA |
| EDA-GTP-DY-647P1 | Jena Bioscience | NU-820-647P1 |
| HEPES pH 7.4 | Thermo | 15630080 |
| NaCl | Shanghai Hushi Chemical Co., Ltd. | 10019318 |
| $MgCl_2$ | Sigma | M8266 |
| DTT | Promega | V3151 |
| BSA | Sigma | B2604 |
| DMSO | Sigma | D4540 |
| Igepal | Sigma | I3021 |

2.1.2 Instruments

| Name | Manufacturer | Model |
|---|---|---|
| Pipette | Thermo | 100-1000 μl |
| Pipette | Thermo | 20-200 μl |
| Pipette | Thermo | 10-100 μl |
| Pipette | RNIN | 2-20 μl |
| Pipette | RNIN | 0.5-10 μl |
| Ultra microsyringe | Tecan | D300 E |

2.2 Nucleotide Exchange Test Procedure

Preparation of His-KRAS G12C: K-Ras4B-G12C (UniProt P01116-2, amino acid 1-169) sequence was subjected to codon optimization and gene synthesis, and finally subcloned to a pET-30a(+) vector and transformed into BL21 (DE3) competence; a proper clone was selected, cultured in a TB medium and induced for expression at low temperature with IPTG; and bacteria were collected. Cell disruption was performed using an ultrasonic disruptor, and the supernatant was collected by centrifugal filtration. Purification was performed by Ni Sepharose HP and Superdex 200 pg (16/60) to give proteins with >90% purity that were assayed for viability.

Preparation of SOS1cat: human SOS1 (UniProt Q07889, amino acid 564-1049) sequence was subjected to codon optimization and gene synthesis, and finally subcloned to a pET-30a(+) vector and transformed into BL21(DE3) competence; a proper clone was selected, cultured in a TB medium and induced for expression at low temperature with IPTG; and bacteria were collected. Cell disruption was performed using an ultrasonic disruptor, and the supernatant was collected by centrifugal filtration. Purification was performed by Ni Sepharose HP, Superdex 200 pg (16/60) and Superdex 200 pg (16/60) to give proteins with >90% purity that were assayed for viability.

Test buffer was prepared with the following components: HEPES pH 7.4: 20 mM; NaCl: 150 mM; $MgCl_2$: 0.5 mM; DTT: 2 mM; BSA: 0.05%; and Igepal: 0.0025%.

KRAS G12C working solution, SOS1cat working solution and blank control solution were prepared with the test buffers; wherein the KRAS G12C working solution contained 100 nM His-KRAS G12C and 2 nM anti-His-terbium; the SOS1cat working solution contained 20 nM SOS1cat and 200 nM EDA-GTP-DY-647P1; and the blank control solution contained 100 nM EDA-GTP-DY-647P1.

The whole test procedures were completed at 20° C. 5 μL of SOS1cat working solution was added to each well of the test group, while 5 μL of blank working solution was added to each well of the control group, and the plate was incubated at 20° C. for 10 min. Then, the compound was loaded using a Tecan D300e ultra microsyringe at a maximum final concentration of 10 μM, and the mixture was diluted 2-fold in sequence to set up 8 concentration gradients and incubated at 20° C. for 30 min. Finally, 5 μL of KRAS G12C working solution was added to each well, the plate was incubated for 15 min at 20° C., and a ratio of fluorescence at 665 nm/620 nm was detected using an Envision microplate reader to reflect the conversion degree of the nucleotide. The inhibition rate was calculated by the following formula: inhibition rate (%)=(mean value of negative control group−mean value of experimental group)/(mean value of negative control group−mean value of blank group)×100%, wherein the negative control group contained no compound and the remaining conditions were the same as those of the test group. $IC_{50}$ values were calculated and analyzed using the four-parameter logistic model with the logarithm of the compound concentration as the abscissa and the phosphorylation inhibition rate as the ordinate, and the results are shown in Table 6.

Test Example 3 KRAS/SOS1 Protein Binding Assay

This assay can be used to detect the efficacy of compounds to inhibit protein-protein interactions between SOS1 and KRAS G12C on the one hand, and to validate the molecular action mode of compounds on the other hand. Low $IC_{50}$ values indicate that the SOS1 inhibitor compounds can inhibit protein interactions with high efficacy.

3.1 Test Reagents and Buffers 3.1.1 Reagents:

GST-SOS1 (564-1049), in-house manufacture: human SOS1 (UniProt Q07889, amino acid 564-1049) sequence was subjected to codon optimization and gene synthesis, and finally subcloned to a pGEX-4T-1 vector and transformed into BL21(DE3) competence; a proper clone was selected, cultured in a TB medium and induced for expression at low temperature with IPTG; and bacteria were collected. Cell disruption was performed using an ultrasonic disruptor, and the supernatant was collected by centrifugal filtration. Purification was performed by Ni Sepharose HP and Superdex 200 pg (16/60) to give proteins with >90% purity that were assayed for viability;

Kras-G12C-6×His (1-169), in-house manufacture: K-Ras4B-G12C (UniProt P01116-2, amino acid 1-169) sequence was subjected to codon optimization and gene synthesis, and finally subcloned to a pET-30a(+) vector and transformed into BL21(DE3) competence; a proper clone was selected, cultured in a TB medium and induced for expression at low temperature with IPTG; and bacteria were collected. Cell disruption was performed using an ultrasonic disruptor, and the supernatant was collected by centrifugal filtration. Purification was performed by Ni Sepharose HP and Superdex 200 pg (16/60) to give proteins with >90% purity that were assayed for viability;

GDP (Sigma, Cat. No. G7127);

MAb Anti-GST-XL665 (Cisbio, Cat. No. 61GSTXLA);

MAb Anti-6HIS-Tb cryptate Gold (Cisbio, Cat. No. 61HI2TLA).

3.1.2 Buffers:

Diluent Buffer (Cisbio, Cat. No. 62DLBDDF);

Detection buffer (Cisbio, Cat. No. 62DB2FDG);

GST-SOS1 working solution: prepared using Diluent Buffer with a concentration of 92 nM;

GDP-Kras-G12C-His working solution: prepared using Diluent Buffer, and the final concentrations of GDP and Kras-G12C-His are 40 μM and 100 nM, respectively;

Antibody working solution: prepared using Detection buffer, and the concentrations of MAb Anti-GST-XL665 and MAb Anti-6HIS-Tb cryptate Gold are both 4× and are mixed at a ratio of 1:1.

3.2 Testing Procedures:

5 μL of GST-SOS1 working solution was added to each well of the test group and the negative group, and 5 μL of Diluent Buffer was added to each well of the control group; then, the compound was loaded using a Tecan D300e ultra microsyringe at a maximum final concentration of 5000 nM, and the mixture was diluted 3-fold in sequence to set up 7 concentration gradients and incubated at room temperature for 30 min; next, 5 μL of GDP-Kras-G12C-His working solution prepared in advance was added into each well (GDP and Kras-G12C-His were incubated for 10 min at room temperature), and incubated for 15 min at room temperature; and finally, 10 μL of antibody working solution was added to each well, the plate was incubated at room temperature for 50 min, and a ratio of fluorescence at 665 nm/620 nm was detected using an Envision microplate reader. The inhibition rate was calculated by the following formula: inhibition rate (%)=(mean value of negative control group−mean value of experimental group)/(mean value of negative control group−mean value of blank group)×100%, wherein the negative control group contained no compound and the remaining conditions were the same as those of the test group. IC 50 values were calculated using the four-parameter logistic model with the logarithm of the compound concentration as the abscissa and the phosphorylation inhibition rate as the ordinate, and the results are shown in Table 6.

Test Example 4 Assay for Proliferation Inhibitory Activity of K562 Cells

The K562 cell line can be purchased from the American Type Culture Collection (ATCC).

The K562 cells in a good growth state were added to a centrifuge tube with the cell density adjusted to $3\times10^4$/mL, and seeded on a 96-well plate (100 μL/well). The cells were cultured overnight in a cell incubator, the compound was loaded using a nanoliter pipettor to allow the final compound concentration to be 10000 nM to 4.6 nM, 2 replicate wells were set and control was set. After the cells were continuously cultured in the cell incubator for 72 h, a detection reagent CCK-8 (Cell Counting Kit-8, Dojindo Laboratories Co., Ltd., 10 μL/well) was added thereto; after the cells were incubated in the cell incubator for 1 h, the absorbance was measured at 450 nm with an Envision microplate reader; and a dose-response curve was fitted by four-parameter analysis, $IC_{50}$ was calculated, and the results are shown in Table 6.

TABLE 6

| Examples | Nucleotide conversion of HTRF $IC_{50}$ (nM) | Inhibition of $IC_{50}$ (nM) by KRAS-G12C/SOS1 binding | K562 cell proliferation inhibition $IC_{50}$ (nM) |
|---|---|---|---|
| 19 | / | 41 | 206 |
| 20 | 482 | 78 | 292 |
| 21 | 481 | 58 | 187 |
| 22 | / | 63 | 836 |
| 23 | 283 | / | 118 |
| 24 | / | 143 | 177 |
| 25 | / | 86 | 247 |
| 26 | / | 103 | / |
| 27 | 542 | 61 | 469 |
| 28 | / | 50 | 239 |
| 29 | / | 63 | 320 |
| 30 | / | 68 | 302 |
| 31 | / | 129 | 513 |
| 32 | / | 90 | 155 |
| 33 | / | 64 | 250 |
| 34 | / | 612 | / |
| 35 | / | 156 | 574 |
| 36 | / | 94 | 346 |
| 37 | / | 97 | 362 |
| 38 | / | 115 | 477 |
| 39 | / | 103 | 561 |
| 40 | / | 179 | 514 |
| 41 | / | 180 | 570 |
| 42 | 572 | 81 | 562 |
| 43 | 717 | 215 | 1068 |
| 44 | 724 | / | / |
| 45 | 694 | / | 1077 |
| 46 | 498 | / | 491 |
| 47 | 573 | / | 440 |
| 48 | 895 | / | 1573 |
| 49 | 1469 | / | 2152 |
| 50 | 456 | / | 334 |
| 51 | / | 100 | 282 |
| 52 | 455 | / | 95 |
| 53 | 504 | / | 93 |
| 54 | 486 | / | 84 |
| 55 | / | 87 | 280 |
| 56 | / | 88 | 507 |
| 57 | / | 204 | 2170 |
| 58 | 433 | / | 31 |
| 59 | 448 | / | 21 |
| 60 | 433 | / | 30 |
| 61 | / | 63 | 421 |
| 62 | / | 45 | 155 |
| 63 | / | 38 | 137 |
| 64 | / | 64 | 281 |
| 65 | 482 | 56 | 433 |
| 66 | / | 79 | 271 |
| 67 | / | 71 | 264 |
| 68 | / | 90 | 720 |
| 69 | / | 49 | 310 |
| 70 | / | 44 | 257 |
| 71 | / | 35 | 139 |

Test Example 5 Pharmacodynamics of SOS1 Inhibitor in MIA PaCa-2 Human Pancreatic Cancer Nude Mouse Xenograft Tumor Model SPF-grade female BALB/C nude mice (from Changzhou Cavens Laboratory Animal Ltd.) were inoculated subcutaneously with $1\times10^7$ MIA PaCa-2 cells (Kras G12C mutant tumor cells, Nanjing Cobioer Biosciences Co., Ltd.). When the mean tumor volume reached about 200 $mm^3$, the animals were divided into administration groups and control groups, 8 animals in each group. The day of grouping was determined as d0, the gavage administration was started on dl, the administration was performed twice a day, and the administration volume of the administration group was 10 mL/kg. Vehicle control was administered to the control group. The mice were consecutively administered, the tumor volume was measured 2-3 times a week, meanwhile, the mice were weighed and the data were recorded; The general behavior of the mice was observed and recorded every day. After the experiment was completed, the tumors were removed, weighed and photographed.

Calculation formula for tumor volume:

$$\text{Tumor volume }(mm^3) = 1/2\times(a\times b^2)$$

(where $a$ represents long diameter and $b$ represents short diameter);

Relative tumor proliferation rate (T/C %) refers to the percentage of the relative tumor volume of the treatment and control groups at a certain time point;

Tumor growth inhibition rate (TGI %) was calculated according to the following formula: TGI %=(1−tumor weight in treatment group/tumor weight in control group)×100%;

The calculation formula for weight change rate (WCR) (%) is: $WCR=(Wt_t-Wt_0)/Wt_0\times100\%$, where $Wt_0$ is the body weight of the animal at grouping (i.e., d0), $Wt_t$ is the body weight of the animal at each measurement.

The compound disclosed herein has good in vivo pharmacodynamic activity.

The invention claimed is:

1. A compound of formula (I), a stereoisomer thereof or a pharmaceutically acceptable salt thereof:

(I)

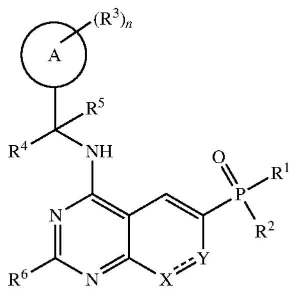

wherein,

X and Y are each independently selected from the group consisting of $CR^a$, C(O), N and $NR^b$;

"------" represents a single bond or a double bond depending on X and Y;

$R^a$ is selected from the group consisting of hydrogen, hydroxy, halogen, cyano, $C_{1-6}$ alkyl and $C_{1-6}$ alkoxy, wherein the $C_{1-6}$ alkyl or $C_{1-6}$ alkoxy is optionally substituted with one or more deuterium or halogens;

$R^b$ is selected from the group consisting of hydrogen, $C_{1-6}$ alkyl and $C_{1-6}$ alkoxy;

$R^1$ and $R^2$ are each independently selected from the group consisting of $C_{1-6}$ alkyl, $NH(R^c)$—$C_{1-6}$ alkyl- and $N(R^c)(C_{1-6}$ alkyl)-$C_{1-6}$ alkyl-, or $R^1$, $R^2$ and the phosphorus atom to which they are both connected together form 5-10 membered heterocyclyl, wherein the $C_{1-6}$ alkyl or 5-10 membered heterocyclyl is optionally substituted with one or more $R^c$;

each $R^c$ is independently selected from the group consisting of hydrogen, O═, HN═, $C_{1-6}$ alkyl-N═, $C_{1-6}$ alkyl-, $C_{1-6}$ alkyl-C(O)—, $C_{1-6}$ alkyl-$S(O)_2$—, 3-6 membered cycloalkyl-$S(O)_2$—, $C_{1-6}$ alkyl OC(O)—, $C_{1-6}$ alkyl-O—$C_{1-6}$ alkyl-, $C_{1-6}$ alkyl-O—$C_{1-6}$ alkyl-C(O)—, amino-C(O)—, mono($C_{1-6}$ alkyl)amino-C(O)—, di($C_{1-6}$ alkyl)amino-C(O)—, amino-$C_{1-6}$ alkyl-C(O)—, mono($C_{1-6}$ alkyl)amino-$C_{1-6}$ alkyl-C(O)—, di($C_{1-6}$ alkyl)amino-$C_{1-6}$ alkyl-C(O)—, amino-C(O)—$C_{1-6}$ alkyl-, mono($C_{1-6}$ alkyl)amino-C(O)—$C_{1-6}$ alkyl-, di($C_{1-6}$ alkyl)amino-C(O)—$C_{1-6}$ alkyl-, 3-6 membered cycloalkyl-, 3-6 membered cycloalkyl-C(O)—, 3-6 membered cycloalkyl-$C_{1-6}$ alkyl-, 3-6 membered heterocycloalkyl-, 3-6 membered heterocycloalkyl-C(O)—, 3-6 membered heterocycloalkyl-$C_{1-6}$ alkyl-, $C_{6-10}$ aryl-$C_{1-6}$ alkyl- and $C_{1-6}$ alkyl-substituted with one or more hydroxy or cyano, wherein the $R^c$ is optionally substituted with one or more halogens when it is not hydrogen and O═;

ring A is selected from the group consisting of $C_{6-10}$ aryl, 5-10 membered heteroaryl, 8-12 membered fused ring and 8-12 membered fused heterocyclic ring;

n is 0, 1, 2 or 3;

each $R^3$ is independently selected from the group consisting of amino, nitro, halogen, $C_{1-8}$ alkyl-, 3-6 membered cycloalkyl- and phenyl, wherein the $C_{1-8}$ alkyl, 3-6 membered cycloalkyl or phenyl is optionally substituted with one or more $R^d$;

$R^d$ is selected from the group consisting of hydroxy, halogen and $C_{1-6}$ alkyl-NH—$C_{1-6}$ alkyl-;

$R^4$ and $R^5$ are each independently selected from the group consisting of hydrogen, deuterium and $C_{1-6}$ alkyl, wherein the $C_{1-6}$ alkyl is optionally substituted with one or more halogens; and $R^6$ is selected from the group consisting of hydrogen, halogen and $C_{1-6}$ alkyl, wherein the $C_{1-6}$ alkyl is optionally substituted with one or more halogens.

2. The compound, stereoisomer thereof, or pharmaceutically acceptable salt thereof of claim 1, wherein X is selected from the group consisting of $CR^a$ and $NR^b$, and Y is selected from the group consisting of $CR^a$, C(O), N and $NR^b$; or, X and Y are both selected from $CR^a$; or, X is selected from CH, and Y is selected from $CR^a$; or, X is selected from CH, and Y is selected from the group consisting of C(OH), $C(OCH_3)$, $C(OCHF_2)$, $C(OCH_2F)$, CF and $C(OCD_3)$; or, X is selected from CH, and Y is selected from N; or, X is selected from $N(CH_3)$, and Y is selected from C(O); or, X is selected from the group consisting of CF and C(CN), and Y is selected from the group consisting of CH and N.

3. The compound, stereoisomer thereof, or pharmaceutically acceptable salt thereof of claim 1, wherein $R^a$ is selected from the group consisting of hydrogen, hydroxy, halogen, cyano, $C_{1-4}$ alkyl and $C_{1-4}$ alkoxy, wherein the $C_{1-4}$ alkyl and $C_{1-4}$ alkoxy are optionally substituted with one or more deuterium or halogens; or, $R^a$ is selected from the group consisting of hydrogen, hydroxy, halogen, cyano and $C_{1-4}$ alkoxy, wherein the $C_{1-4}$ alkoxy is optionally substituted with 3 deuterium, or one or more fluorine; or, $R^a$ is selected from the group consisting of hydrogen, hydroxy, halogen, cyano and $C_{1-4}$ alkoxy, wherein the $C_{1-4}$ alkoxy is optionally substituted with 3 deuterium, or 1 or 2 fluorine; or, $R^a$ is selected from the group consisting of hydrogen, hydroxy, fluorine, cyano, methoxy, monofluorinemethoxy and difluorinemethoxy, wherein the methoxy is optionally substituted with 3 deuterium; or, $R^a$ is selected from the group consisting of hydrogen, hydroxy, fluorine, cyano, $CH_3O$—, $CD_3O$—, $CH_2FO$— and $CHF_2O$—.

4. The compound, stereoisomer thereof, or pharmaceutically acceptable salt thereof of claim 1, wherein $R^b$ is selected from $C_{1-6}$ alkyl; or, $R^b$ is selected from $C_{1-4}$ alkyl; or, $R^b$ is selected from $C_{1-3}$ alkyl; or, $R^b$ is selected from methyl.

5. The compound, stereoisomer thereof, or pharmaceutically acceptable salt thereof of claim 1, wherein $R^1$ and $R^2$ are each independently selected from the group consisting of $C_{1-3}$ alkyl, $NH(R^c)$—$C_{1-3}$ alkyl- and $N(R^c)(C_{1-3}$ alkyl)-$C_{1-3}$ alkyl-; or, $R^1$ and $R^2$ are each independently selected from $C_{1-3}$ alkyl; or, $R^1$ and $R^2$ are each independently selected from the group consisting of methyl and ethyl.

6. The compound, stereoisomer thereof, or pharmaceutically acceptable salt thereof of claim 1, wherein $R^1$, $R^2$ and the phosphorus atom to which they are both connected together form 5-10 membered heterocyclyl, wherein the ring atoms of the 5-10 membered heterocyclyl optionally contain one or more heteroatoms selected from the group consisting of N, O and S atoms, and the 5-10 membered heterocyclyl is optionally substituted with one or more $R^c$, and when the ring atoms contain an N atom, N is connected to $R^c$; or, $R^1$, $R^2$ and the phosphorus atom to which they are both connected together form 5-8 membered heterocyclyl, wherein the ring atoms of the 5-8 membered heterocyclyl optionally contain one heteroatom selected from the group consisting of N and O atoms, and when the ring atoms contain an N atom, N is connected to $R^c$; or, $R^1$, $R^2$ and the phosphorus atom to which they are both connected together form 5 membered or 6 membered heterocyclyl, wherein the ring atoms of the 5 membered or 6 membered heterocyclyl optionally contain one heteroatom selected from the group consisting of N and O atoms, and when the ring atoms contain an N atom, N is connected to $R^c$; or, structural unit

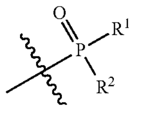

is selected from the group consisting of structural units

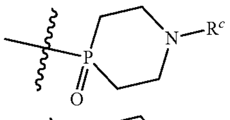
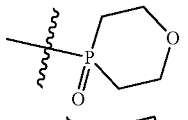
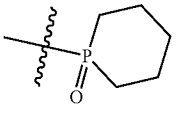
and
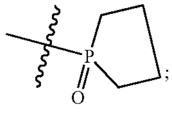
;

or, structural unit

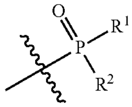

is structural unit

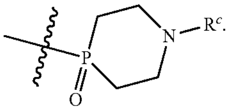

7. The compound, stereoisomer thereof, or pharmaceutically acceptable salt thereof of claim 1, wherein each $R^c$ is independently selected from the group consisting of $C_{1-3}$ alkyl-, $C_{1-3}$ alkyl-C(O)—, $C_{1-3}$ alkyl-$S(O)_2$—, 3-5 membered cycloalkyl-$S(O)_2$—, $C_{1-3}$ alkyl OC(O)—, $C_{1-3}$ alkyl-O—$C_{1-3}$ alkyl-, $C_{1-3}$ alkyl-O—$CH_2$—C(O)—, di($C_{1-3}$ alkyl)amino-C(O)—, di($C_{1-3}$ alkyl)amino-$CH_2$—C(O)—, di($C_{1-3}$ alkyl)amino-C(O)—$CH_2$—, 3-5 membered cycloalkyl-, 3-5 membered cycloalkyl-C(O)—, 3-5 membered cycloalkyl-$CH_2$—, 3-5 membered heterocycloalkyl-, phenyl-$CH_2$— and $C_{1-3}$ alkyl-substituted with one hydroxy or cyano, wherein the $R^c$ is optionally substituted with 1, 2 or 3 halogens when it is not hydrogen; or, each $R^c$ is independently selected from the group consisting of hydrogen, methyl, ethyl, isopropyl,

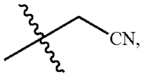 [SMILES: *CC#N]

acetyl,

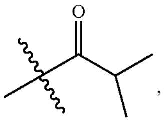 , 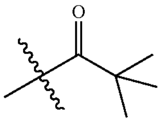 , 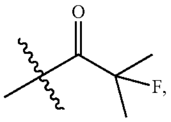

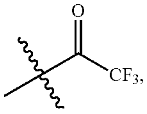 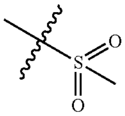 , 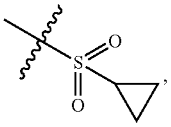 ,

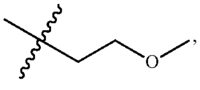 , 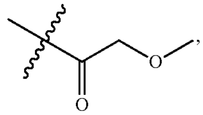 ,

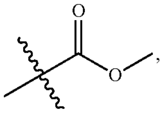 , 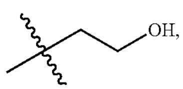 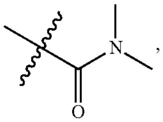 ,

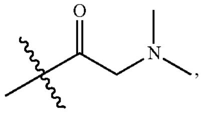 , 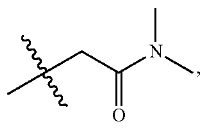 ,

-continued

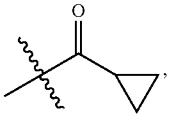 , 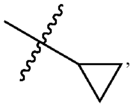 , 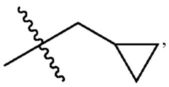 ,

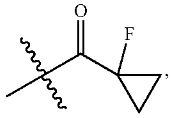 , 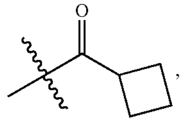 ,

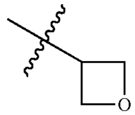 and 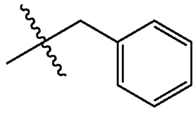 .

8. The compound, stereoisomer thereof, or pharmaceutically acceptable salt thereof of claim 1, wherein ring A is selected from the group consisting of $C_{6-10}$ aryl, 5-10 membered heteroaryl, 8-10 membered fused ring and 8-10 membered fused heterocyclic ring; or, ring A is selected from the group consisting of $C_{6-10}$ aryl, 5-10 membered heteroaryl, 8-10 membered benzocycloalkyl and 8-10 membered benzoheterocycloalkyl; or, ring A is selected from the group consisting of phenyl, thienyl, 2,3-dihydro-1H-indenyl, 2,3-dihydrobenzofuranyl and benzofuranyl.

9. The compound, stereoisomer thereof, or pharmaceutically acceptable salt thereof of claim 1, wherein n is 0, 1 or 2; or, n is 1, 2 or 3; or, n is 2.

10. The compound, stereoisomer thereof, or pharmaceutically acceptable salt thereof of claim 1, wherein each $R^3$ is independently selected from the group consisting of amino, nitro, halogen, $C_{1-4}$ alkyl and phenyl, wherein the $C_{1-4}$ alkyl or phenyl is optionally substituted with one or more $R^d$, and $R^d$ is selected from the group consisting of hydroxy, halogen and $C_{1-3}$ alkyl-NH—$C_{1-3}$ alkyl-; or, each $R^3$ is independently selected from the group consisting of amino, nitro, halogen, $C_{1-4}$ alkyl and phenyl, wherein the $C_{1-4}$ alkyl or phenyl is optionally substituted with 1, 2 or 3 $R^d$, and $R^d$ is selected from the group consisting of hydroxy, fluorine and methyl-NH-methyl-; or, each $R^3$ is independently selected from the group consisting of amino, nitro, fluorine, methyl, trifluoromethyl, —$CF_2CH_2OH$, —$CHF_2$, —$CF_2CH_3$, —$CF_2C(CH_3)_2OH$ and

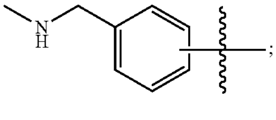 ;

or, each $R^3$ is independently selected from the group consisting of amino, fluorine, methyl, trifluoromethyl, —$CF_2CH_2OH$, —$CHF_2$, —$CF_2CH_3$, —$CF_2C(CH_3)_2OH$ and

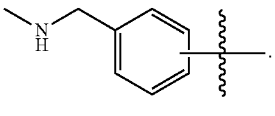 .

11. The compound of formula (I), the stereoisomer thereof or the pharmaceutically acceptable salt thereof according to claim 1, wherein structural unit

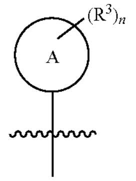

is selected from the group consisting of

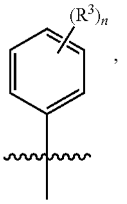
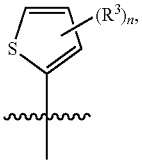
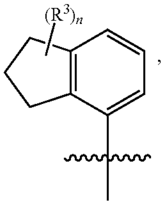
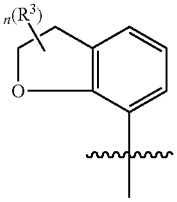

and

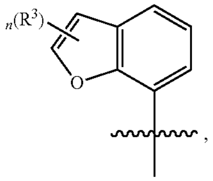

further selected from the group consisting of

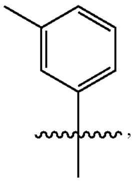
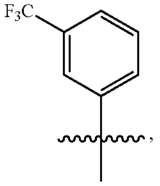
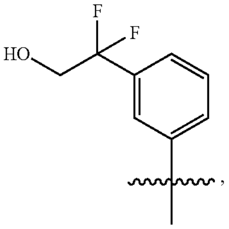
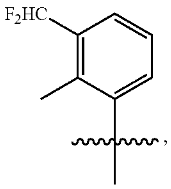
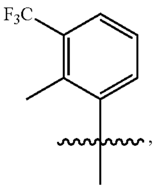
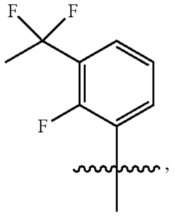
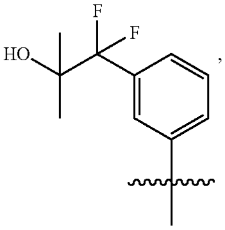
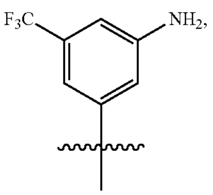
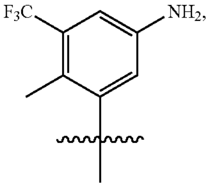
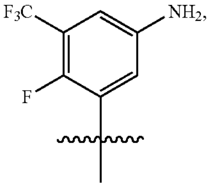

-continued

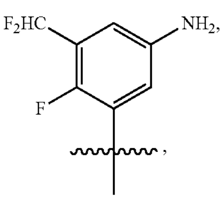
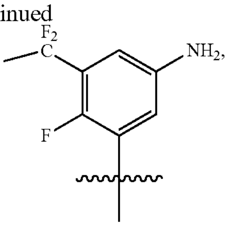
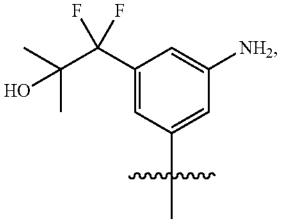
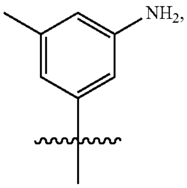
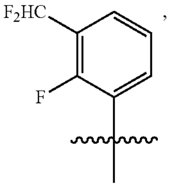
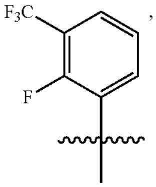
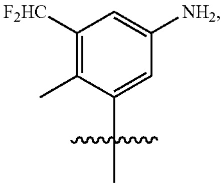
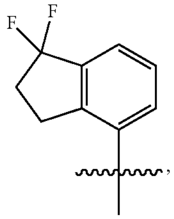
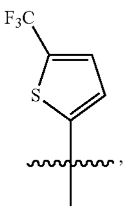
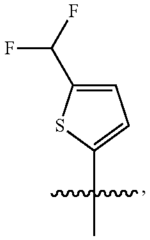
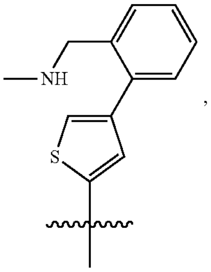
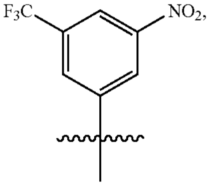
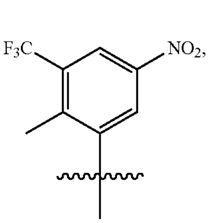
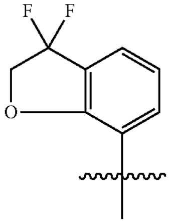

and

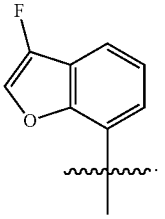

12. The compound, stereoisomer thereof, or pharmaceutically acceptable salt thereof of claim 1, wherein $R^4$ and $R^5$ are each independently selected from the group consisting of hydrogen, deuterium and $C_{1-3}$ alkyl, wherein the $C_{1-3}$ alkyl is optionally substituted with one or more halogens; or, $R^4$ is selected from methyl, and $R^5$ is selected from the group consisting of hydrogen and deuterium, wherein the methyl is optionally substituted with one or more fluorine; or, $R^4$ is selected from the group consisting of methyl and —$CH_2F$, and $R^5$ is selected from the group consisting of hydrogen and deuterium; or, $R^5$ is selected from $C_{1-3}$ alkyl, and $R^4$ is selected from the group consisting of hydrogen and deuterium, wherein the $C_{1-3}$ alkyl is optionally substituted with one or more halogens; or, $R^5$ is selected from the group consisting of methyl and —$CH_2F$, and $R^4$ is selected from the group consisting of hydrogen and deuterium.

13. The compound, stereoisomer thereof, or pharmaceutically acceptable salt thereof of claim 1, wherein $R^6$ is selected from the group consisting of hydrogen, halogen and $C_{1-3}$ alkyl, wherein the $C_{1-3}$ alkyl is optionally substituted with one or more halogens; or, $R^6$ is selected from the group consisting of hydrogen, fluorine, chlorine and methyl, wherein the methyl is optionally substituted with 1, 2 or 3 fluorine; or, $R^6$ is selected from the group consisting of hydrogen, fluorine, methyl and —$CH_2F$; or, $R^6$ is selected from methyl.

14. The compound, stereoisomer thereof, or pharmaceutically acceptable salt thereof of claim 1, wherein:

X and Y are each independently selected from the group consisting of $CR^a$ and N;

$R^a$ is selected from the group consisting of hydrogen and $C_{1-4}$ alkoxy;

"------" represents a double bond;

$R^1$, $R^2$ and the phosphorus atom to which they are both connected together form 6 membered heterocyclyl, wherein the ring atoms of the 6 membered heterocyclyl at least contain one N atom or O atom, and when the ring atoms contain an N atom, N is connected to $R^c$;

$R^c$ is selected from the group consisting of $C_{1-4}$ alkyl-S$(O)_2$— and $C_{3-6}$ cycloalkyl-S$(O)_2$—;

ring A is selected from $C_{6-10}$ aryl;

n is 0, 1, 2 or 3;

each $R^3$ is independently selected from the group consisting of halogen and $C_{1-8}$ alkyl, wherein the $C_{1-8}$ alkyl is optionally substituted with one or more halogens;

$R^4$ and $R^5$ are each independently selected from the group consisting of hydrogen and $C_{1-3}$ alkyl, wherein the $C_{1-3}$ alkyl is optionally substituted with one or more fluorine; and $R^6$ is selected from the group consisting of hydrogen, halogen and $C_{1-6}$ alkyl, wherein the $C_{1-6}$ alkyl is optionally substituted with one or more halogens.

15. The compound, stereoisomer thereof, or pharmaceutically acceptable salt thereof of claim 1, wherein the compound of formula (I), the stereoisomer thereof or the pharmaceutically acceptable salt thereof is selected from a compound of formula (II), a stereoisomer thereof or a pharmaceutically acceptable salt thereof:

(II)

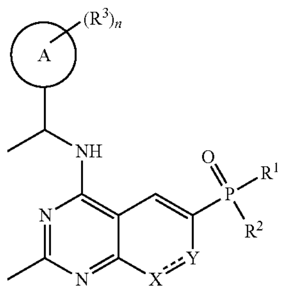

wherein,

X and Y are each independently selected from the group consisting of $CR^a$, C(O), N and $NR^b$;

"------" represents a single bond or a double bond depending on X and Y;

$R^a$ is selected from the group consisting of hydrogen, hydroxy, halogen, $C_{1-6}$ alkyl and $C_{1-6}$ alkoxy, wherein the $C_{1-6}$ alkyl is optionally substituted with one or more halogens, and the $C_{1-6}$ alkoxy is optionally substituted with one or more deuterium or halogens;

$R^b$ is selected from the group consisting of hydrogen, $C_{1-6}$ alkyl and $C_{1-6}$ alkoxy;

$R^1$ and $R^2$ are each independently selected from the group consisting of $C_{1-6}$ alkyl, $NH(R^c)$—$C_{1-6}$ alkyl- and $N(R^c)(C_{1-6}$ alkyl)-$C_{1-6}$ alkyl-, or $R^1$, $R^2$ and the phosphorus atom to which they are both connected together form 5-8 membered heterocyclyl, wherein the ring atoms of the 5-8 membered heterocyclyl at least contain one N atom, and N is connected to $R^c$;

each $R^c$ is independently selected from the group consisting of hydrogen, $C_{1-6}$ alkyl-, $C_{1-6}$ alkyl-C(O)—, $C_{1-6}$ alkyl OC(O)—, $C_{1-6}$ alkyl-O—$C_{1-6}$ alkyl-, $C_{1-6}$ alkyl-O—$C_{1-6}$ alkyl-C(O)—, amino-C(O)—, mono($C_{1-6}$ alkyl)amino-C(O)—, di($C_{1-6}$ alkyl)amino-C(O)—, amino-$C_{1-6}$ alkyl-C(O)—, mono($C_{1-6}$ alkyl)amino-$C_{1-6}$ alkyl-C(O)—, di($C_{1-6}$ alkyl)amino-$C_{1-6}$ alkyl-C(O)—, amino-C(O)—$C_{1-6}$ alkyl-, mono($C_{1-6}$ alkyl)amino-C(O)—$C_{1-6}$ alkyl-, di($C_{1-6}$ alkyl)amino-C(O)—$C_{1-6}$ alkyl-, 3-6 membered cycloalkyl-, 3-6 membered cycloalkyl-C(O)—, 3-6 membered cycloalkyl-$C_{1-6}$ alkyl-, $C_{6-10}$ aryl-$C_{1-6}$ alkyl-, and $C_{1-6}$ alkyl-substituted with one or more hydroxy, wherein the $R^c$ is optionally substituted with one or more halogens when it is not hydrogen;

ring A is selected from the group consisting of $C_{6-10}$ aryl, 5-10 membered heteroaryl and 8-12 membered fused ring;

n is 0, 1, 2 or 3;

each $R^3$ is independently selected from the group consisting of amino, nitro, halogen, $C_{1-8}$ alkyl and 3-6 membered cycloalkyl, wherein the $C_{1-8}$ alkyl and 3-6 membered cycloalkyl are optionally substituted with one or more $R^d$; and $R^d$ is selected from the group consisting of hydroxy and halogen;

or, the compound of formula (I), the stereoisomer thereof or the pharmaceutically acceptable salt thereof is selected from a compound of formula (III), a stereoisomer thereof or a pharmaceutically acceptable salt thereof:

(III)

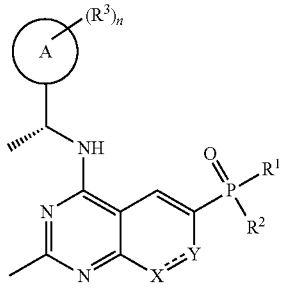

wherein,
$R^1$, $R^2$, $R^3$, X, Y, n, ring A and ------ are defined as in claim 1; or, structural unit
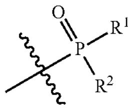
is selected from the group consisting of structural units
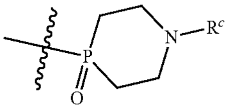
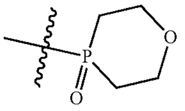
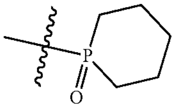
and
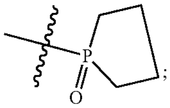
;
or, structural unit
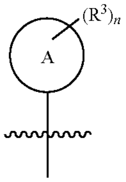
is selected from the group consisting of
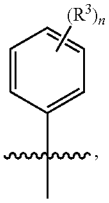
,
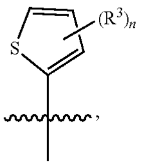
,
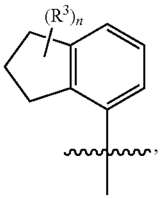
,
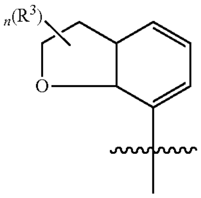
and
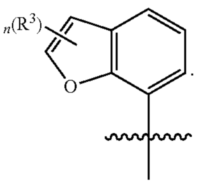
.
16. The compound, stereoisomer thereof, or pharmaceutically acceptable salt thereof of claim 1, selected from:
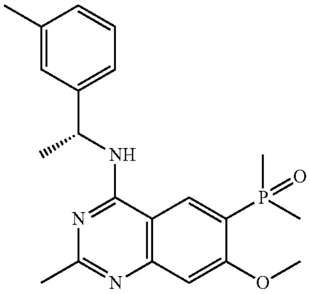
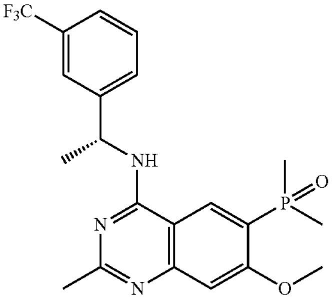
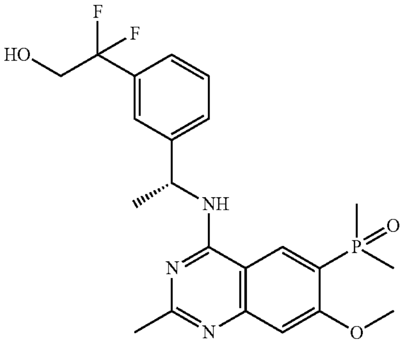
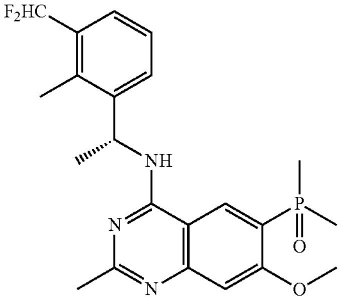
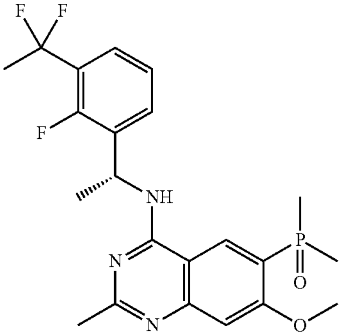

-continued
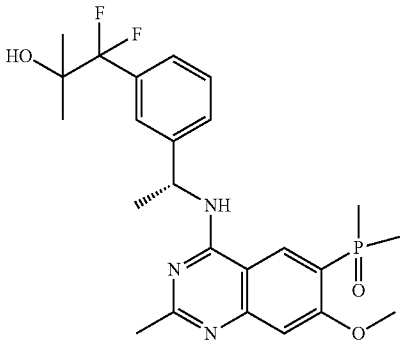
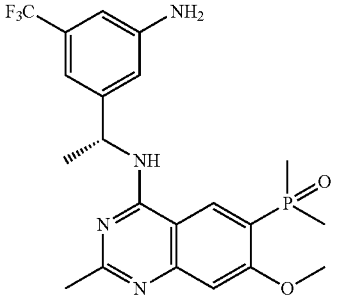
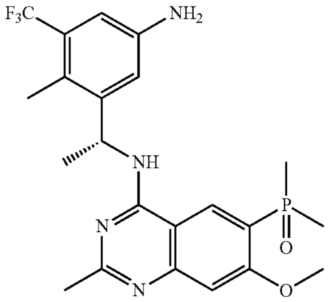
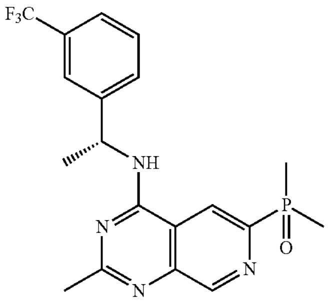
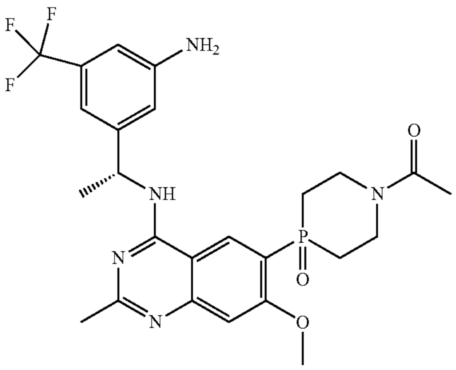
-continued
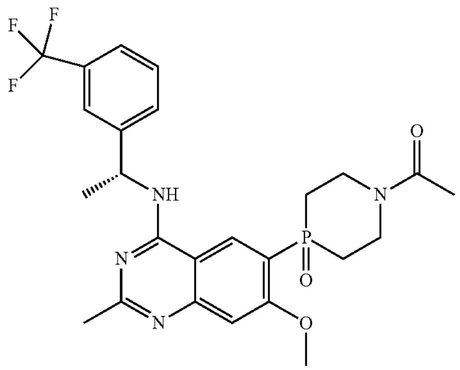
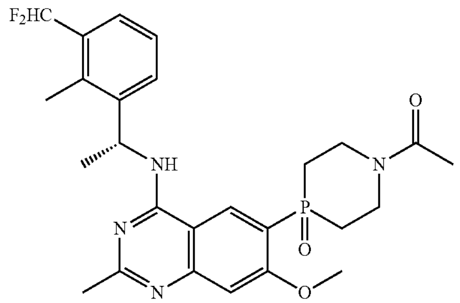
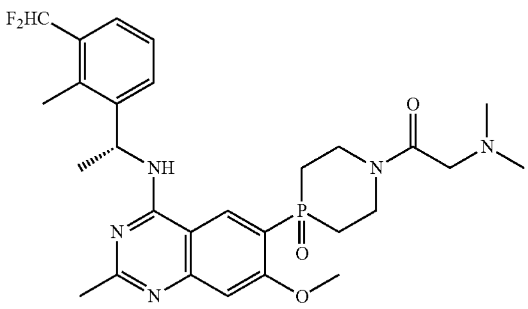
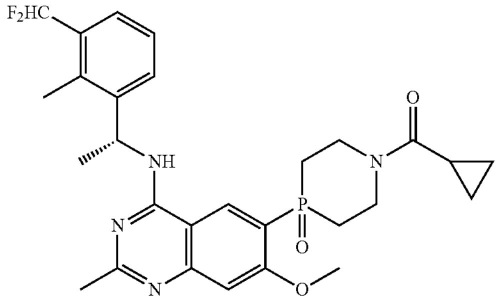
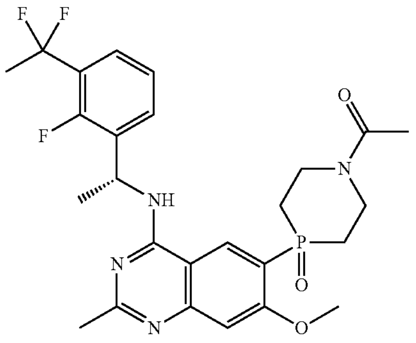

-continued
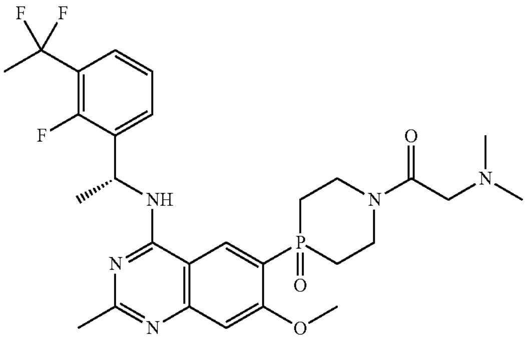
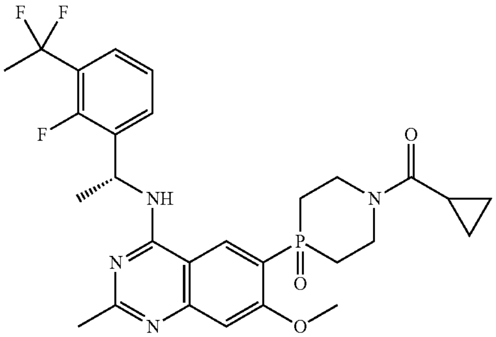
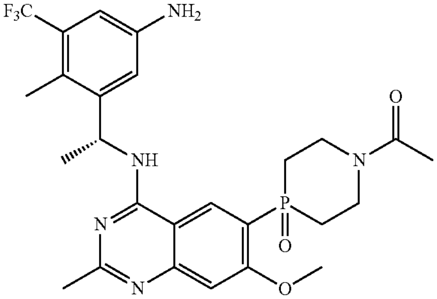
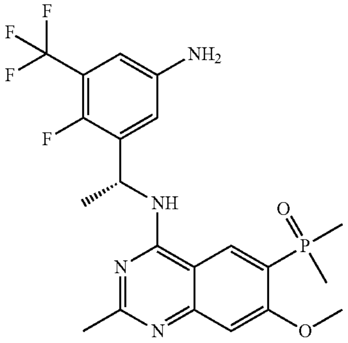
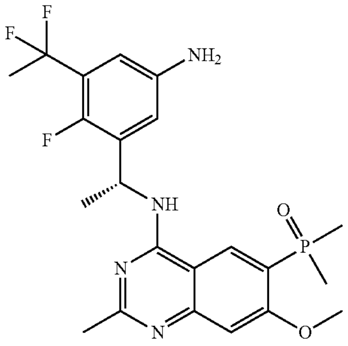
-continued
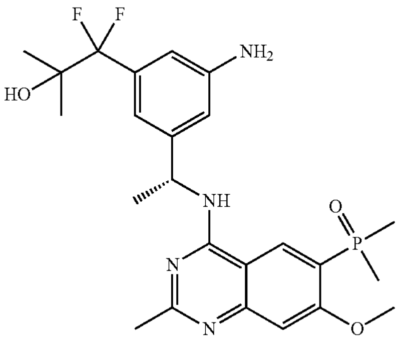
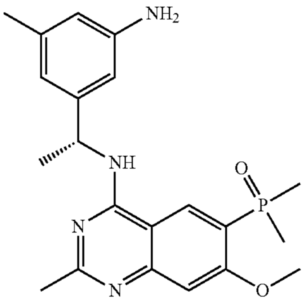
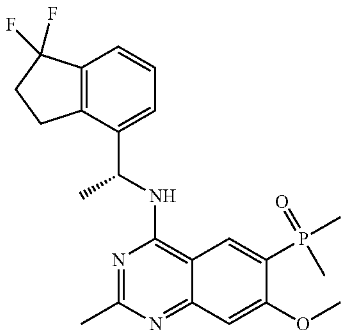
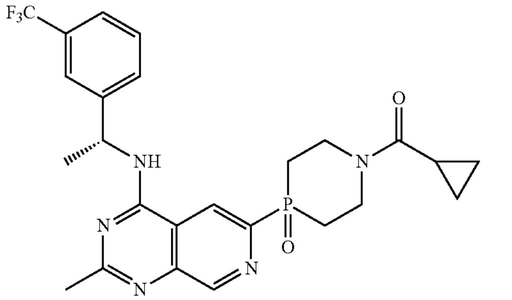
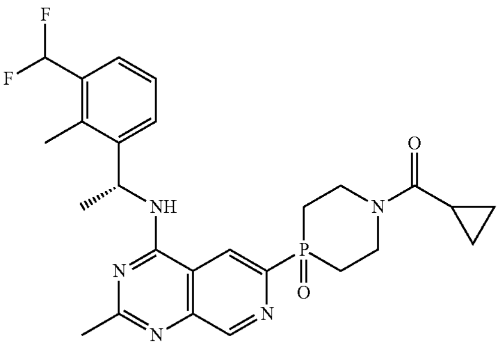

-continued
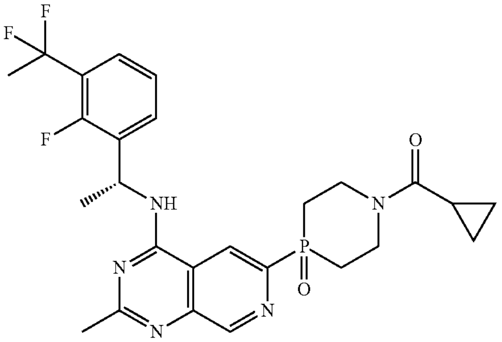
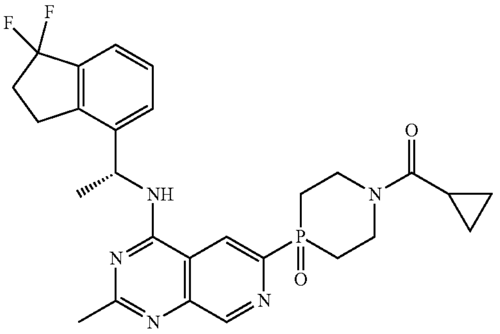
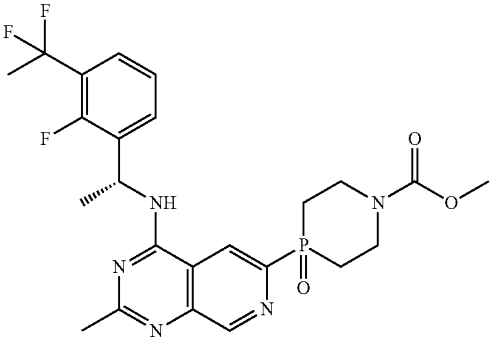
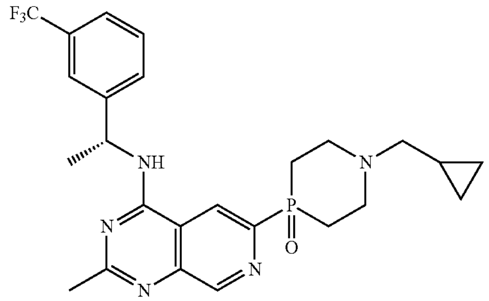
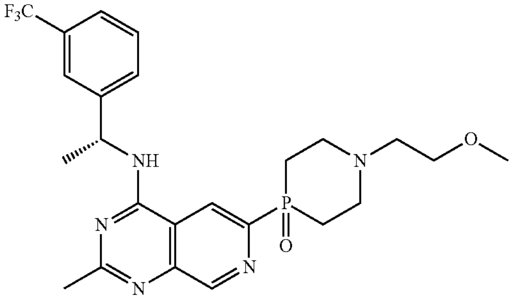
-continued
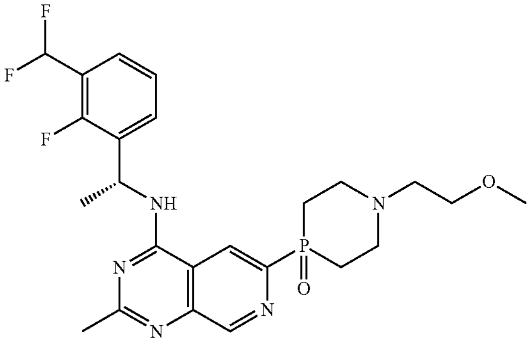
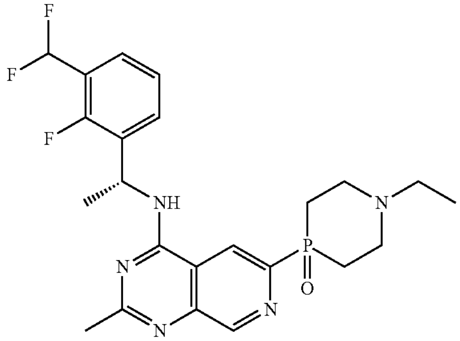
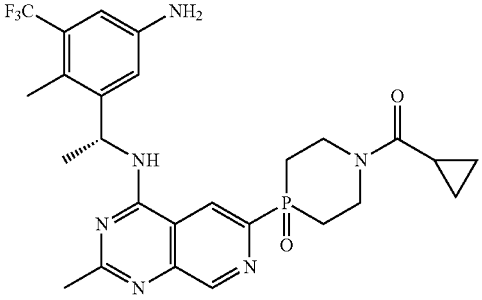
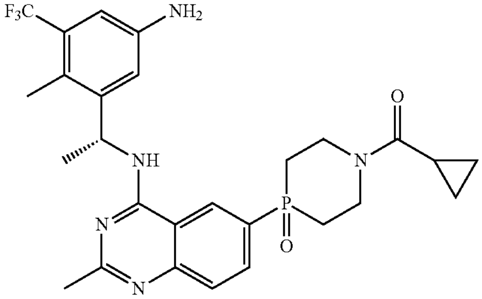
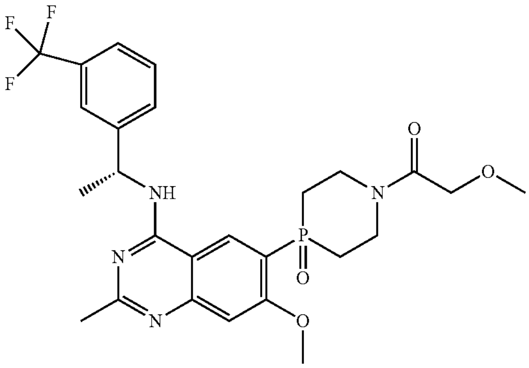

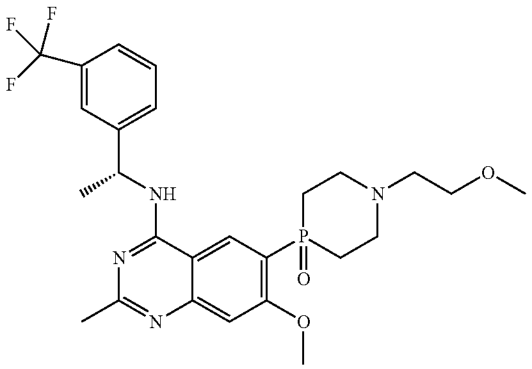
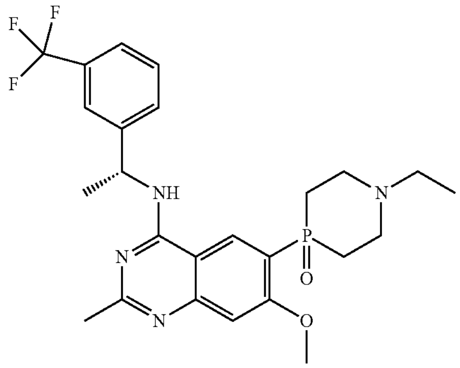
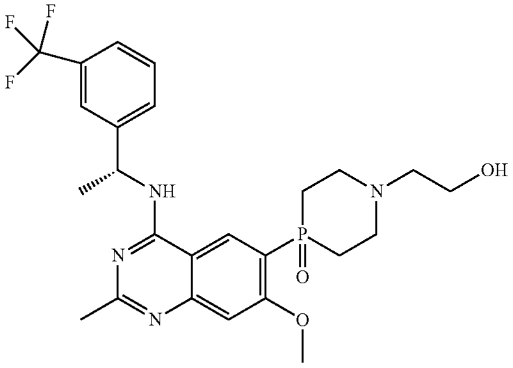
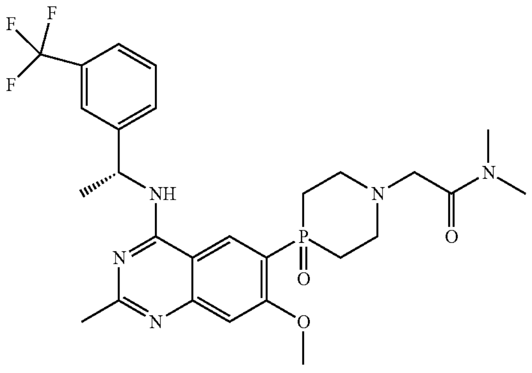
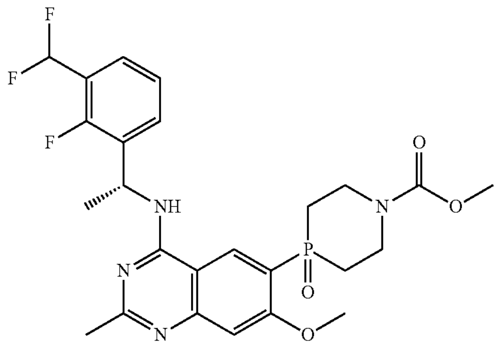
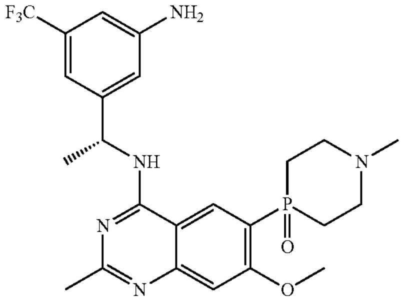
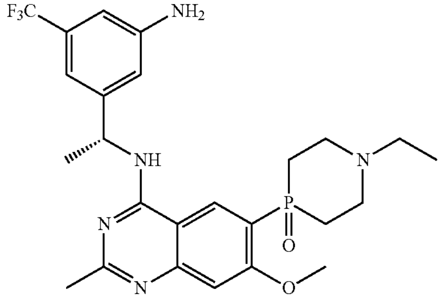
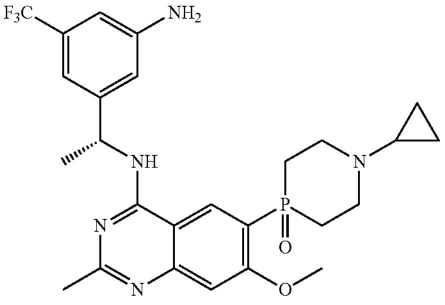
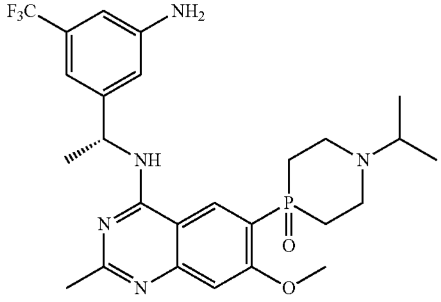

-continued
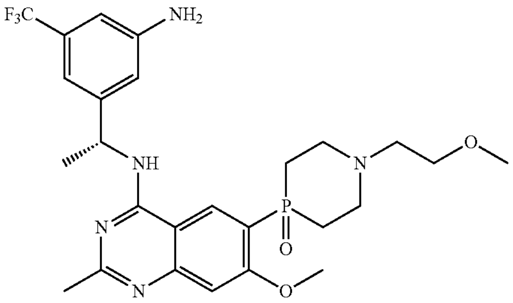
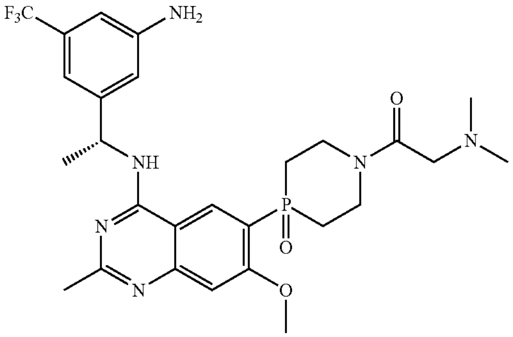
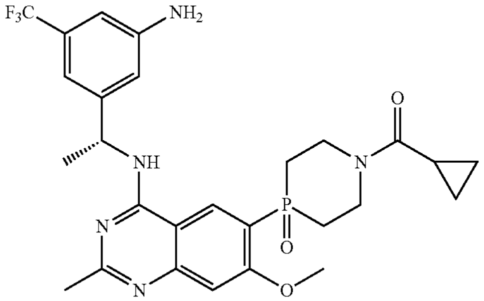
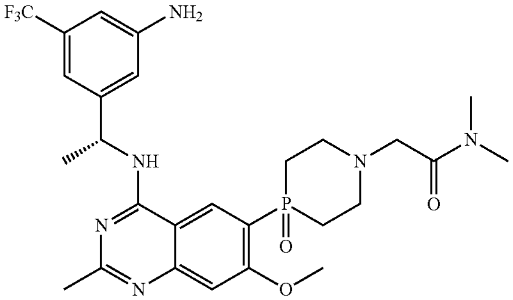
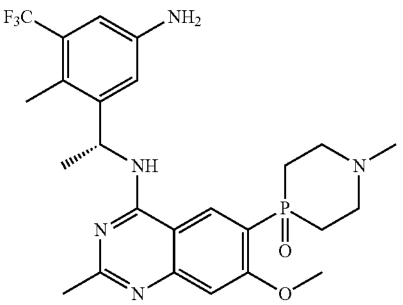
-continued
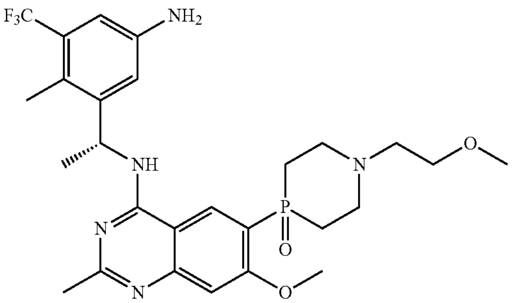
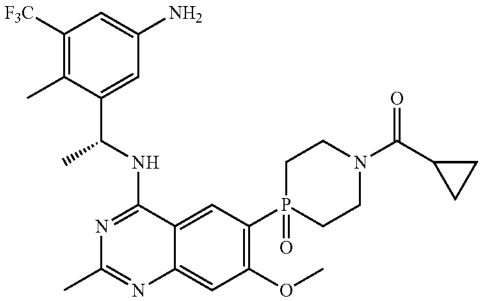
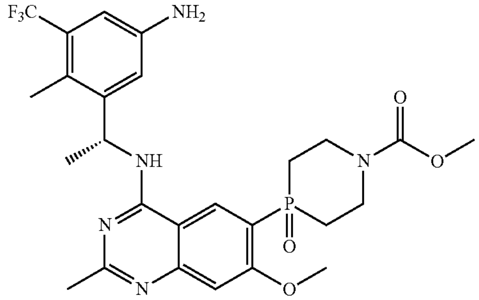
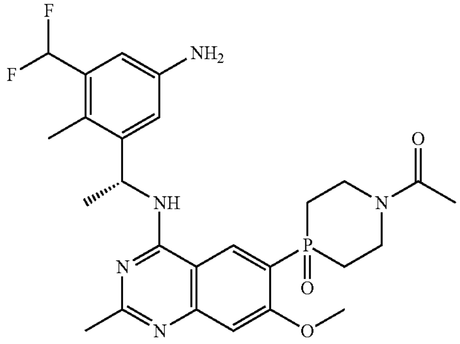
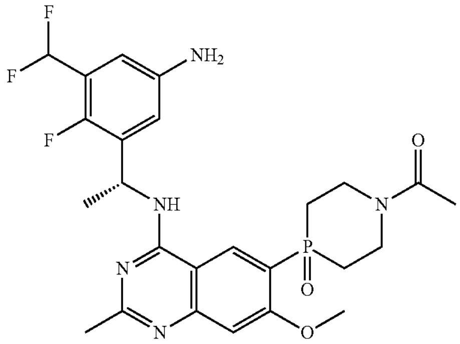

-continued
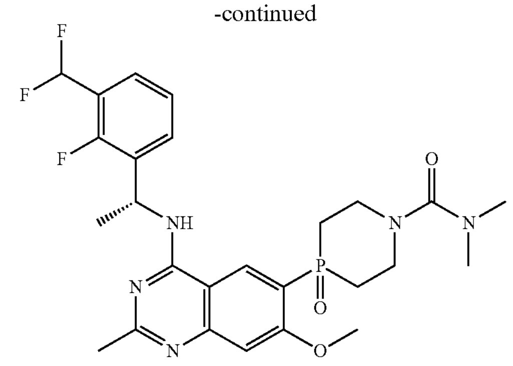
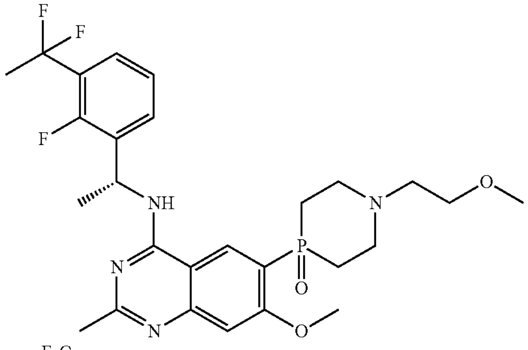
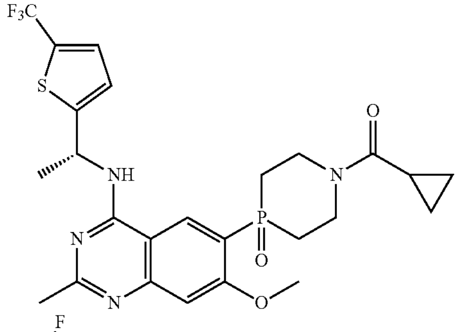
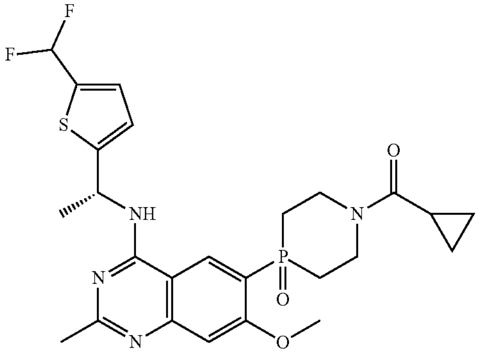
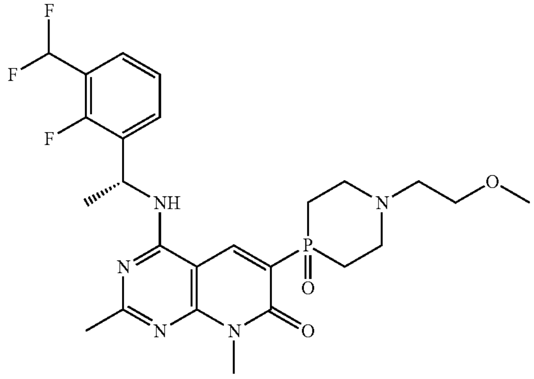
-continued
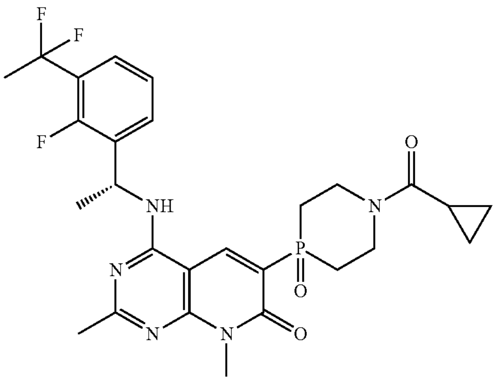
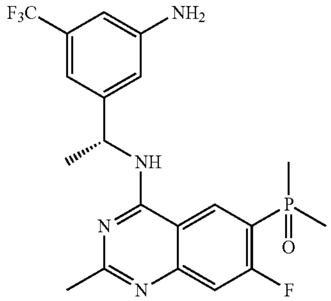
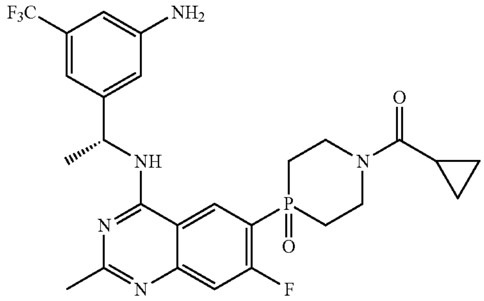
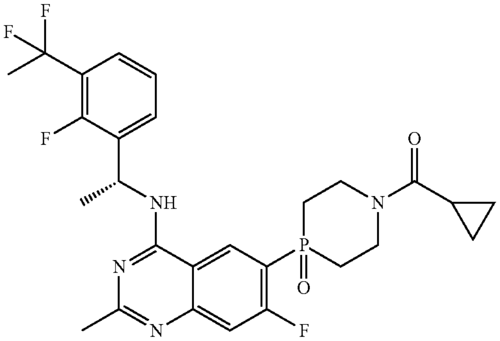
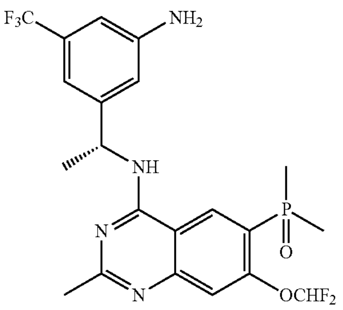

-continued
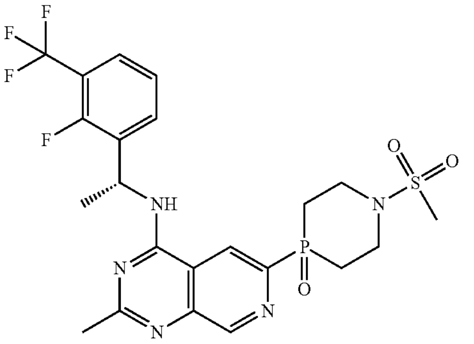
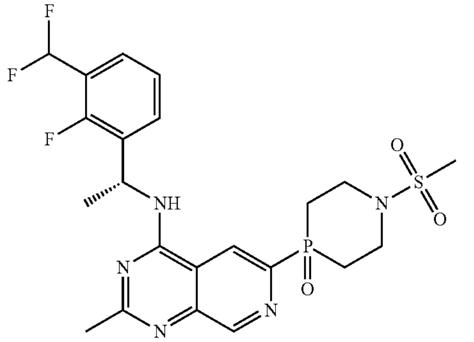
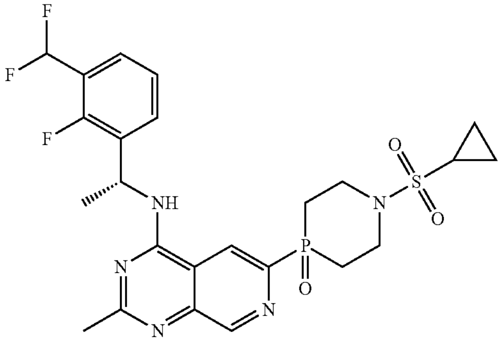
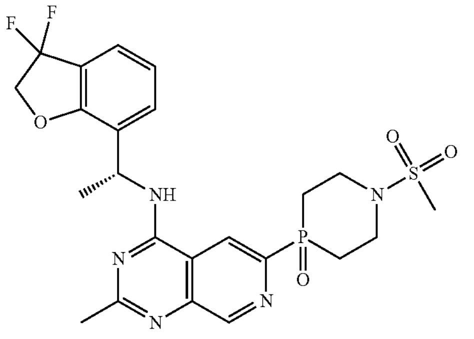
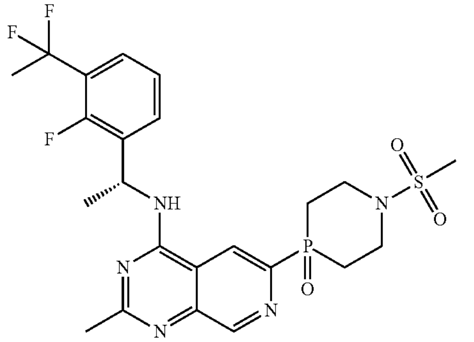
-continued
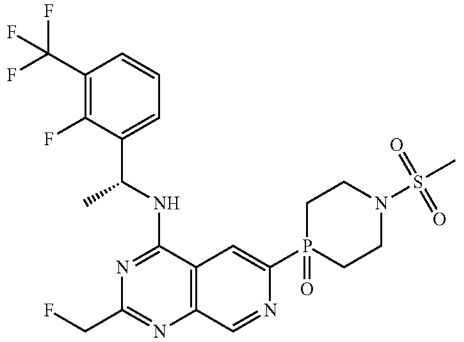
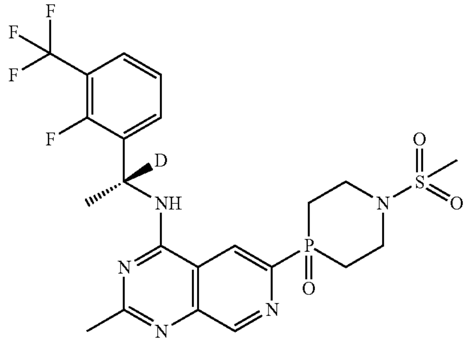
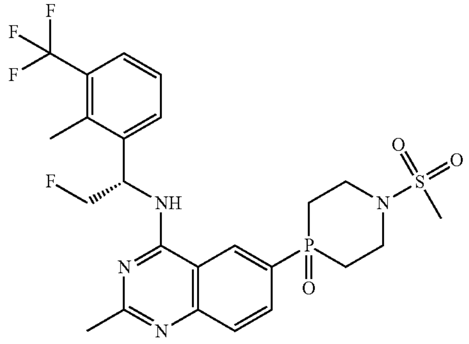
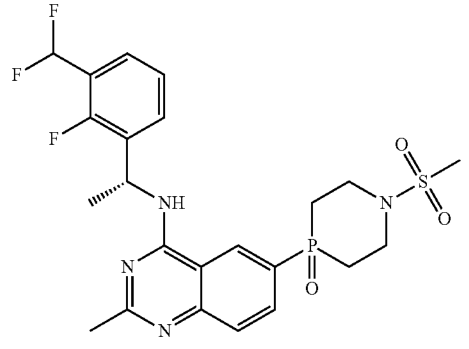
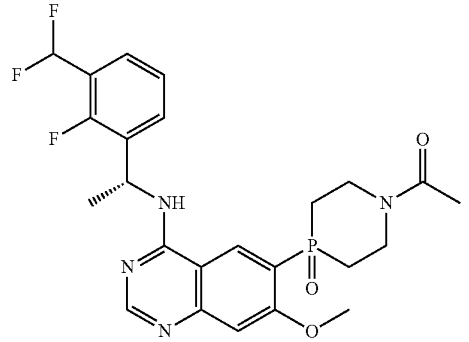

-continued
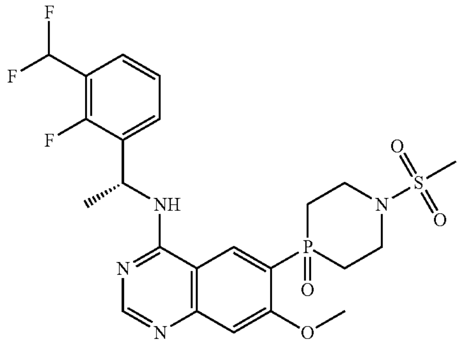
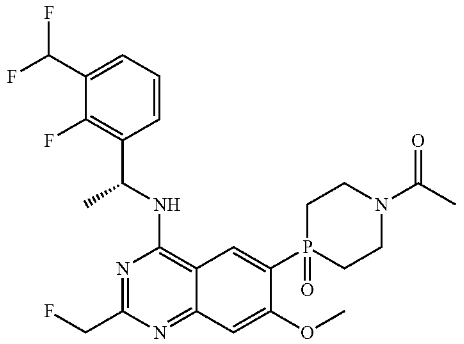
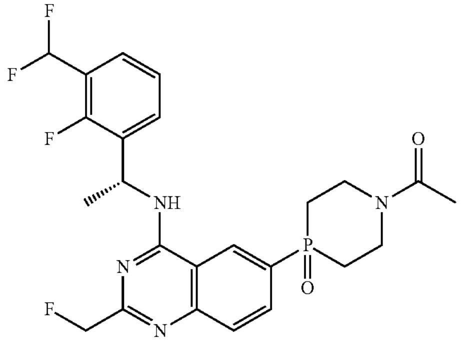
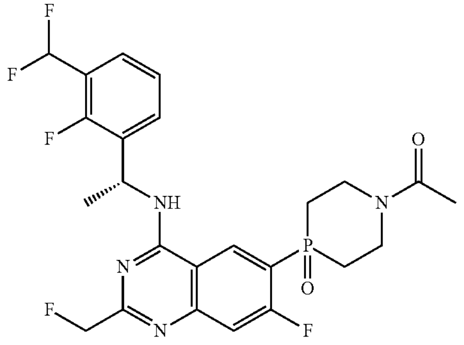
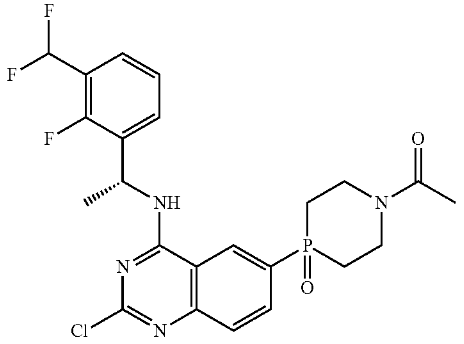
-continued
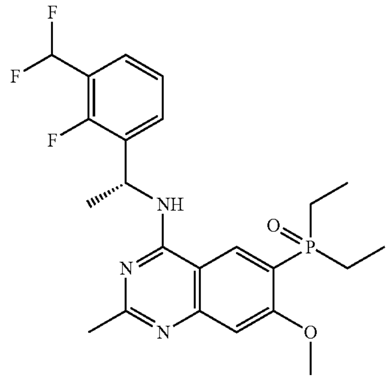
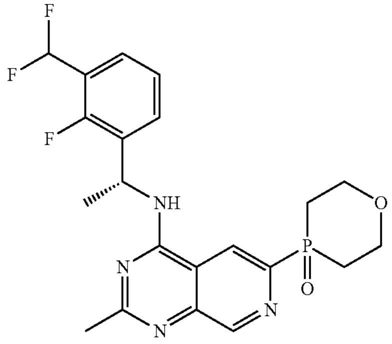
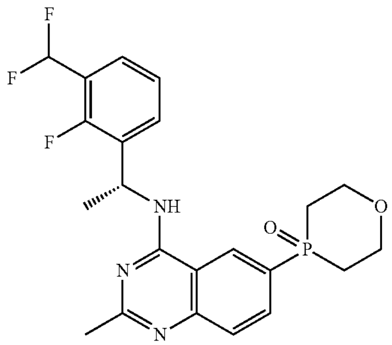
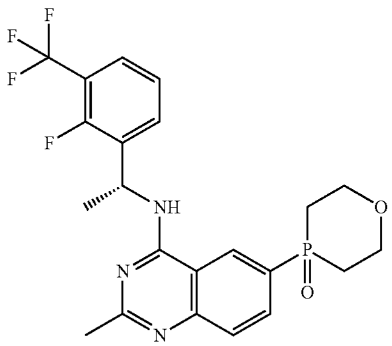

-continued
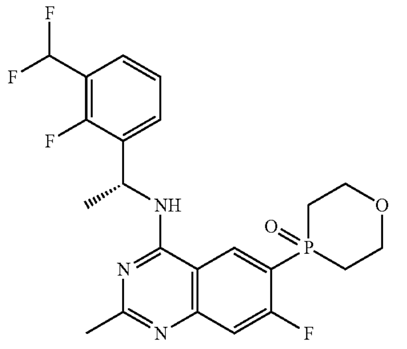
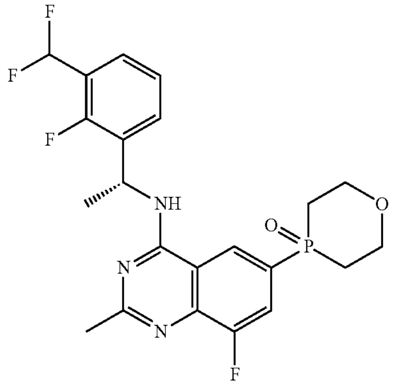
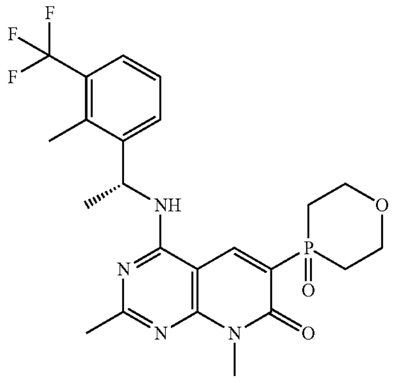
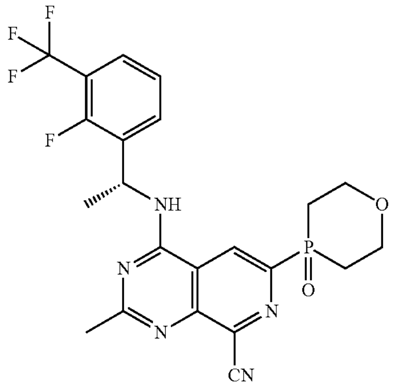
-continued
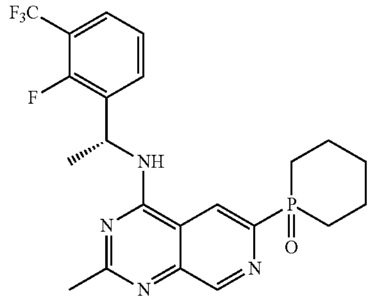
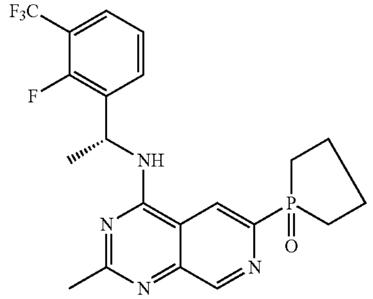
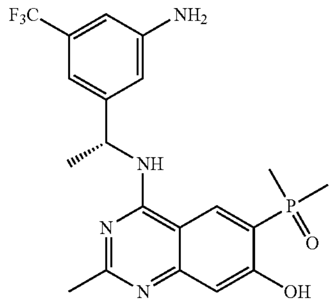
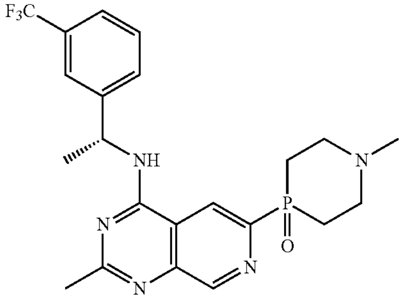
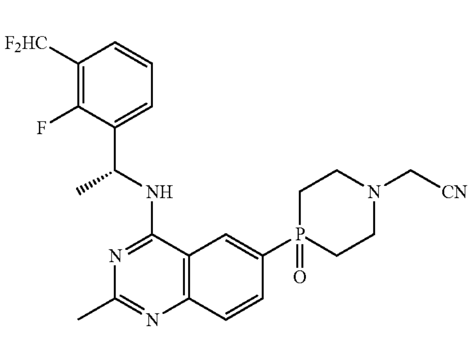

-continued
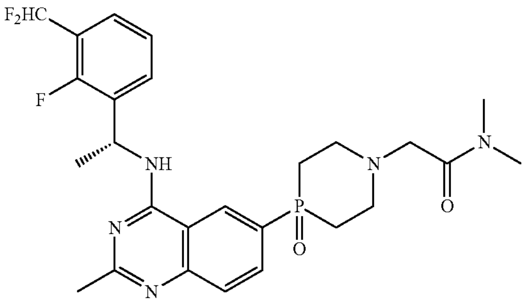
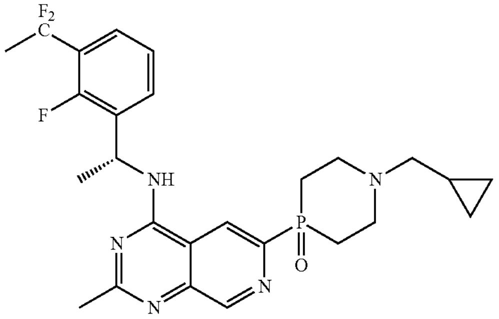
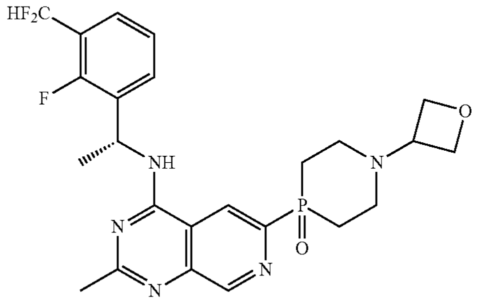
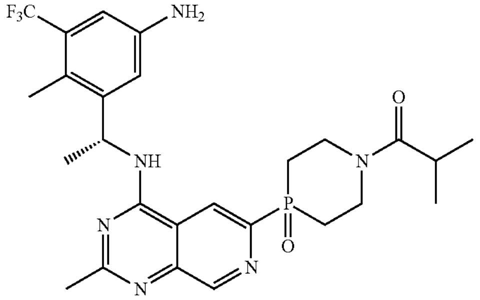
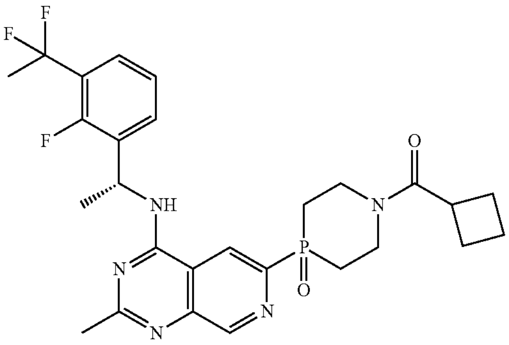
-continued
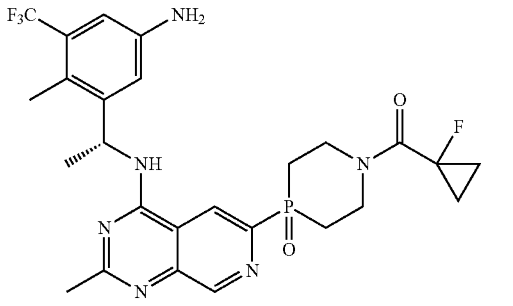
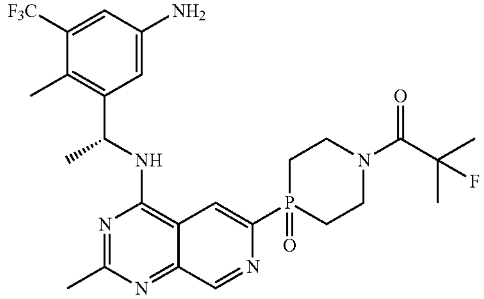
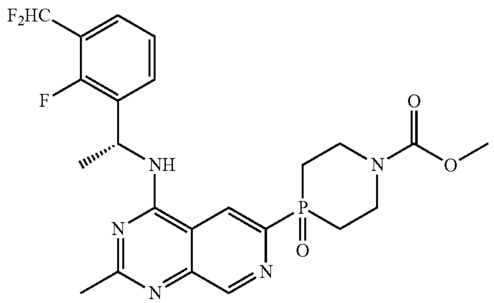
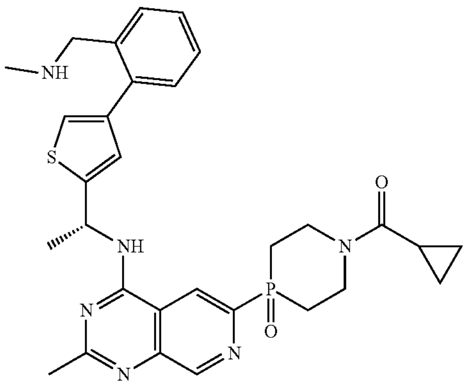
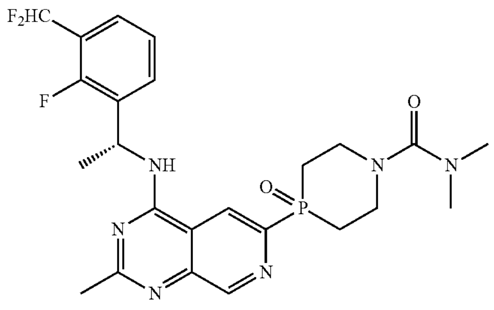

-continued
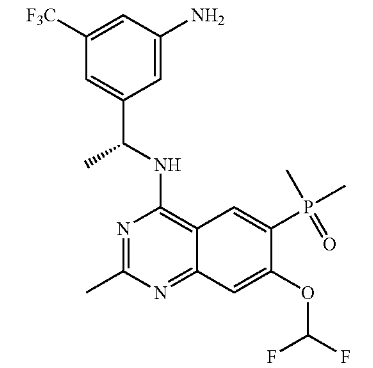
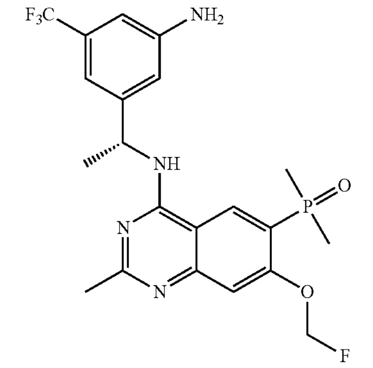
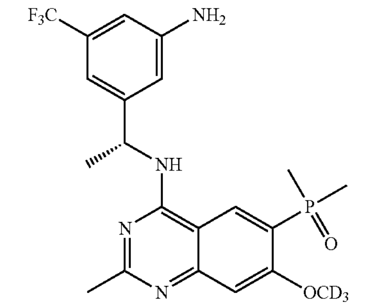
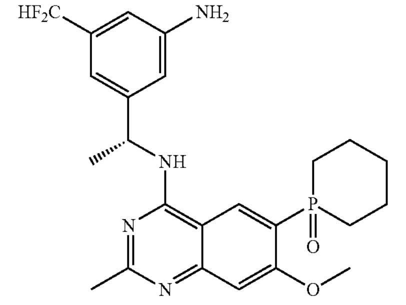
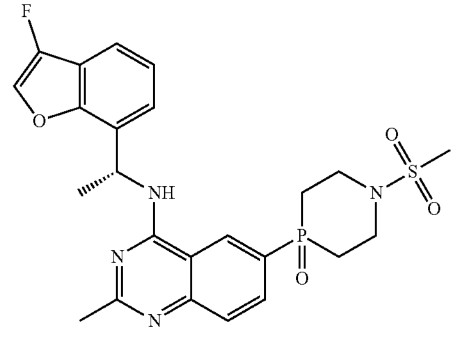
-continued
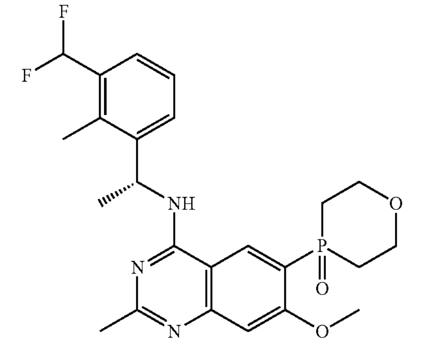
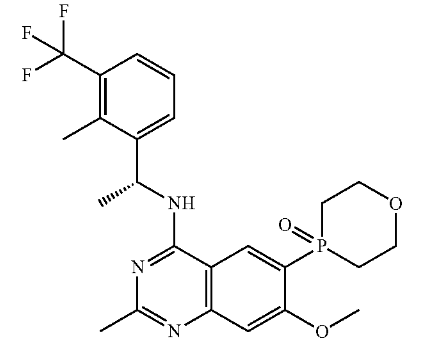
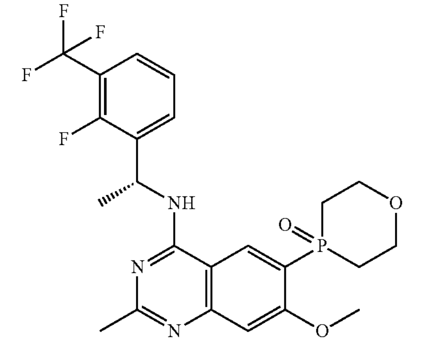
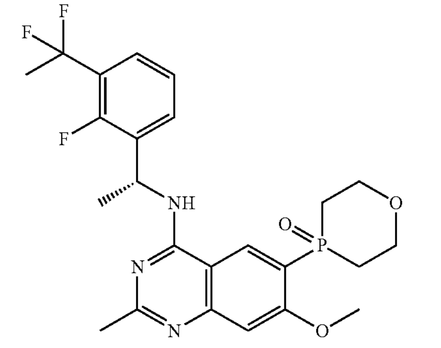
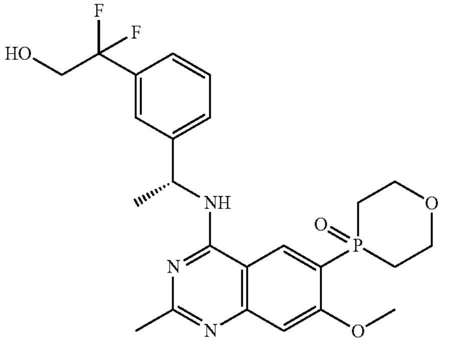

-continued
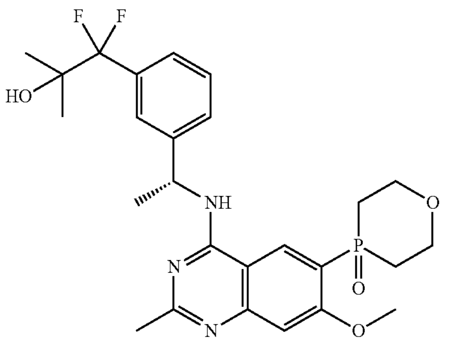
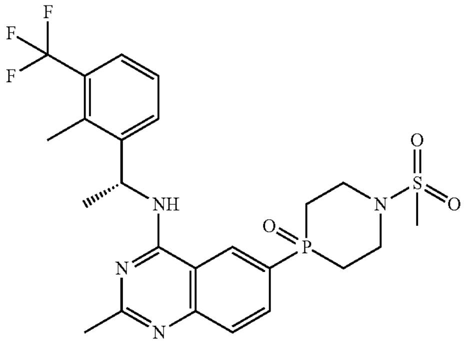
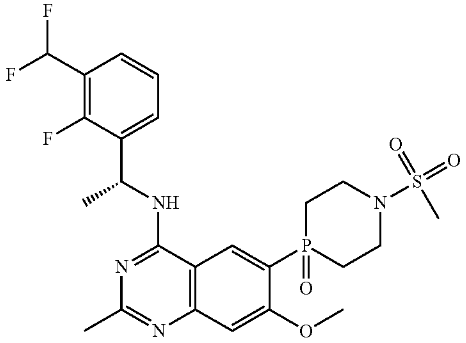
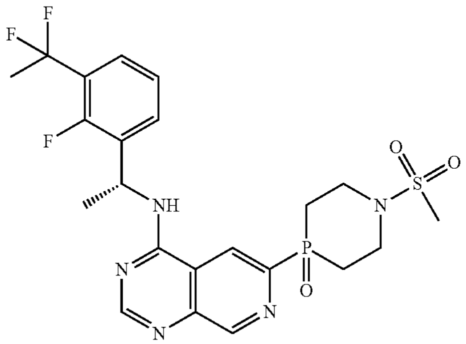
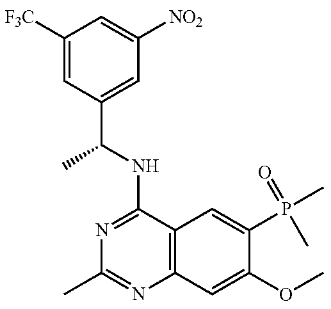
-continued
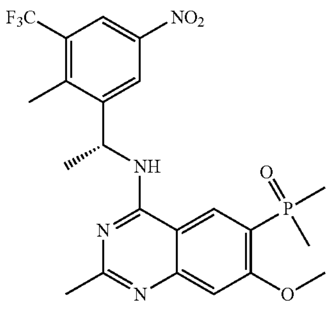
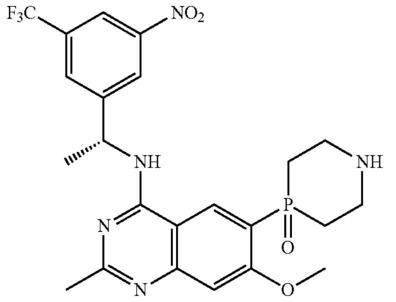
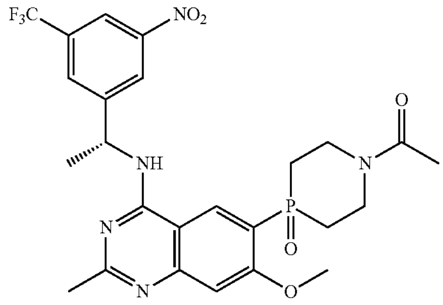
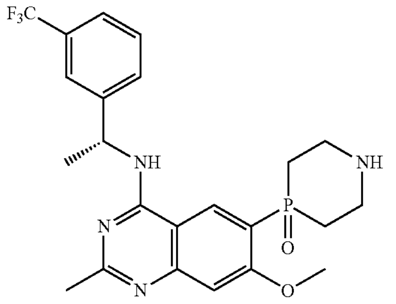
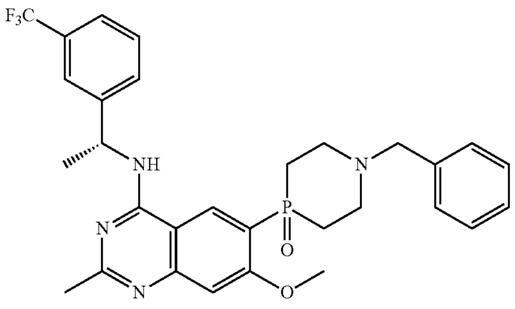

-continued
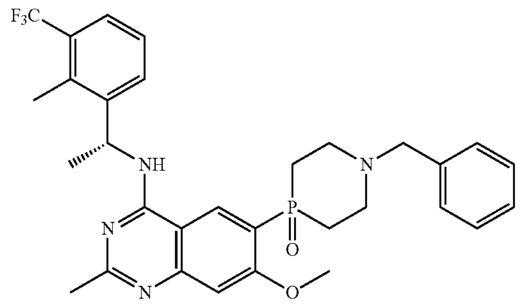
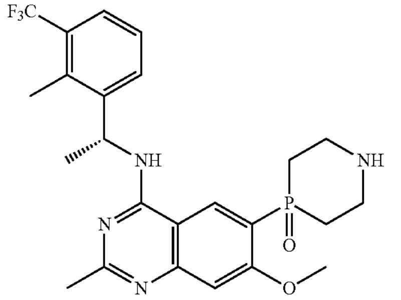
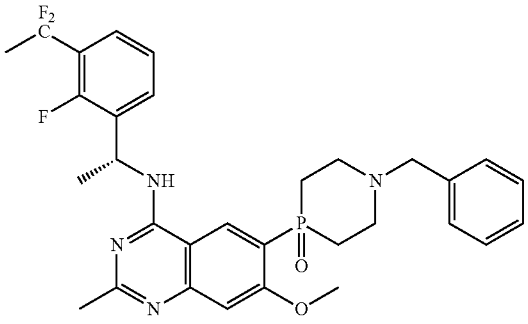
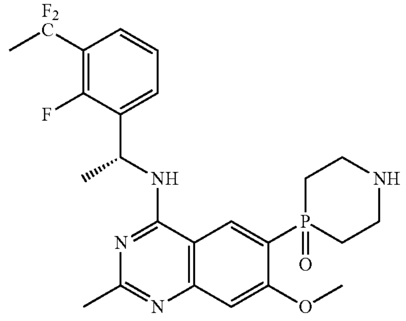
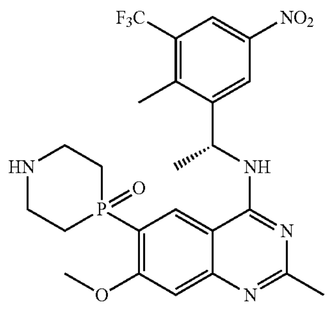
-continued
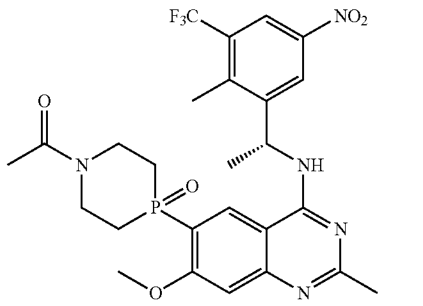
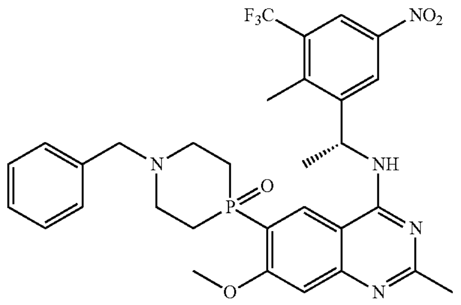
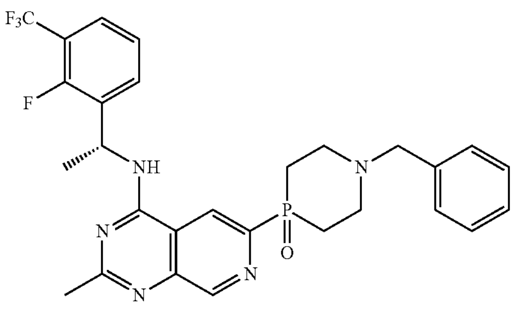
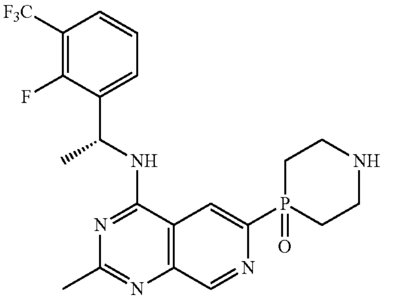
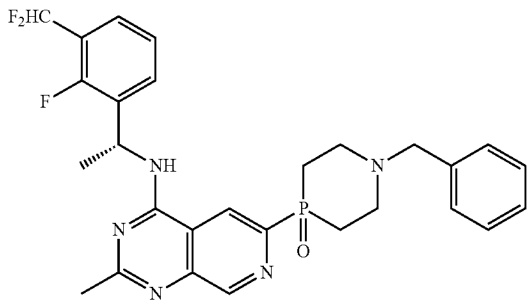

-continued
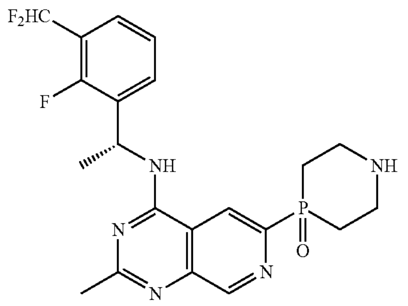
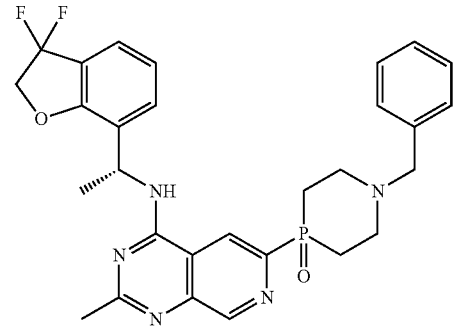
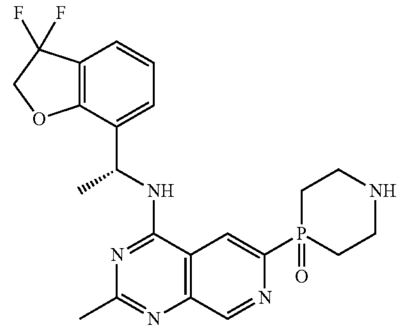
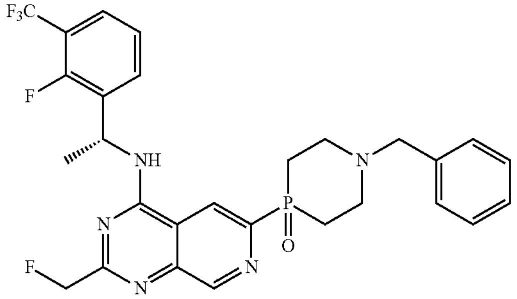
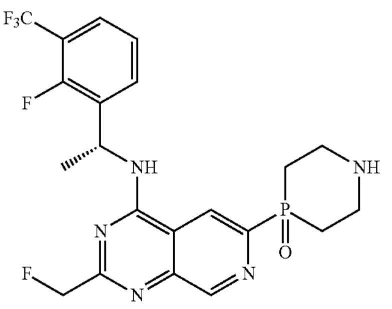
-continued
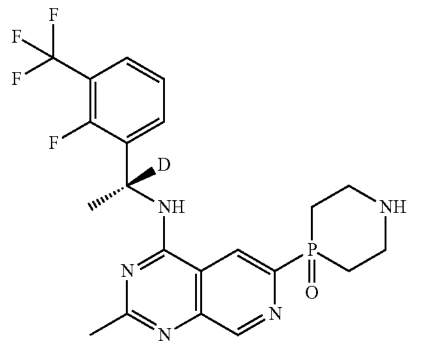
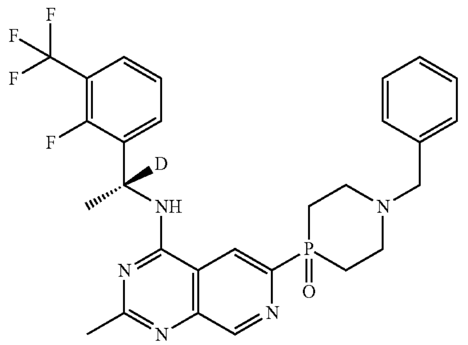
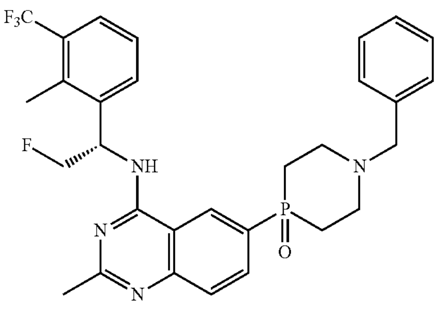
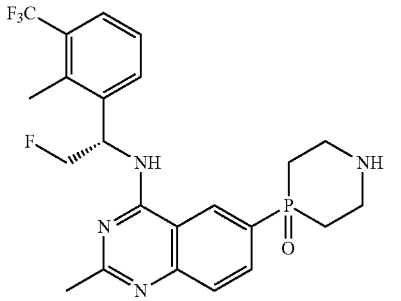
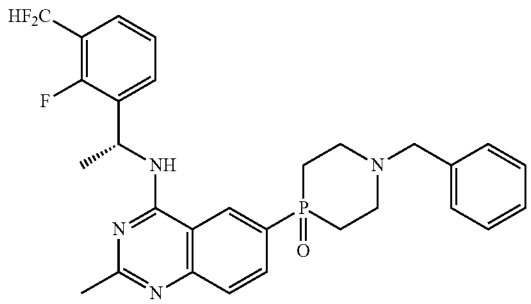

-continued

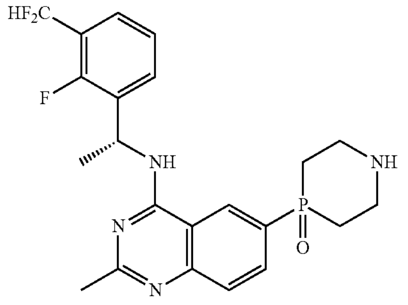

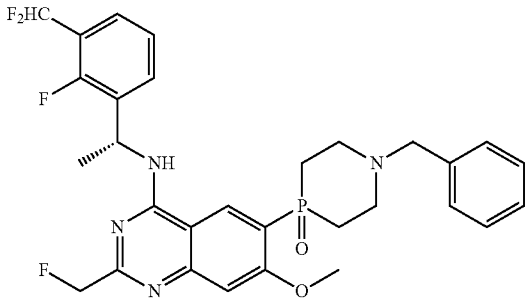

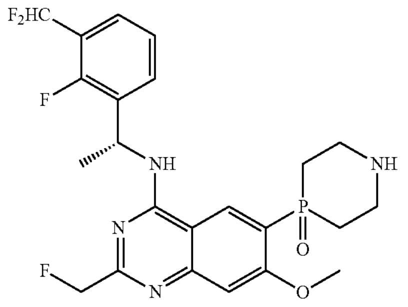

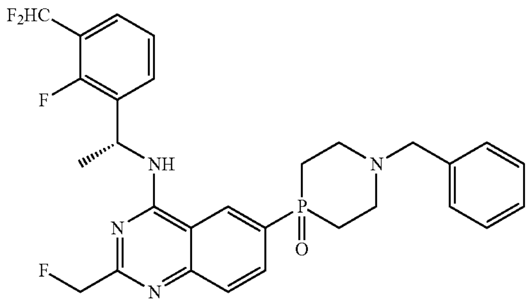

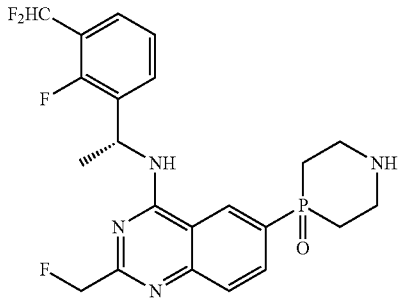

-continued

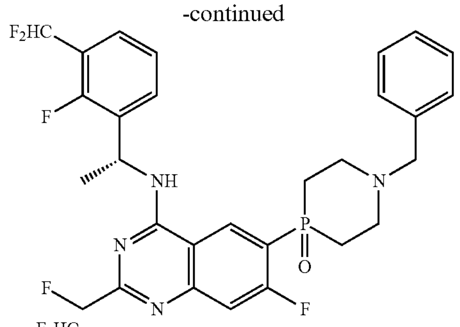

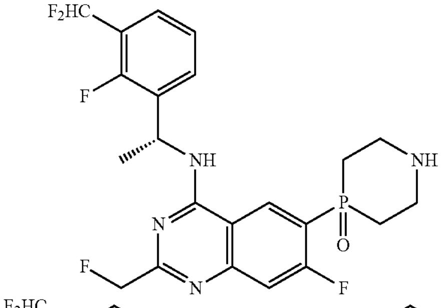

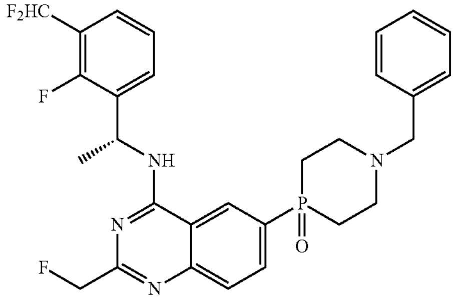

or

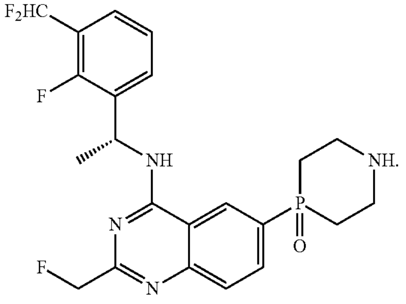 [SMILES: C[C@@H](Nc1nc(CF)nc2ccc(P3(=O)CCNCC3)cc12)c1cccc(C(F)F)c1F]

17. A pharmaceutical composition comprising the compound, the stereoisomer thereof or the pharmaceutically acceptable salt thereof according to claim 1.

18. A method of treating a disease or disorder related to SOS1 or regulated by SOS1, comprising administering to a mammal in need of such treatment a therapeutically effective amount of the compound, the stereoisomer or the pharmaceutically acceptable salt thereof according to claim 1, or the pharmaceutical composition thereof.

19. The method according to claim 18, wherein the disease or disorder related to SOS1 or regulated by SOS1 is a cancer.

* * * * *